US012509464B2

(12) United States Patent
Suh et al.

(10) Patent No.: US 12,509,464 B2
(45) Date of Patent: Dec. 30, 2025

(54) ORGANIC LIGHT EMITTING DEVICE

(71) Applicant: LG CHEM, LTD., Seoul (KR)

(72) Inventors: Sang Duk Suh, Daejeon (KR); Min Woo Jung, Daejeon (KR); Jungha Lee, Daejeon (KR); Su Jin Han, Daejeon (KR); Seulchan Park, Daejeon (KR); Sunghyun Hwang, Daejeon (KR); Dong Hoon Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 869 days.

(21) Appl. No.: 17/611,991

(22) PCT Filed: Dec. 4, 2020

(86) PCT No.: PCT/KR2020/017667
§ 371 (c)(1),
(2) Date: Nov. 17, 2021

(87) PCT Pub. No.: WO2021/125649
PCT Pub. Date: Jun. 24, 2021

(65) Prior Publication Data
US 2022/0259208 A1 Aug. 18, 2022

(30) Foreign Application Priority Data
Dec. 19, 2019 (KR) ........................ 10-2019-0170947
Dec. 3, 2020 (KR) ........................ 10-2020-0167777

(51) Int. Cl.
*H10K 85/60* (2023.01)
*C07D 487/04* (2006.01)
*H10K 50/11* (2023.01)

(52) U.S. Cl.
CPC ......... *C07D 487/04* (2013.01); *H10K 85/615* (2023.02); *H10K 85/6572* (2023.02);
(Continued)

(58) Field of Classification Search
CPC ...... C07D 487/04; H10K 50/11; H10K 71/00; H10K 85/342; H10K 85/615;
(Continued)

(56) References Cited

U.S. PATENT DOCUMENTS

2002/0076576 A1* 6/2002 Li ......................... H10K 85/00 428/917
2004/0251816 A1 12/2004 Leo et al.
(Continued)

FOREIGN PATENT DOCUMENTS

CN 103875092 A 6/2014
CN 103890991 A 6/2014
(Continued)

*Primary Examiner* — Elizabeth M. Dahlburg
(74) *Attorney, Agent, or Firm* — Bryan Cave Leighton Paisner LLP

(57) ABSTRACT

Provided is an organic light emitting device having improved driving voltage, efficiency and lifetime, the device including a light emitting layer comprising a first compound
(Continued)

of Chemical Formula 1 and a second compound of Chemical Formula 2:

<Chemical Formula 1>

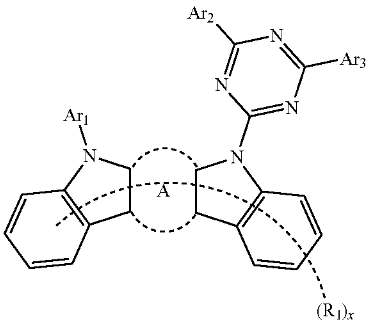

A is a benzene ring fused with the two pentagonal rings;

$Ar_1$ to $Ar_3$ are each independently a substituted or unsubstituted $C_{6-20}$ aryl or $C_{5-60}$ heteroaryl containing one or more of N, O and S;

provided that at least one of $Ar_1$-$Ar_3$, and $R_1$ is substituted with at least one deuterium, or at least one of $R_1$ is deuterium, and the first compound comprises at least 5 deuteriums;

<Chemical Formula 2>

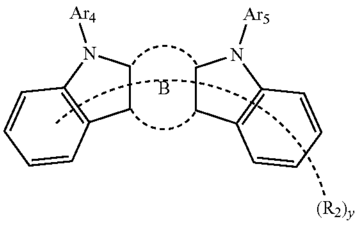

B is a benzene ring fused with the two pentagonal rings;

$Ar_4$ is a substituted or unsubstituted $C_{6-60}$ aryl; and $Ar_5$ is a substituted or unsubstituted $C_{6-60}$ aryl or $C_{5-50}$ heteroaryl containing one of N, O and S.

11 Claims, 1 Drawing Sheet

(52) U.S. Cl.
CPC ..... *H10K 85/6574* (2023.02); *H10K 85/6576* (2023.02); *H10K 50/11* (2023.02)

(58) Field of Classification Search
CPC ............ H10K 85/654; H10K 85/6572; H10K 85/6574; H10K 85/6576; H10K 2101/10; H10K 2101/90
See application file for complete search history.

(56) References Cited

U.S. PATENT DOCUMENTS

| | | | |
|---|---|---|---|
| 2011/0101312 | A1 | 5/2011 | LeCloux et al. |
| 2013/0248849 | A1 | 9/2013 | Feldman et al. |
| 2014/0231796 | A1 | 8/2014 | Wang |
| 2014/0239285 | A1 | 8/2014 | Wang |
| 2016/0130194 | A1 | 5/2016 | Howard, Jr. et al. |
| 2017/0025618 | A1 | 1/2017 | Zheng et al. |
| 2017/0194569 | A1 | 7/2017 | Kim et al. |
| 2017/0263869 | A1 | 9/2017 | Tada et al. |
| 2017/0271598 | A1 | 9/2017 | Zeng et al. |
| 2018/0019409 | A1 | 1/2018 | Ryu et al. |
| 2018/0138425 | A1 | 5/2018 | Ma et al. |
| 2018/0312514 | A1 | 11/2018 | Ma et al. |
| 2018/0331304 | A1 | 11/2018 | Ma et al. |
| 2019/0013490 | A1 | 1/2019 | Cho et al. |
| 2020/0161563 | A1 | 5/2020 | Jang et al. |
| 2020/0176688 | A1 | 6/2020 | Cho et al. |
| 2020/0212310 | A1 | 7/2020 | Kim et al. |
| 2021/0143344 | A1 | 5/2021 | Han et al. |
| 2024/0023355 | A1 | 1/2024 | Cho et al. |

FOREIGN PATENT DOCUMENTS

| | | | |
|---|---|---|---|
| CN | 107623073 | | 1/2018 |
| CN | 108323172 | | 7/2018 |
| CN | 111211234 | | 5/2020 |
| EP | 3862355 | A1 | 8/2021 |
| JP | 2013-509406 | A | 3/2013 |
| JP | 2014-509067 | | 4/2014 |
| JP | 2014-532983 | A | 12/2014 |
| JP | 2014-532984 | A | 12/2014 |
| JP | 5784621 | | 9/2015 |
| KR | 10-2017-0052487 | | 5/2017 |
| KR | 10-2017-0059985 | | 5/2017 |
| KR | 10-2017-0075877 | | 7/2017 |
| KR | 10-2018-0007617 | | 1/2018 |
| KR | 10-2018-0121835 | | 11/2018 |
| KR | 10-2018-0124766 | | 11/2018 |
| KR | 10-2018-0137772 | | 12/2018 |
| KR | 10-2019-0034074 | | 4/2019 |
| KR | 10-2019-0139782 | A | 12/2019 |
| KR | 10-2054806 | | 12/2019 |
| WO | 2003-012890 | A2 | 2/2003 |
| WO | 2011-059463 | | 5/2011 |
| WO | 2017-078403 | | 5/2017 |
| WO | 2018123783 | | 7/2018 |
| WO | 2019-017618 | | 1/2019 |
| WO | 2021-025328 | A1 | 2/2021 |

* cited by examiner

【FIG. 1】
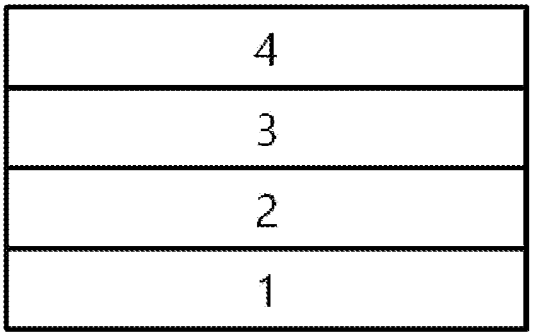
【FIG. 2】
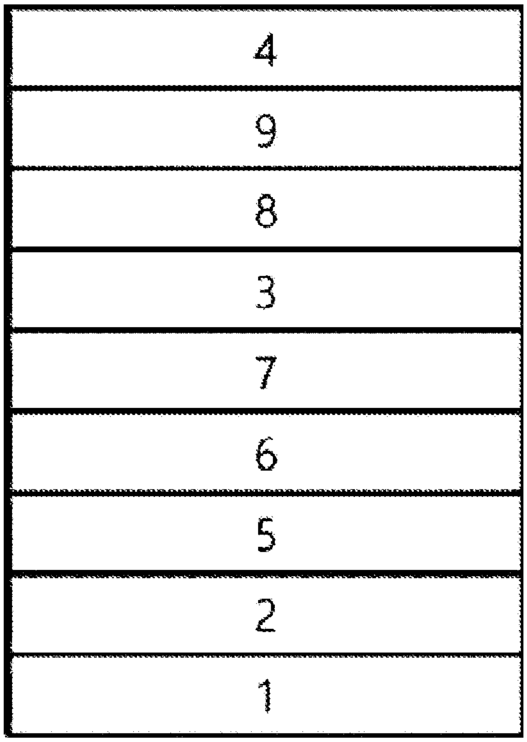

ORGANIC LIGHT EMITTING DEVICE

CROSS-REFERENCE TO RELATED APPLICATION(S)

This application is a National Stage Application of International Application No. PCT/KR2020/017667 filed on Dec. 4, 2020, which claims the benefit of Korean Patent Application No. 10-2019-0170947 filed on Dec. 19, 2019 and Korean Patent Application No. 10-2020-0167777 filed on Dec. 3, 2020 in the Korean Intellectual Property Office, each of which is incorporated herein by reference in its entirety.

TECHNICAL FIELD

The present disclosure relates to an organic light emitting device having improved driving voltage, efficiency and lifetime.

BACKGROUND

In general, an organic light emitting phenomenon refers to a phenomenon where electric energy is converted into light energy by using an organic material. The organic light emitting device using the organic light emitting phenomenon has characteristics such as a wide viewing angle, an excellent contrast, a fast response time, an excellent luminance, driving voltage and response speed, and thus many studies have proceeded.

The organic light emitting device generally has a structure which comprises an anode, a cathode, and an organic material layer interposed between the anode and the cathode. The organic material layer frequently has a multilayered structure that comprises different materials in order to enhance efficiency and stability of the organic light emitting device, and for example, the organic material layer can be formed of a hole injection layer, a hole transport layer, a light emitting layer, an electron transport layer, an electron injection layer and the like. In the structure of the organic light emitting device, if a voltage is applied between two electrodes, the holes are injected from an anode into the organic material layer and the electrons are injected from the cathode into the organic material layer, and when the injected holes and electrons meet each other, an exciton is formed, and light is emitted when the exciton falls to a ground state again.

In the above-mentioned organic light emitting devices, there is a continuing need for the development of an organic light emitting device having improved driving voltage, efficiency and lifetime.

BRIEF DESCRIPTION

Technical Problem

It is an object of the present disclosure to provide an organic light emitting device having improved driving voltage, efficiency and lifetime.

Technical Solution

Provided herein is the following organic light emitting device:

An organic light emitting device including: an anode, a cathode, and a light emitting layer interposed between the anode and the cathode, wherein the light emitting layer includes a first compound of the following Chemical Formula 1 and a second compound of the following Chemical Formula 2.

Organic Light Emitting Device

<Chemical Formula 1>

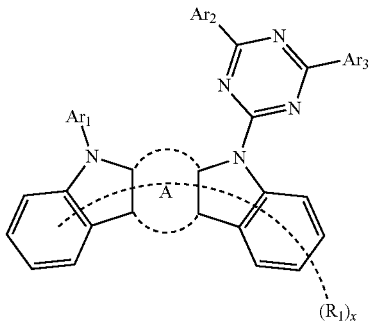

wherein in the Chemical Formula 1:

A is a benzene ring fused with two adjacent pentagonal rings;

$Ar_1$ to $Ar_3$ are each independently a substituted or unsubstituted $C_{6-60}$ aryl or a substituted or unsubstituted $C_{5-60}$ heteroaryl containing any one or more heteroatoms selected from the group consisting of N, O and S;

each $R_1$ is independently hydrogen, deuterium, halogen, cyano, a substituted or unsubstituted $C_{1-60}$ alkyl, a substituted or unsubstituted $C_{1-60}$ alkoxy, a substituted or unsubstituted $C_{2-60}$ alkenyl, a substituted or unsubstituted $C_{2-60}$ alkynyl, a substituted or unsubstituted $C_{3-60}$ cycloalkyl, a substituted or unsubstituted $C_{6-60}$ aryl, or a substituted or unsubstituted $C_{2-60}$ heteroaryl containing any one or more heteroatoms selected from the group consisting of N, O and S;

x is an integer of 1 to 10;

provided that at least one of $Ar_1$ to $Ar_3$, and $R_1$ is substituted with at least one deuterium, or at least one of $R_1$ is deuterium, and the first compound comprises at least 5 deuteriums;

<Chemical Formula 2>

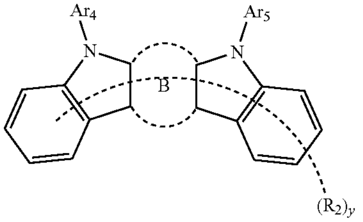

wherein in the Chemical Formula 2:

B is a benzene ring fused with two adjacent pentagonal rings:

$Ar_4$ is a substituted or unsubstituted $C_{6-60}$ aryl;

$Ar_5$ is a substituted or unsubstituted $C_{6-60}$ aryl or a substituted or unsubstituted $C_{5-60}$ heteroaryl containing one heteroatom selected from the group consisting of N, O and S;

each $R_2$ is independently hydrogen, deuterium, halogen, cyano, a substituted or unsubstituted $C_{1-60}$ alkyl, a substituted or unsubstituted $C_{1-60}$ alkoxy, a substituted or unsubstituted $C_{2-60}$ alkenyl, a substituted or unsubstituted $C_{2-60}$ alkynyl, a substituted or unsubstituted $C_{3-60}$ cycloalkyl, a substituted or unsubstituted $C_{6-60}$ aryl, or a substituted or unsubstituted $C_{2-60}$ heteroaryl containing any one or more heteroatoms selected from the group consisting of N, O and S; and y is an integer of 1 to 10.

Advantageous Effects

The above-mentioned organic light emitting device has excellent driving voltage, efficiency, and lifetime by containing the first compound of Chemical Formula 1 and the second compound of Chemical Formula 2 in the light emitting layer.

DESCRIPTION OF THE DRAWINGS

FIG. 1 shows an example of an organic light emitting device comprising a substrate 1, an anode 2, a light emitting layer 3, and a cathode 4.

FIG. 2 shows an example of an organic light emitting device comprising a substrate 1, an anode 2, a hole injection layer 5, a hole transport layer 6, an electron blocking layer 7, a light emitting layer 3, a hole blocking layer 8, an electron injection and transport layer 9, and a cathode 4.

DETAILED DESCRIPTION

Hereinafter, embodiments of the present disclosure will be described in more detail to facilitate understanding of the invention.

As used herein, the notation

or means a bond linked to another substituent group.

As used herein, the term "substituted or unsubstituted" means being unsubstituted or substituted with one or more substituents selected from the group consisting of deuterium, a halogen group, a nitrile group, a nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a heterocyclic group containing at least one of N, O and S atoms, or being unsubstituted or substituted with a substituent to which two or more substituents of the above-exemplified substituents are connected. For example, "a substituent in which two or more substituents are connected" can be a biphenyl group. Namely, a biphenyl group can be an aryl group, or it can be interpreted as a substituent in which two phenyl groups are connected.

In the present disclosure, the carbon number of a carbonyl group is not particularly limited, but is preferably 1 to 40. Specifically, the carbonyl group can be a group having the following structural formulas, but is not limited thereto:

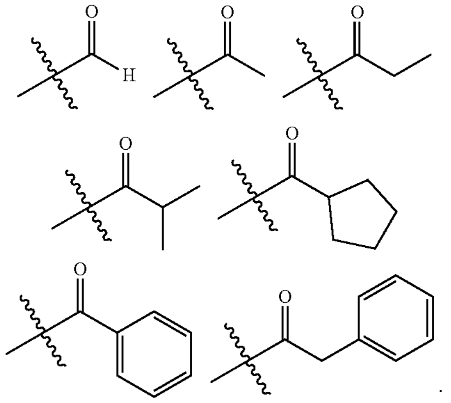

In the present disclosure, an ester group can have a structure in which oxygen of the ester group can be substituted by a straight-chain, branched-chain, or cyclic alkyl group having 1 to 25 carbon atoms, or an aryl group having 6 to 25 carbon atoms. Specifically, the ester group can be a group having the following structural formulas, but is not limited thereto:

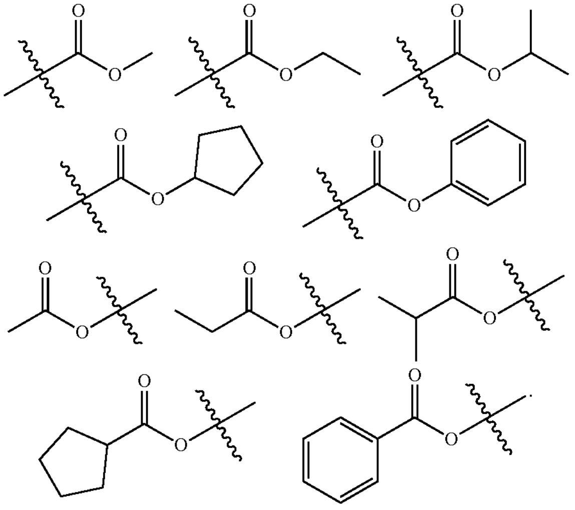

In the present disclosure, the carbon number of an imide group is not particularly limited, but is preferably 1 to 25. Specifically, the imide group can be a group having the following structural formulas, but is not limited thereto:

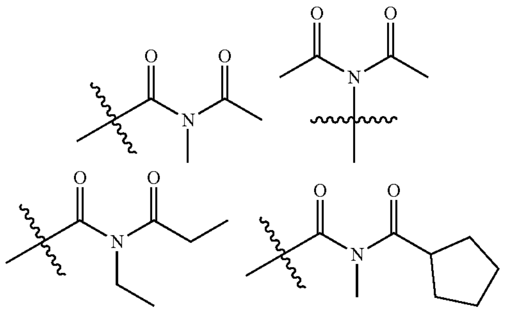

-continued

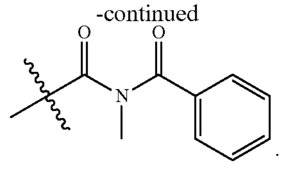

In the present disclosure, a silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but is not limited thereto.

In the present disclosure, a boron group specifically includes a trimethylboron group, a triethylboron group, a t-butyldimethylboron group, a triphenylboron group, and a phenylboron group, but is not limited thereto.

In the present disclosure, examples of a halogen group include fluorine, chlorine, bromine, or iodine.

In the present disclosure, the alkyl group can be straight-chain or branched-chain, and the carbon number thereof is not particularly limited, but is preferably 1 to 40. According to one embodiment, the carbon number of the alkyl group is 1 to 20. According to another embodiment, the carbon number of the alkyl group is 1 to 10. According to another embodiment, the carbon number of the alkyl group is 1 to 6. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methyl-hexyl, and the like, but are not limited thereto.

In the present disclosure, the alkenyl group can be straight-chain or branched-chain, and the carbon number thereof is not particularly limited, but is preferably 2 to 40. According to one embodiment, the carbon number of the alkenyl group is 2 to 20. According to another embodiment, the carbon number of the alkenyl group is 2 to 10. According to still another embodiment, the carbon number of the alkenyl group is 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present disclosure, a cycloalkyl group is not particularly limited, but the carbon number thereof is preferably 3 to 60. According to one embodiment, the carbon number of the cycloalkyl group is 3 to 30. According to another embodiment, the carbon number of the cycloalkyl group is 3 to 20. According to still another embodiment, the carbon number of the cycloalkyl group is 3 to 6. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present disclosure, an aryl group is not particularly limited, but the carbon number thereof is preferably 6 to 60, and it can be a monocyclic aryl group or a polycyclic aryl group. According to one embodiment, the carbon number of the aryl group is 6 to 30. According to one embodiment, the carbon number of the aryl group is 6 to 20. The aryl group can be a phenyl group, a biphenyl group, a terphenyl group or the like as the monocyclic aryl group, but is not limited thereto. The polycyclic aryl group includes a naphthyl group, an anthracenyl group, a phenanthrenyl group, a pyrenyl group, a perylenyl group, a chrysenyl group, or the like, but is not limited thereto.

In the present disclosure, the fluorenyl group can be substituted, and two substituents can be linked with each other to form a spiro structure. In the case where the fluorenyl group is substituted,

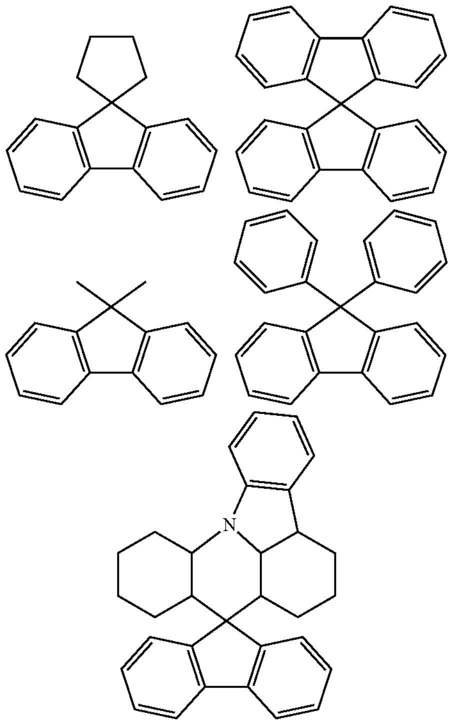

and the like can be formed. However, the structure is not limited thereto.

In the present disclosure, a heterocyclic group is a heterocyclic group containing one or more of O, N, Si and S as a heteroatom, and the carbon number thereof is not particularly limited, but is preferably 2 to 60. Examples of the heterocyclic group include a thiophene group, a furan group, a pyrrole group, an imidazole group, a thiazole group, an oxazol group, an oxadiazol group, a triazol group, a pyridyl group, a bipyridyl group, a pyrimidyl group, a triazine group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzoimidazole group, a benzothiazol group, a benzocarbazole group, a benzothiophene group, a dibenzothiophene group, a benzofuranyl group, a phenanthroline group, an isoxazolyl group, a thiadiazolyl group, a phenothiazinyl group, a dibenzofuranyl group, and the like, but are not limited thereto.

In the present disclosure, the aryl group in the aralkyl group, the aralkenyl group, the alkylaryl group and the arylamine group is the same as the aforementioned examples of the aryl group. In the present disclosure, the alkyl group in the aralkyl group, the alkylaryl group and the alkylamine group is the same as the aforementioned examples of the alkyl group. In the present disclosure, the heteroaryl in the heteroarylamine group can be applied to the aforementioned description of the heterocyclic group. In the present disclosure, the alkenyl group in the aralkenyl group is the same as the aforementioned examples of the alkenyl group. In the present disclosure, the aforementioned description of the aryl group can be applied except that the arylene is a divalent group. In the present disclosure, the aforementioned description of the heterocyclic group can be applied except that the heteroarylene is a divalent group. In the present disclosure, the aforementioned description of the aryl group or cycloalkyl group can be applied except that the hydrocarbon ring is not a monovalent group but formed by combining two substituent groups. In the present disclosure, the aforementioned description of the heterocyclic group can be applied, except that the heterocycle is not a monovalent group but formed by combining two substituent groups.

The organic light emitting device according to the present disclosure can be a normal type organic light emitting device in which an anode, a light emitting layer and a cathode are sequentially stacked on a substrate, or an inverted type organic light emitting device in which a cathode, a light emitting layer and an anode are sequentially stacked on a substrate. Further, the organic light emitting device can further selectively include at least one of a hole injection layer, a hole transport layer, and an electron blocking layer between the anode and the light emitting layer, and can further include at least one of a hole blocking layer, an electron injection layer, and an electron transport layer between the cathode and the light emitting layer. In addition, the electron injection layer and the electron transport layer can be included in the form of a single layer of the electron injection and transport layer instead of a separate layer.

Hereinafter, the present disclosure will be described in detail for each configuration.

Anode and Cathode

An anode and a cathode used in the present disclosure mean electrodes used in an organic light emitting device.

As the anode material, generally, a material having a large work function is preferably used so that holes can be smoothly injected into the organic material layer. Specific examples of the anode material include metals such as vanadium, chrome, copper, zinc, and gold, or an alloy thereof; metal oxides such as zinc oxides, indium oxides, indium tin oxides (ITO), and indium zinc oxides (IZO); a combination of metals and oxides, such as ZnO:Al or $SNO_2$:Sb; conductive polymers such as poly(3-methylthiophene), poly[3,4-(ethylene-1,2-dioxy)thiophene](PEDOT), polypyrrole, and polyaniline, and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or an alloy thereof; a multilayered structure material such as LiF/Al or $LiO_2$/Al, and the like, but are not limited thereto.

Hole Injection Layer

The organic light emitting device according to the present disclosure can further include a hole injection layer on the anode, if necessary.

The hole injection layer is a layer for injecting holes from the electrode, and the hole injection material is preferably a compound which has a capability of transporting the holes, thus has a hole injecting effect in the anode and an excellent hole injecting effect to the light emitting layer or the light emitting material, prevents excitons produced in the light emitting layer from moving to an electron injection layer or the electron injection material, and further is excellent in the ability to form a thin film. Further, it is preferable that a HOMO (highest occupied molecular orbital) of the hole injection material is between the work function of the anode material and a HOMO of a peripheral organic material layer.

Specific examples of the hole injection material include metal porphyrine, oligothiophene, an arylamine-based organic material, a hexanitrilehexaazatriphenylene-based organic material, a quinacridone-based organic material, a perylene-based organic material, anthraquinone, polyaniline and polythiophene-based conductive compound, and the like, but are not limited thereto.

Hole Transport Layer

The organic light emitting device according to the present disclosure can include a hole transport layer on the anode (or on the hole injection layer if the hole injection layer exists), if necessary.

The hole transport layer is a layer that can receive the holes from the anode or the hole injection layer and transport the holes to the light emitting layer, and the hole transport material is suitably a material having large mobility to the holes, which can receive holes from the anode or the hole injection layer and transfer the holes to the light emitting layer.

Specific examples thereof include an arylamine-based organic material, a conductive polymer, a block copolymer in which a conjugate portion and a non-conjugate portion are present together, and the like, but are not limited thereto.

Light Emitting Layer

The light emitting layer used in the present disclosure is a layer that can emit light in the visible light region by combining holes and electrons transported from the anode and the cathode. Generally, the light emitting layer includes a host material and a dopant material, and in the present disclosure, the first compound of Chemical Formula 1 and the second compound of Chemical Formula 2 are included as a host.

Preferably, the first compound of Chemical Formula 1 can be substituted with 5 or more deuteriums. Specifically, at least one of $Ar_1$ to $Ar_3$ and $R_1$ in Chemical Formula 1 is substituted with at least one deuterium, or at least one of $R_1$ becomes deuterium, whereby the first compound can include 5 or more, or 6 or more, or 7 or more, or 8 or more, or 10 or more deuteriums in the compound, or the first compound can be completely substituted with deuterium.

Preferably, the Chemical Formula 1 can be any one selected from the group consisting of the following Chemical Formulas 1-1 to 1-6:

<Chemical Formula 1-1>

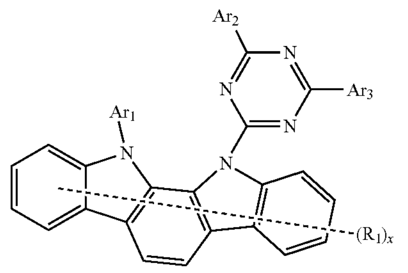

<Chemical Formula 1-2>

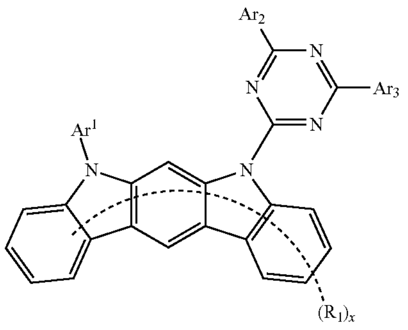

<Chemical Formula 1-3>

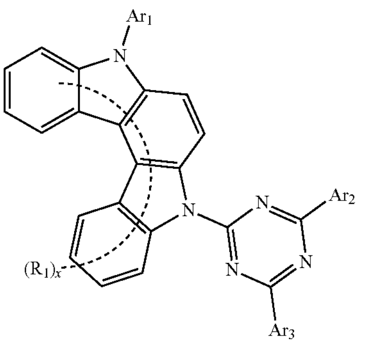

<Chemical Formula 1-4>

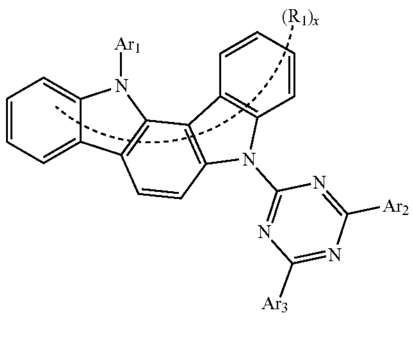

-continued

<Chemical Formula 1-5>

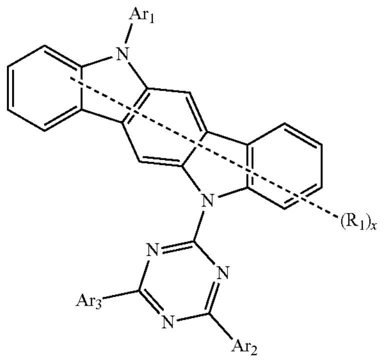

<Chemical Formula 1-6>

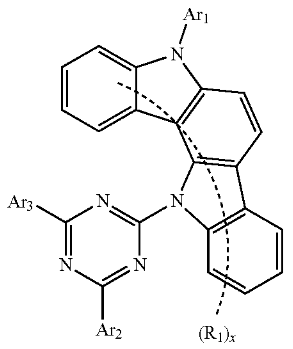

wherein in the Chemical Formulas 1-1 to 1-6, $Ar_1$ to $Ar_3$, $R_1$, and x are as defined above.

In Chemical Formula 1, preferably, $Ar_1$ to $Ar_3$ can be each independently phenyl, biphenyl, terphenyl, dibenzofuranyl, dibenzothiophenyl, fluorenyl, 9,9-dimethylfluorenyl, 9,9-diphenylfluorenyl, carbazol-9-yl, or 9-phenyl-9H-carbazolyl.

In Chemical Formula 1, more preferably, at least one of $Ar_1$ to $Ar_3$ can be phenyl, and the rest can be each independently phenyl, biphenyl, terphenyl, dibenzofuranyl, dibenzothiophenyl, fluorenyl, 9,9-dimethylfluorenyl, 9,9-diphenylfluorenyl, carbazol-9-yl, or 9-phenyl-9H-carbazolyl.

Further, at least one of the $Ar_1$ to $Ar_3$ can be substituted with at least one deuterium. For example, at least one of the $Ar_1$ to $Ar_3$ can be selected from the group consisting of the following structures:

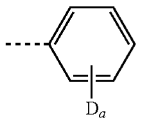

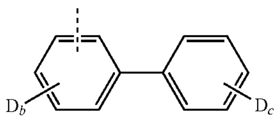

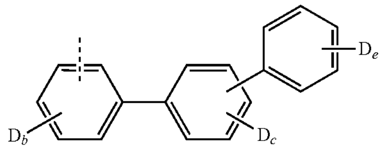

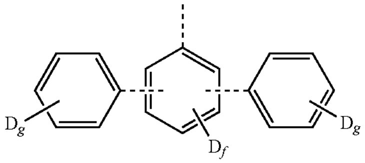

-continued

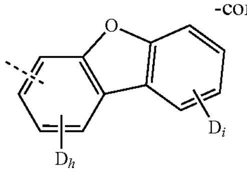
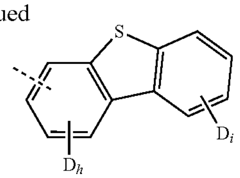
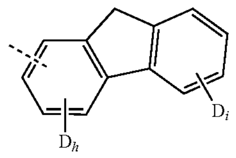
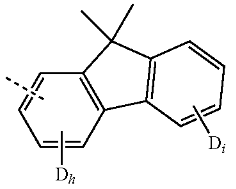
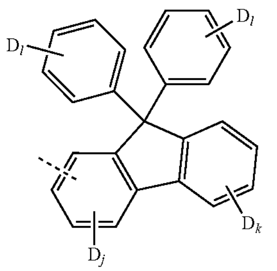
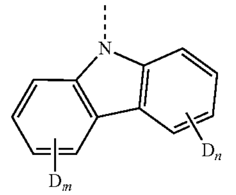
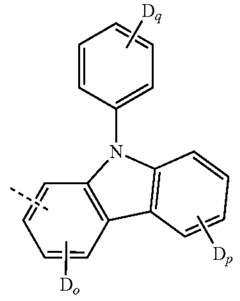

wherein in the above formula, a is an integer of 1 to 5, b is an integer of 0 to 4, c is an integer of 0 to 5, provided that b and c are not 0 at the same time, each d is independently an integer of 0 to 3, e is an integer of 0 to 5, provided that d and e are not 0 at the same time, f is an integer of 0 to 3, each g is independently an integer of 0 to 5, provided that f and g are not 0 at the same time, h is an integer of 0 to 3, i is an integer of 0 to 4, provided that h and i are not 0 at the same time, j is an integer of 0 to 3, k is an integer of 0 to 4, each 1 is independently an integer of 0 to 5, provided that j, k and 1 are not 0 at the same time, m is an integer of 0 to 4, n is an integer of 0 to 4, provided that m and n are not 0 at the same time, and is an integer of 0 to 3, p is an integer of 0 to 4, q is an integer of 0 to 5, provided that o, p, and q are not 0 at the same time.

Further, preferably, at least one of the $Ar_1$ to $Ar_3$ can be substituted with 5 or more deuteriums.

More preferably, in Chemical Formula 1, at least one of the $Ar_1$ to $Ar_3$ can be phenyl substituted with 5 deuteriums, and the rest can be phenyl, biphenyl, terphenyl, dibenzofuranyl, dibenzothiophenyl, fluorenyl, 9,9-dimethylfluorenyl, 9,9-diphenylfluorenyl, carbazol-9-yl, or 9-phenyl-9H-carbazolyl, each of which is unsubstituted.

As an example, all of the $Ar_1$ to $Ar_3$ are phenyl, provided that at least one of the $Ar_1$ to $Ar_3$, specifically any one, two, or all three of $Ar_1$ to $Ar_3$ can be substituted with 5 deuteriums.

As another example, one of the $Ar_1$ to $Ar_3$ is biphenyl, terphenyl, dibenzofuranyl, dibenzothiophenyl, fluorenyl, 9,9-dimethylfluorenyl, 9,9-diphenylfluorenyl, carbazol-9-yl, or 9-phenyl-9H-carbazolyl, each of which is unsubstituted, and the rest can be phenyl, provided that at least one of the rest, that is, one or both of the rest can be substituted with 5 deuteriums.

Further, preferably, at least one of the $Ar_1$ to $Ar_3$ can be biphenyl, terphenyl, dibenzofuranyl, dibenzothiophenyl, fluorenyl, 9,9-dimethylfluorenyl, 9,9-diphenylfluorenyl, carbazol-9-yl, or 9-phenyl-9H-carbazolyl, each of which is substituted with 5 or more deuteriums, and the rest can be each independently an unsubstituted phenyl or an unsubstituted biphenyl.

As an example, one of the $Ar_1$ to $Ar_3$ can be biphenyl substituted with 5 deuteriums, and the rest can be each independently an unsubstituted phenyl or an unsubstituted biphenyl. At this time, those in which biphenyl is substituted with 5 deuteriums can be the following structure as an example:

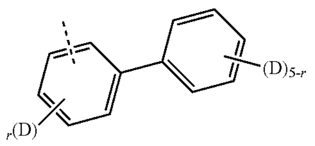

wherein in the above formula, r is an integer of 0 to 4, more specifically 0.

As another example, two of the $Ar_1$ to $Ar_3$ can be biphenyl substituted with 5 deuteriums, and the rest can be unsubstituted phenyl. At this time, those in which biphenyl is substituted with 5 deuteriums can be the above-mentioned structure.

As another example, one of the $Ar_1$ to $Ar_3$ can be biphenyl, terphenyl, dibenzofuranyl, dibenzothiophenyl, fluorenyl, 9,9-dimethylfluorenyl, 9,9-diphenylfluorenyl, carbazol-9-yl, or 9-phenyl-9H-carbazolyl, each of which is completely substituted with deuterium, and all the rest can be an unsubstituted phenyl.

Further, preferably, the $Ar_1$ to $Ar_3$ can be each independently phenyl, biphenyl, terphenyl, dibenzofuranyl, dibenzothiophenyl, fluorenyl, 9,9-dimethylfluorenyl, 9,9-diphenylfluorenyl, carbazol-9-yl, or 9-phenyl-9H-carbazolyl, and all of the $Ar_1$ to $Ar_3$ can be completely substituted with deuterium.

Further, in Chemical Formula 1, preferably, all of the $R_1$ can be hydrogen. At this time, in Chemical Formula 1, x is an integer of 10, and at least one of $Ar_1$ to $Ar_3$ is substituted with 5 or more deuteriums.

Further, in Chemical Formula 1, preferably, at least 5 of $R_1$ can be deuterium, and the rest can be hydrogen. At this time, in Chemical Formula 1, x is an integer of 10. For example, in Chemical Formula 1, 5, or 6, or 7, or 8 of the $R_1$ are deuterium, and the rest can be hydrogen, or all 10 $R_1$s can be deuterium.

Representative examples of the first compound of Chemical Formula 1 are as follows:
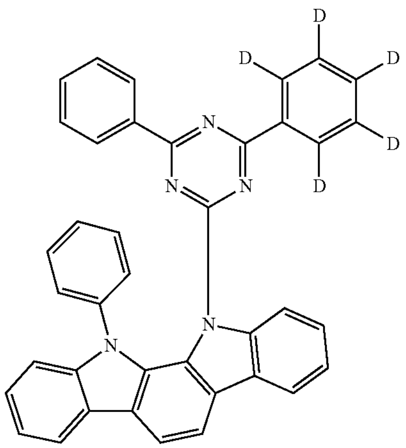
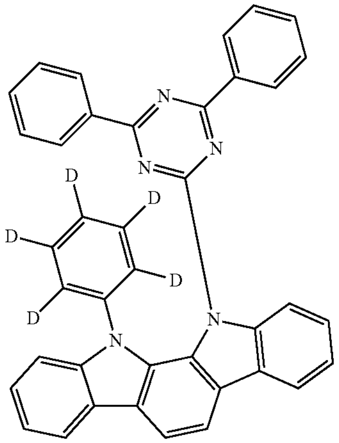
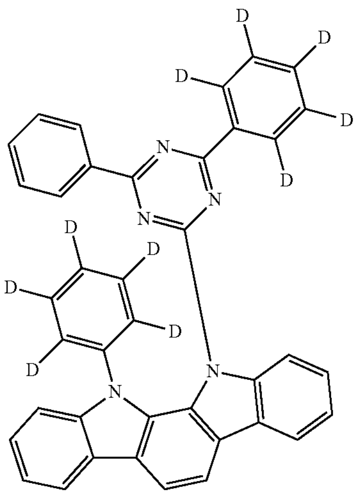
-continued
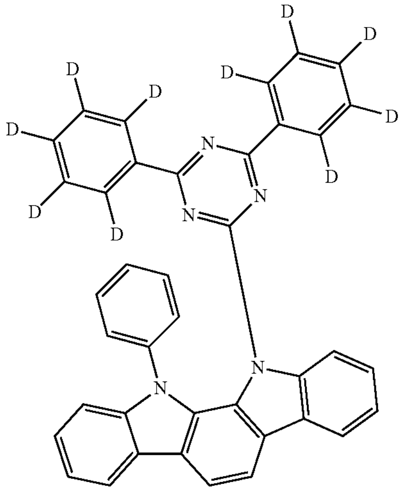
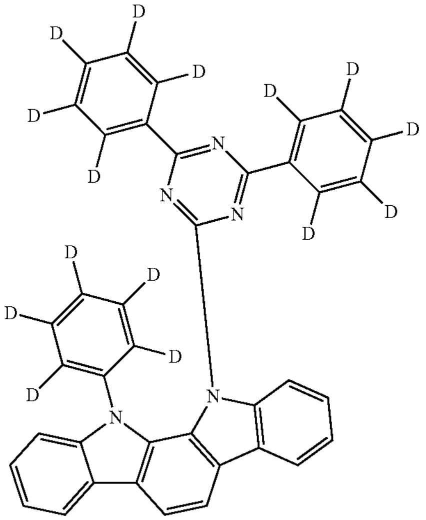
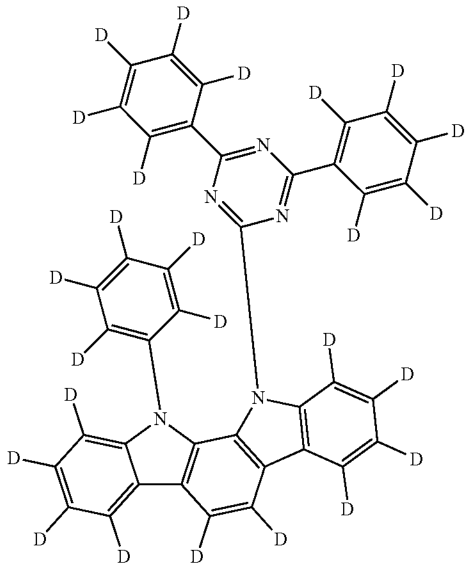

-continued
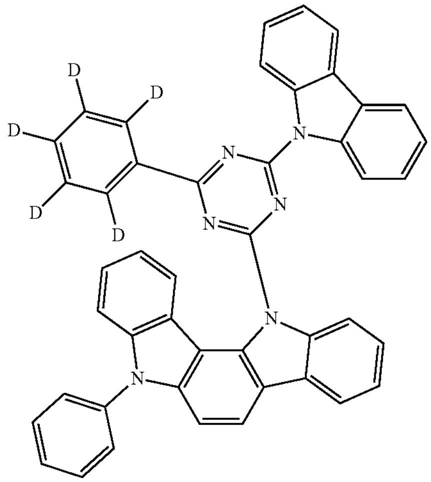
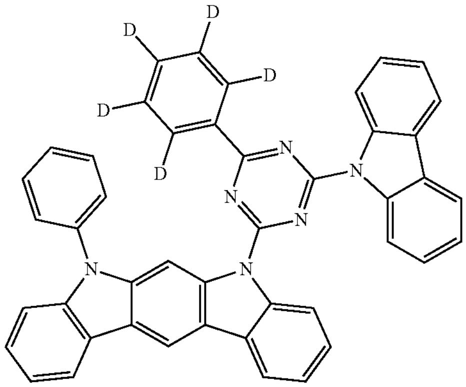
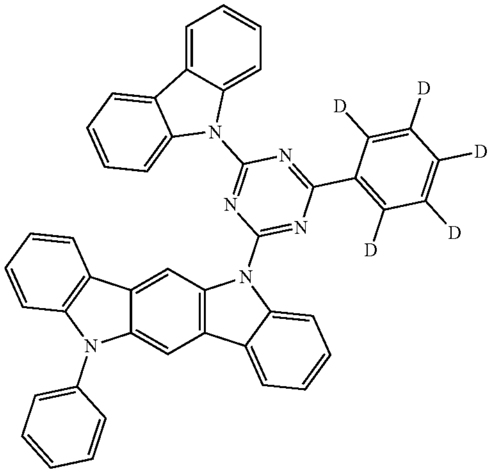
-continued
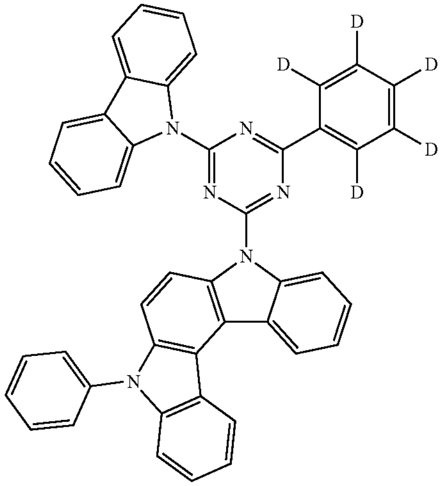
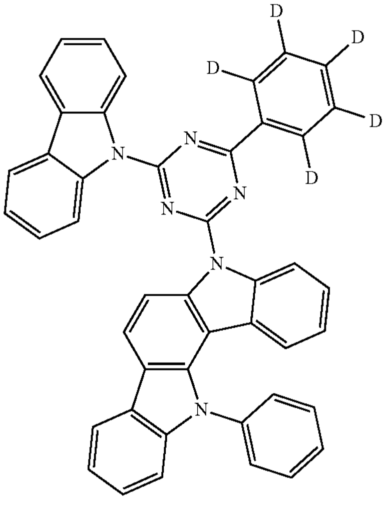
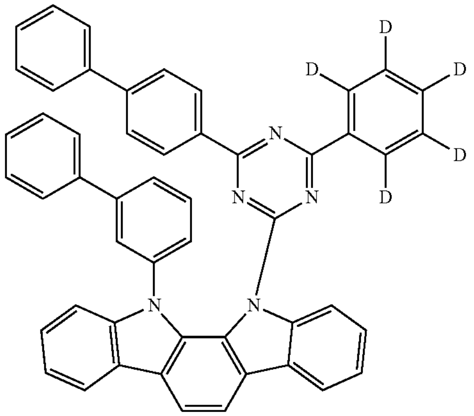

-continued
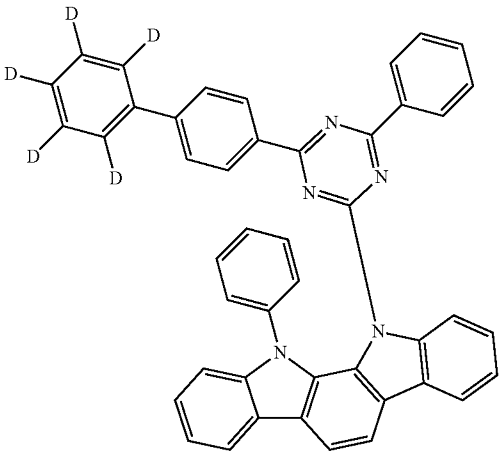
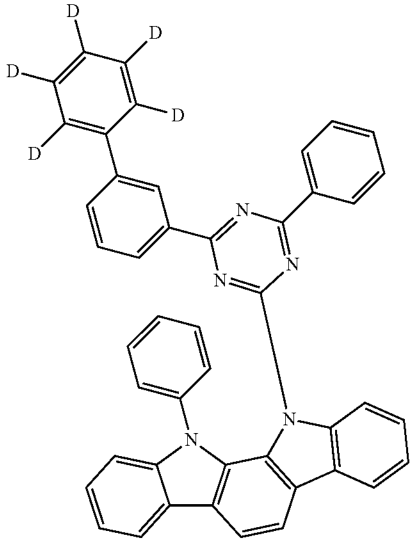
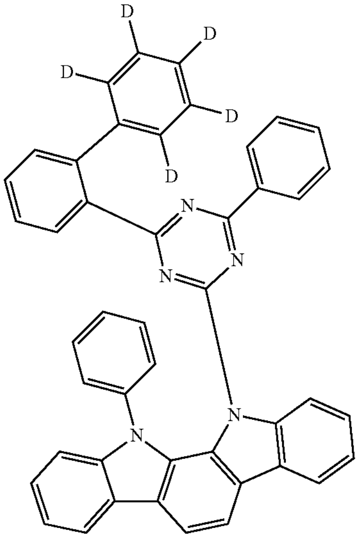
-continued
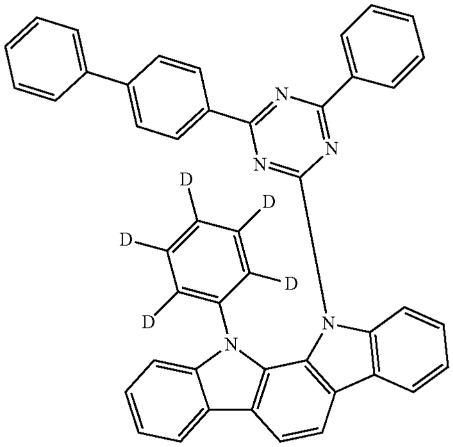
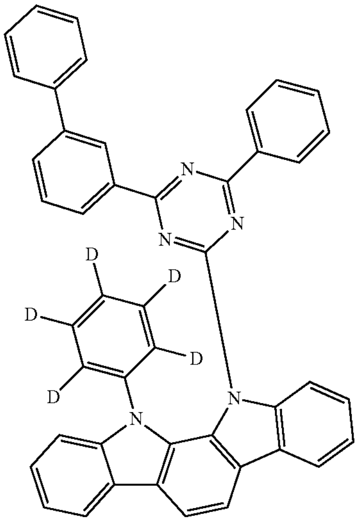
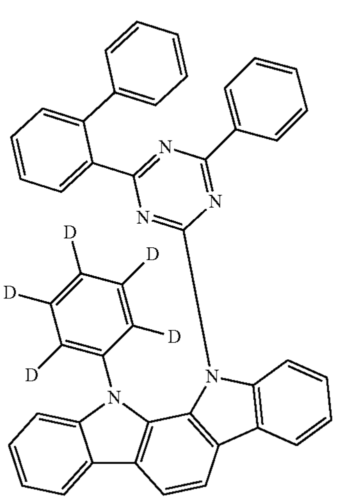

-continued
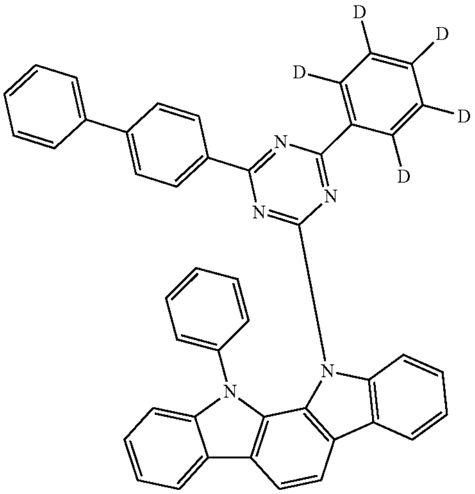
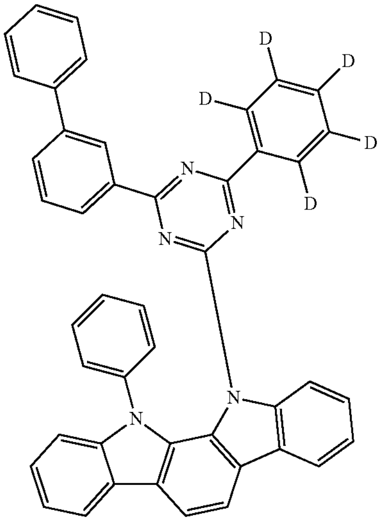
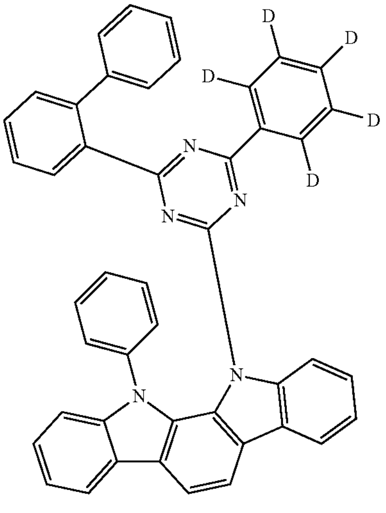
-continued
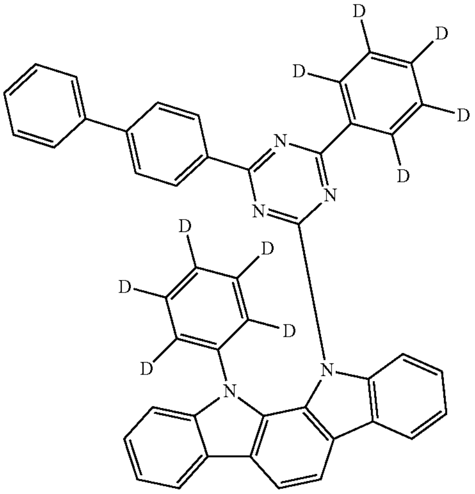
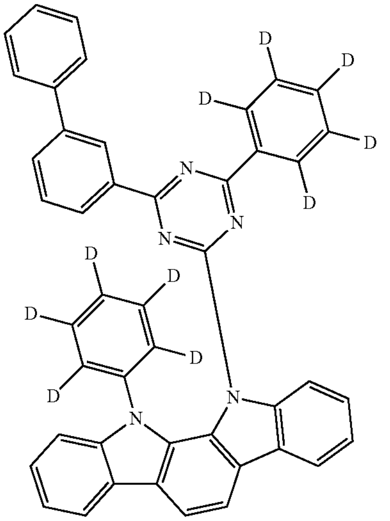
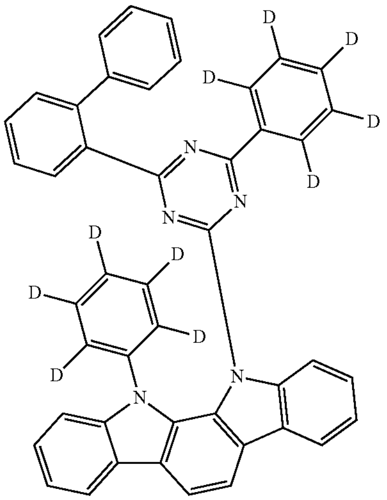

-continued
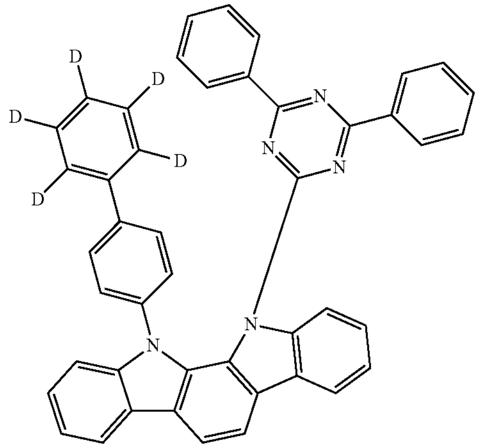
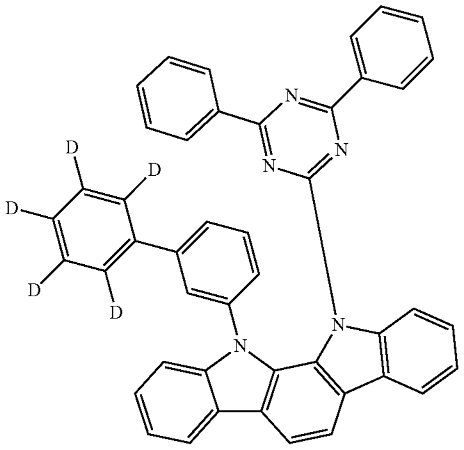
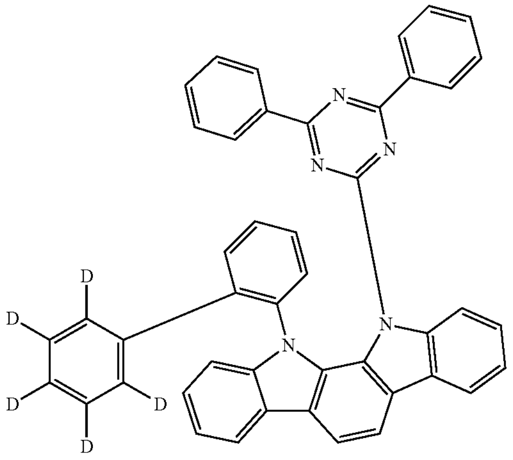
-continued
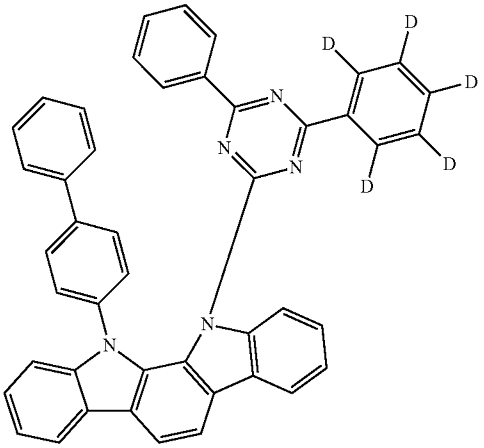
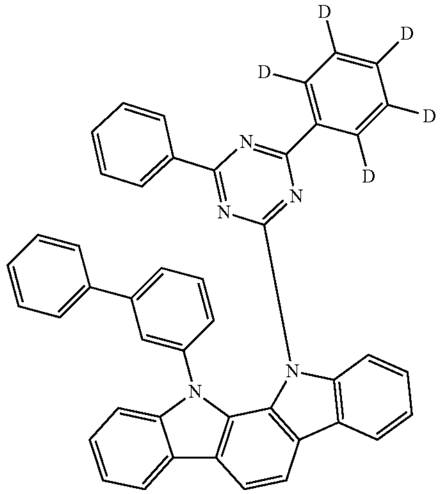
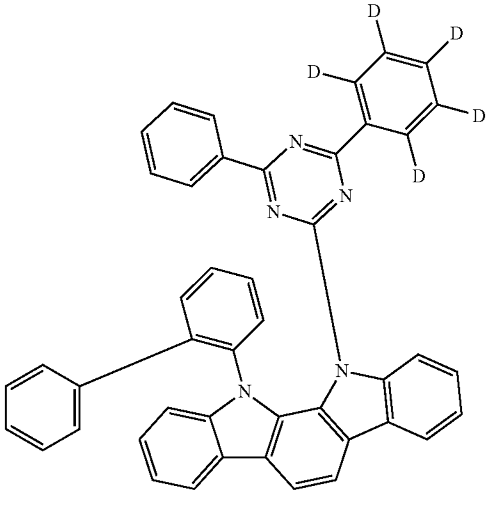

-continued
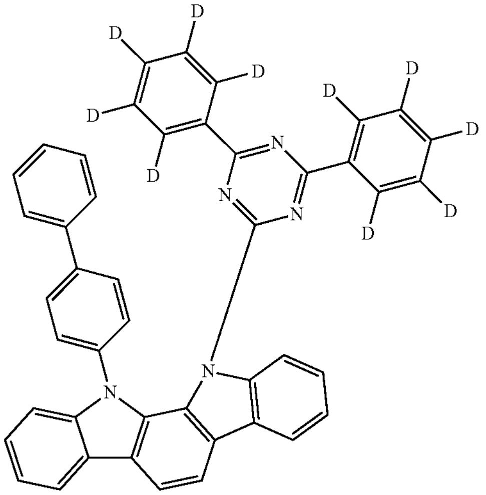
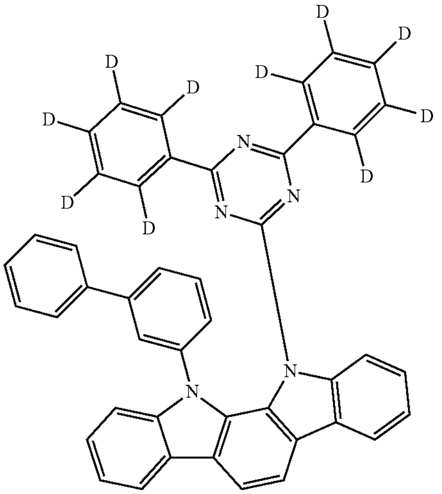
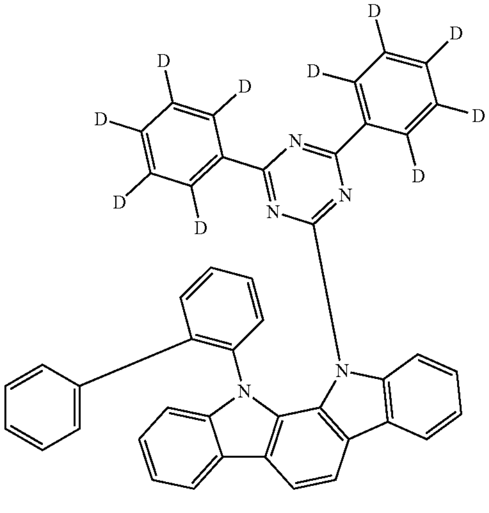
-continued
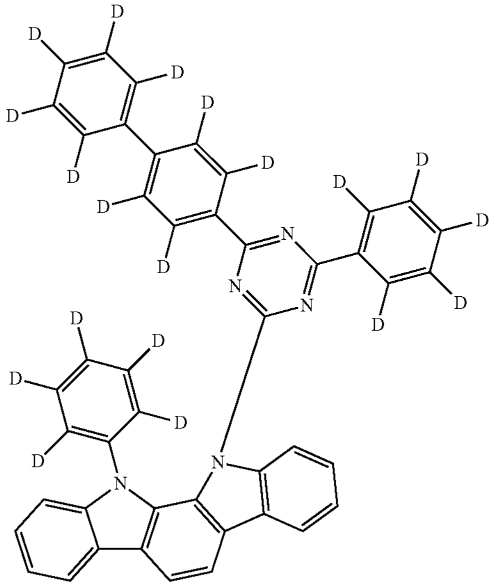
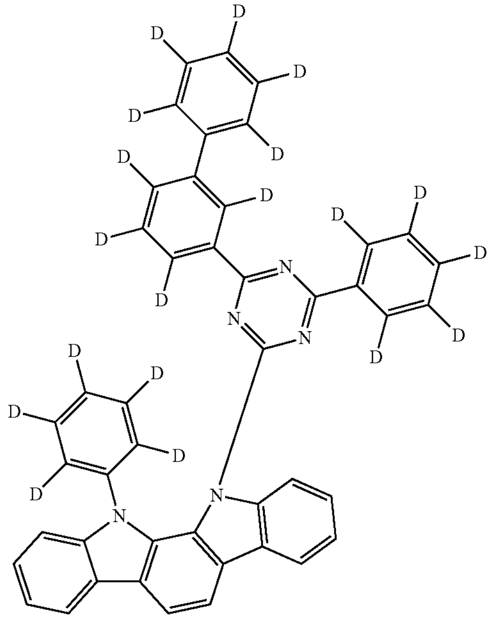

-continued
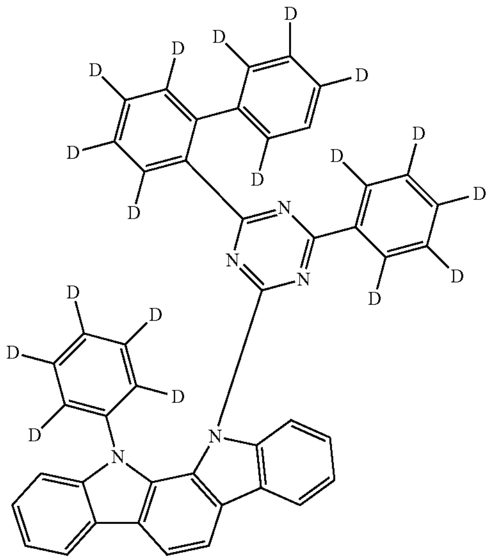
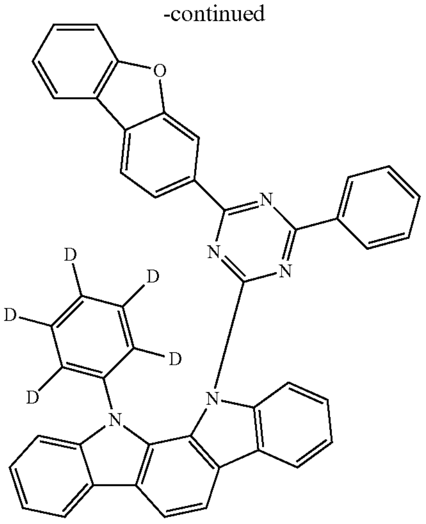
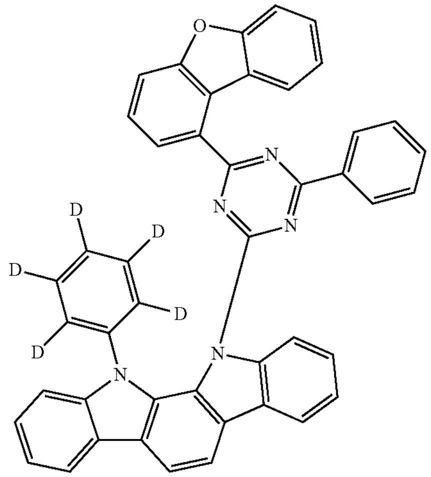
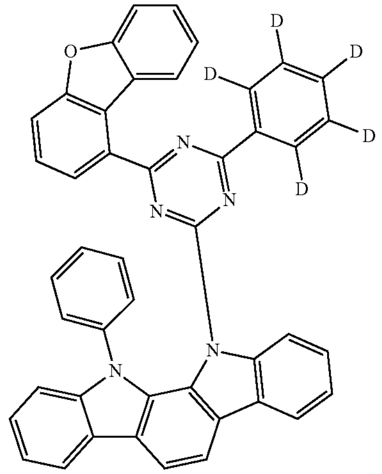
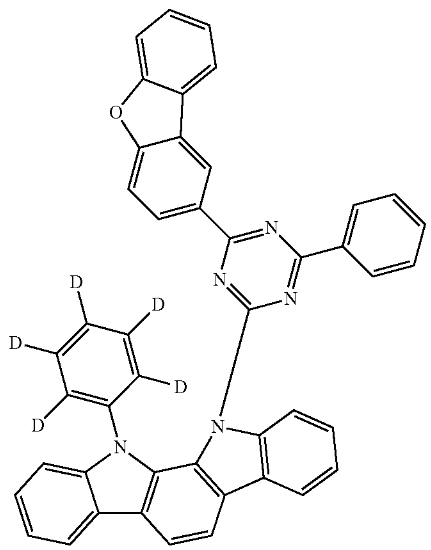
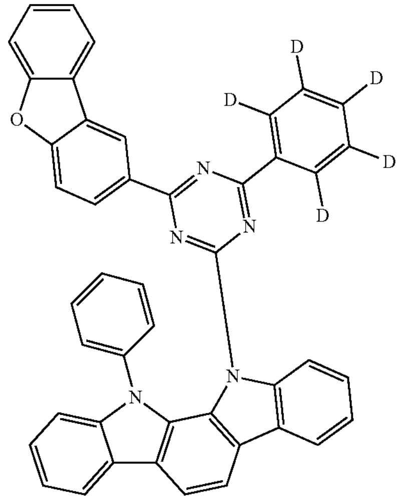

-continued
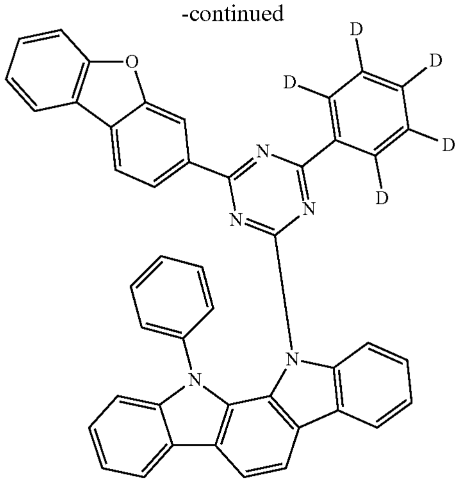
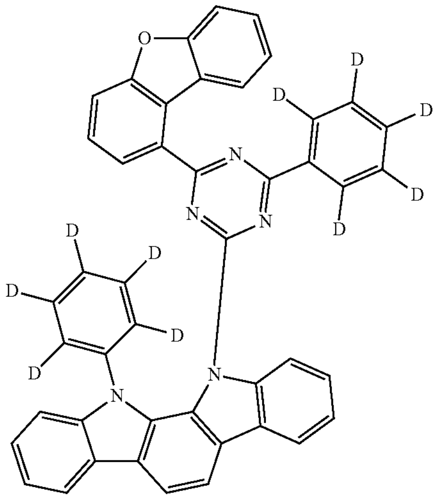
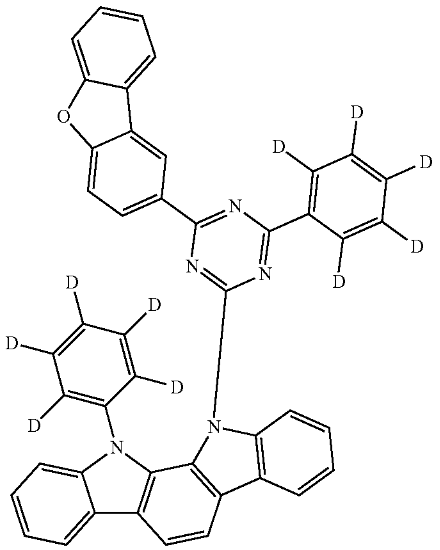
-continued
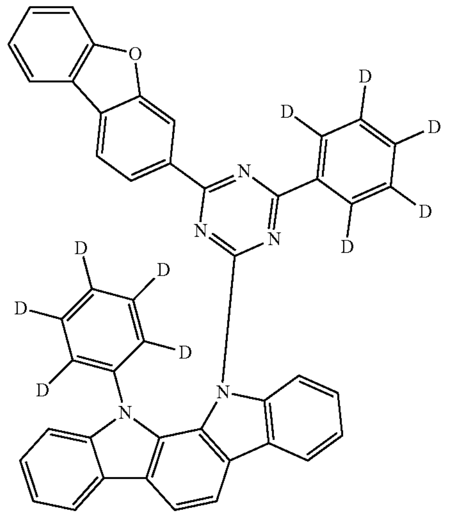
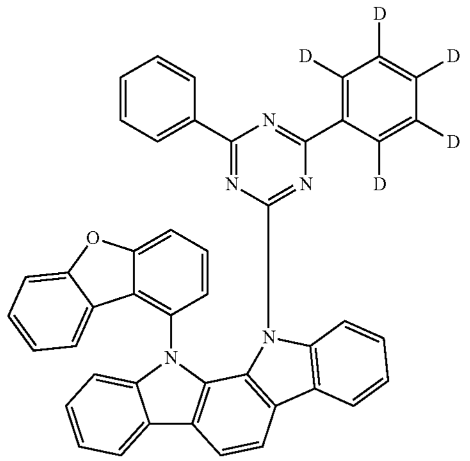
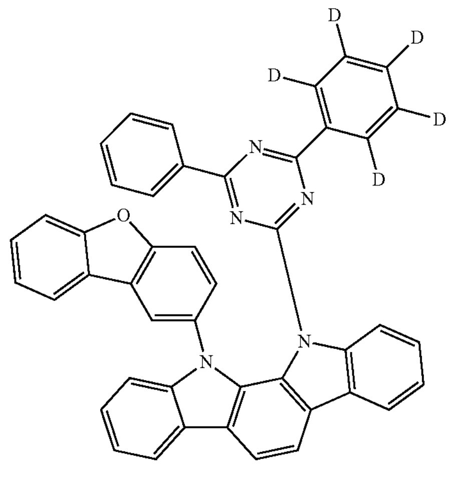

-continued
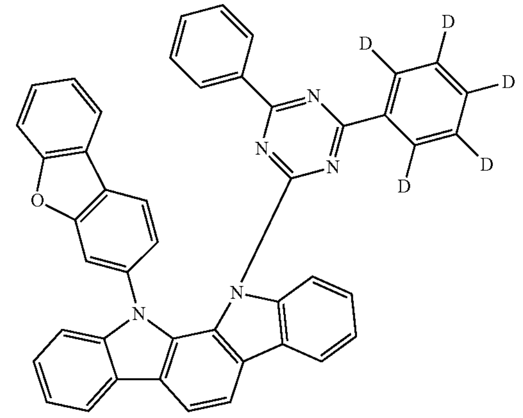
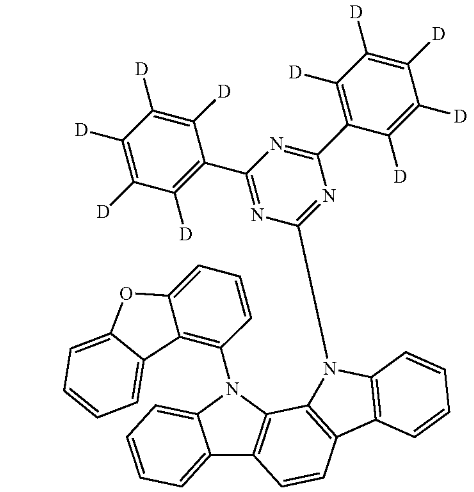
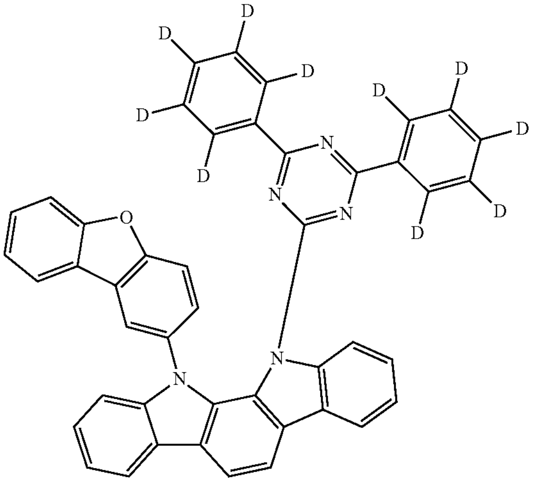
-continued
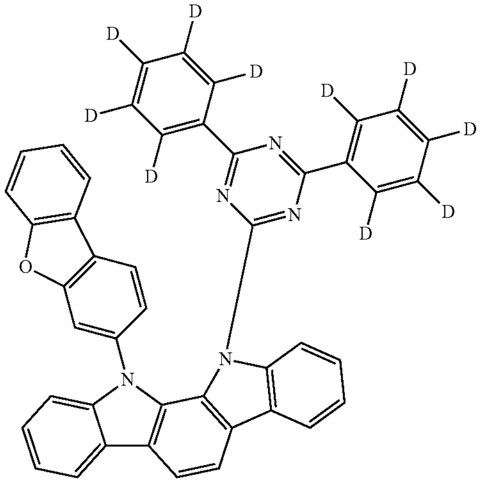
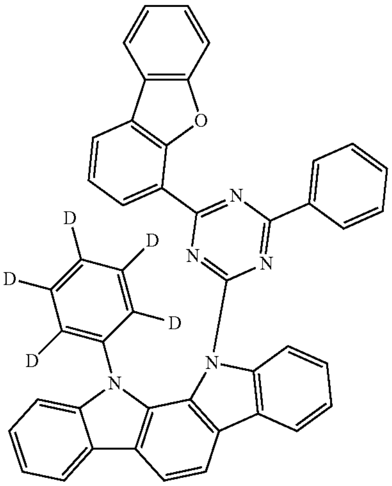
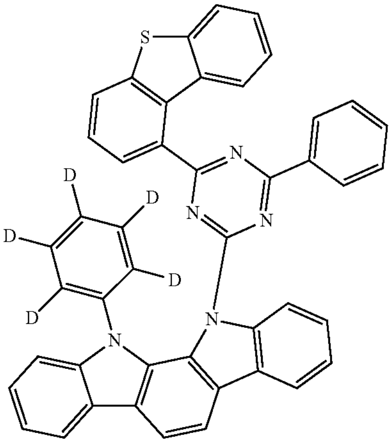

-continued
-continued
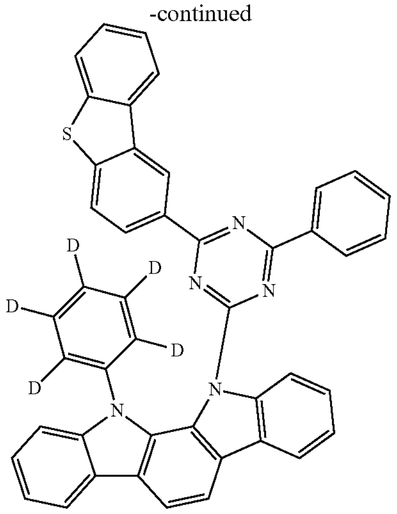
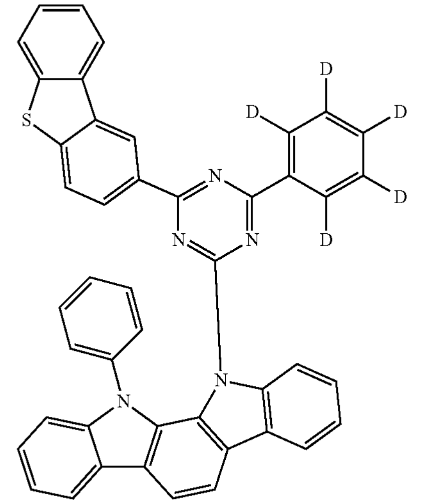
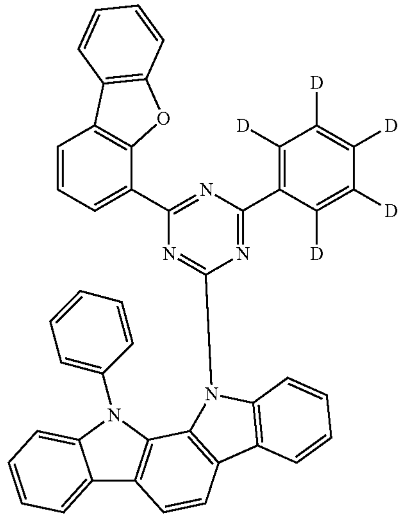
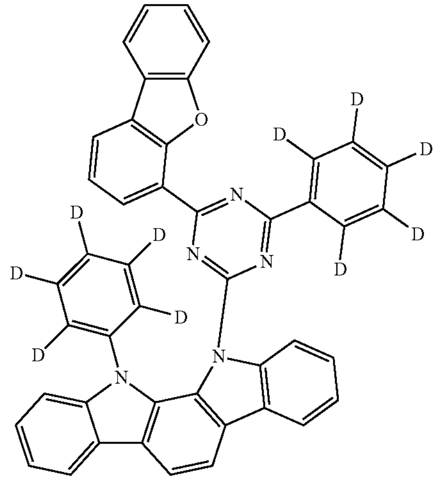
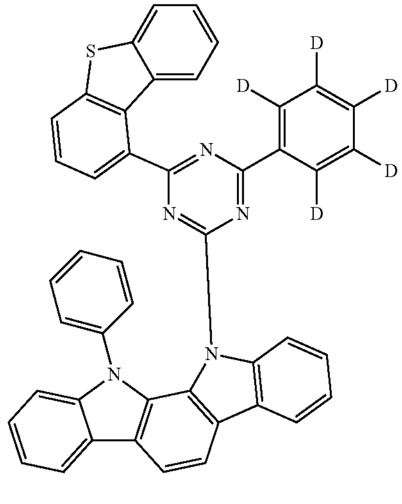
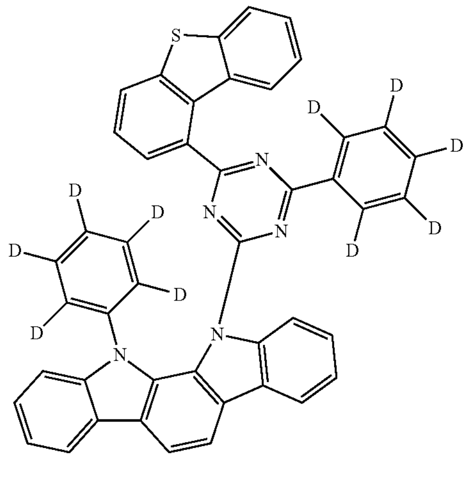

-continued
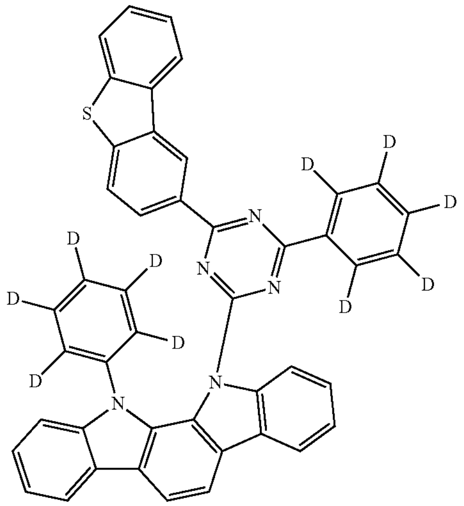
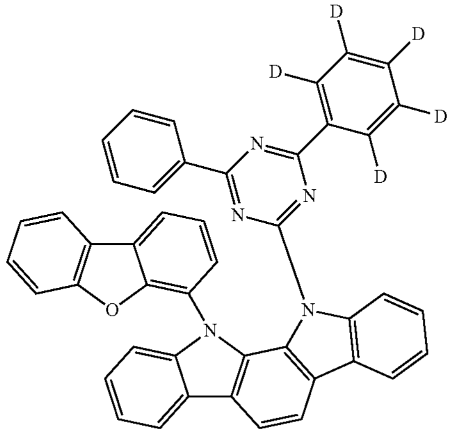
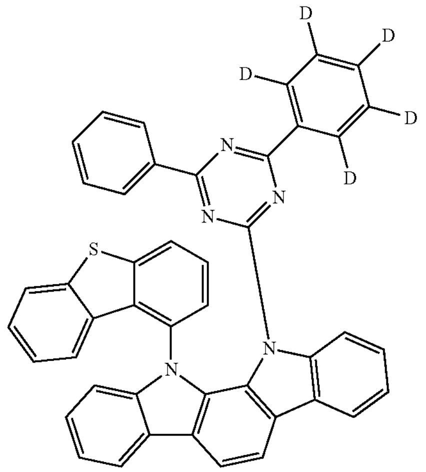
-continued
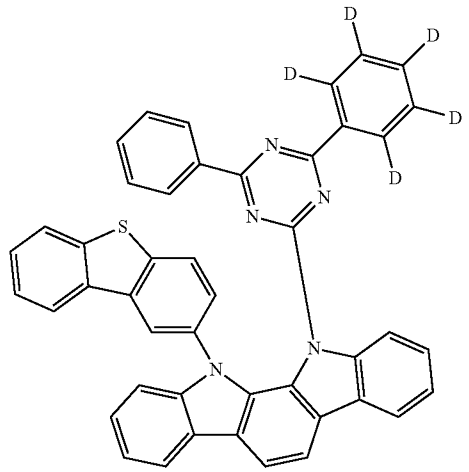
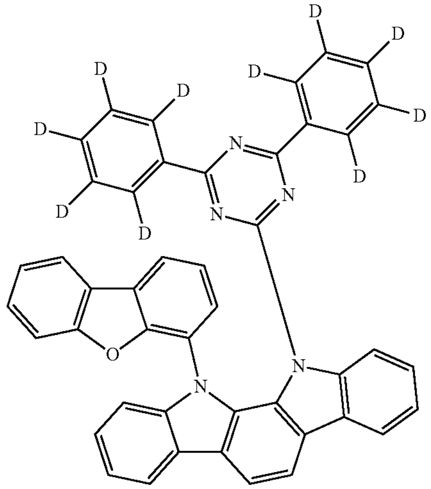
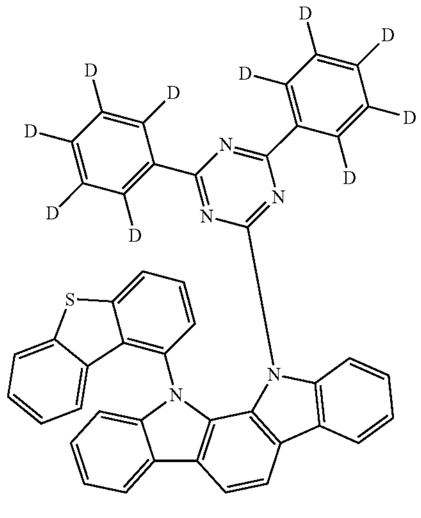

-continued
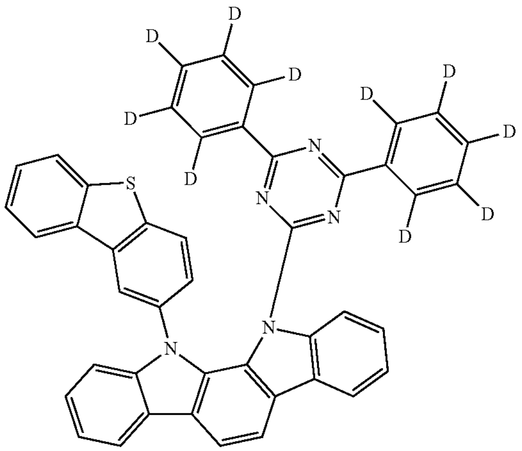
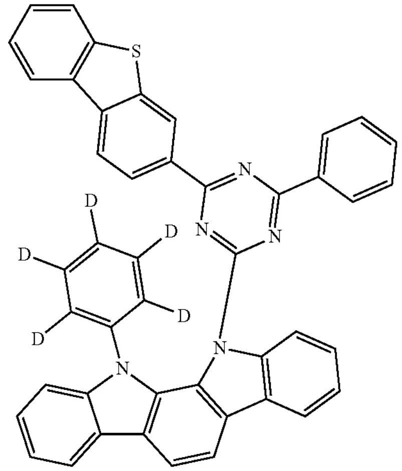
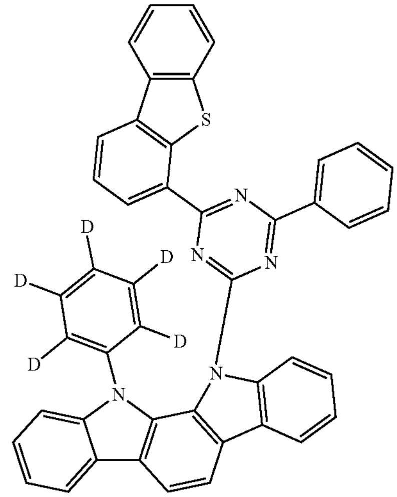
-continued
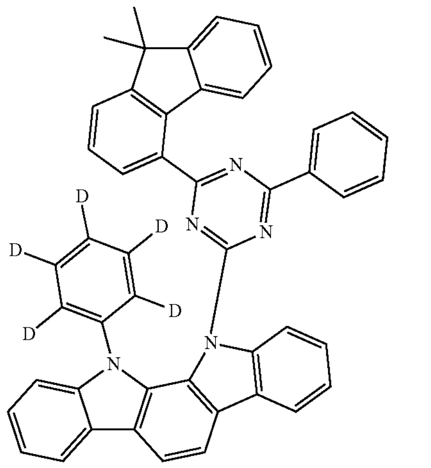
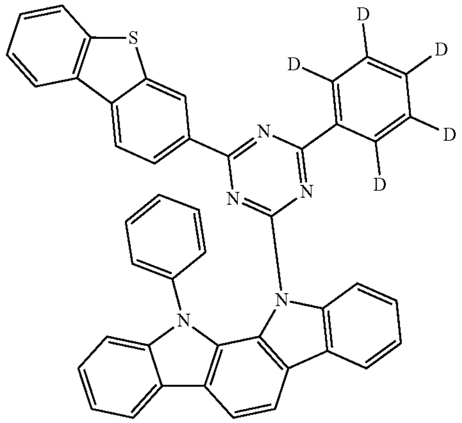
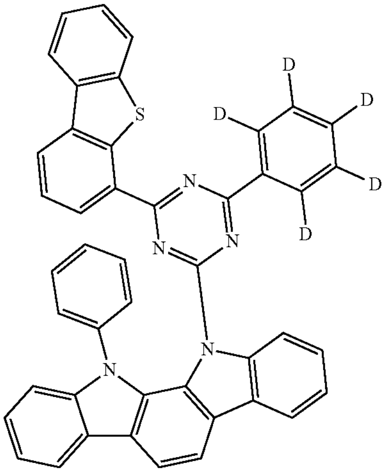

-continued
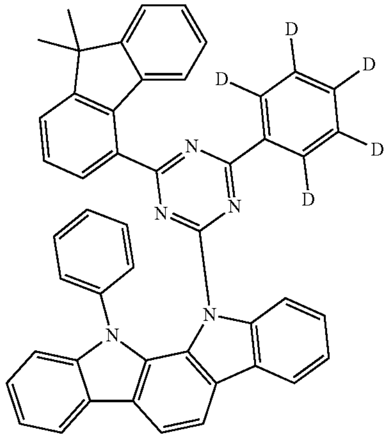
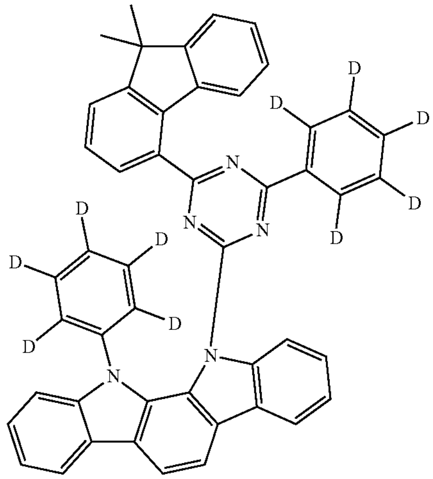
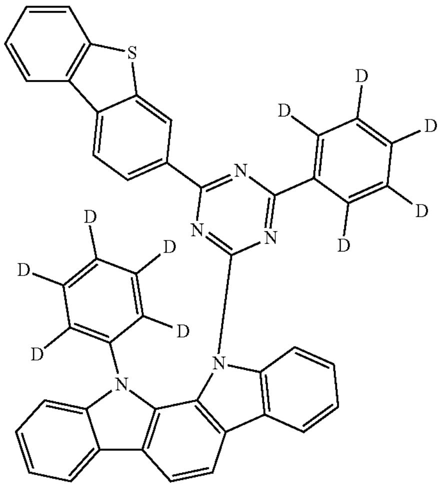
-continued
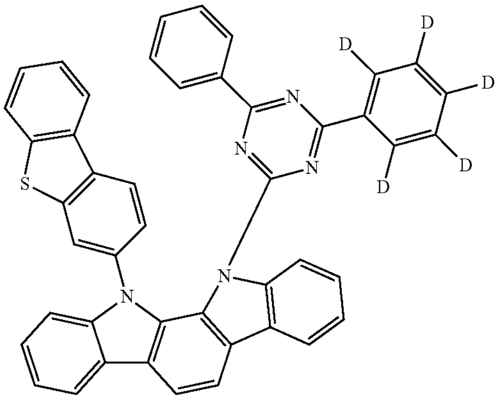
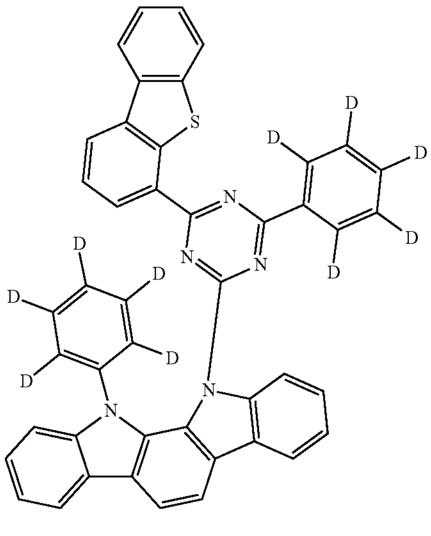
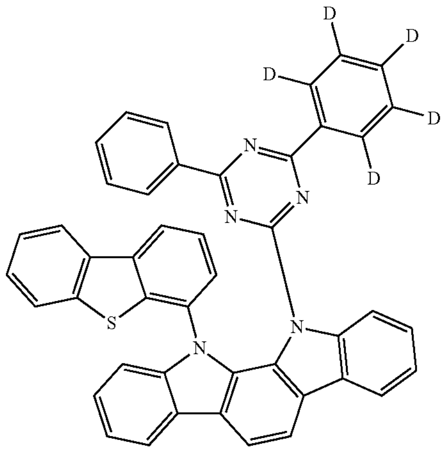

-continued
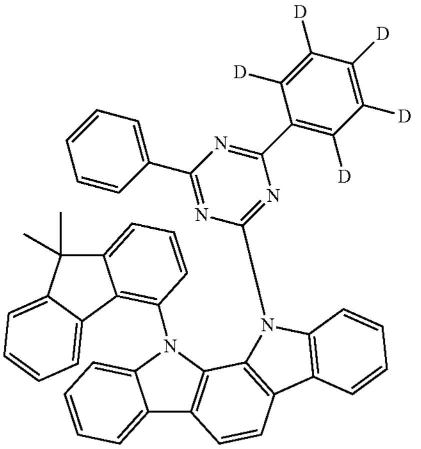
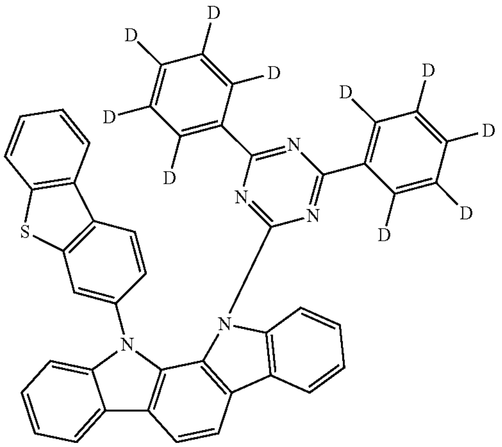
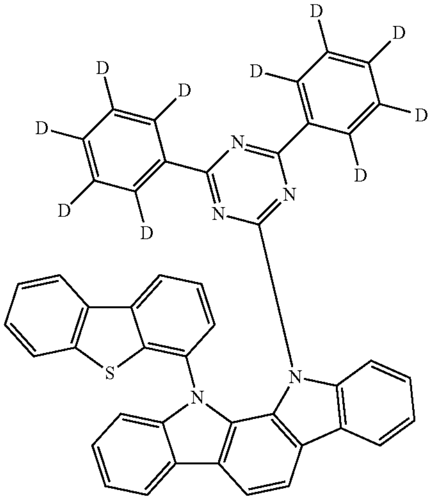
-continued
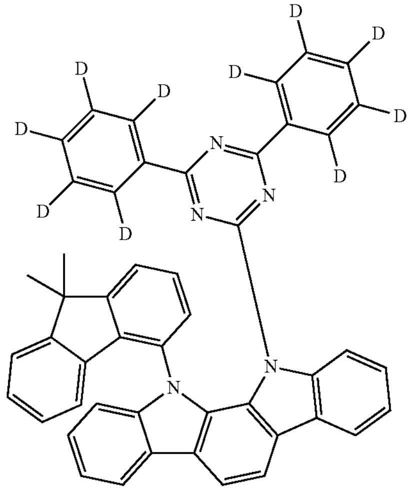
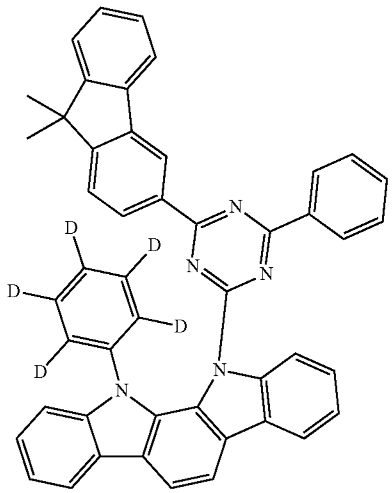
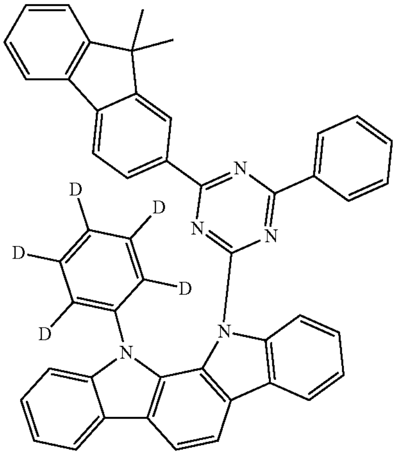

-continued
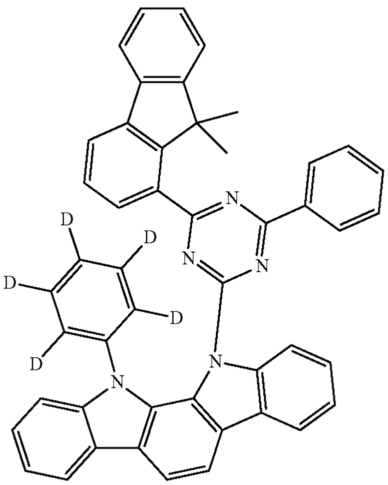
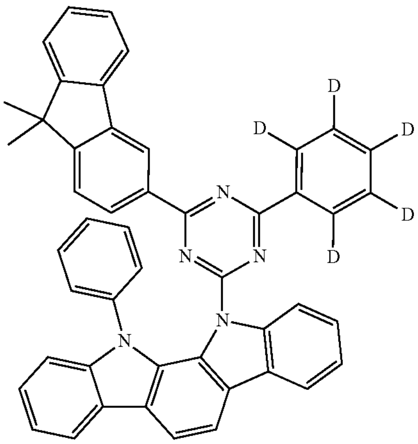
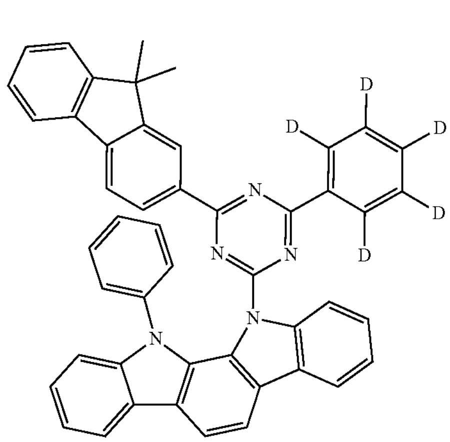
-continued
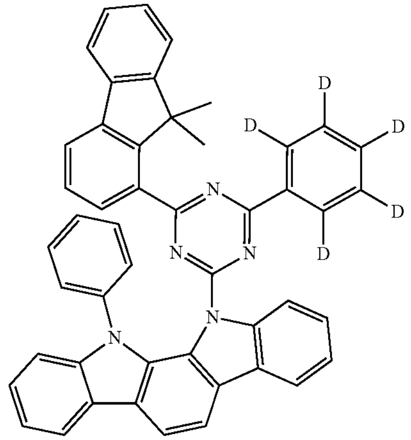
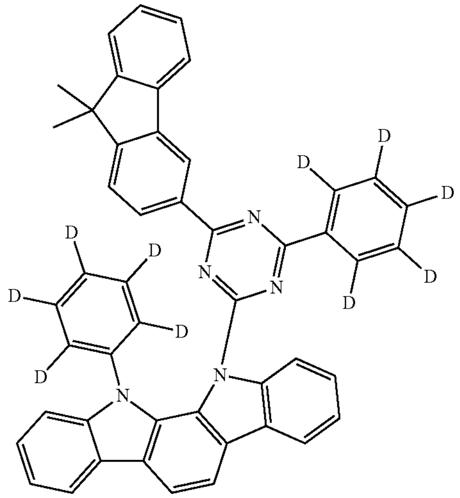
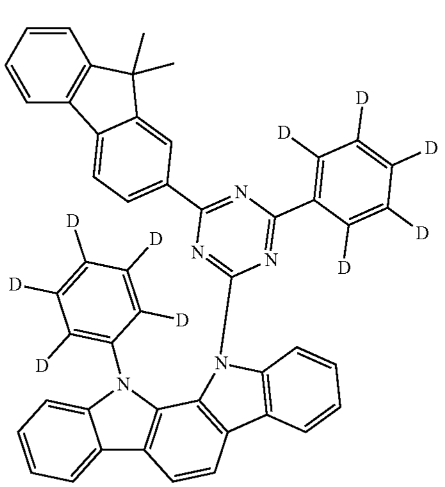

-continued
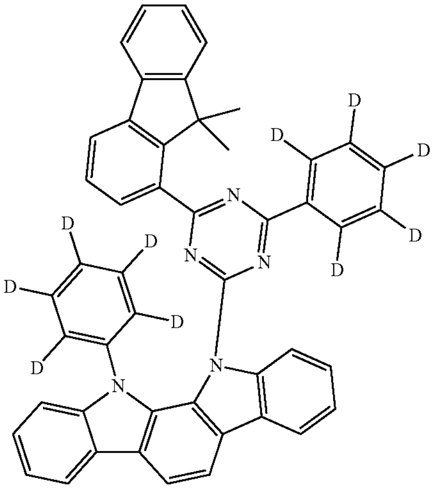
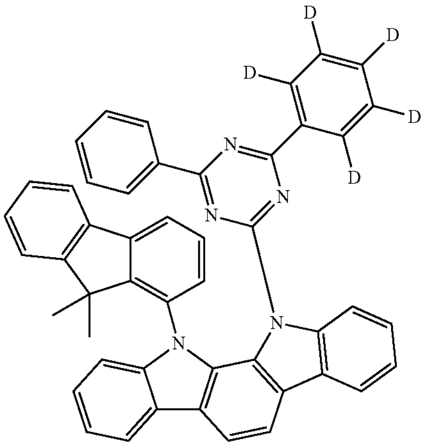
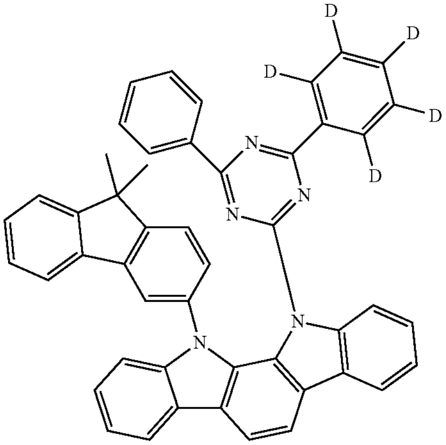
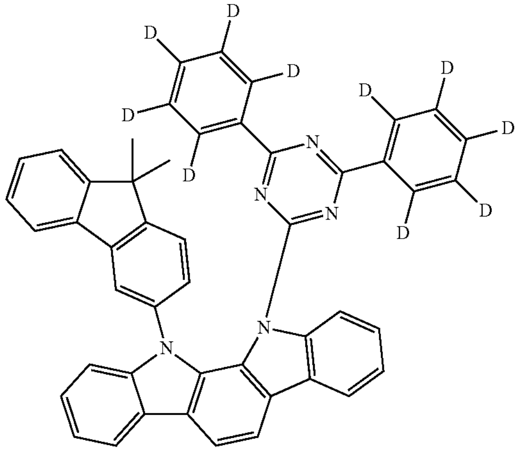
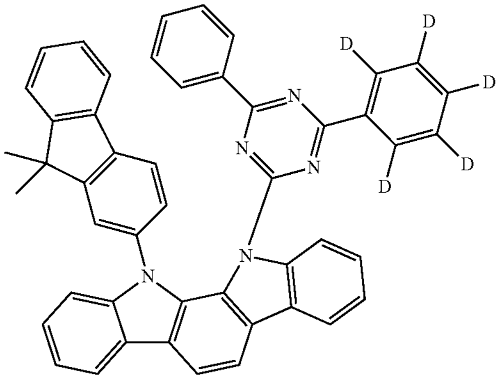
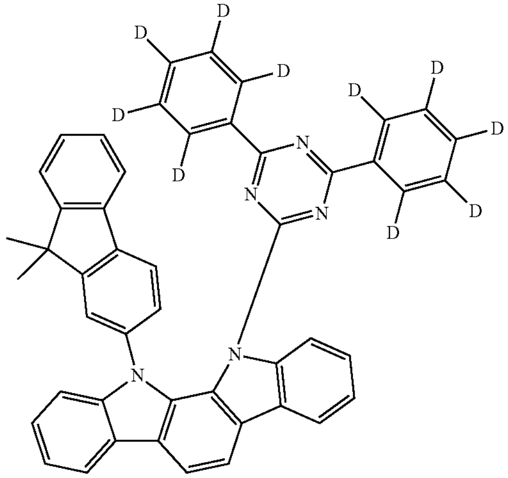

-continued
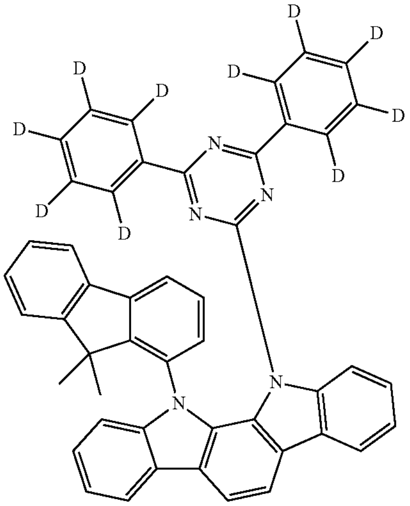
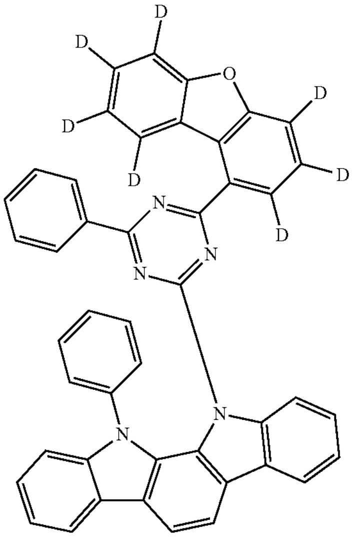
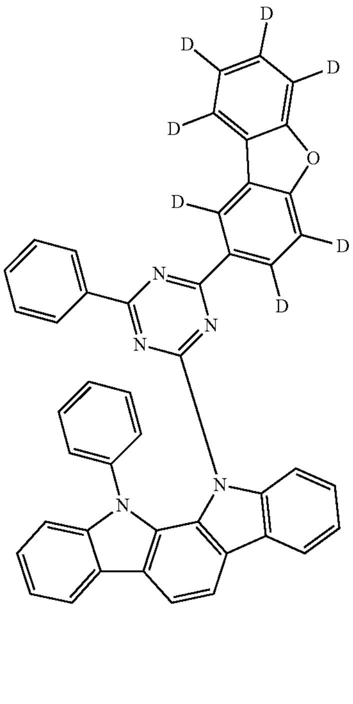
-continued
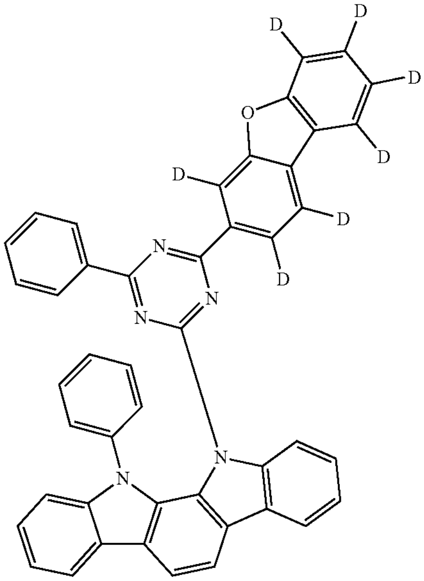
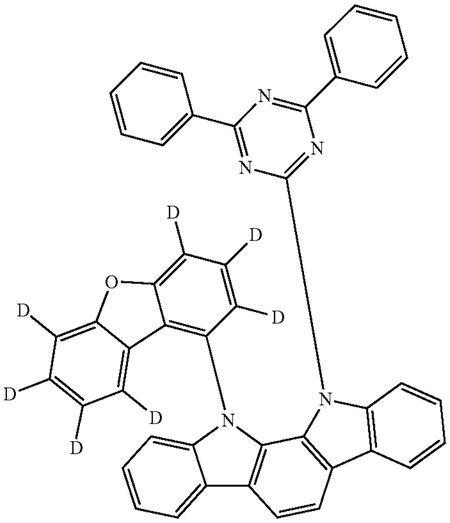
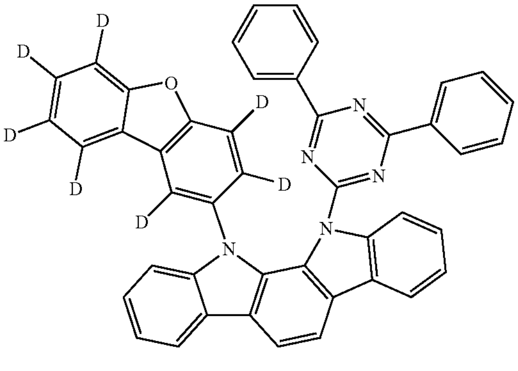

-continued
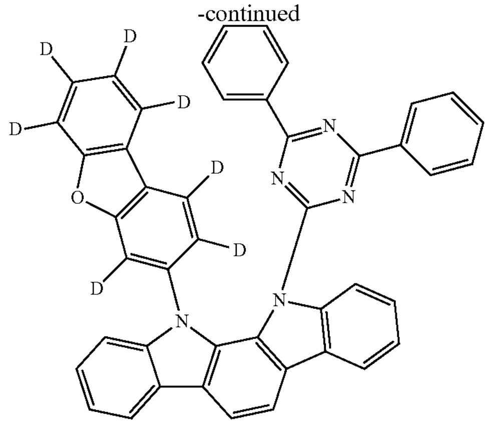
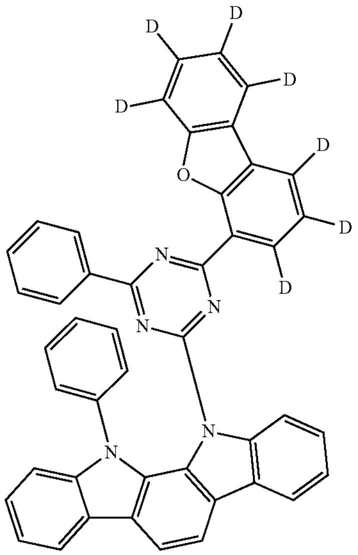
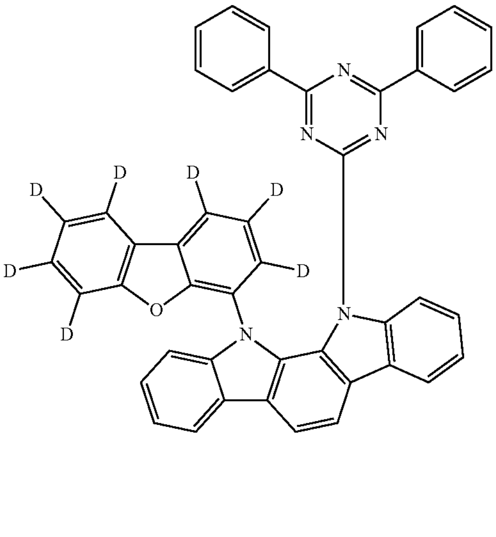
-continued
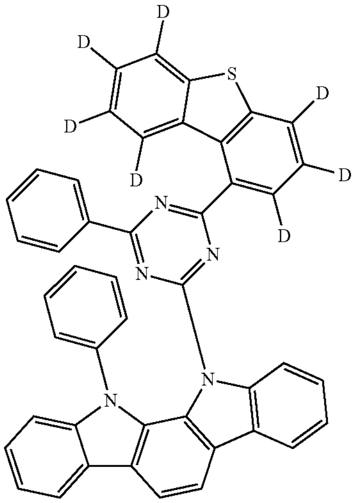
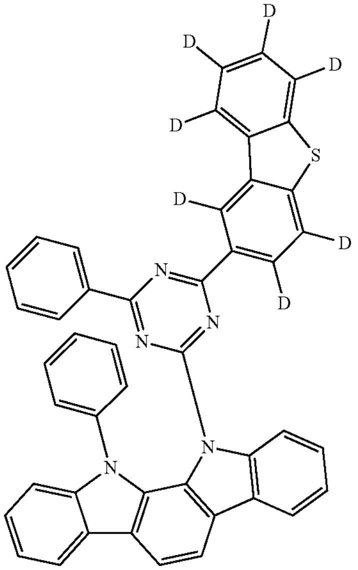
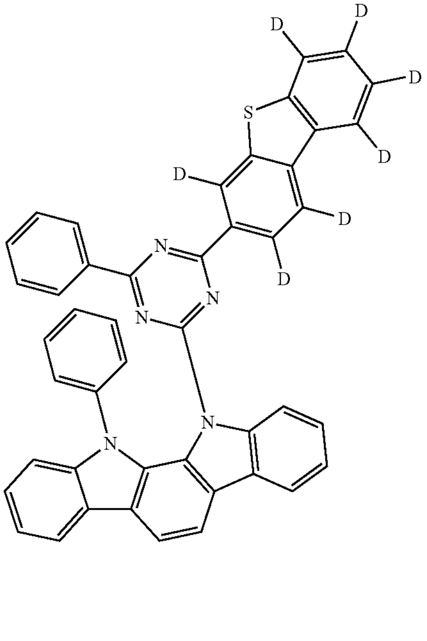

-continued
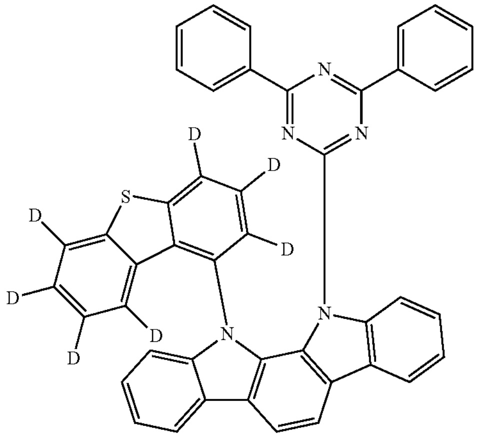
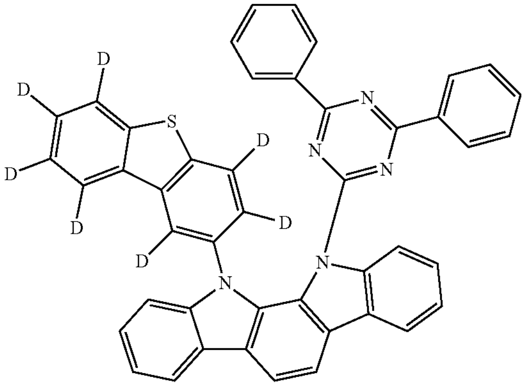
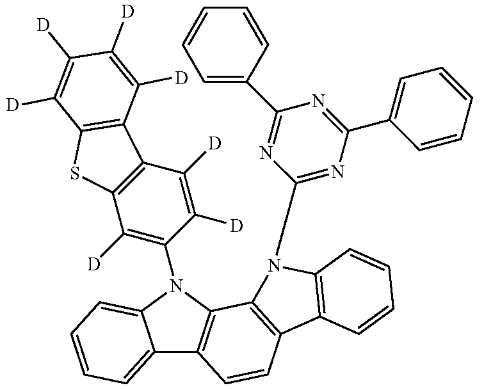
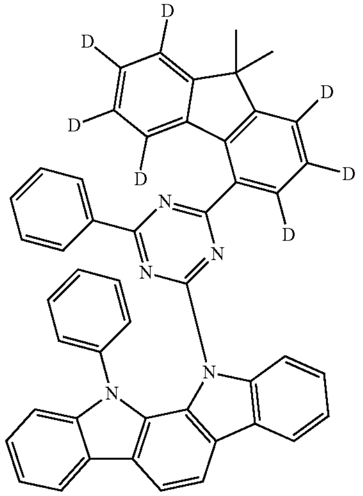
-continued
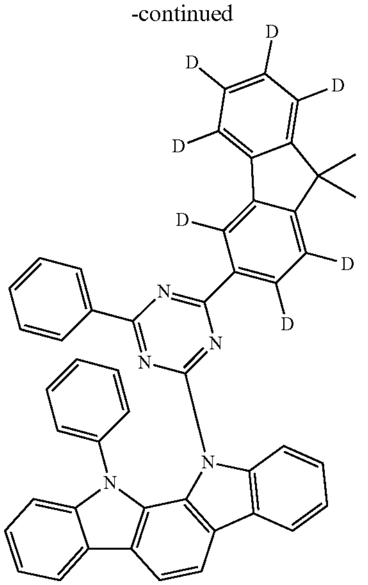
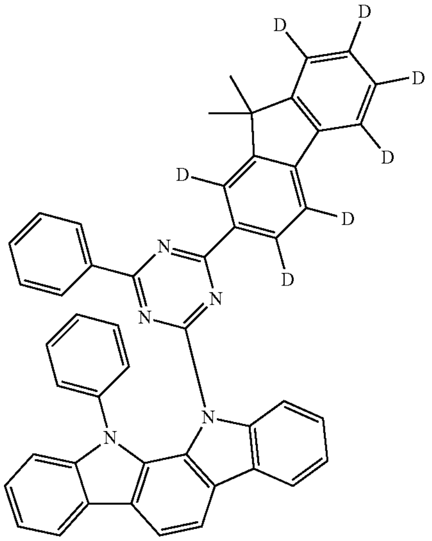
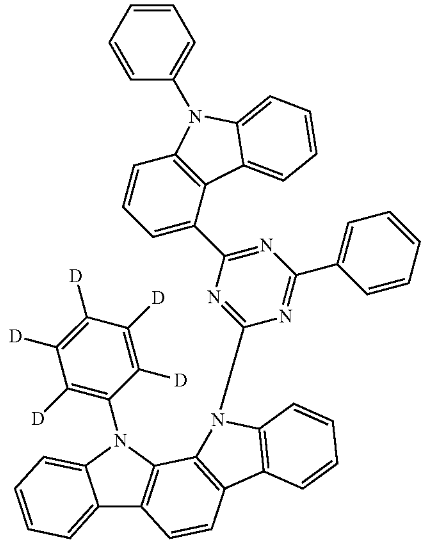

-continued
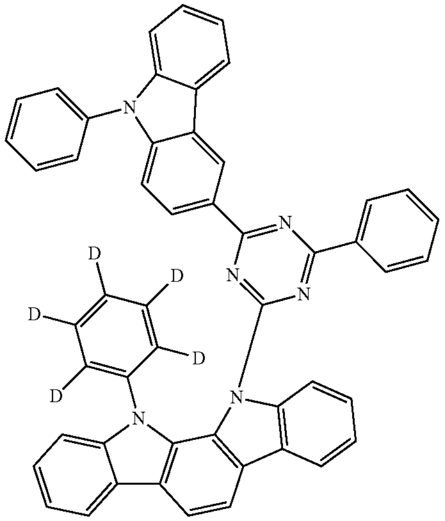
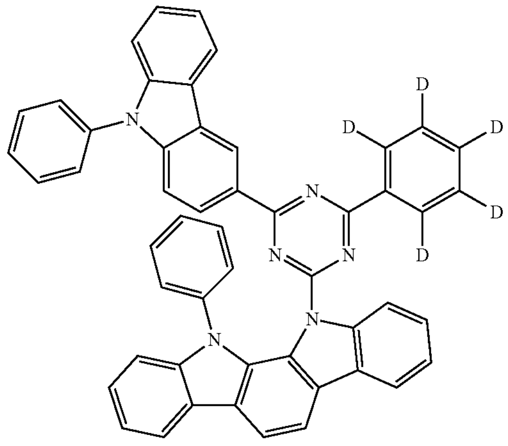
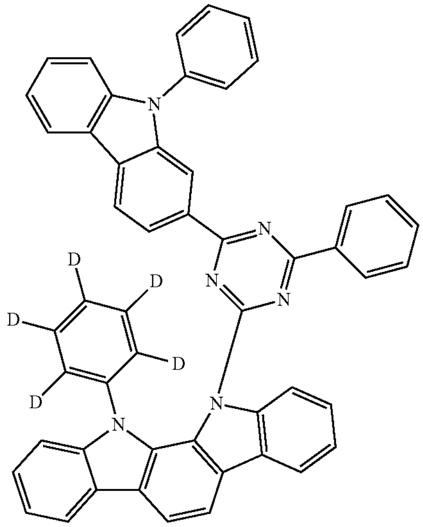
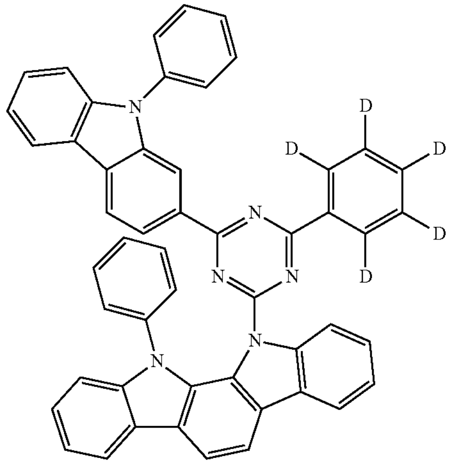
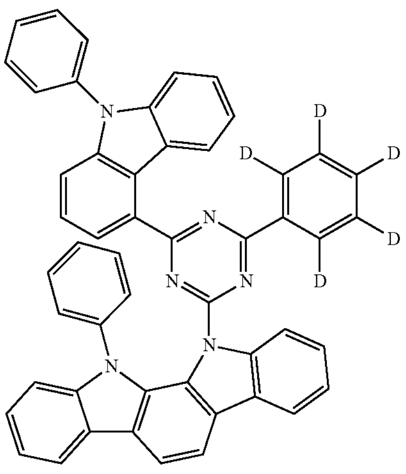
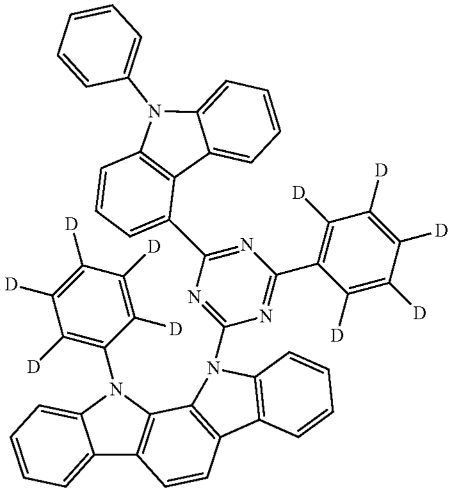
-continued -continued
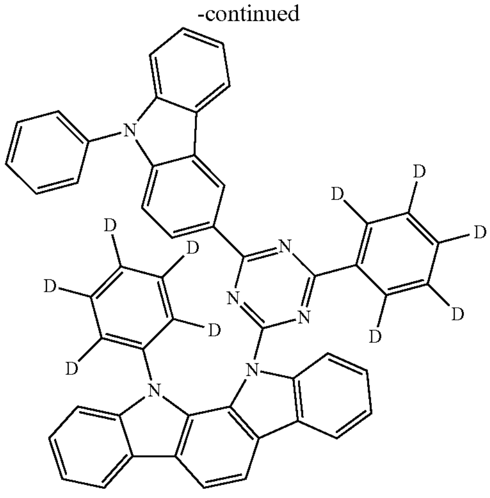
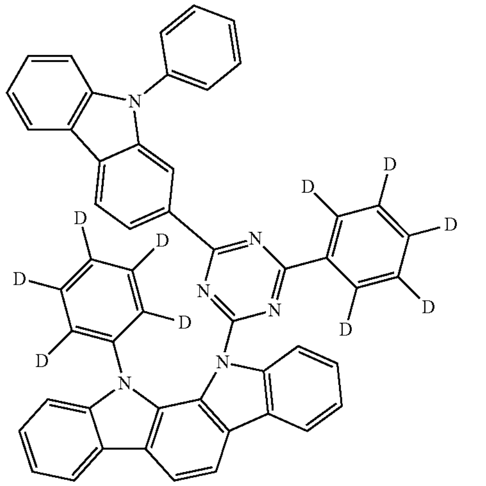
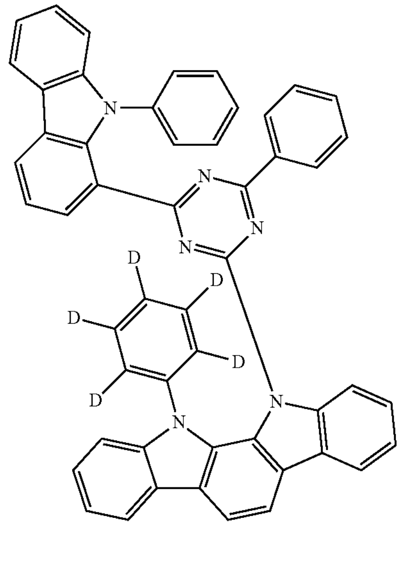
-continued
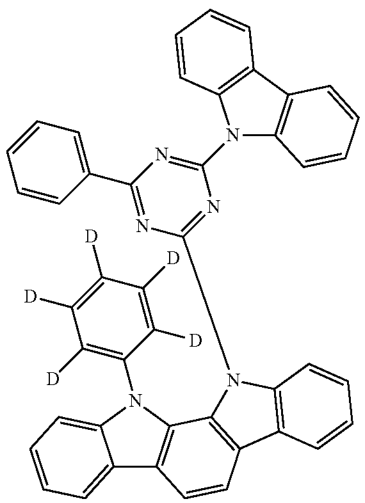
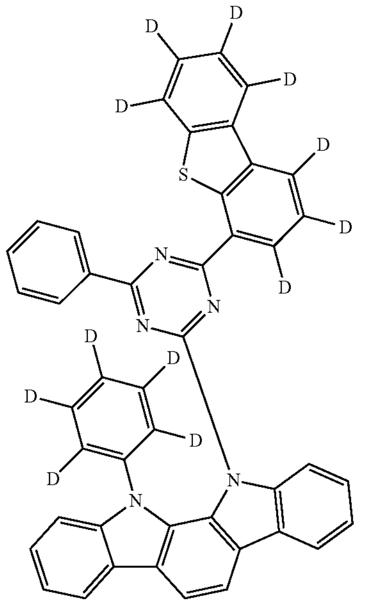
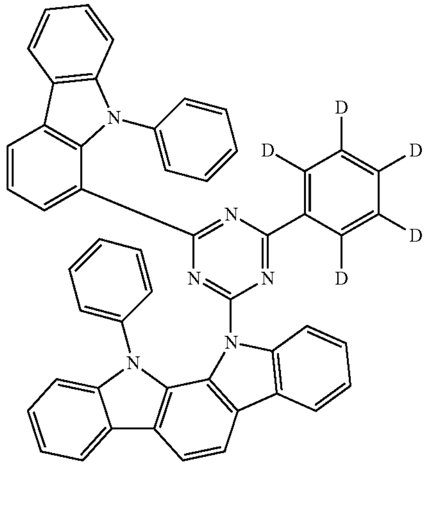

-continued
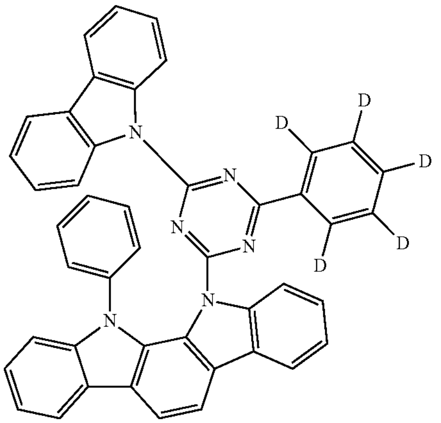
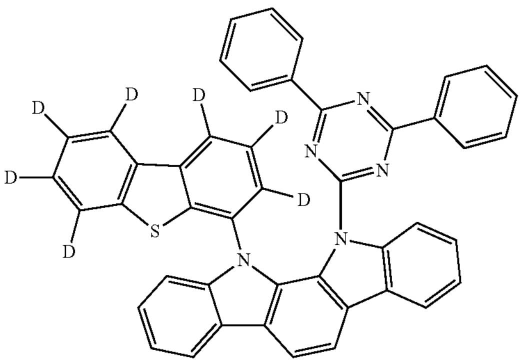
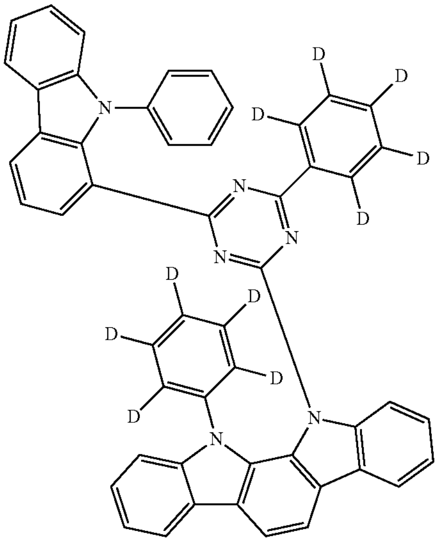
-continued
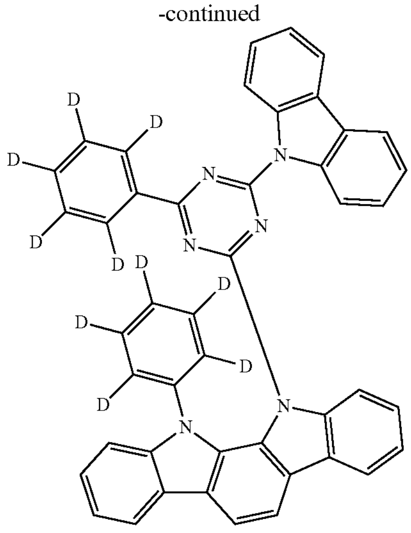
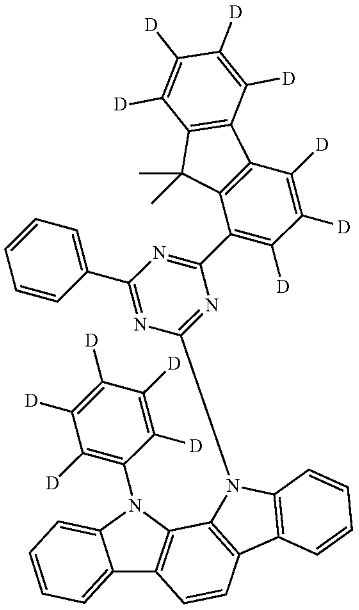
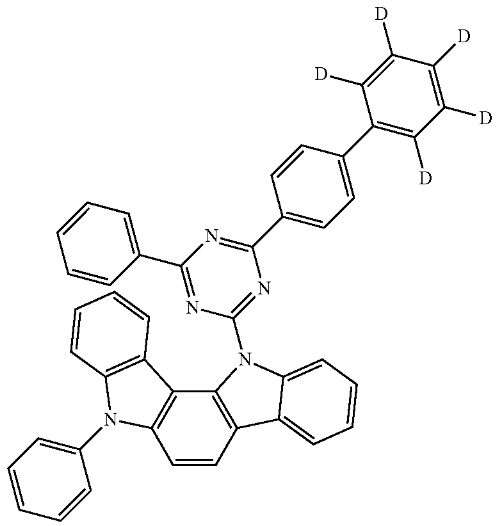

-continued
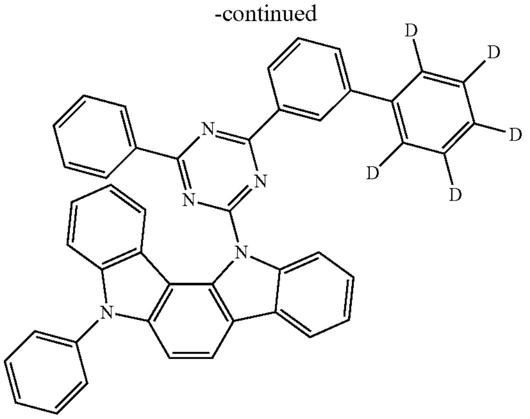
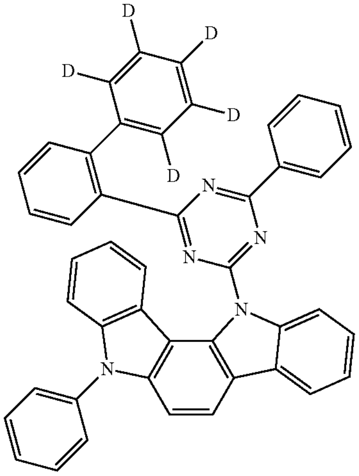
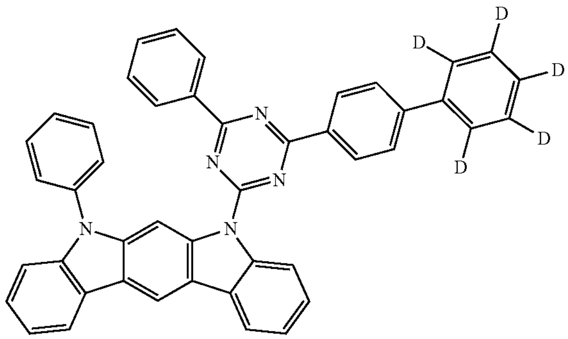
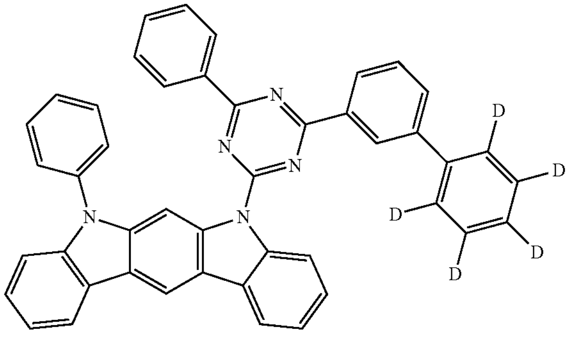
-continued
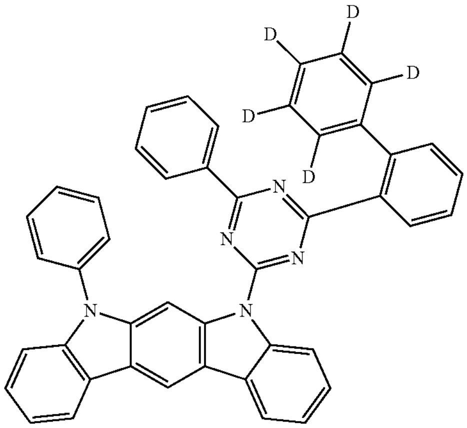
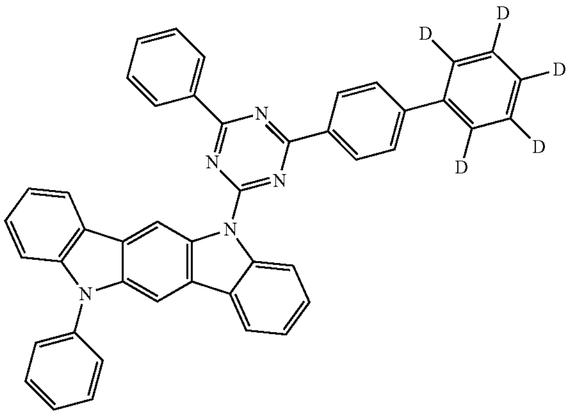
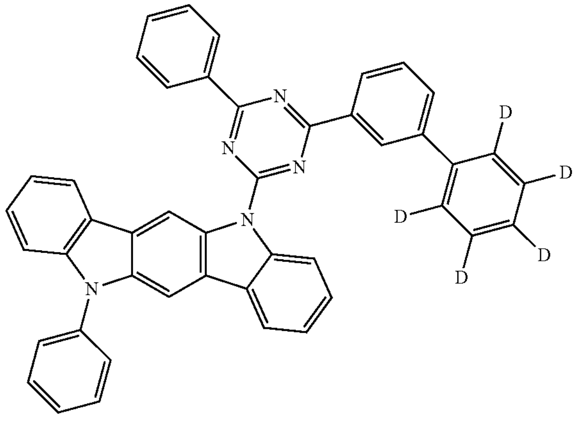

-continued
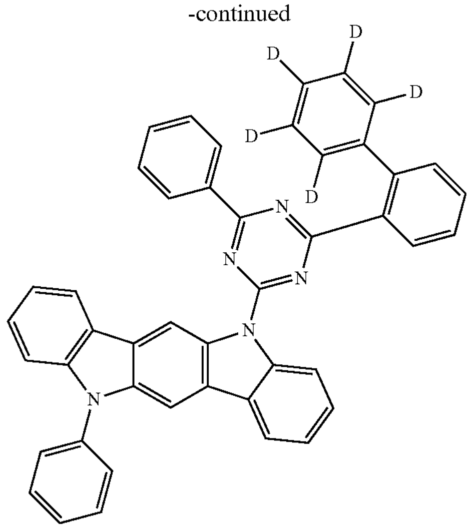
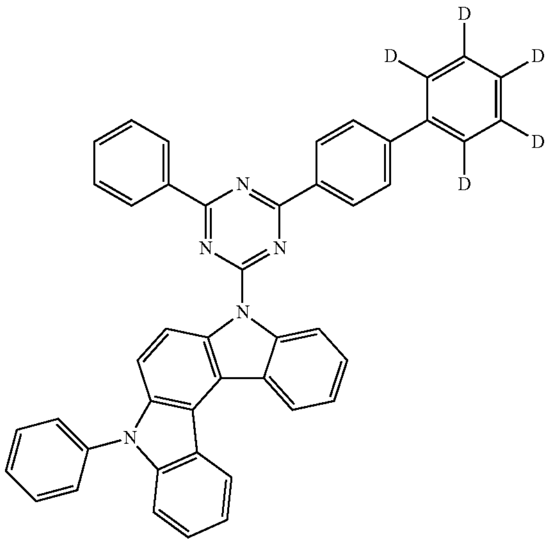
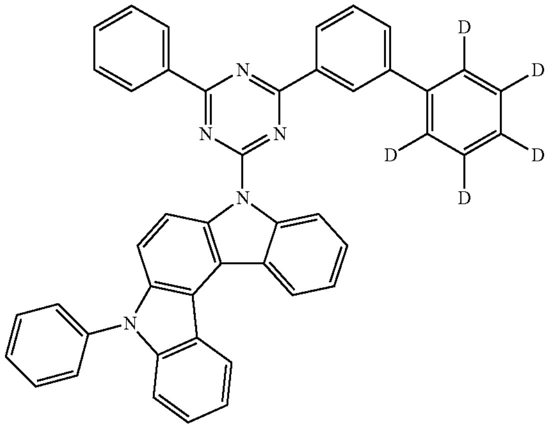
-continued
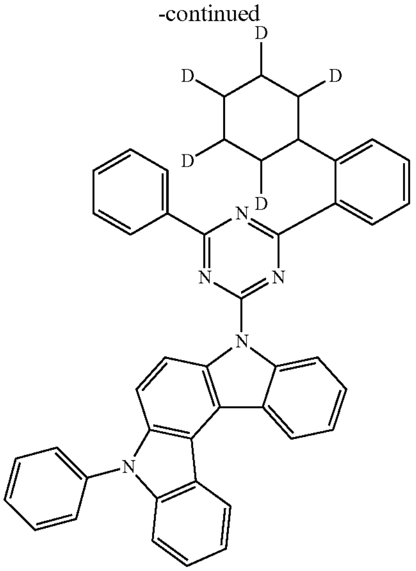
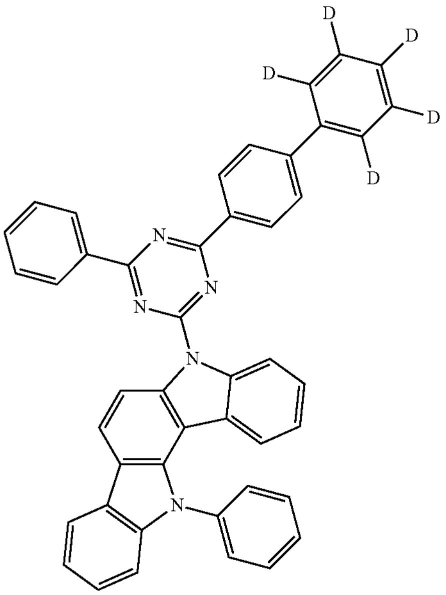
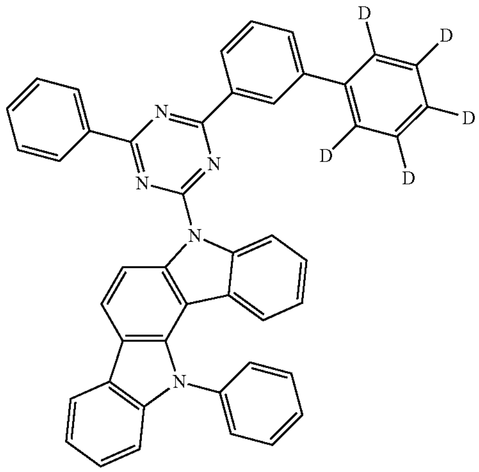

-continued
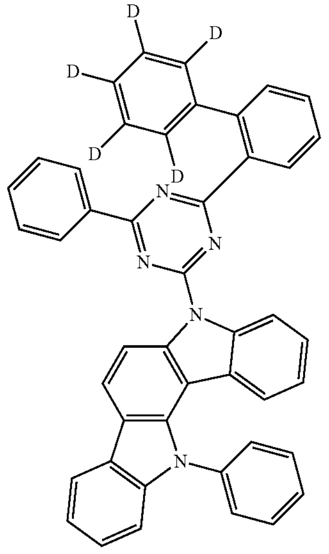
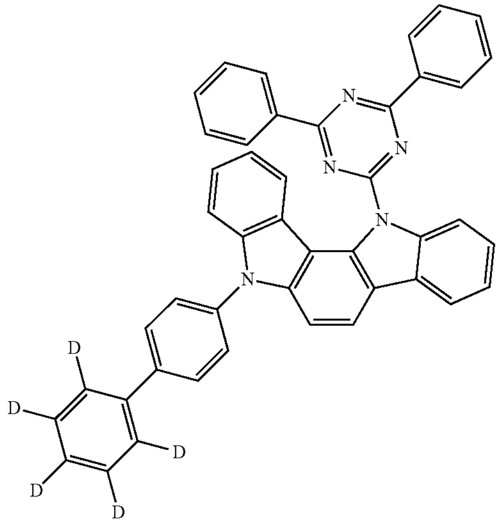
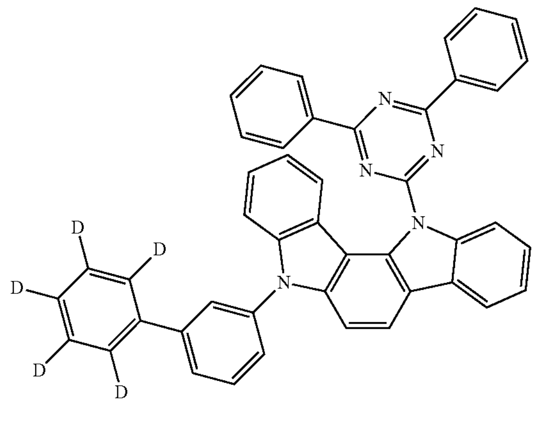
-continued
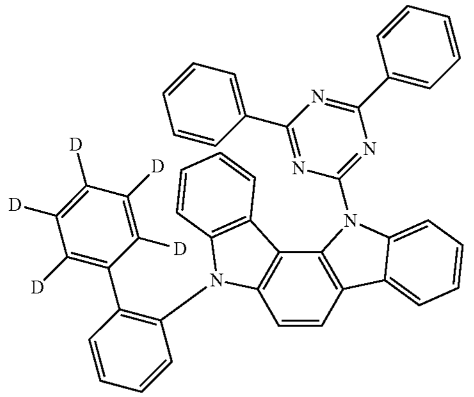
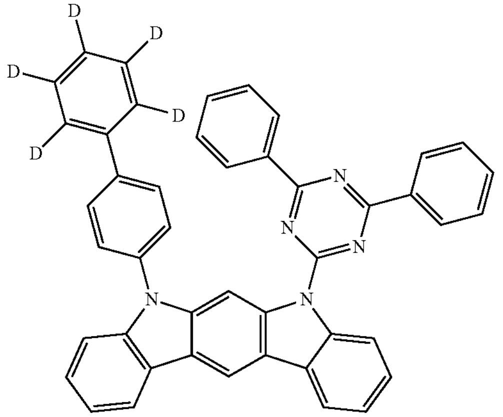
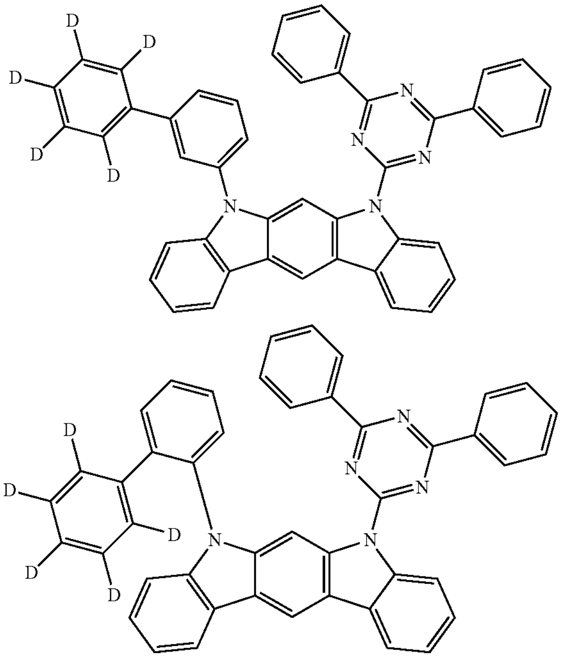

-continued
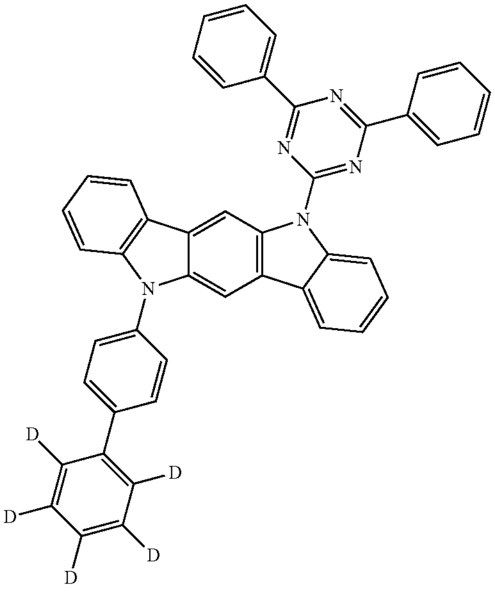
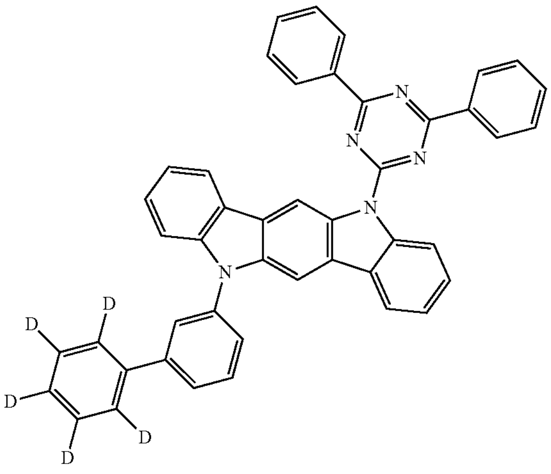
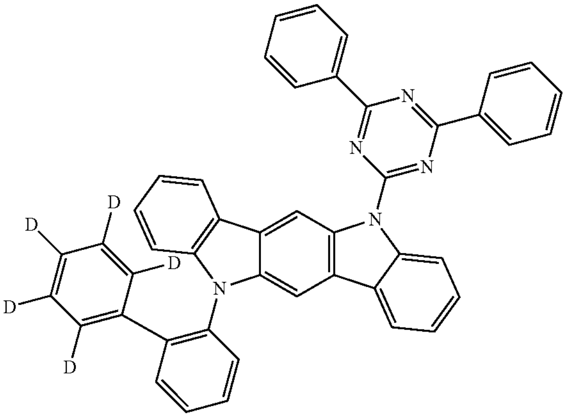
-continued
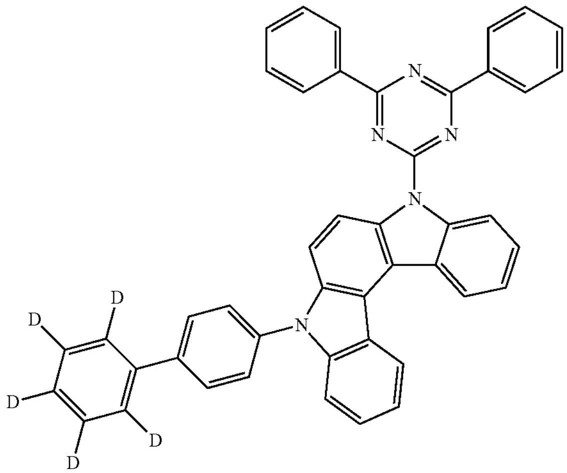
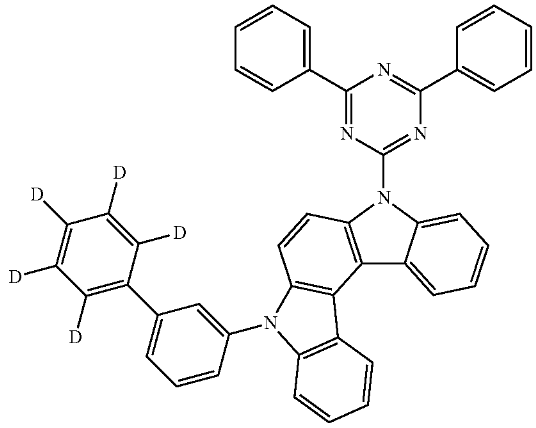
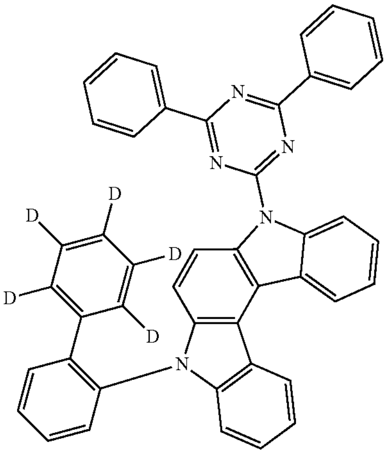

-continued
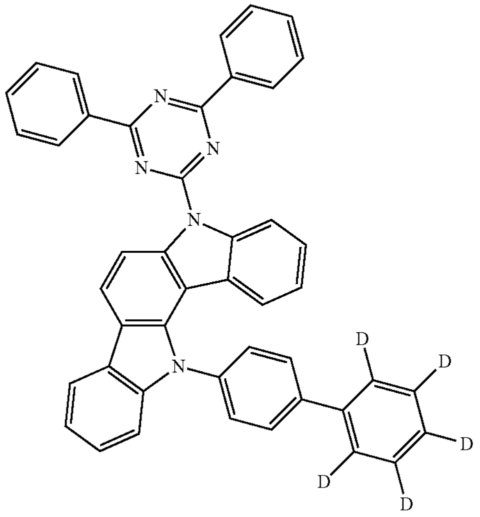
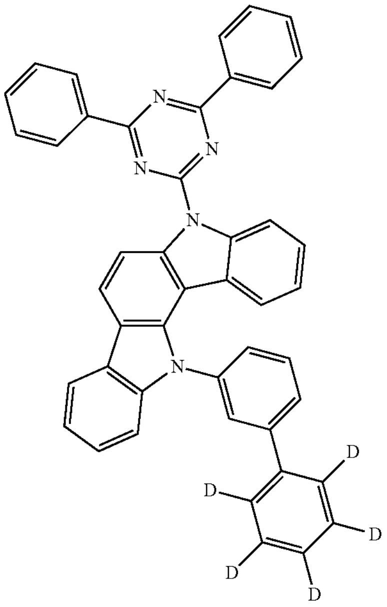
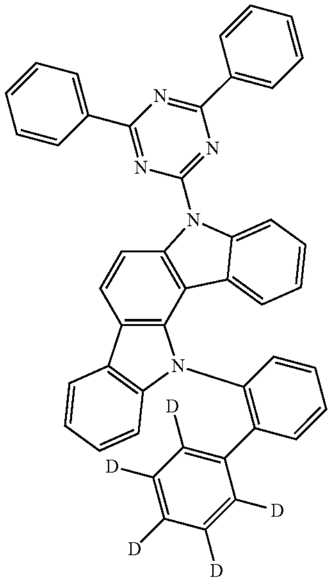
-continued
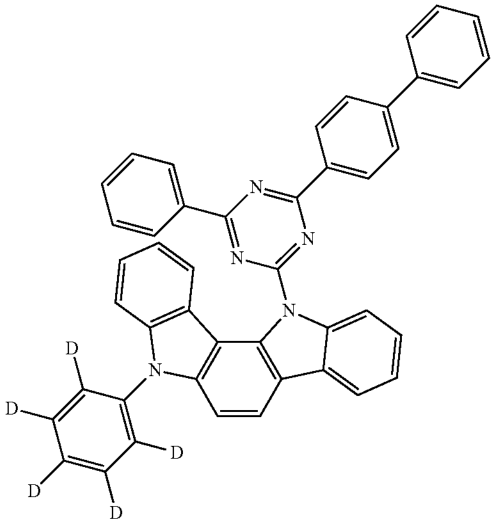
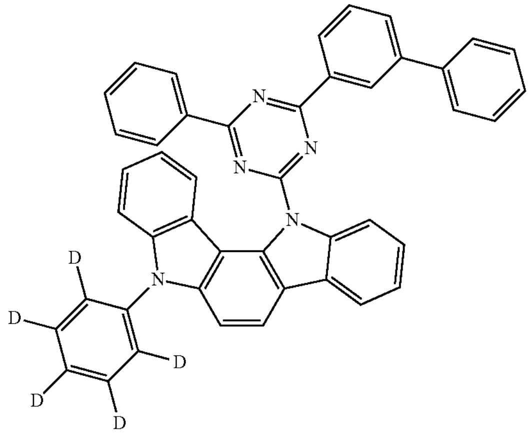
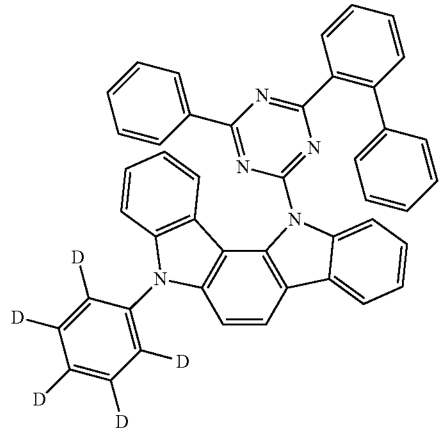
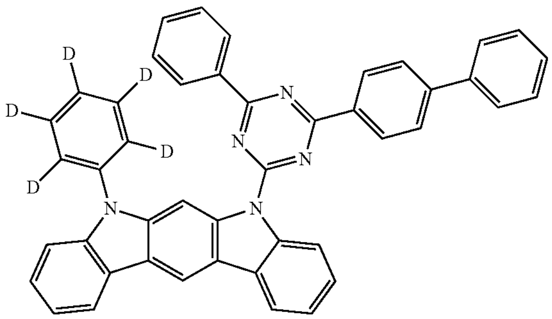

-continued
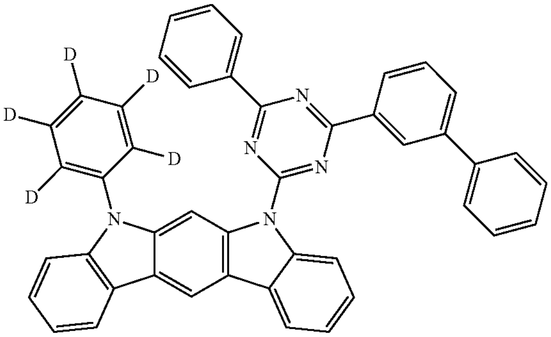
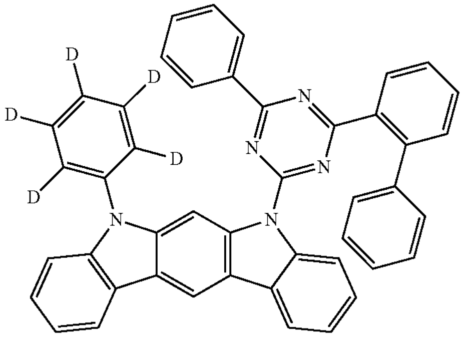
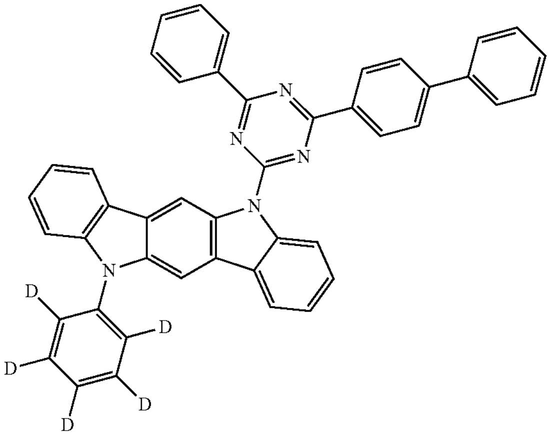
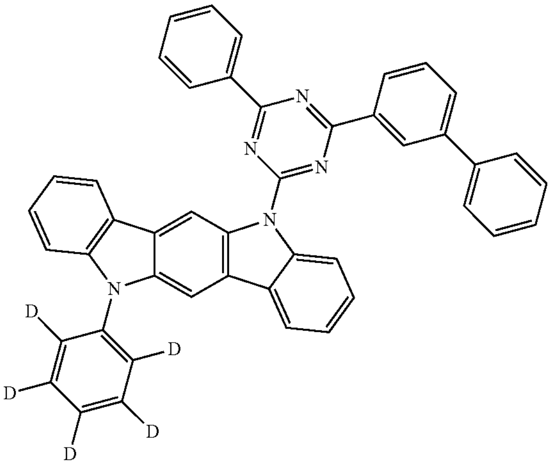
-continued
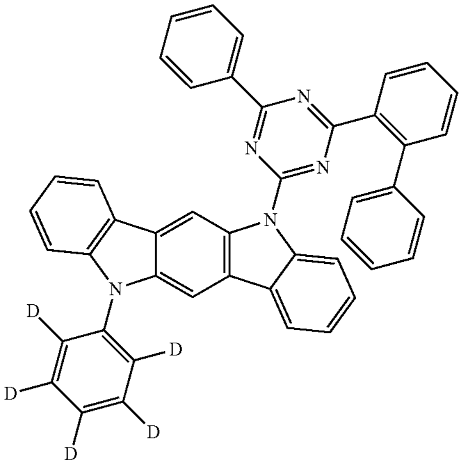
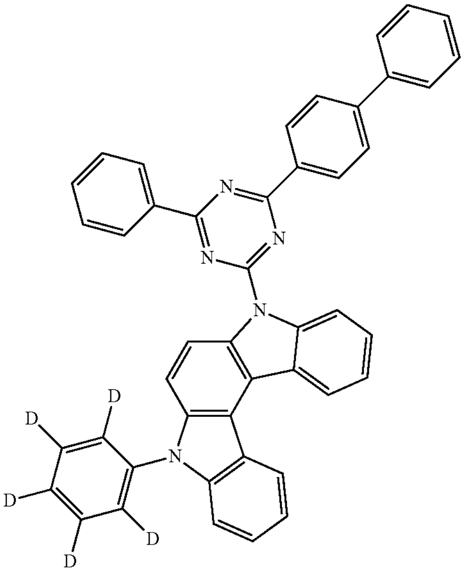
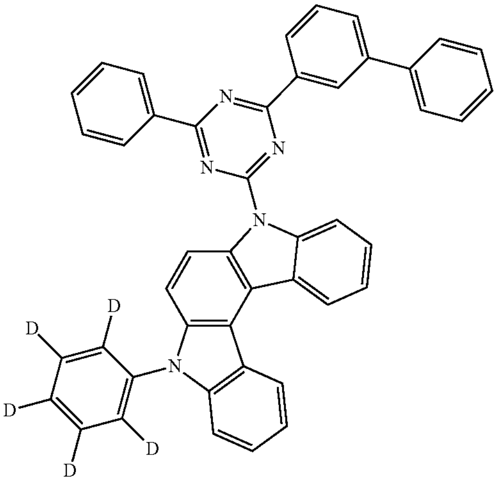

-continued
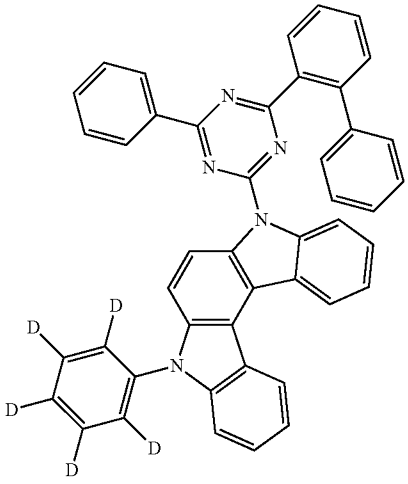
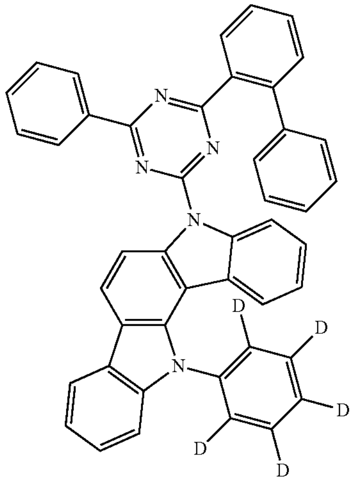
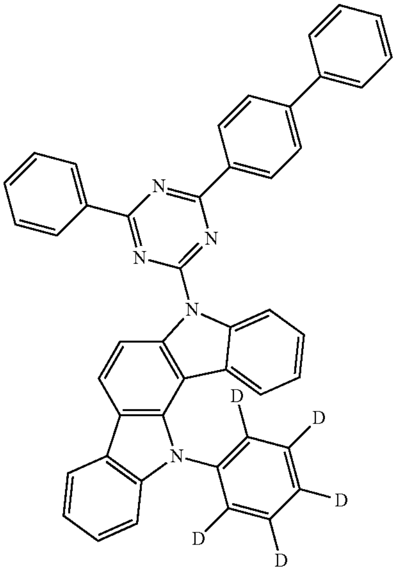
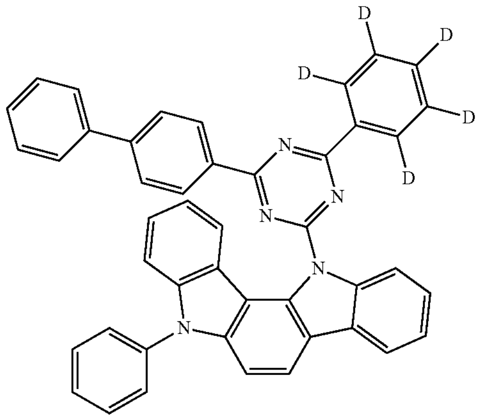
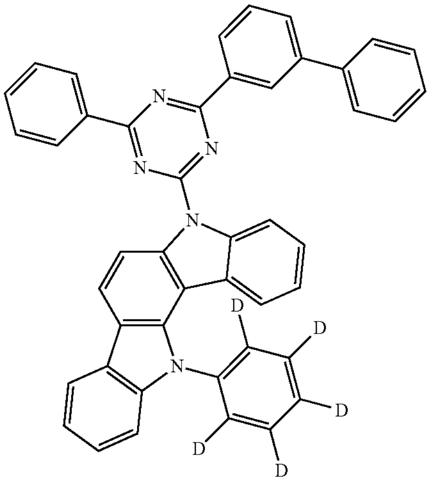
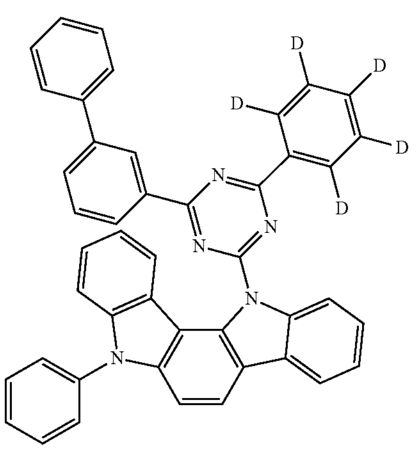
-continued -continued
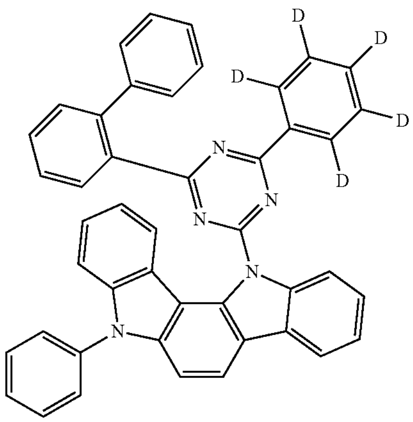
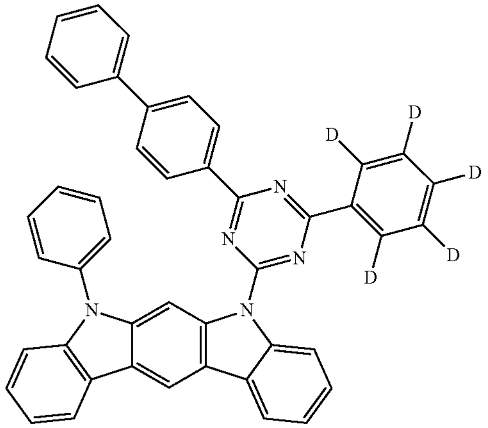
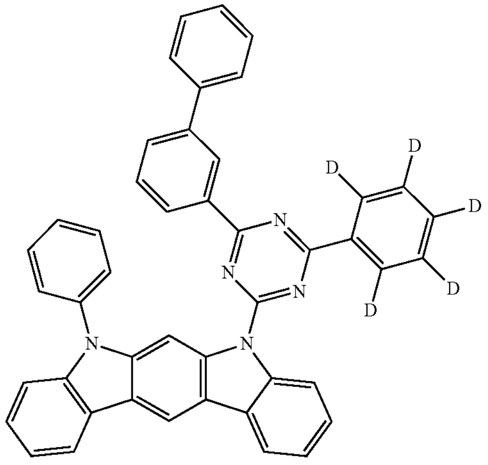
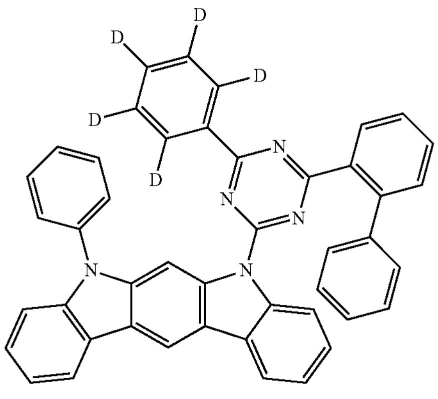
-continued
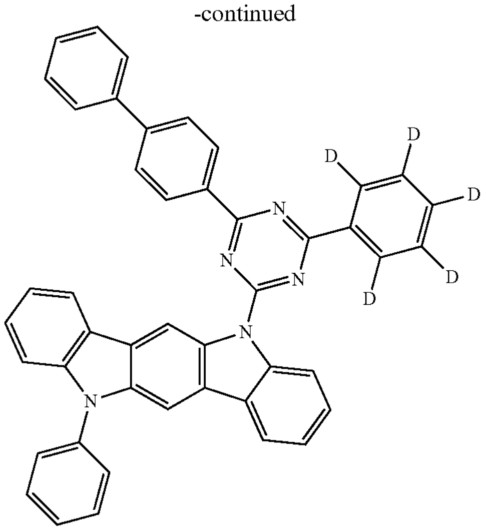
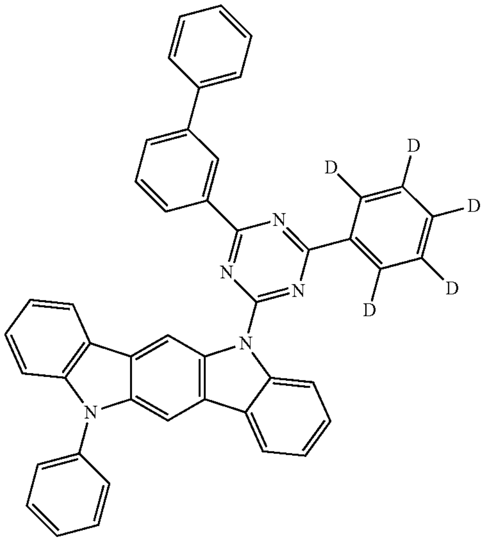
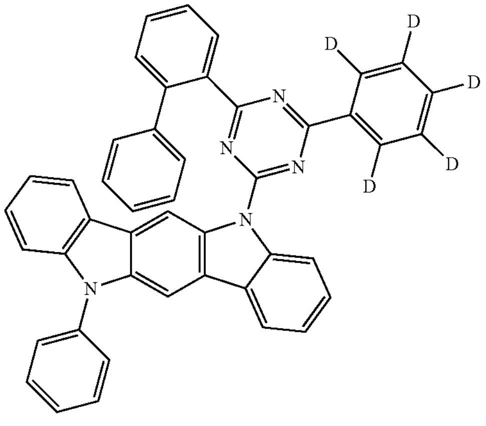

-continued
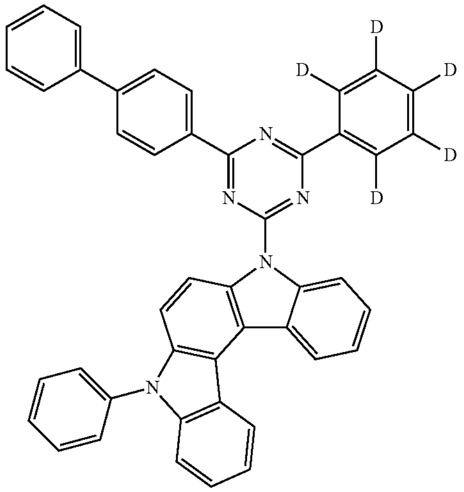
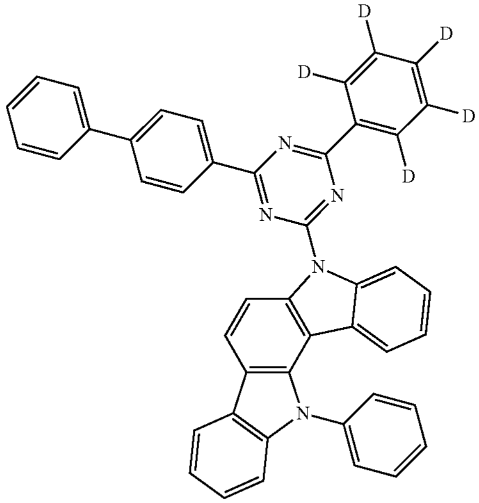
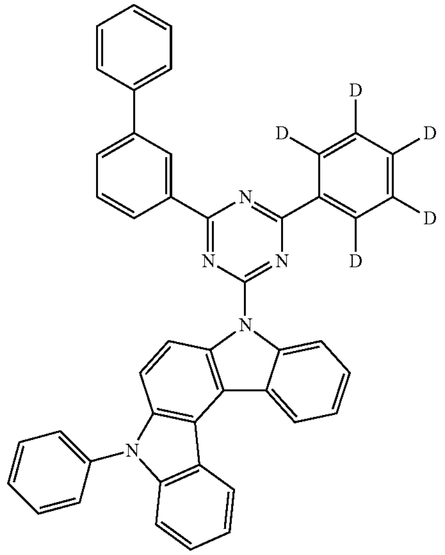
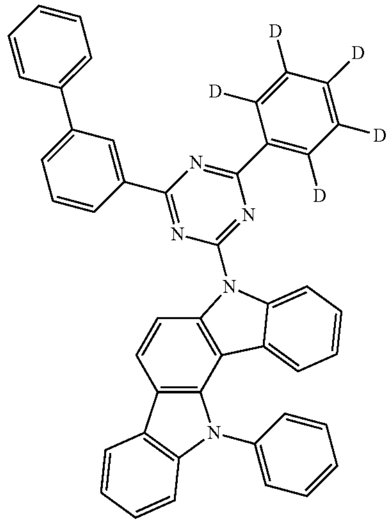
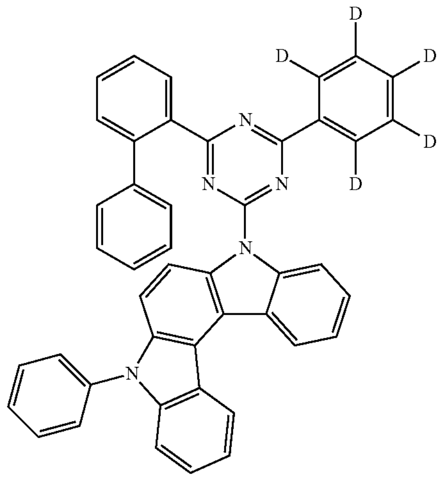
-continued
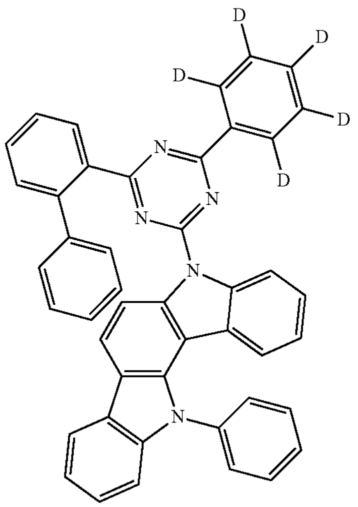

-continued
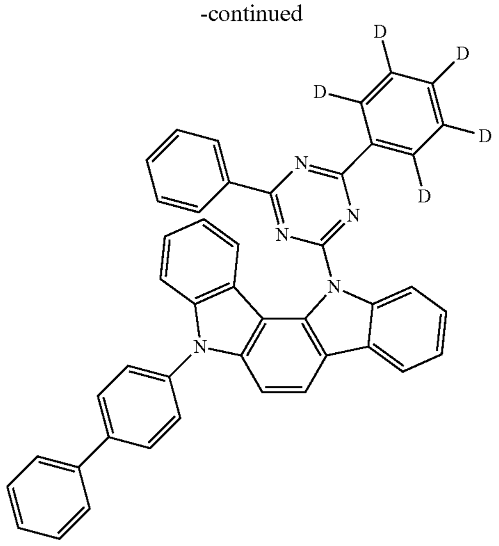
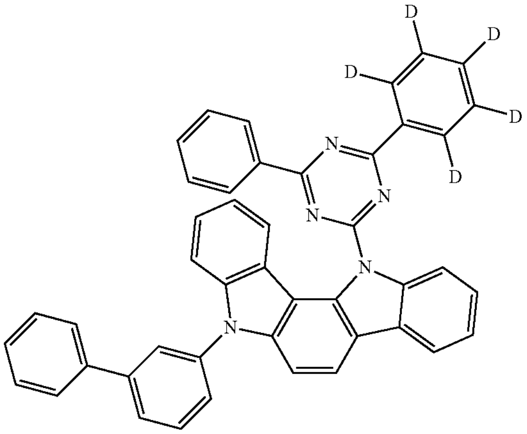
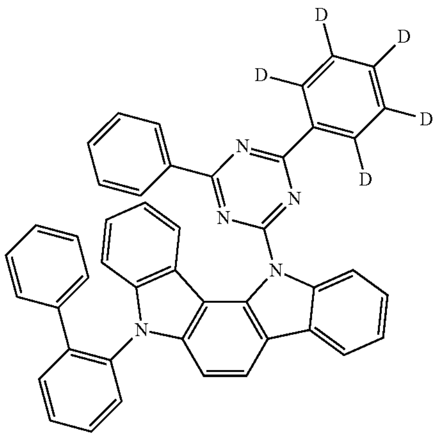
-continued
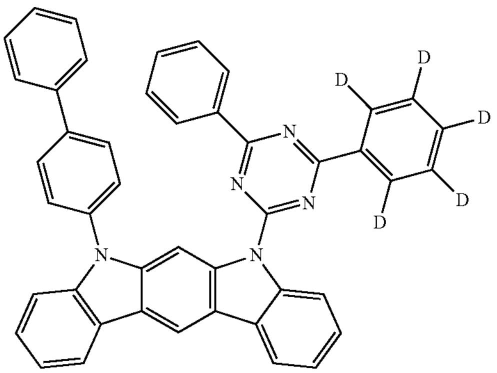
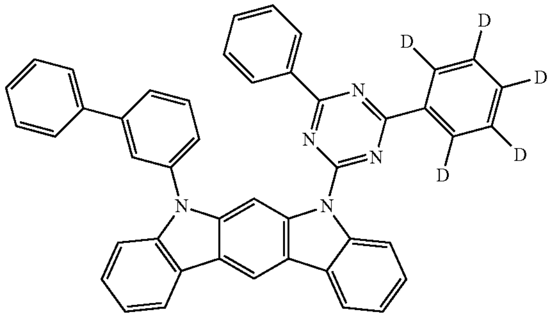
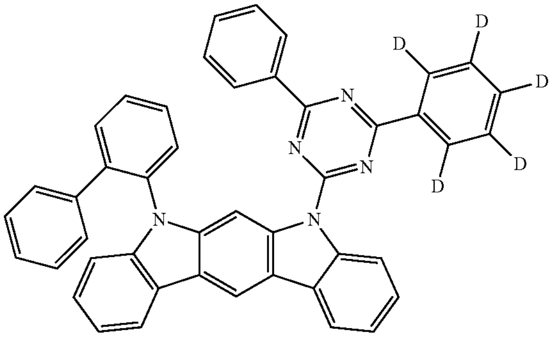
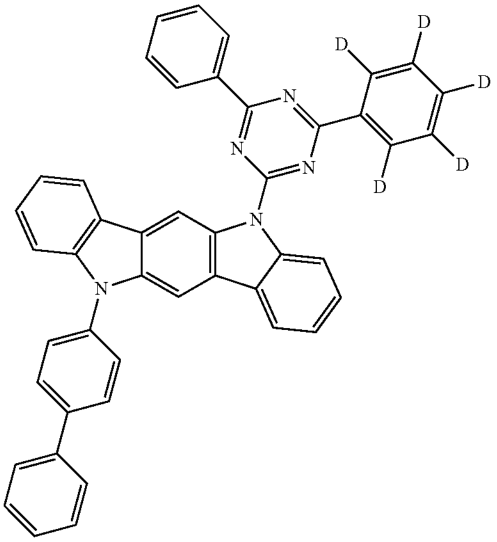

-continued
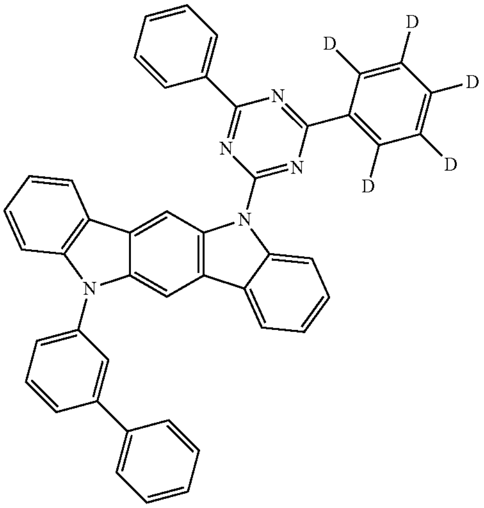
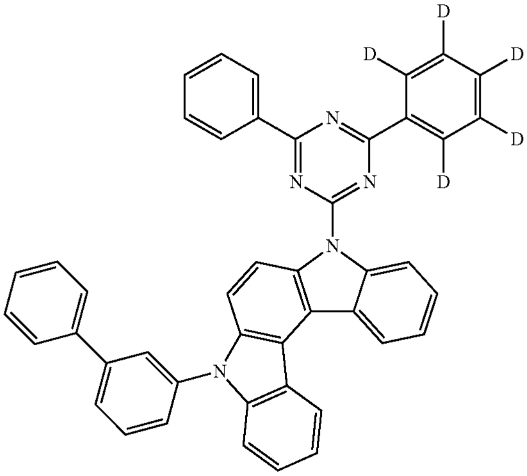
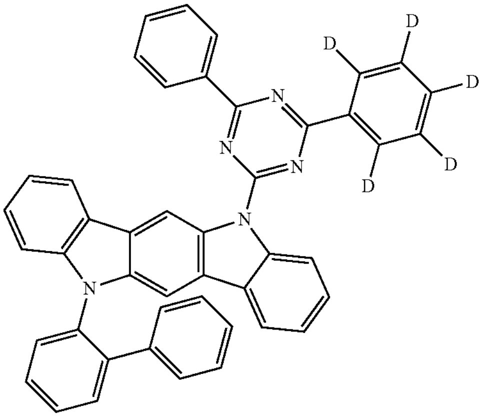
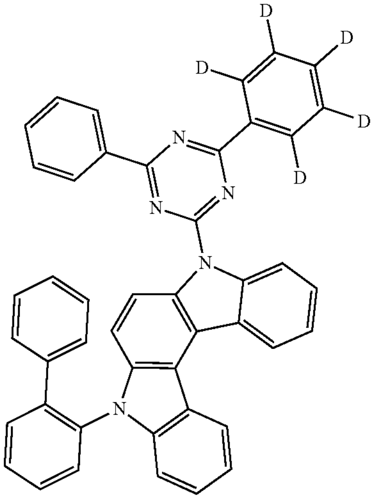
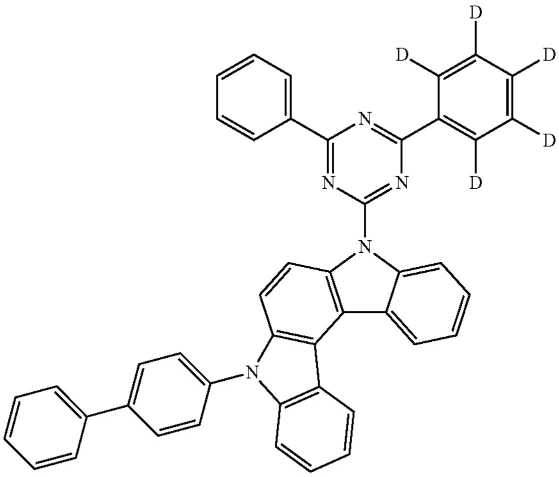
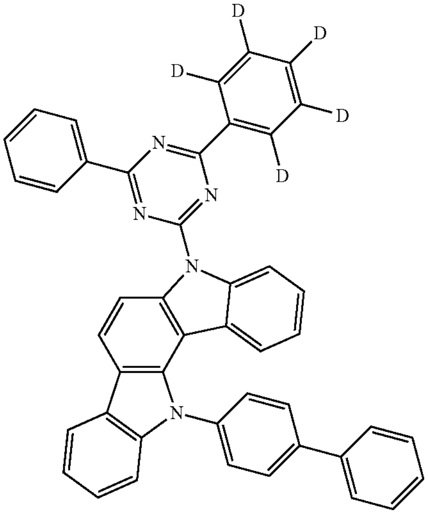
-continued -continued
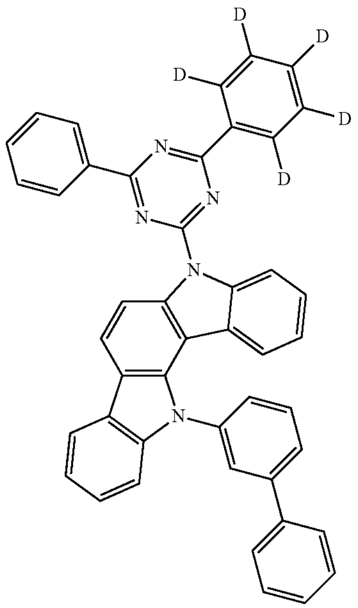
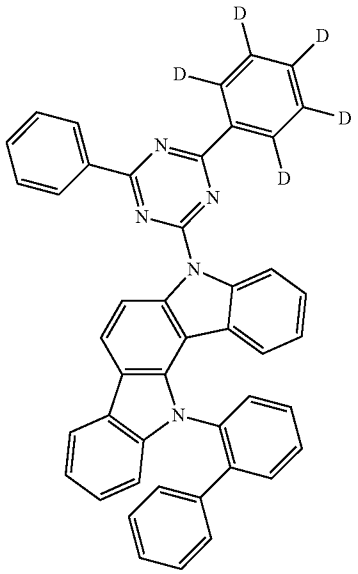
-continued
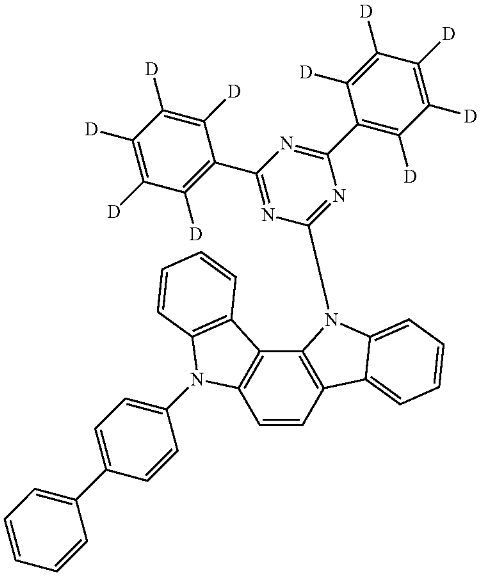
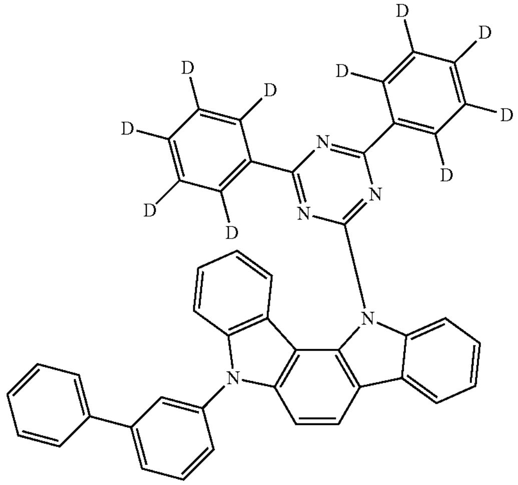
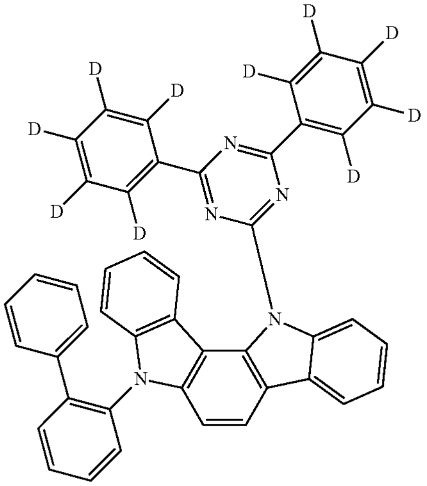

-continued
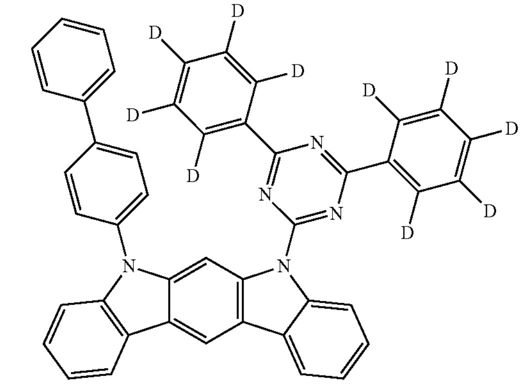
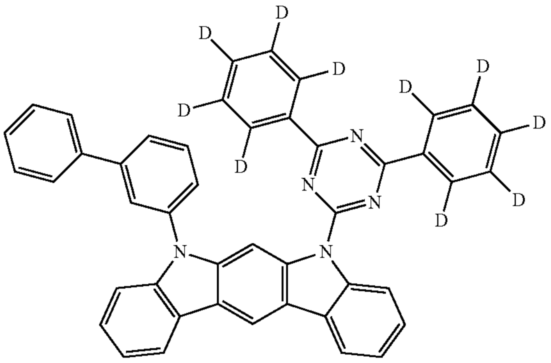
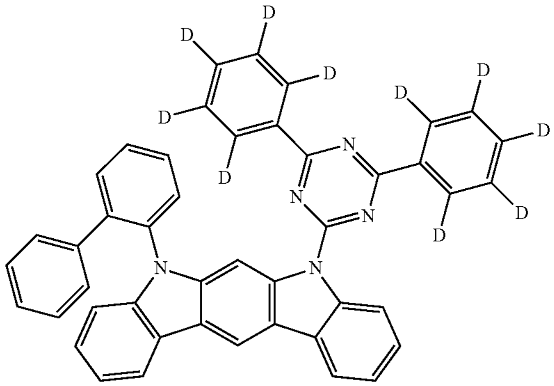
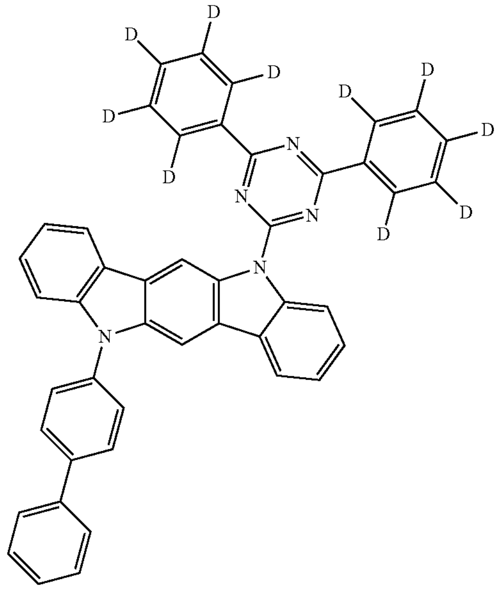
-continued
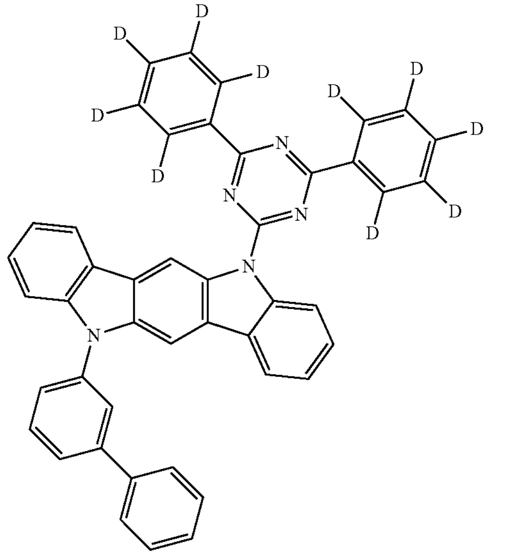
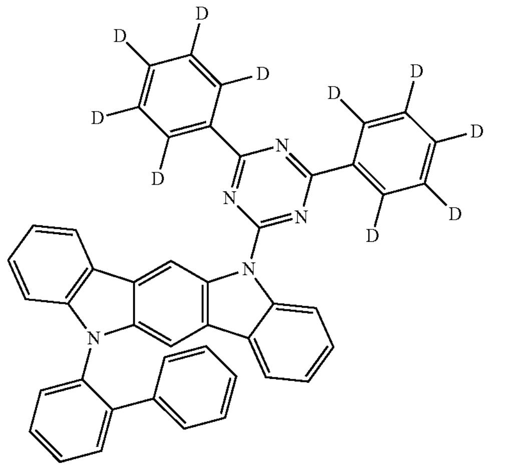
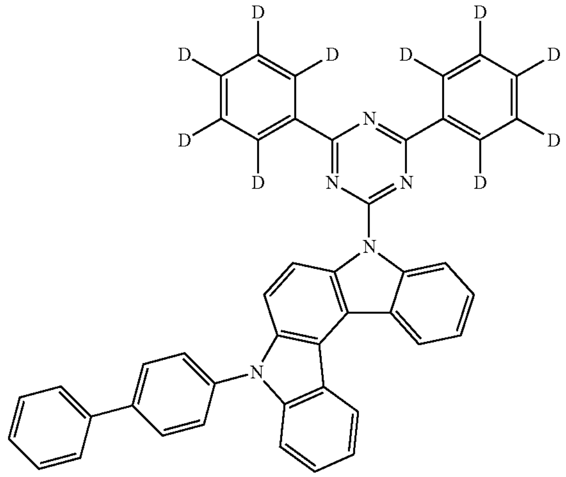

-continued
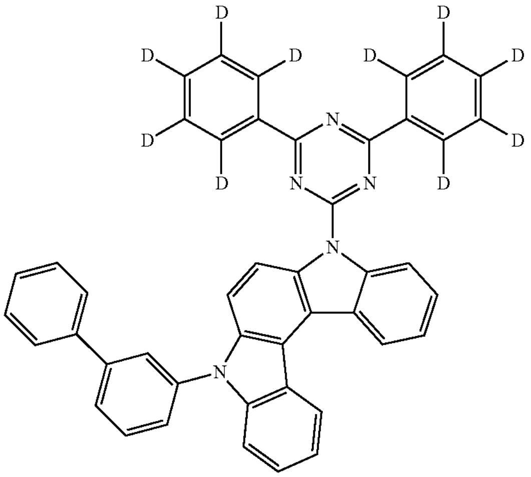
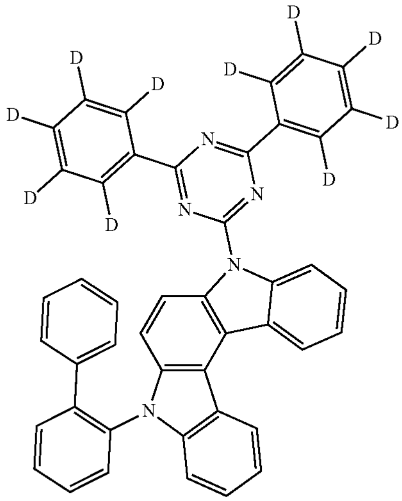
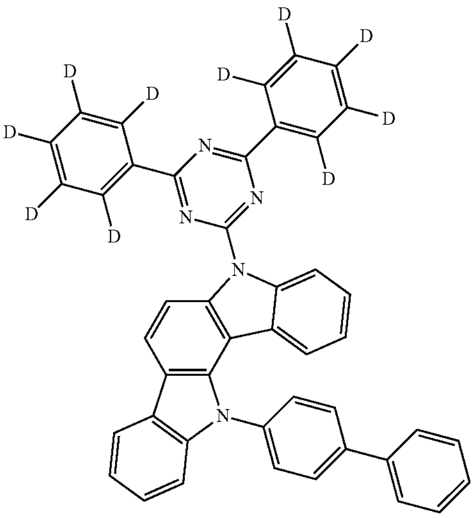
-continued
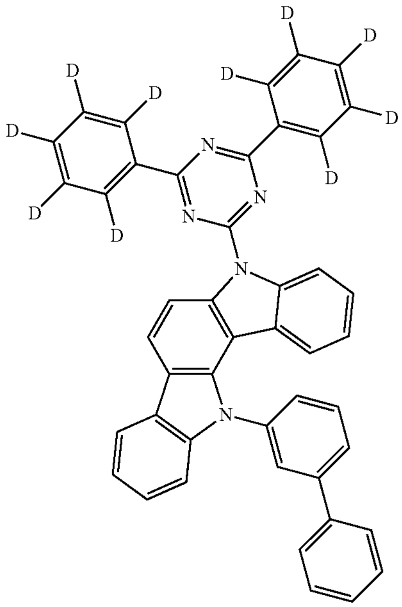
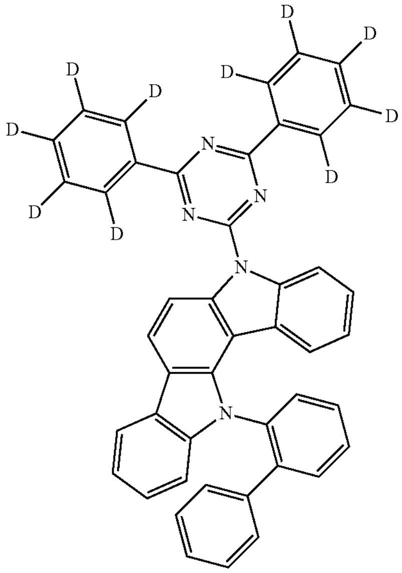
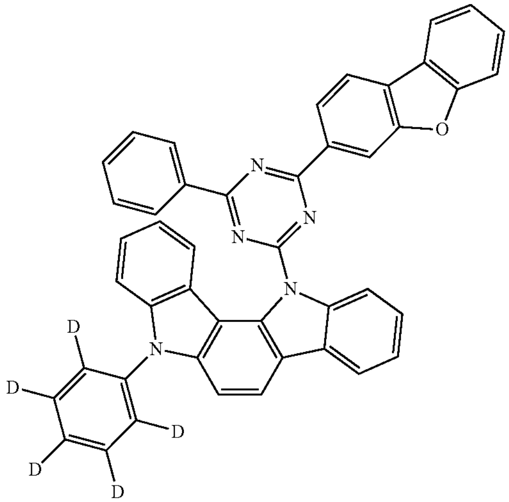

-continued
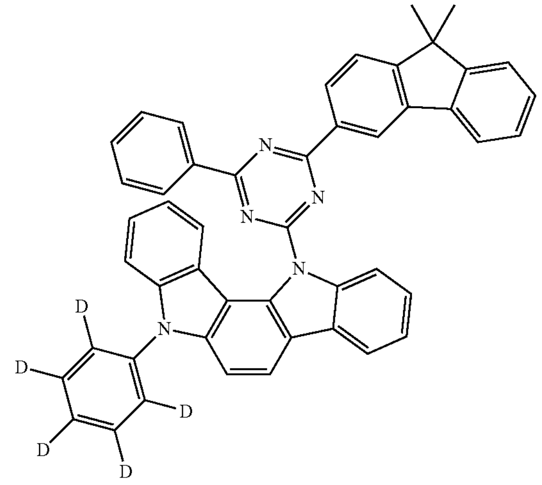
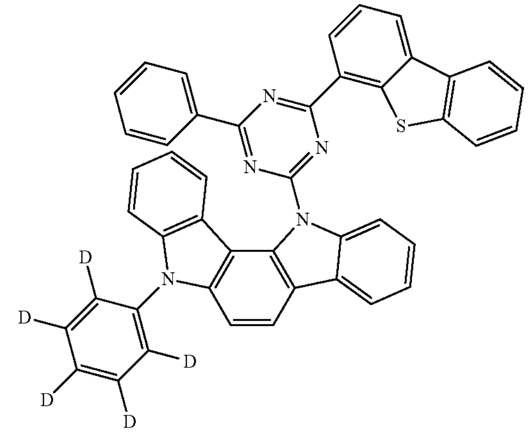
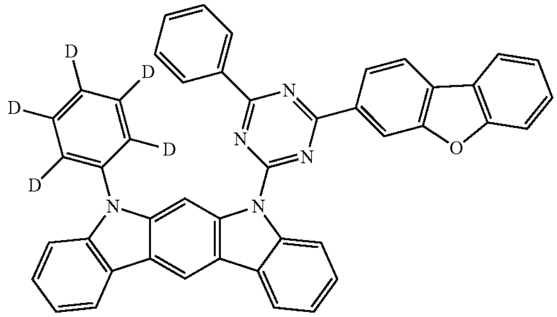
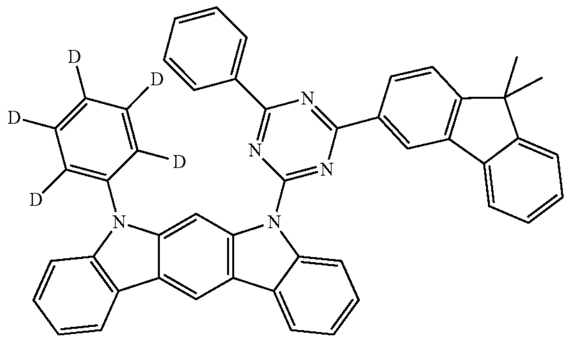
-continued
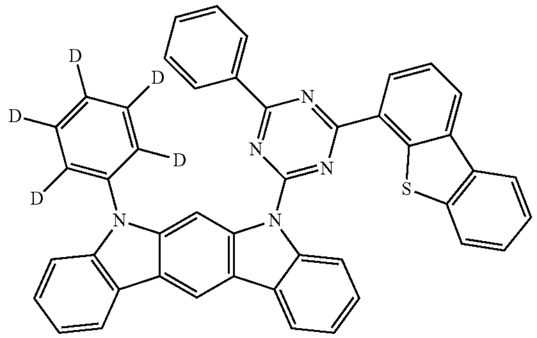
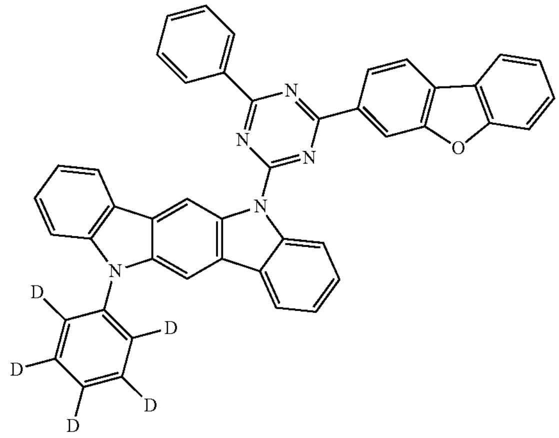
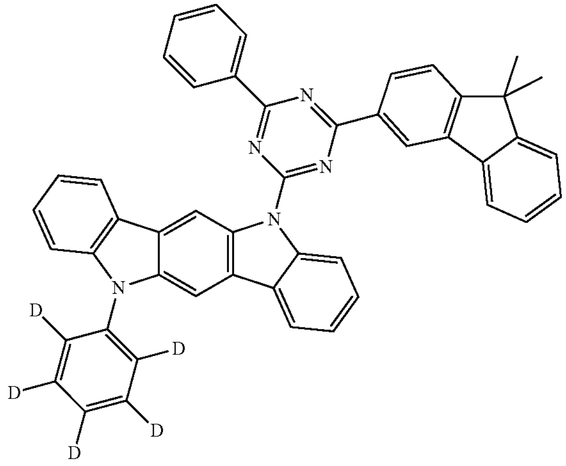
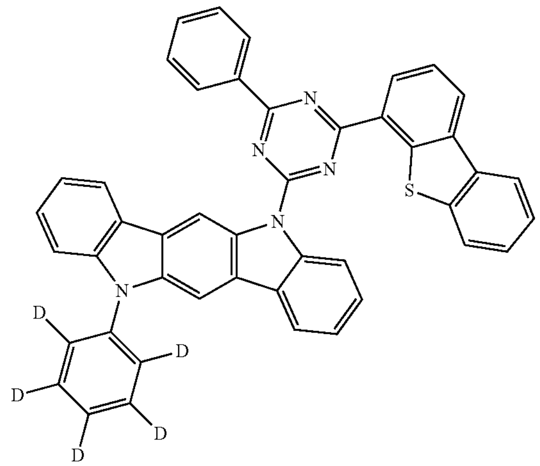

-continued
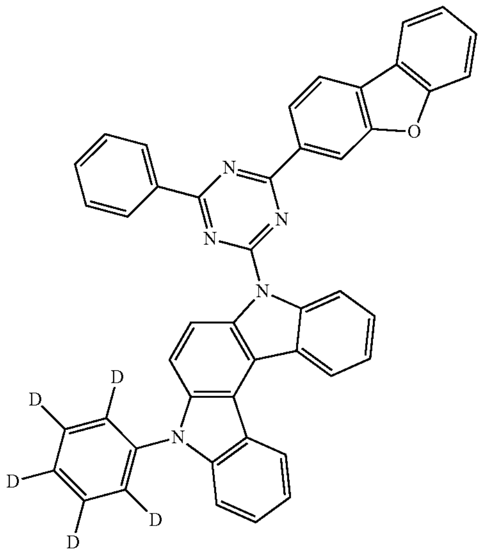
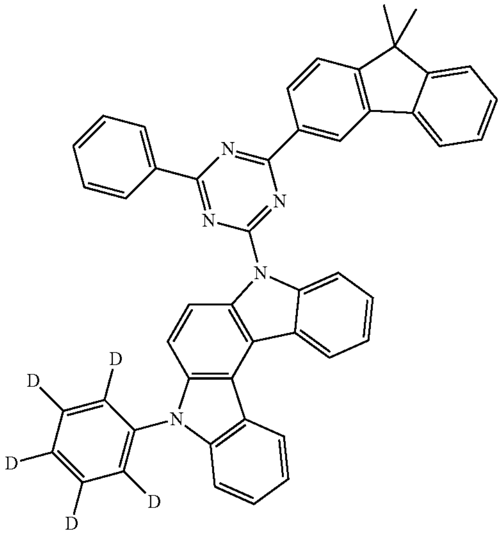
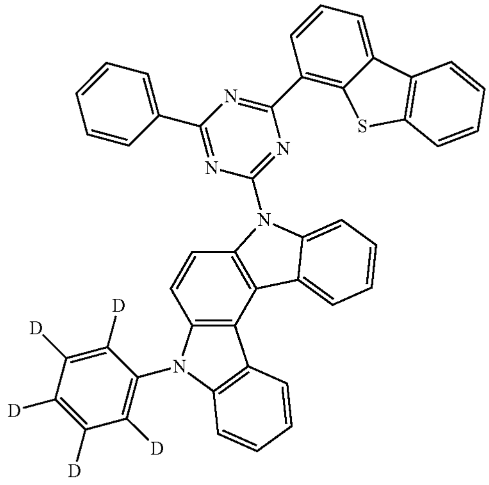
-continued
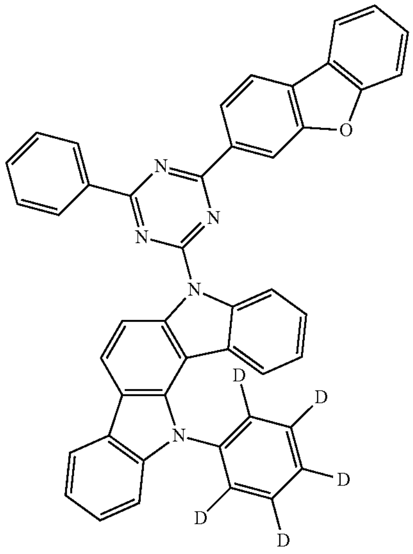
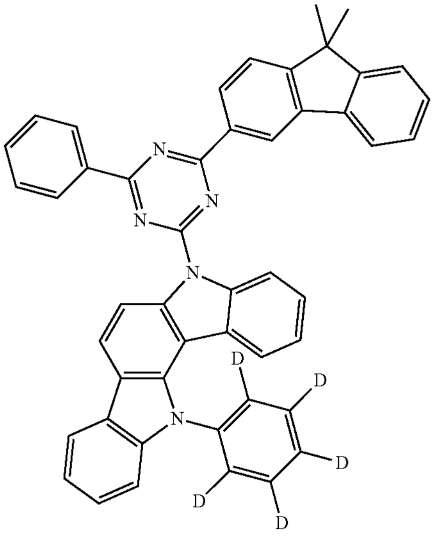
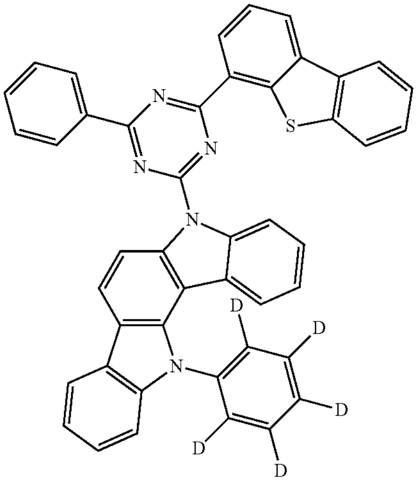

-continued
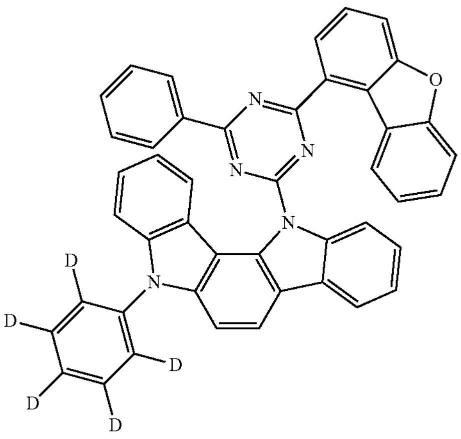
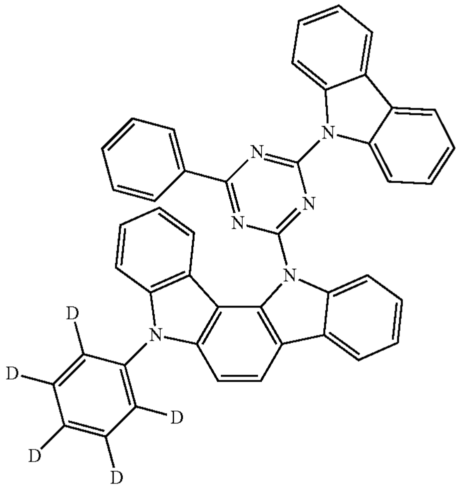
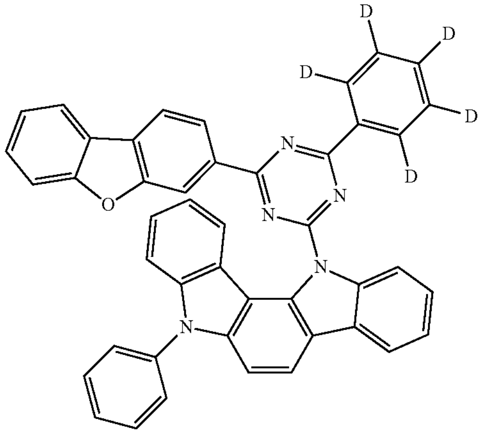
-continued
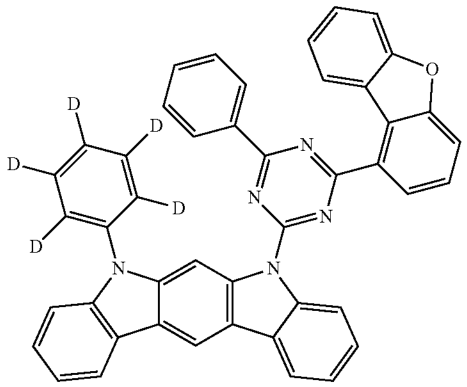
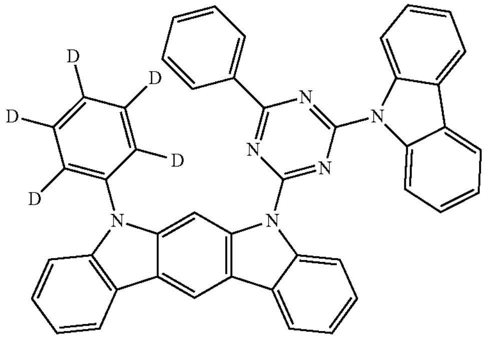
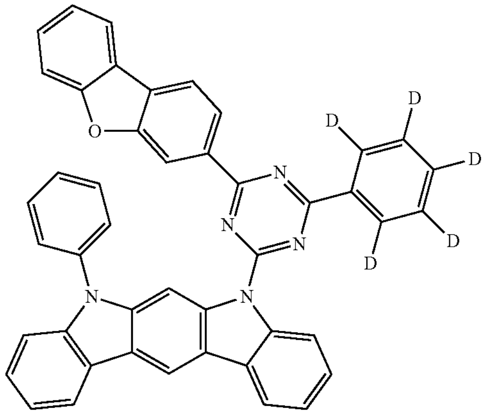
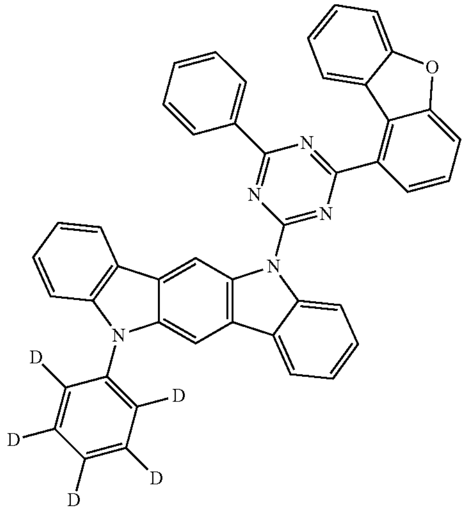

-continued
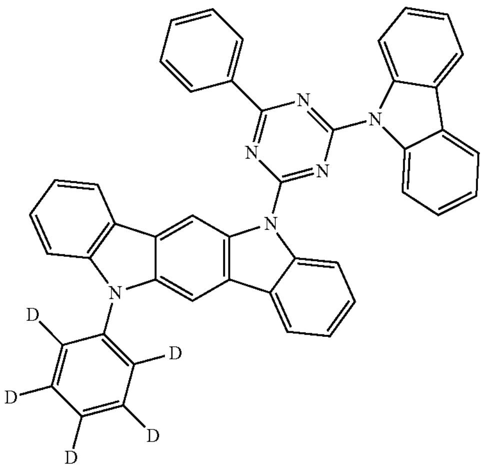
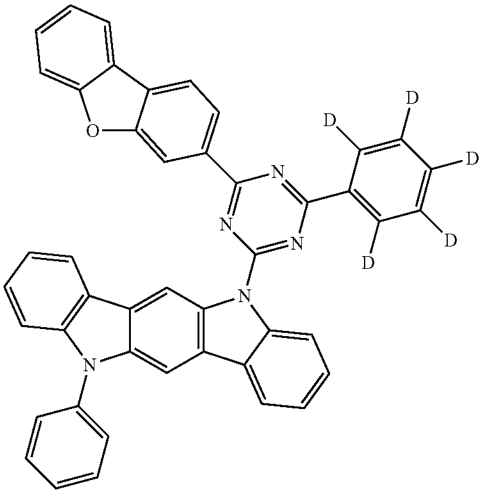
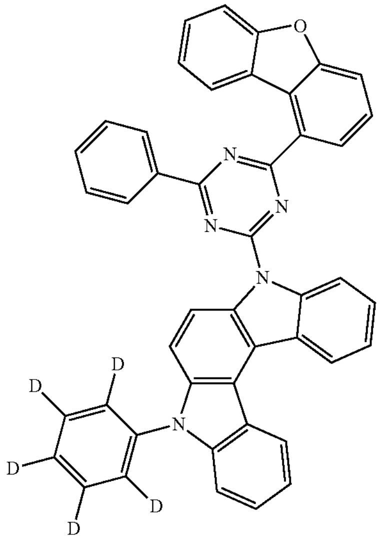
-continued
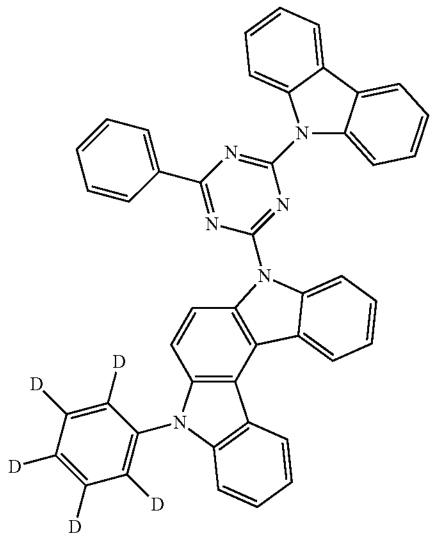
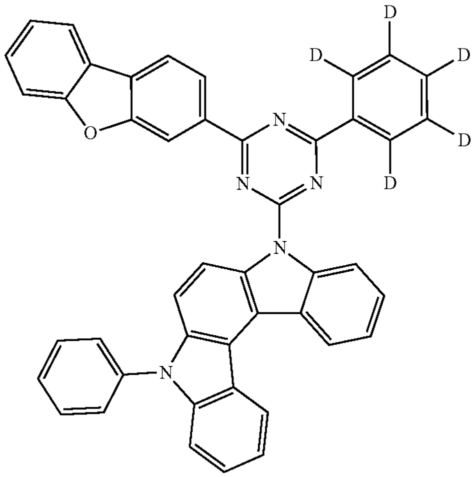
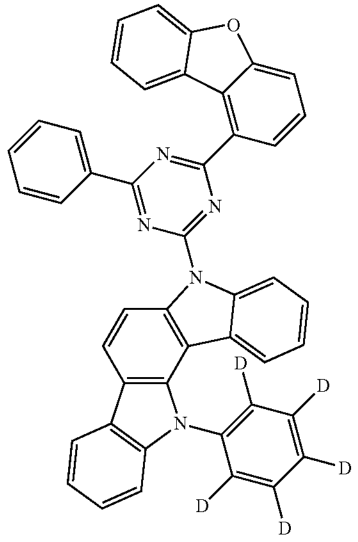

-continued
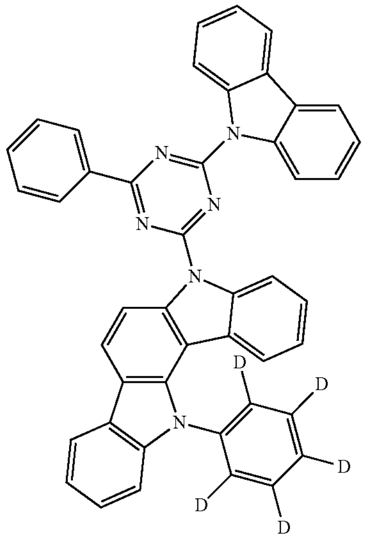
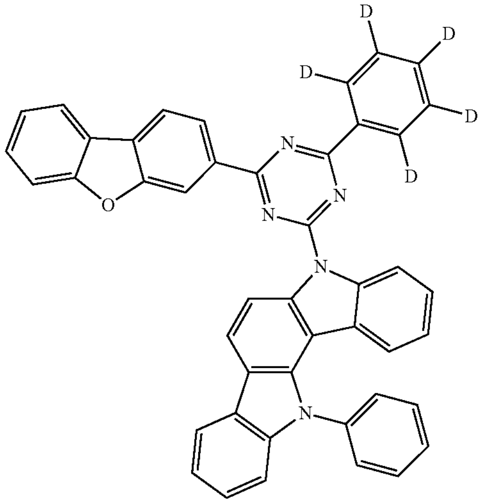 [SMILES: [2H]c1c([2H])c([2H])c(-c2nc(-c3ccc4c(c3)oc3ccccc34)nc(-n3c4ccccc4c4c3ccc3c5ccccc5n(-c5ccccc5)c34)n2)c([2H])c1[2H]]
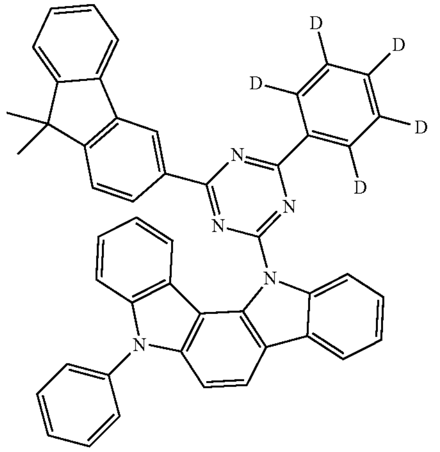
-continued
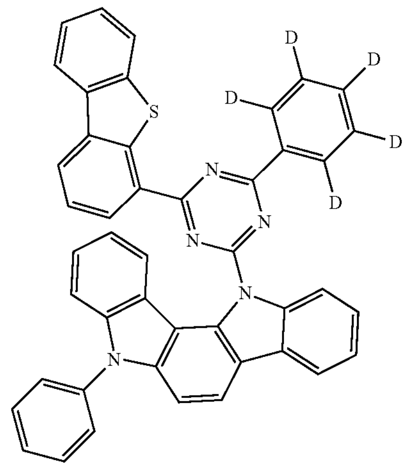
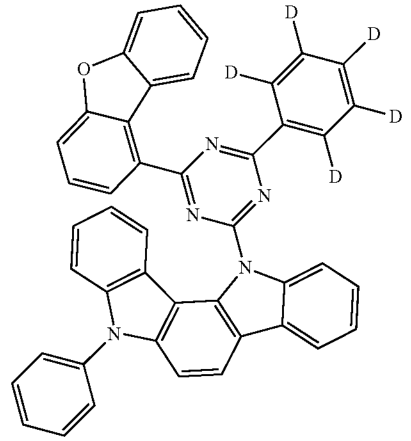
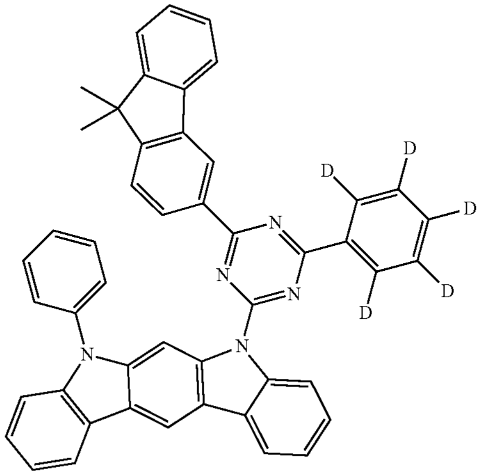

-continued
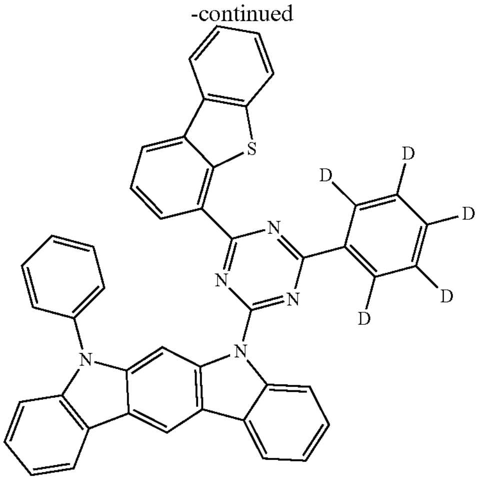
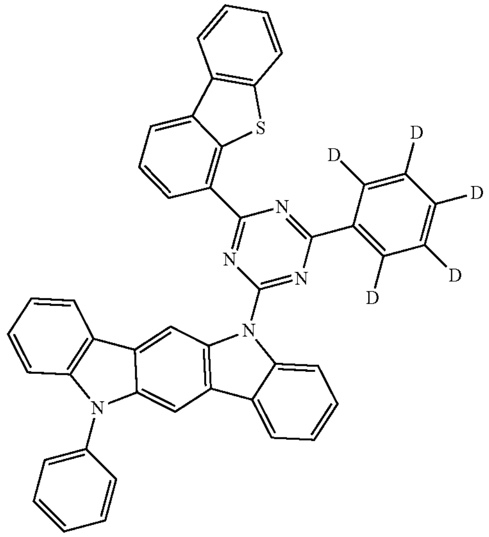
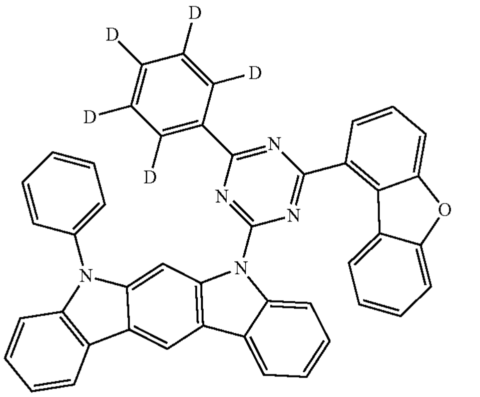
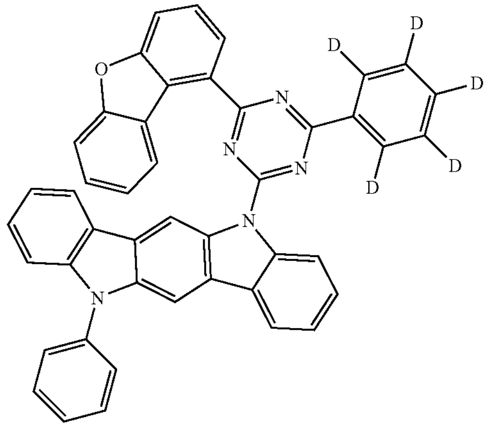
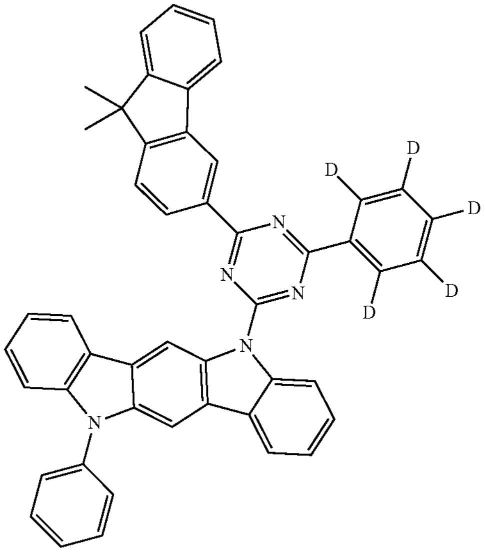
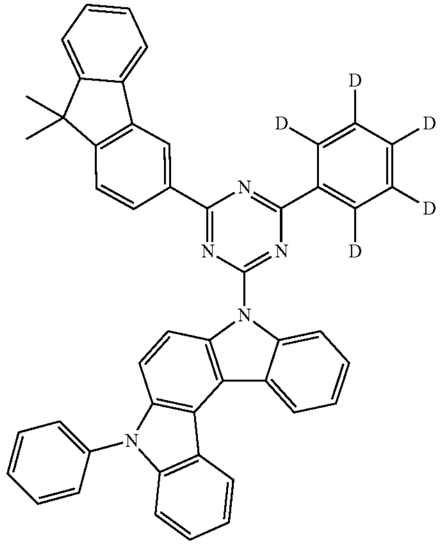
-continued -continued
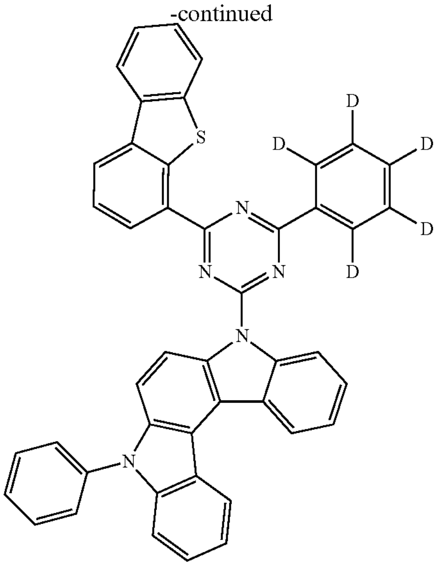
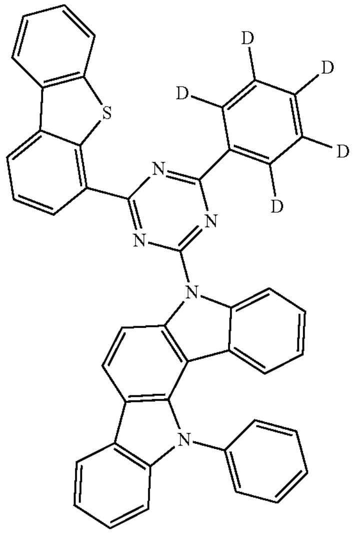
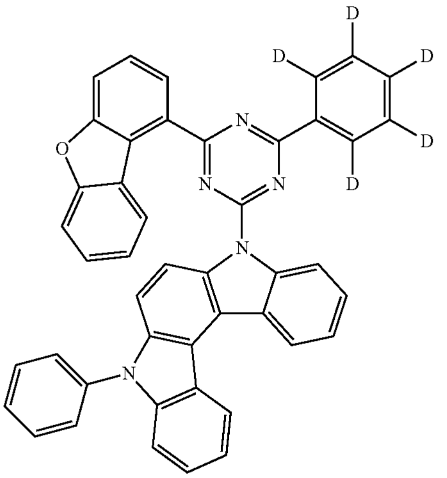
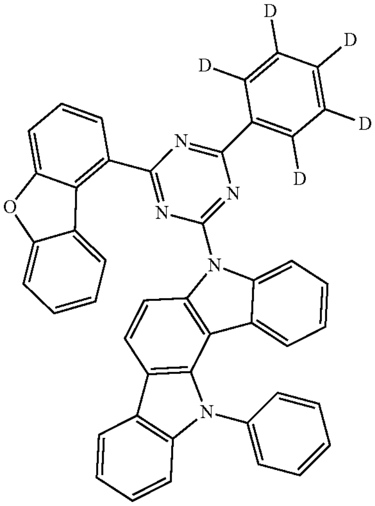
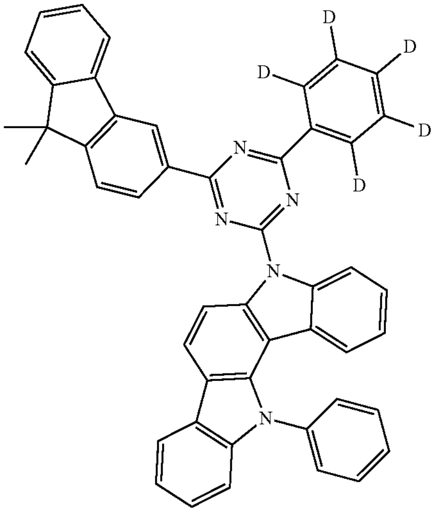
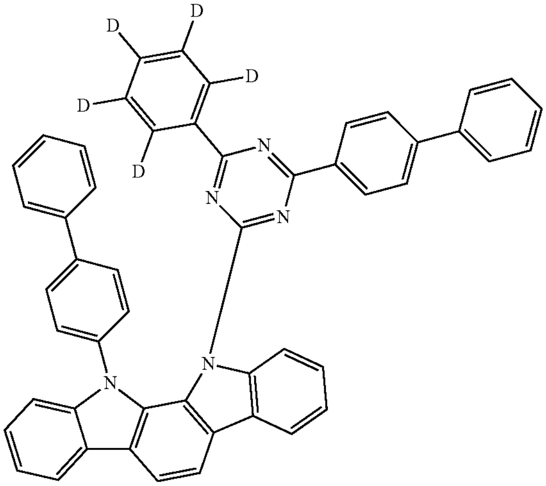
-continued -continued
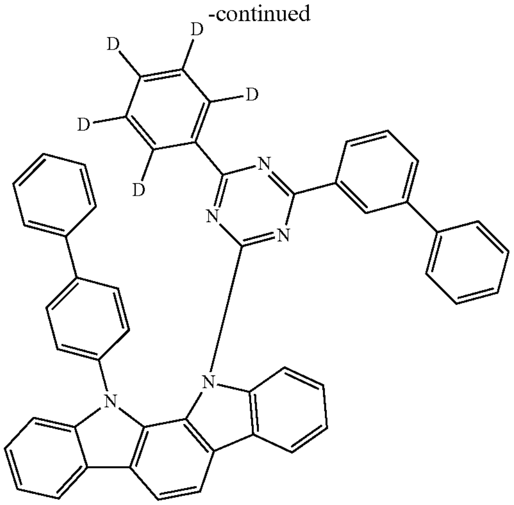
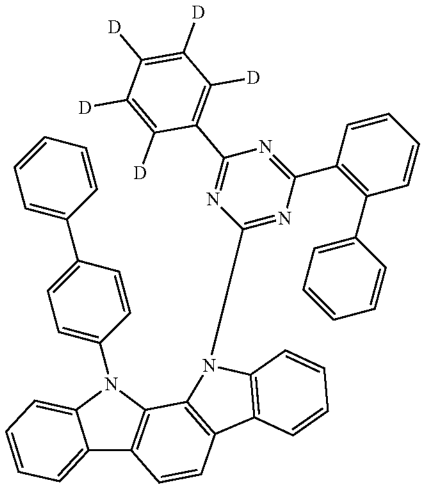
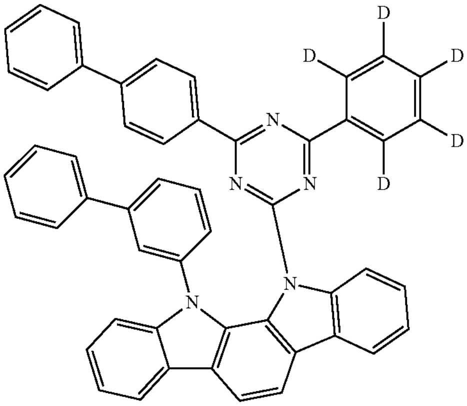
-continued
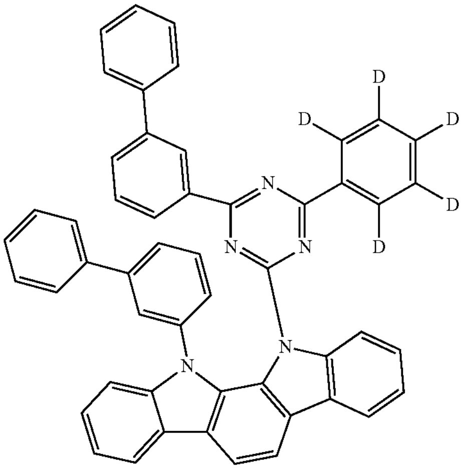
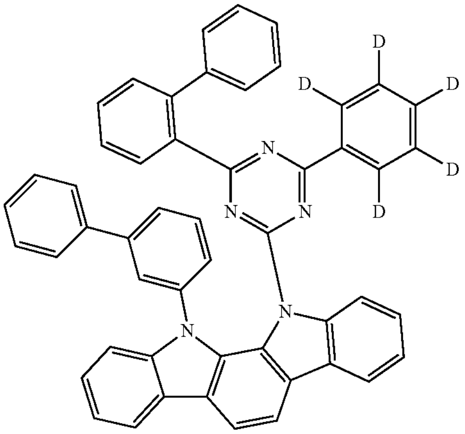
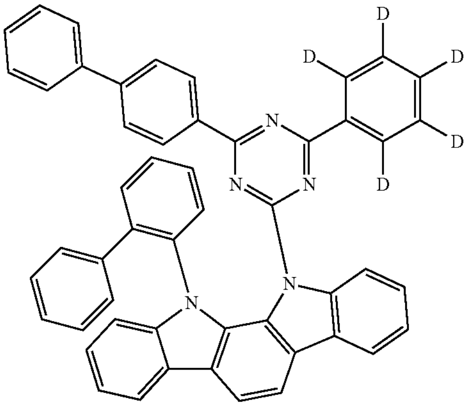

-continued
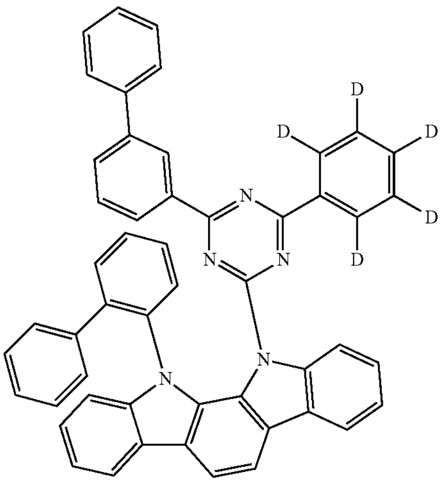
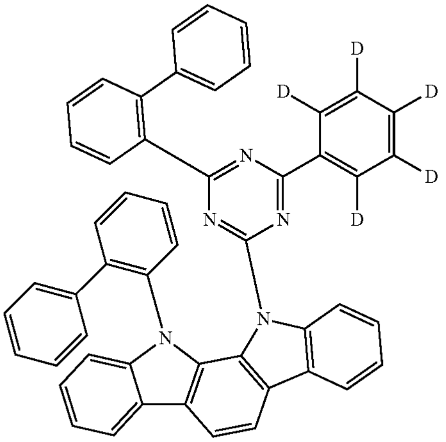
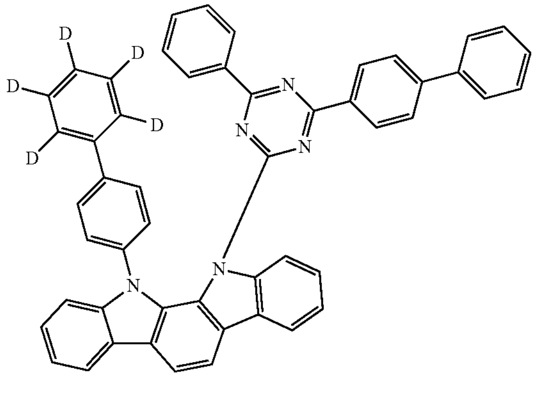
-continued
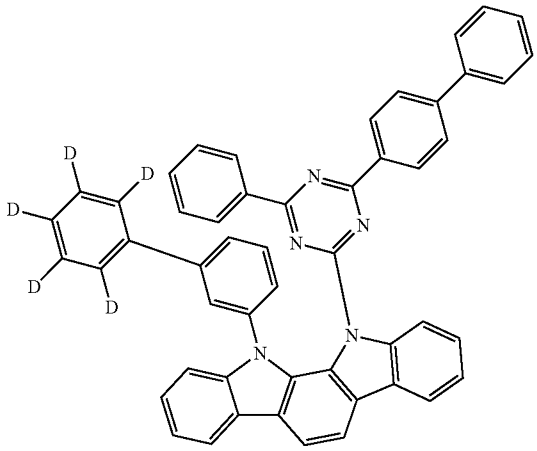
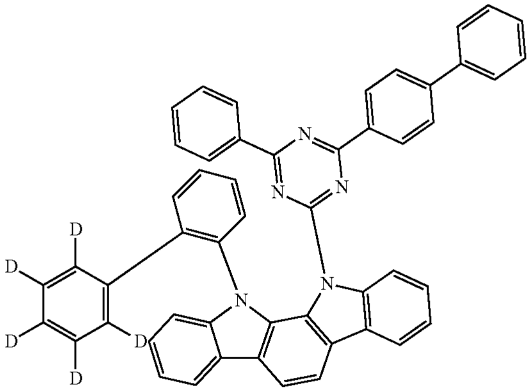
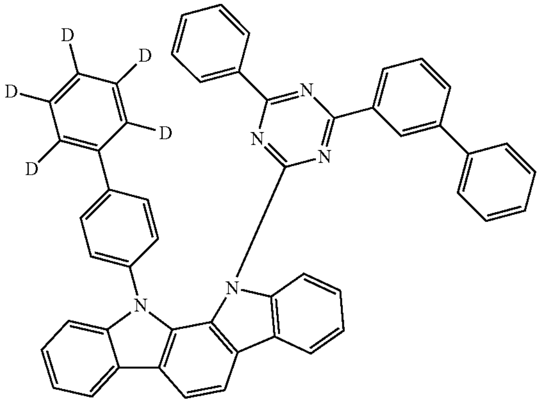
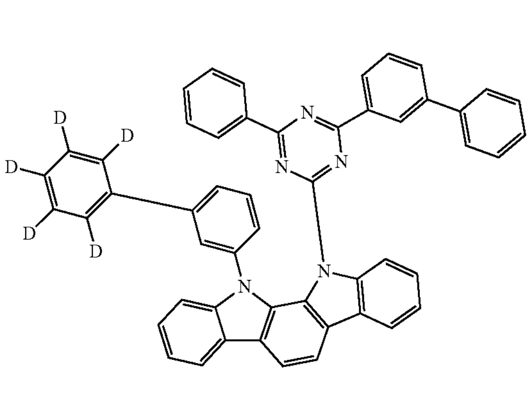

-continued
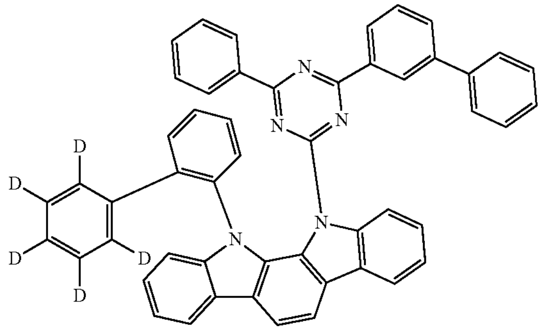
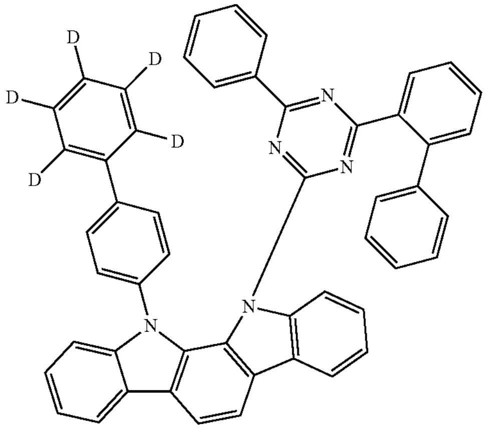
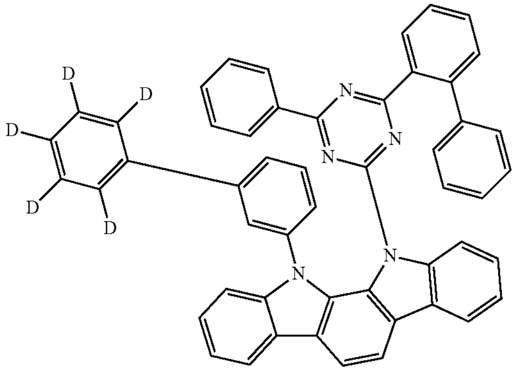
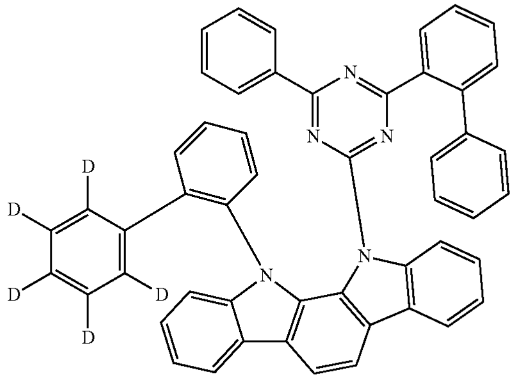
-continued
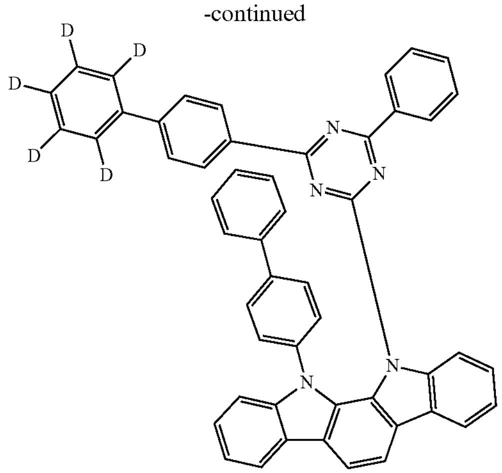
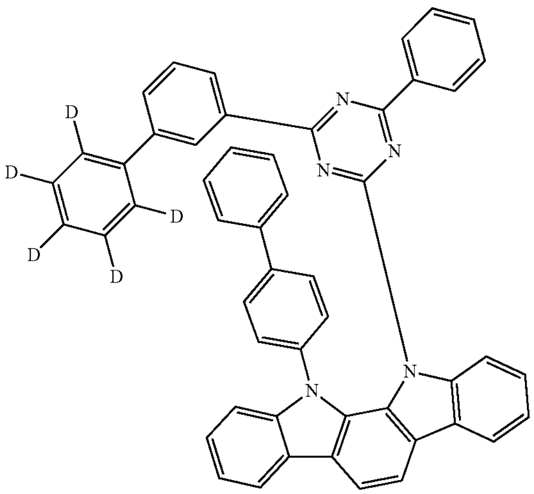
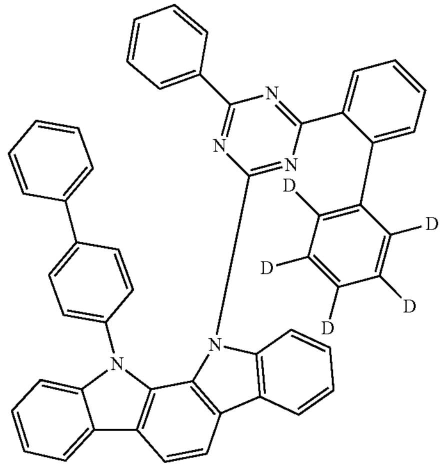

-continued
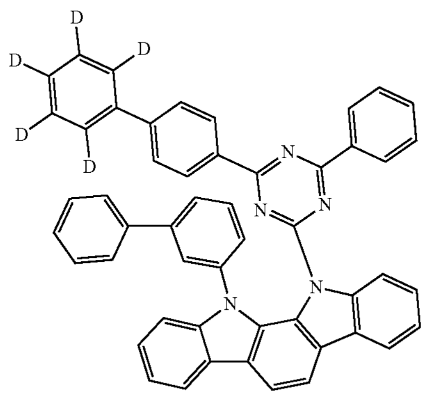
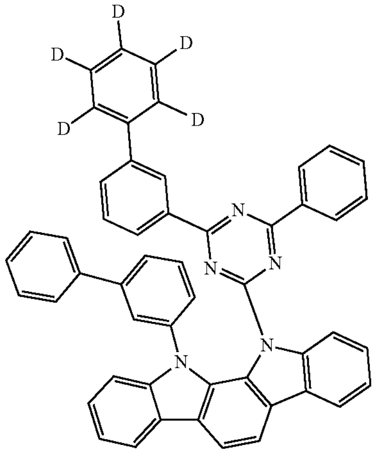
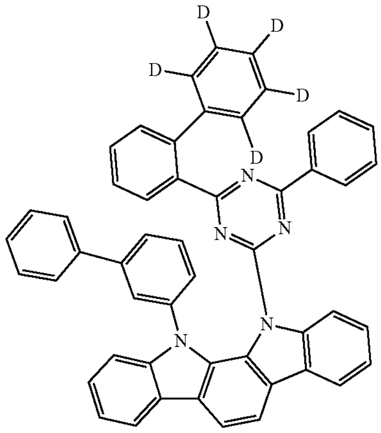
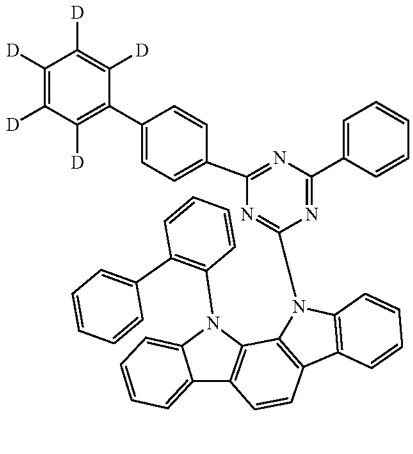
-continued
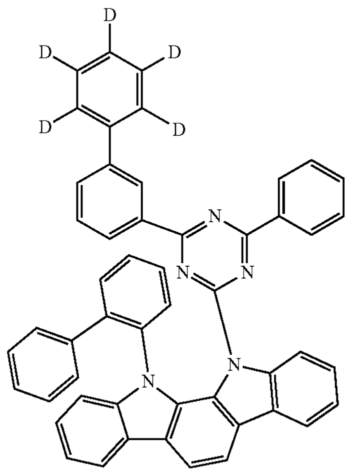
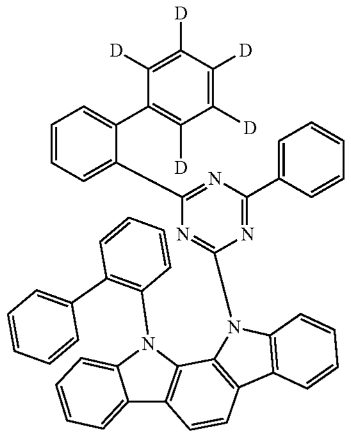
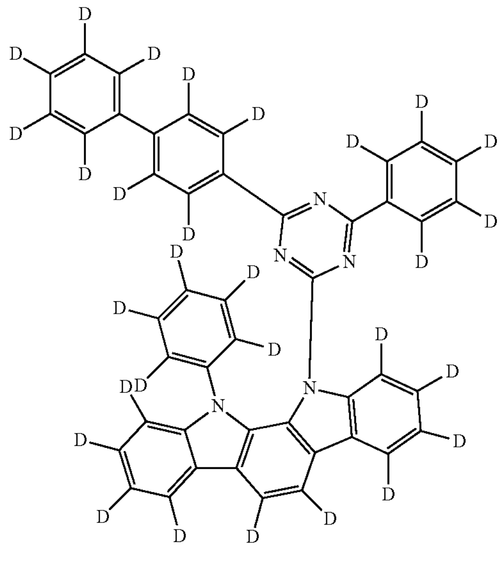

-continued
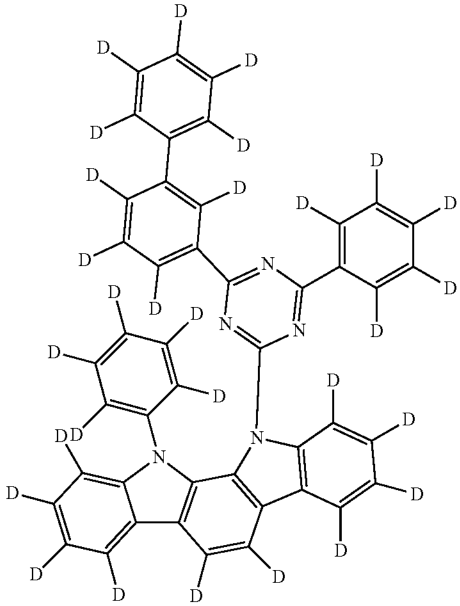
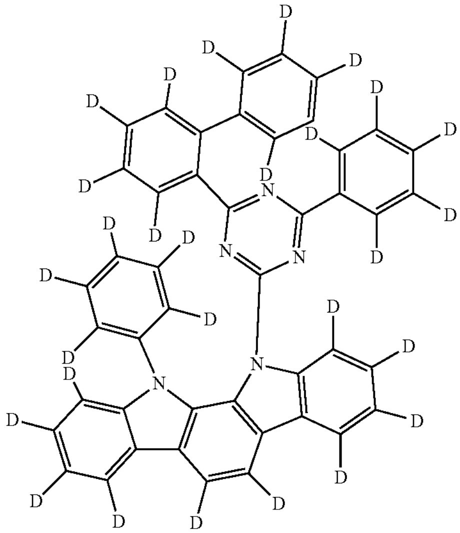
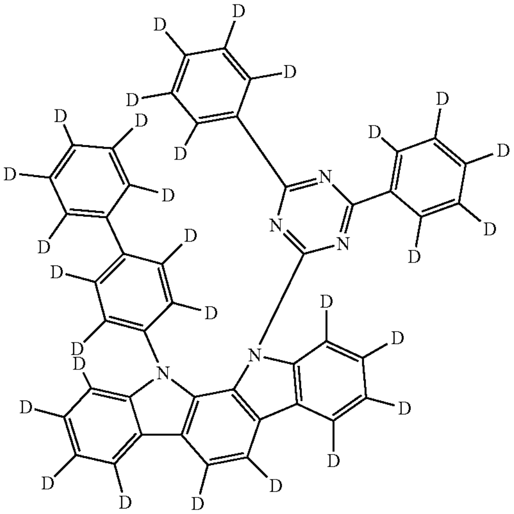
-continued
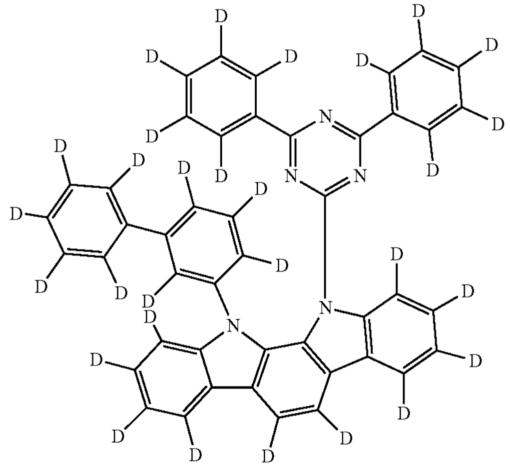
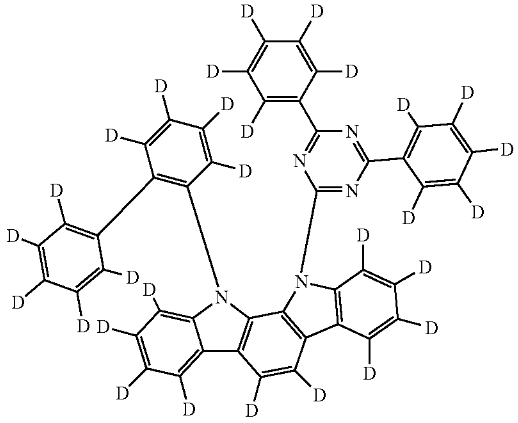
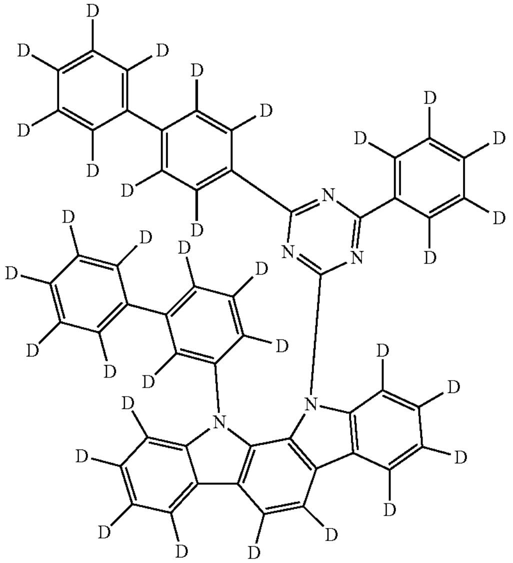

-continued
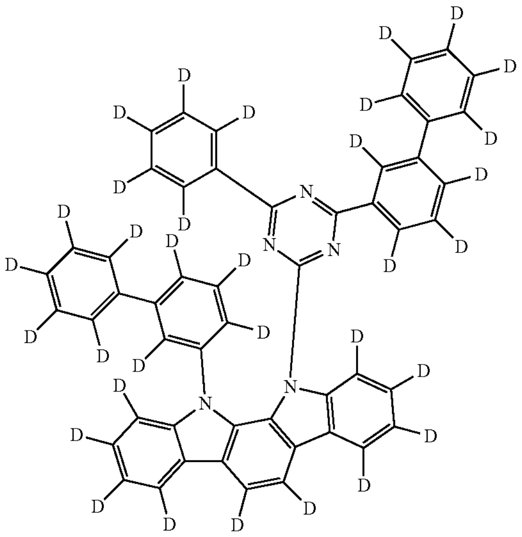
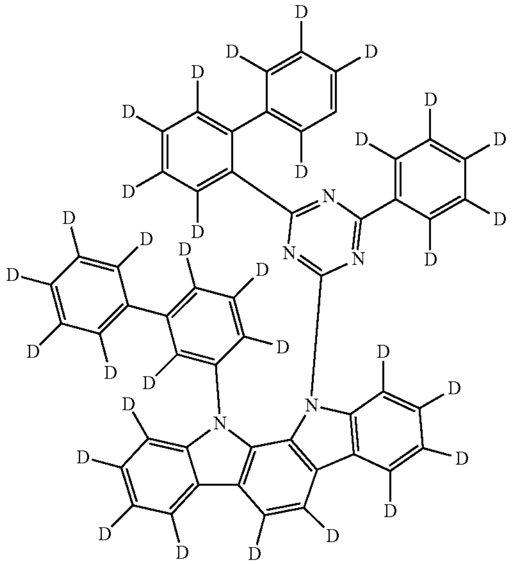
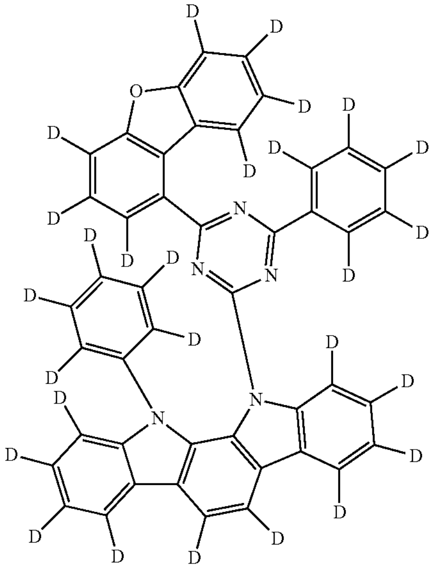
-continued
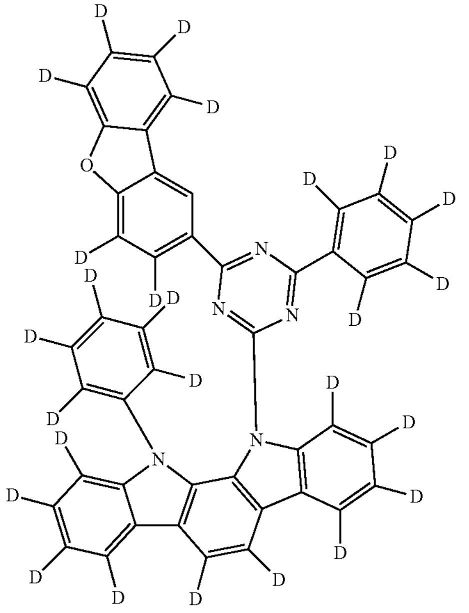
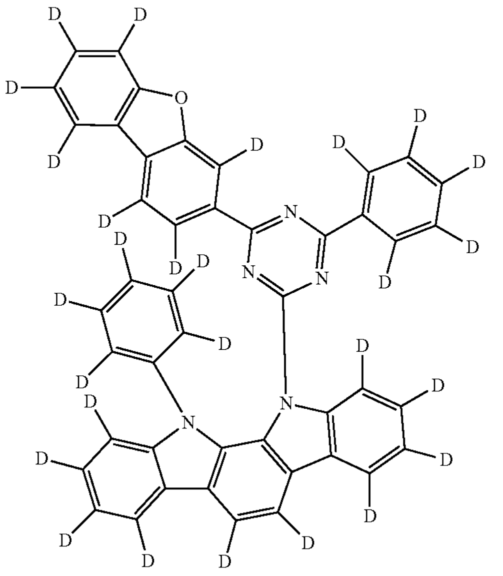

-continued
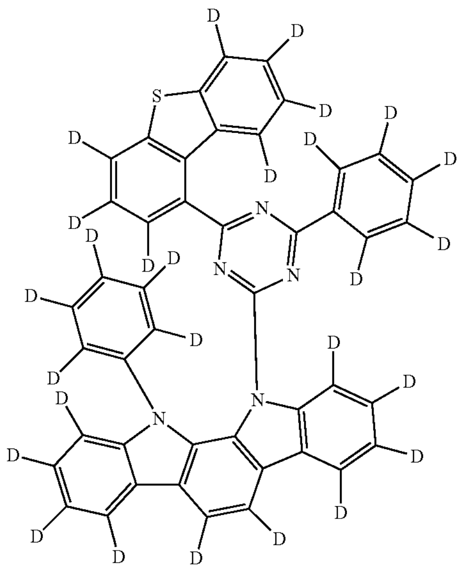
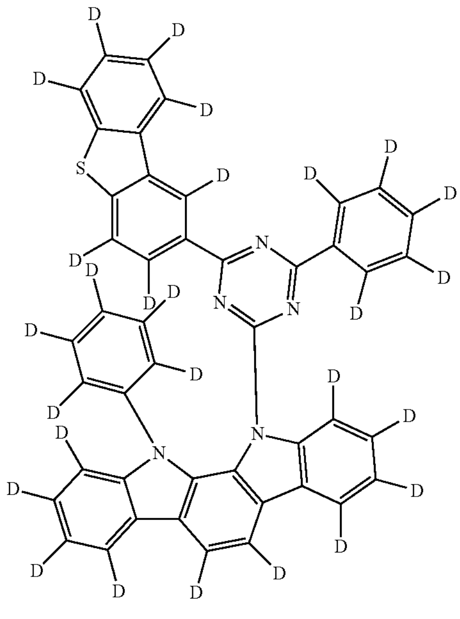
-continued
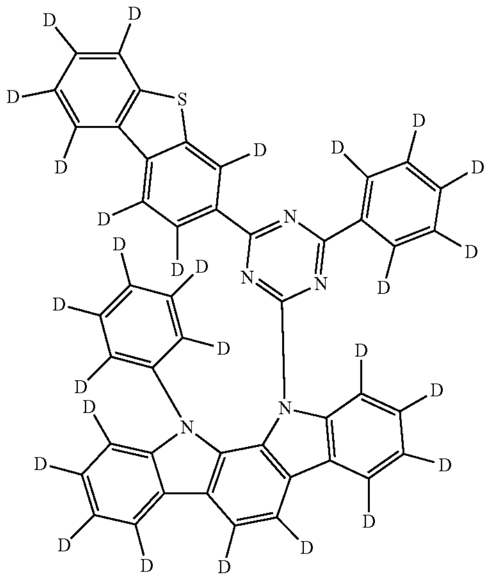
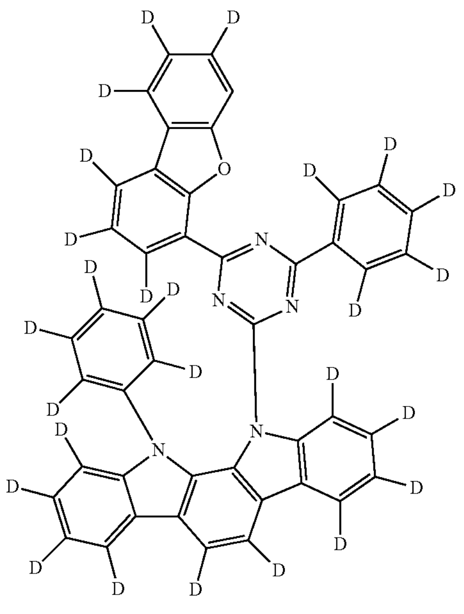

-continued
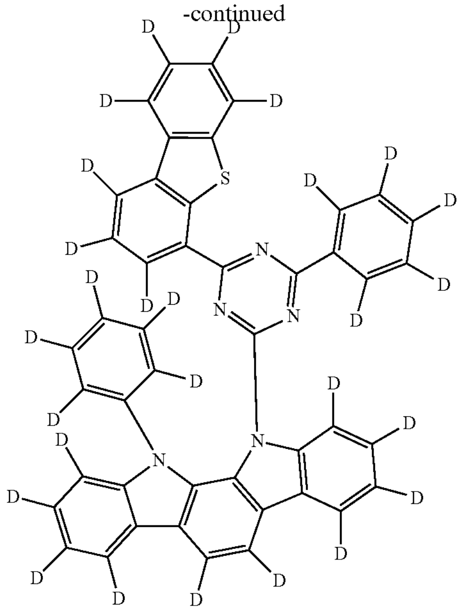
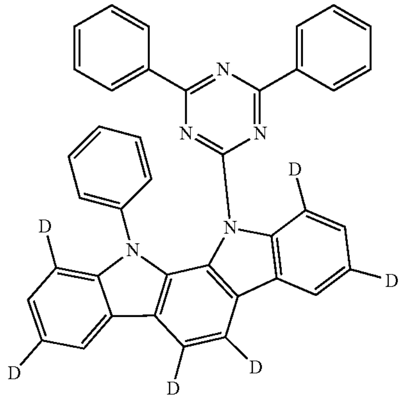
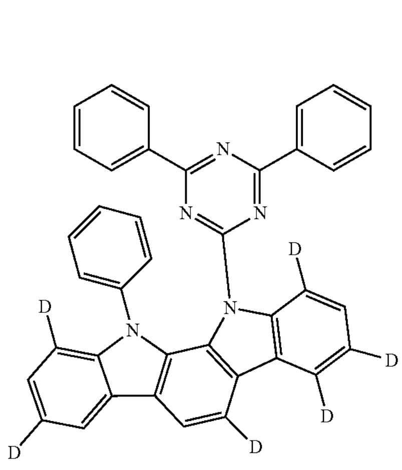
-continued
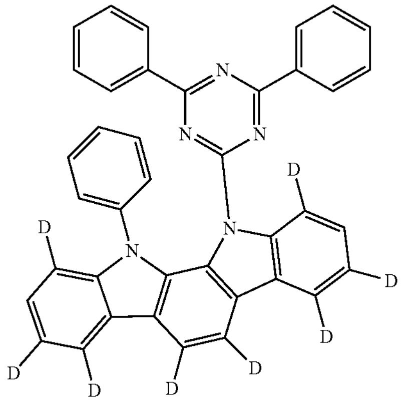
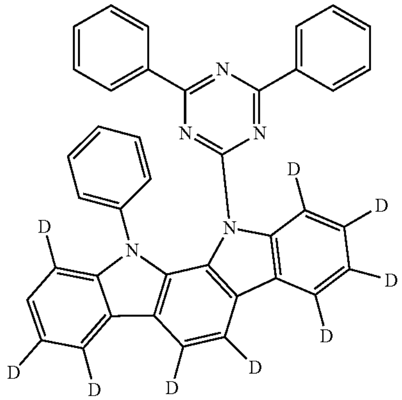
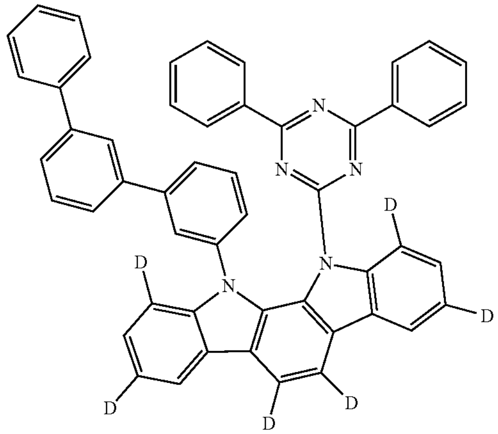
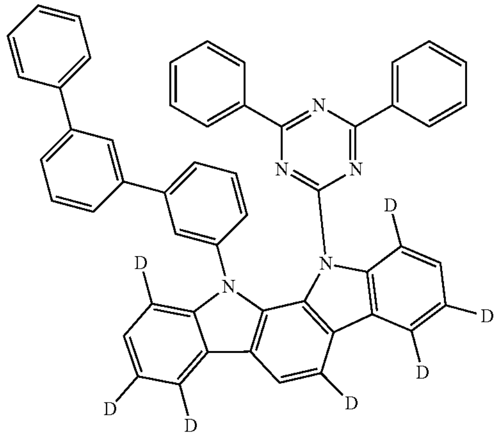

-continued
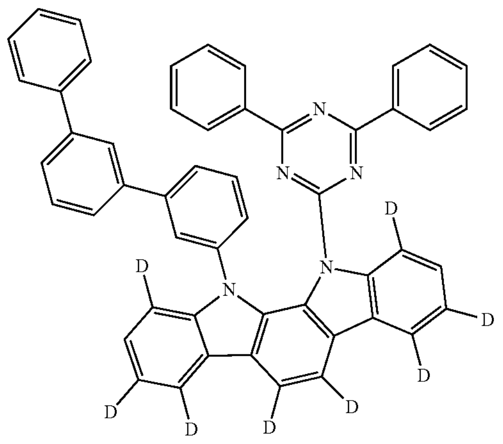
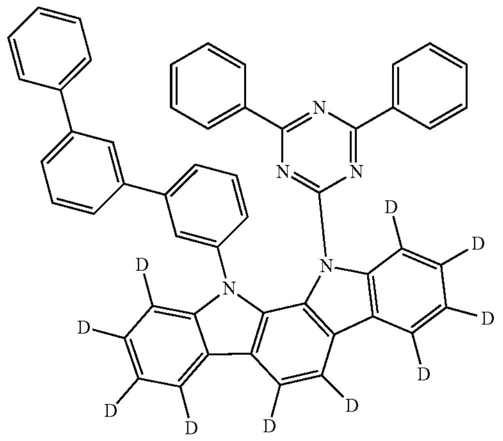
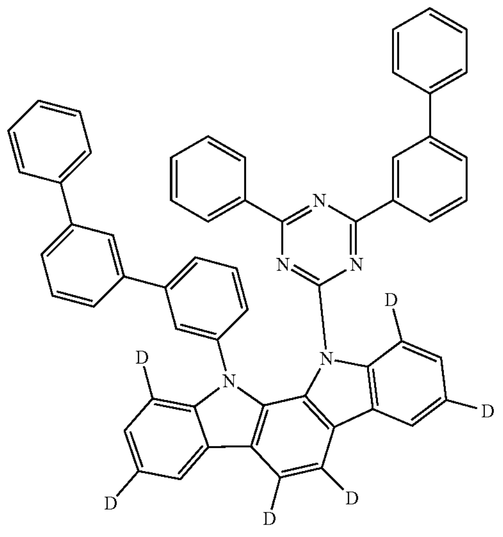
-continued
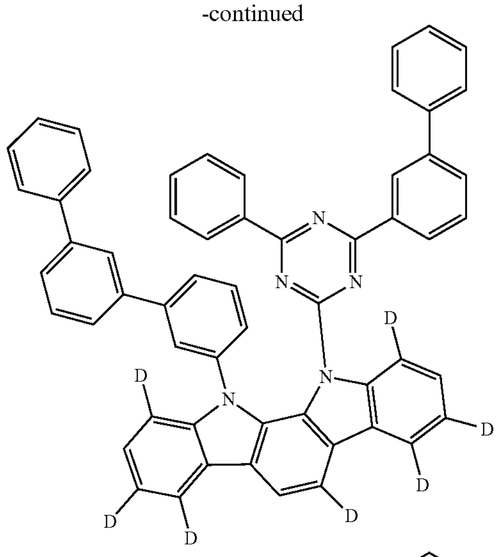
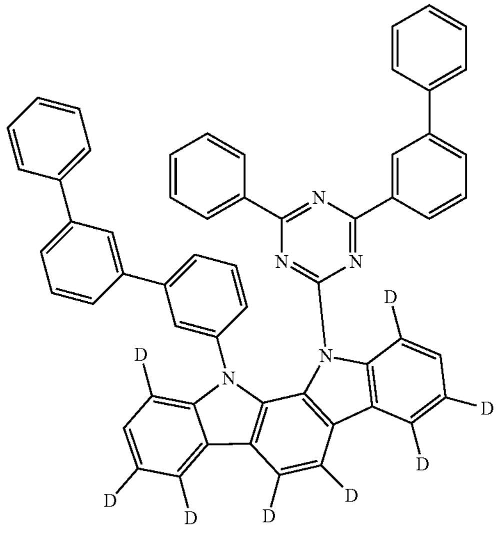
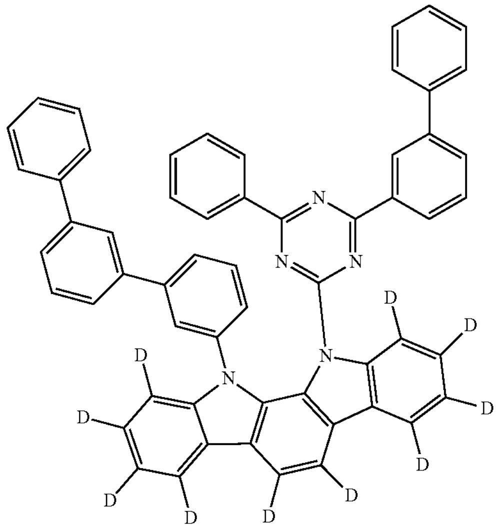

-continued
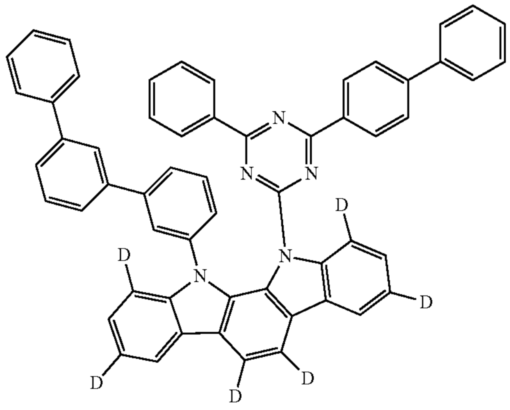
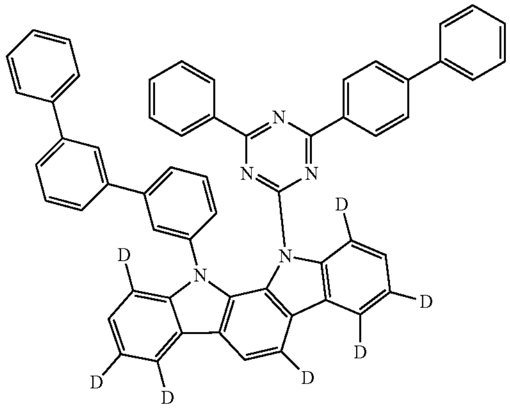
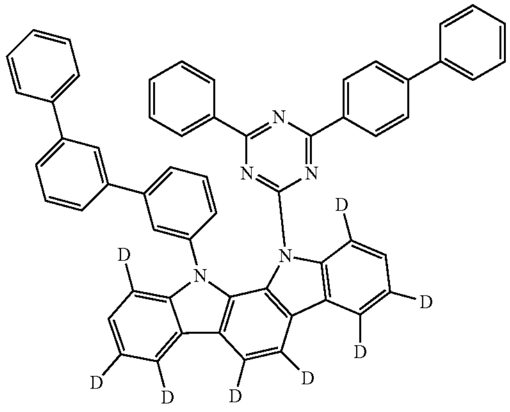
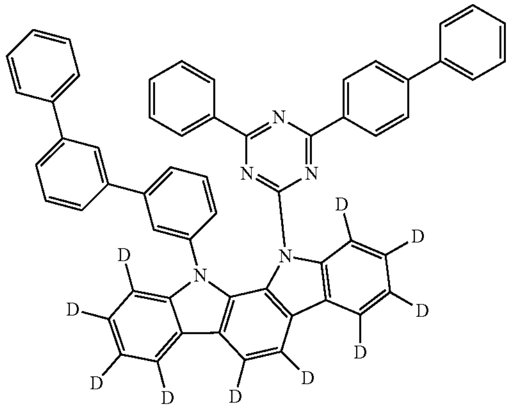
-continued
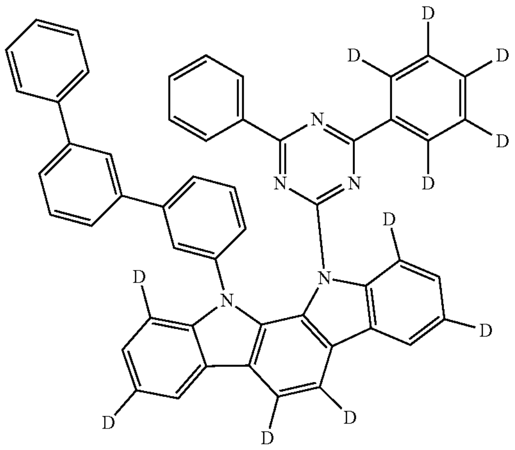
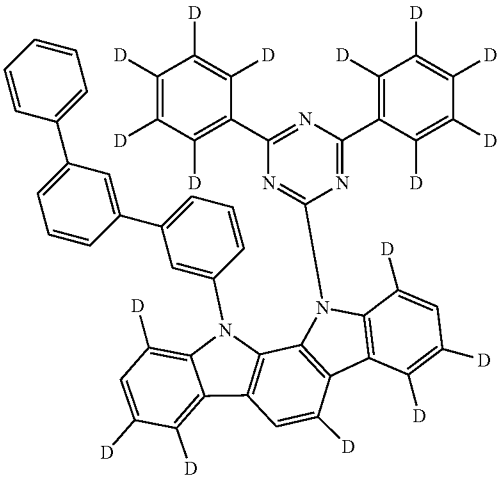
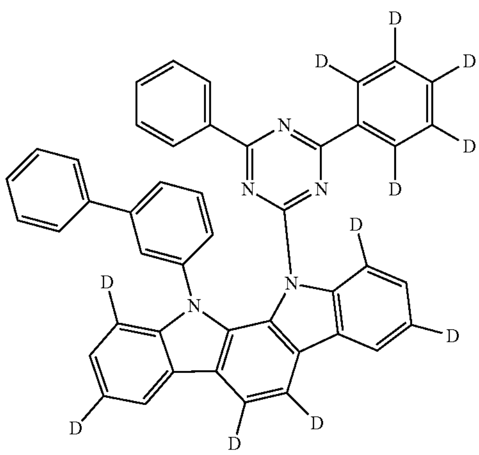

-continued
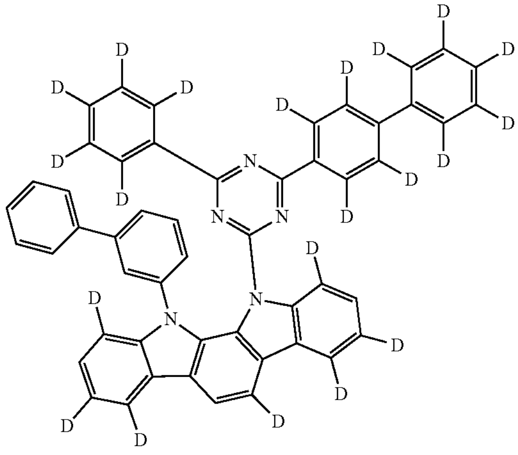
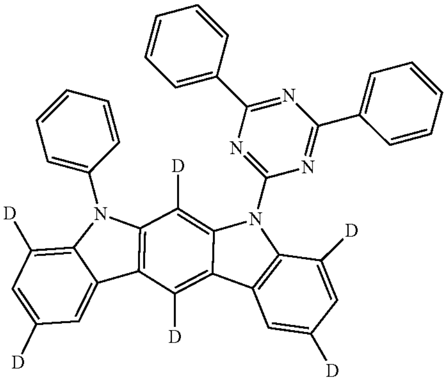
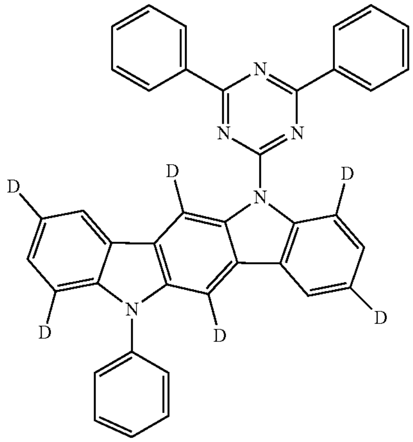
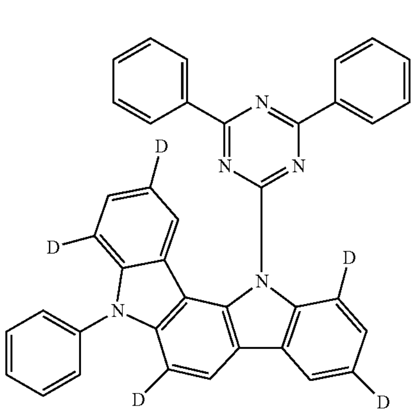
-continued
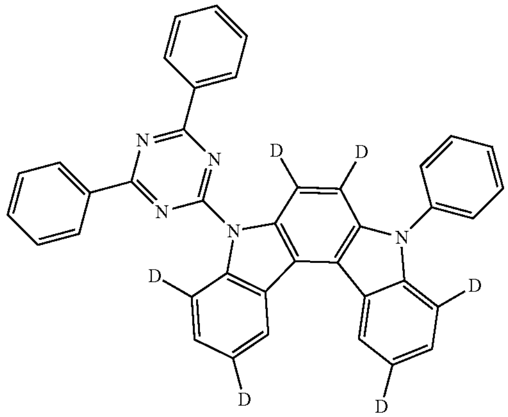
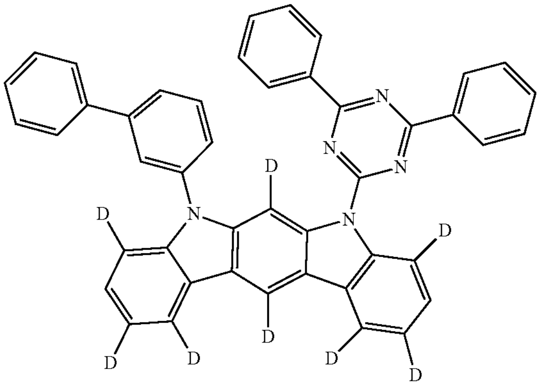
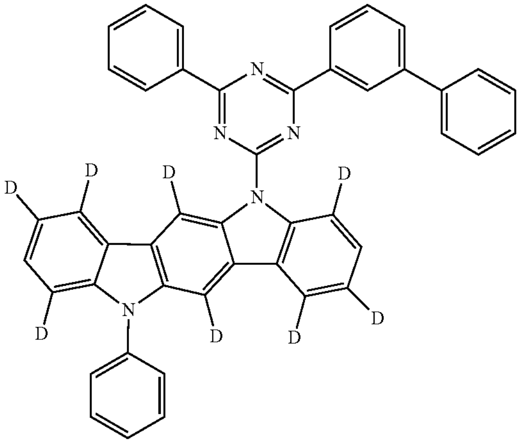
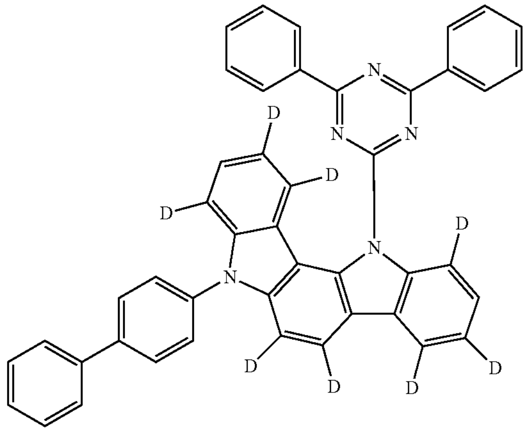

-continued
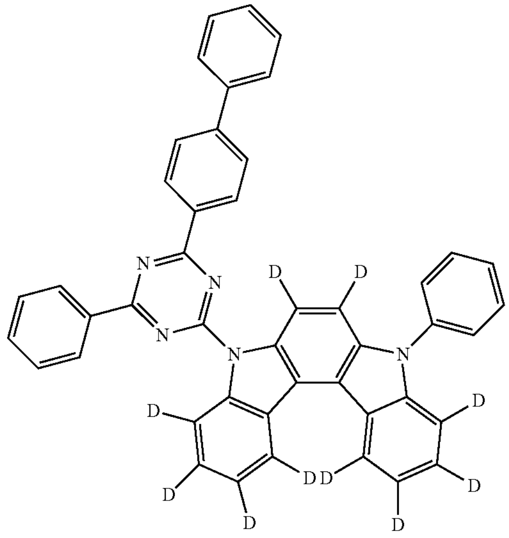
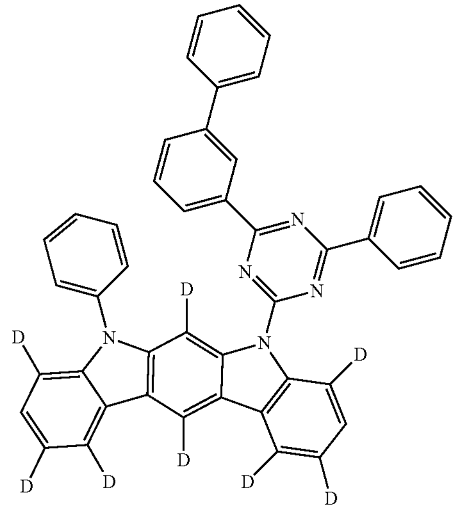
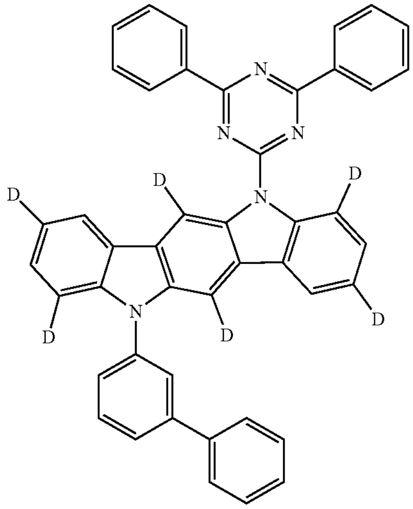
-continued
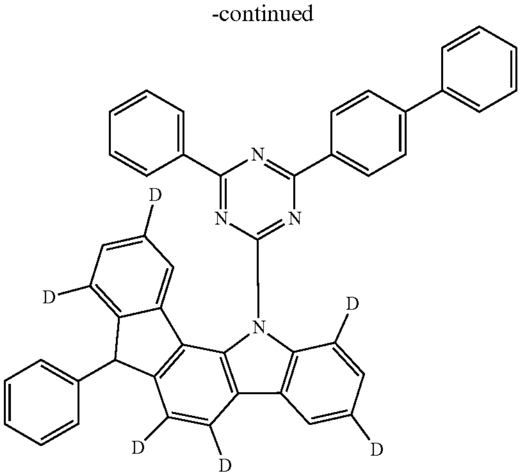
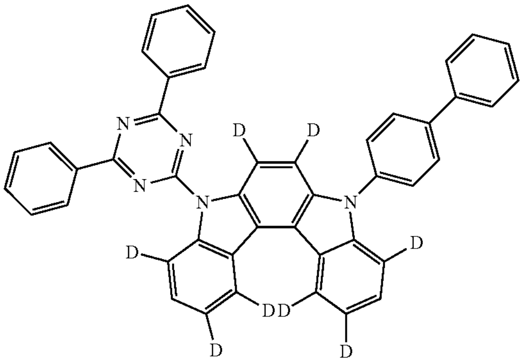
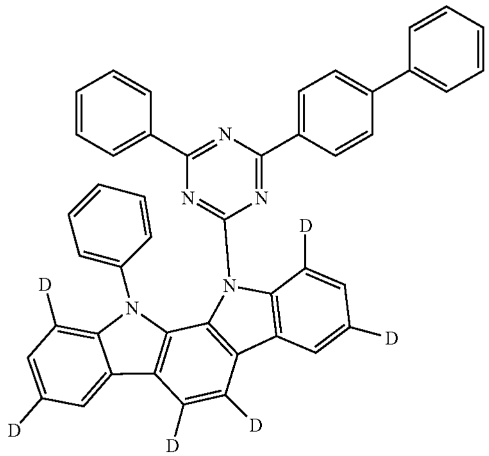
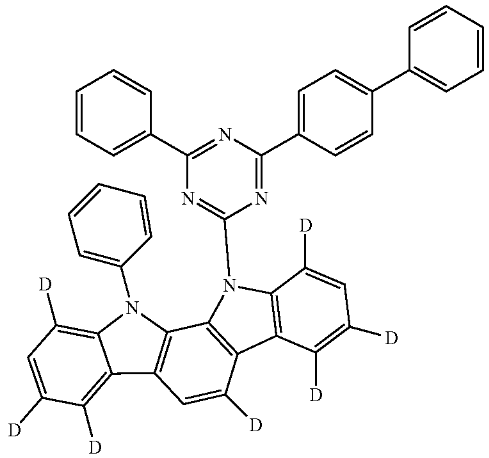

-continued
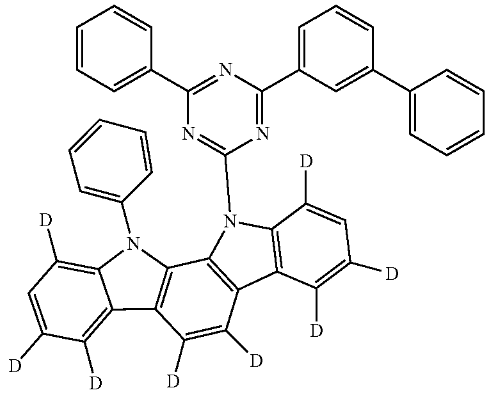
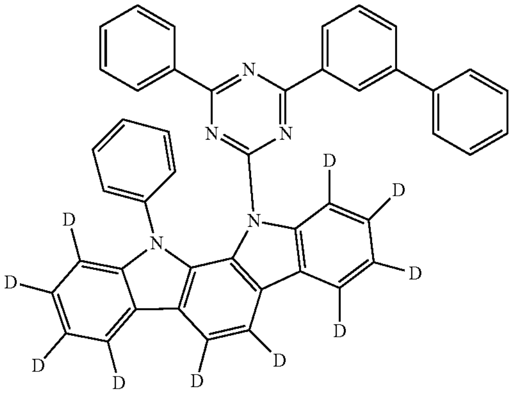
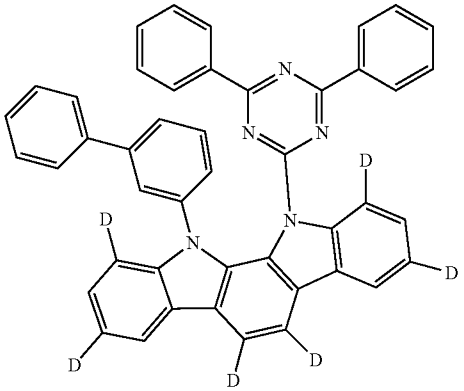
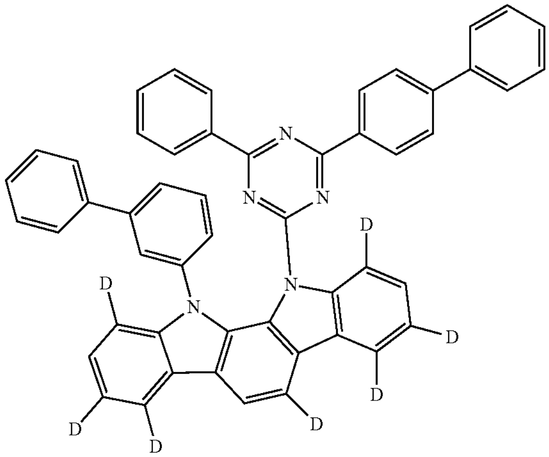
-continued
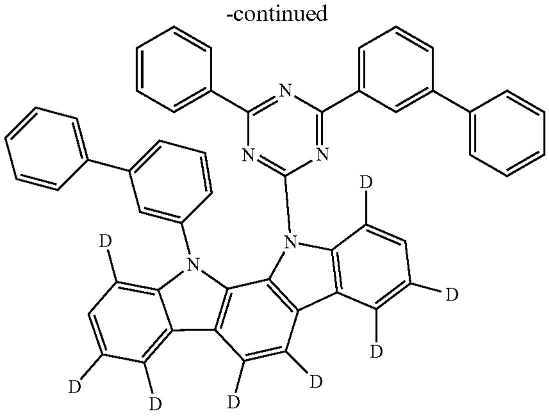
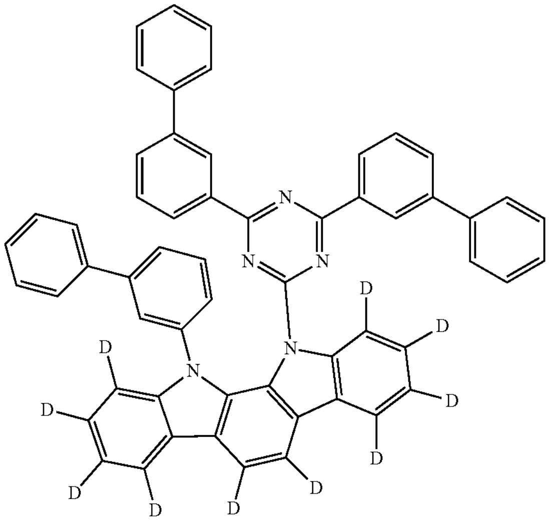
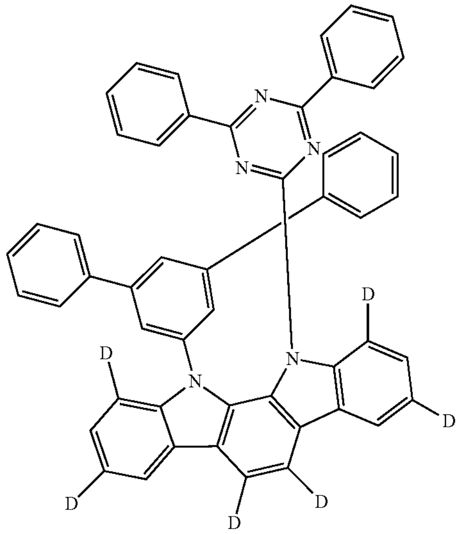

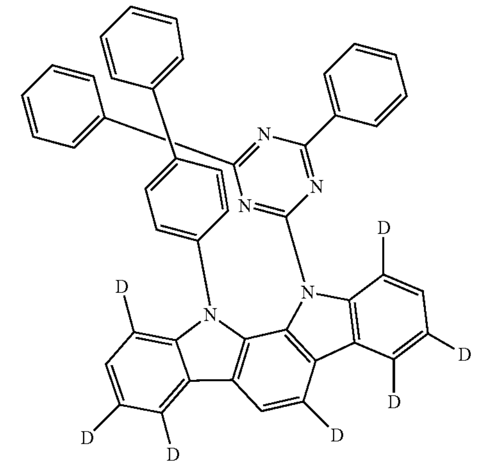
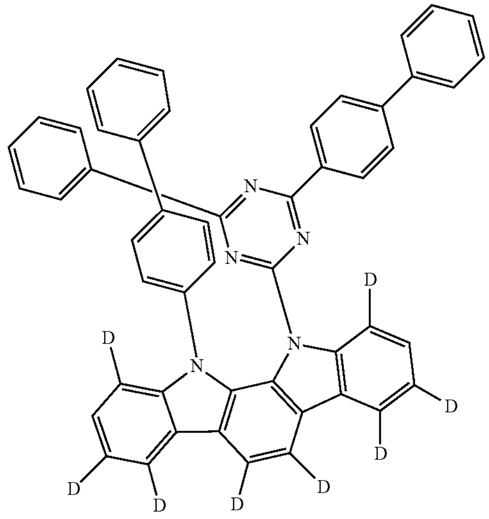
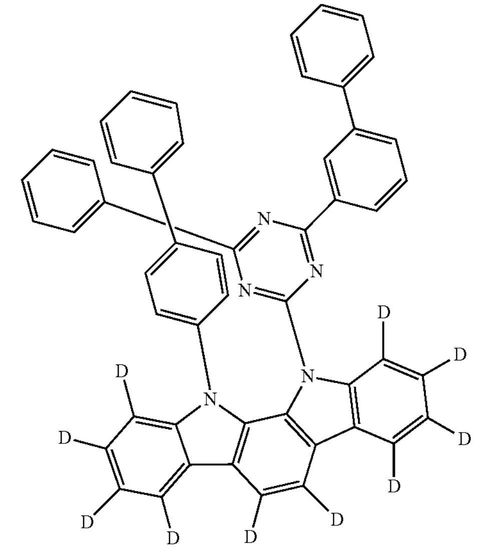
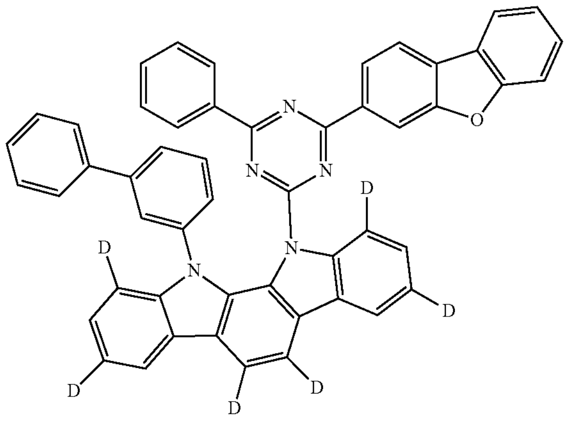
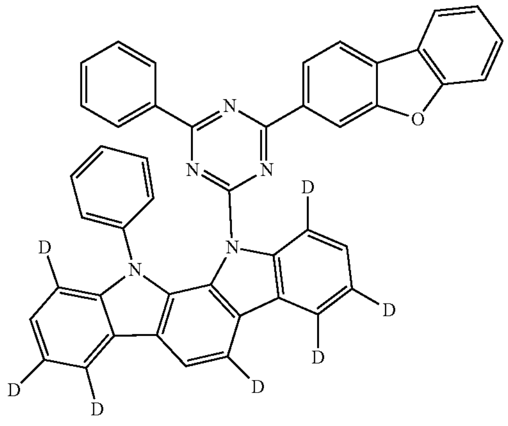
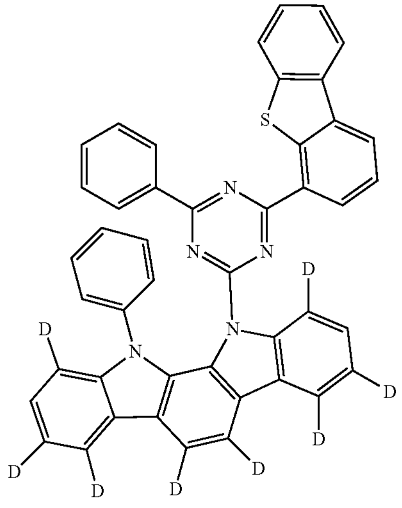

-continued
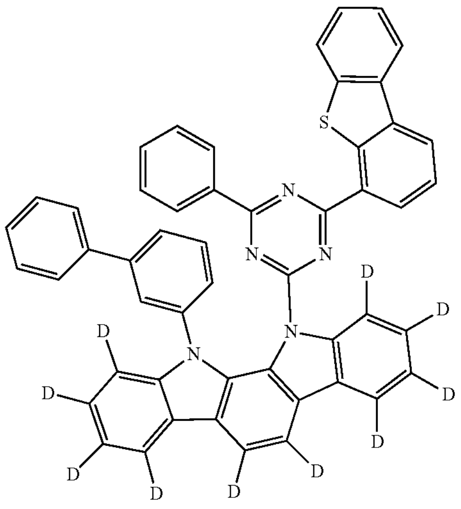
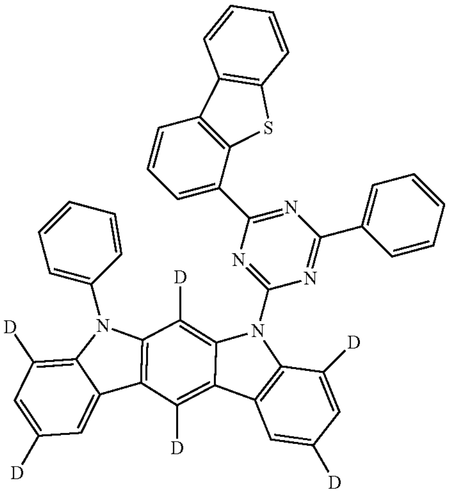
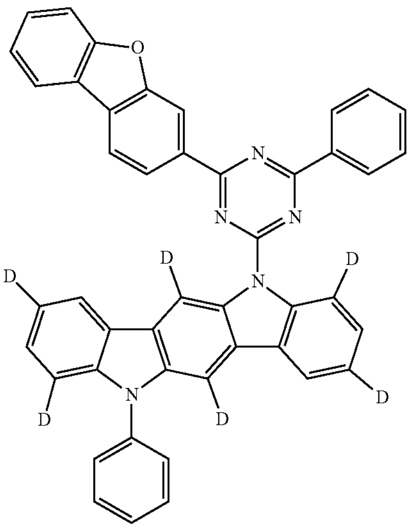
-continued
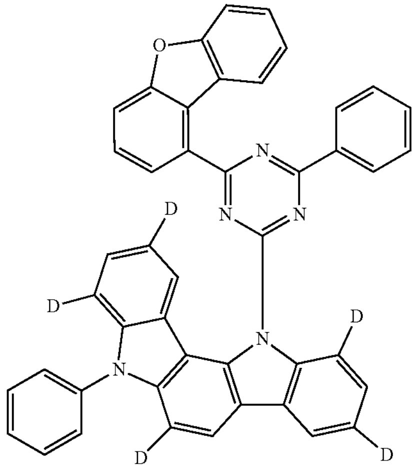
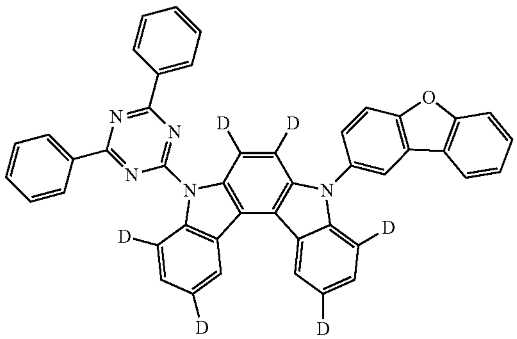
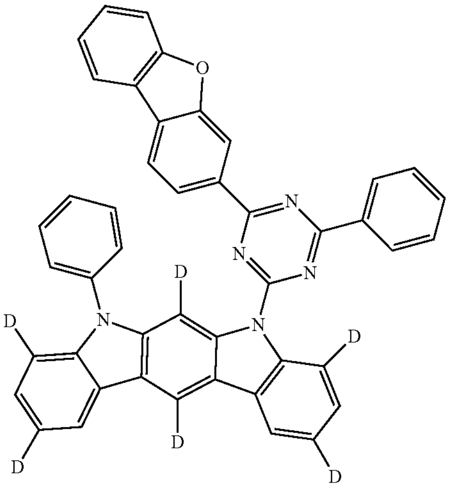

-continued
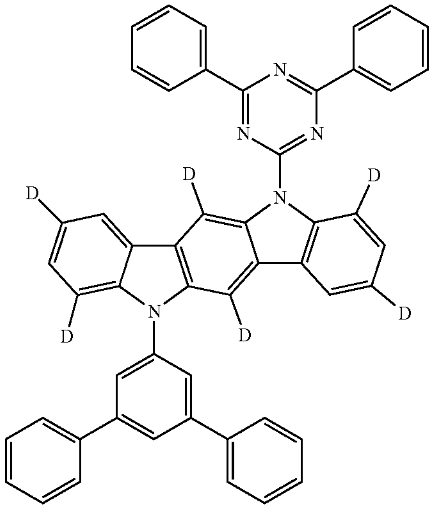
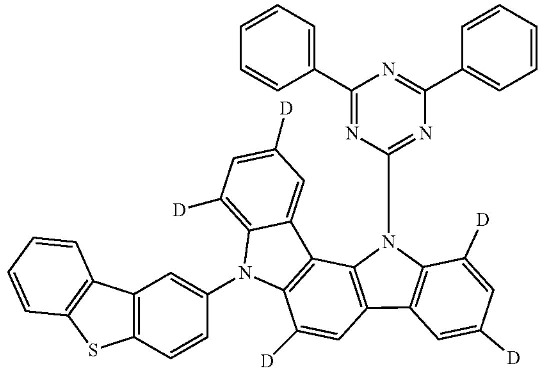
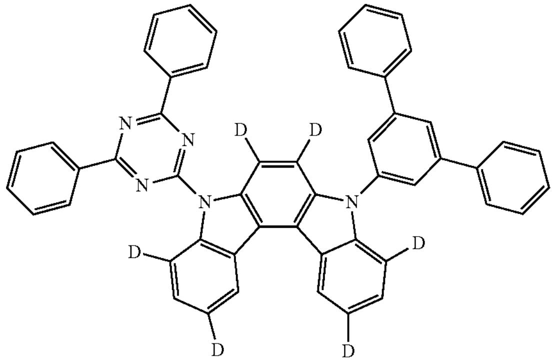
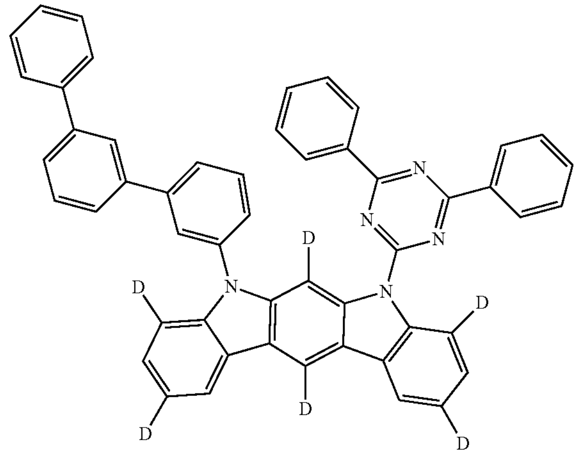
-continued
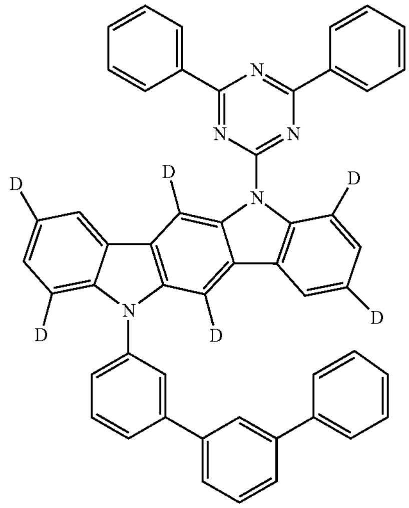
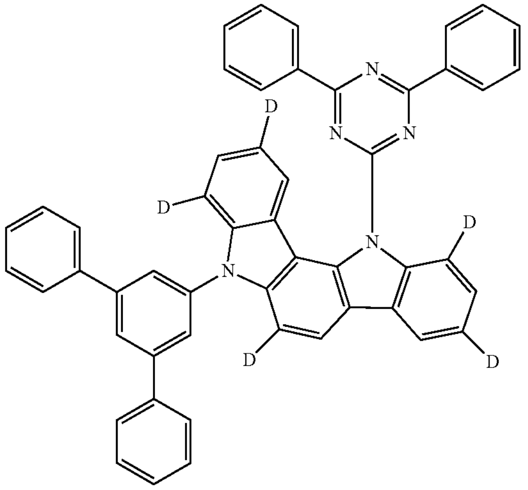
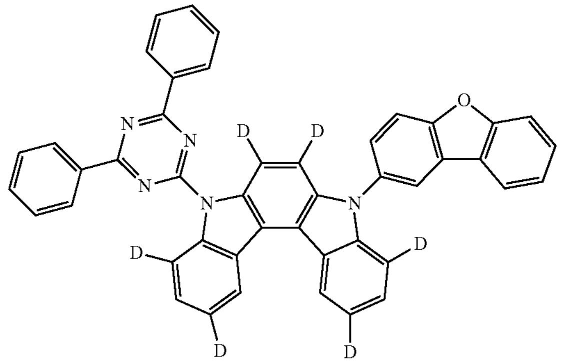

-continued

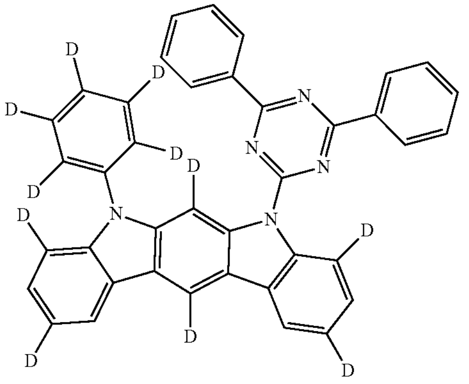

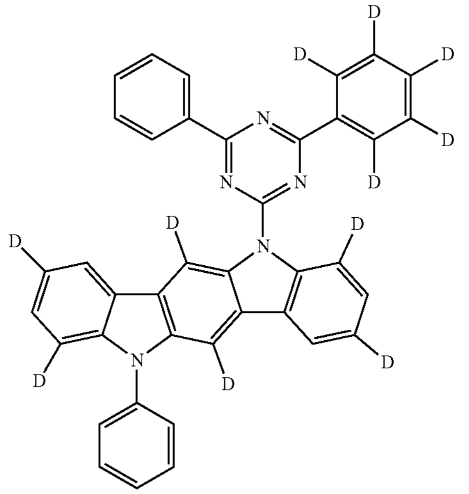

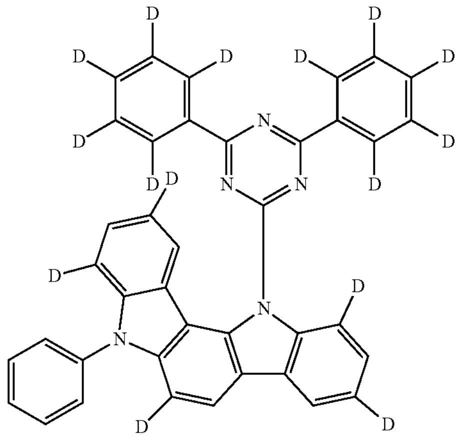

-continued

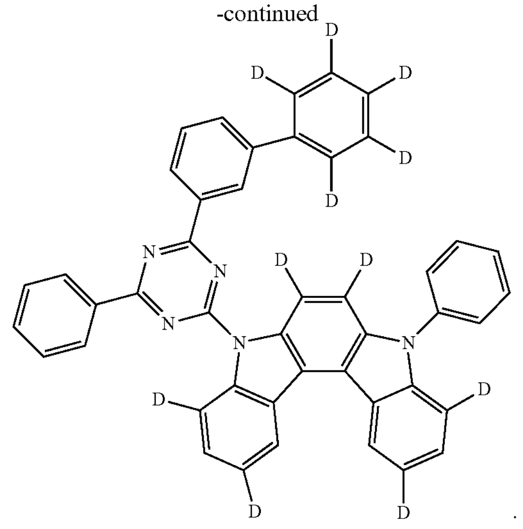

The first compound of Chemical Formula 1 can be prepared for example, by the preparation method as shown in the following Reaction Scheme 1.

<Reaction Scheme 1>

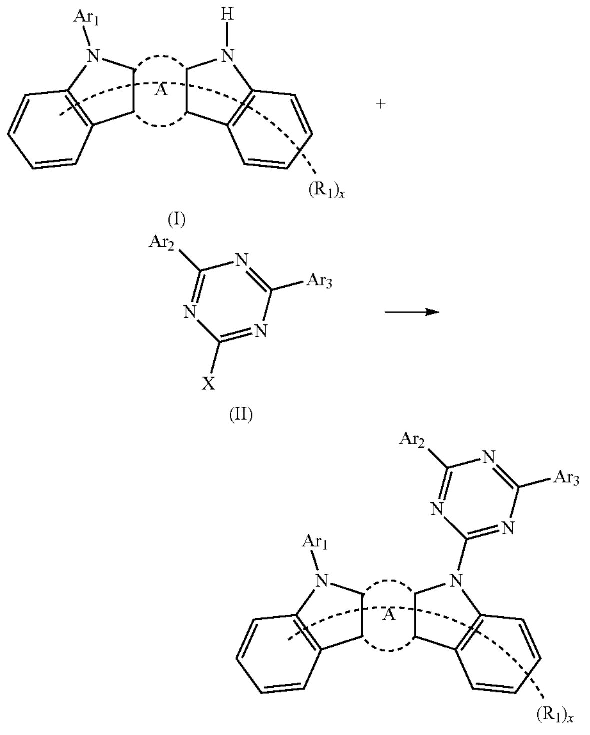

(I)

(II)

(1)

In Reaction Scheme 1, $Ar_1$ to $Ar_3$, R1, and x are as defined in Chemical Formula 1, and X is halogen, preferably chloro or bromo.

The Reaction Scheme 1 is an amine substitution reaction, which is preferably carried out in the presence of a palladium catalyst and a base, and a reactive group for the amine substitution reaction can be modified as known in the art. The above preparation method can be further specified in Preparation Examples described hereinafter.

Meanwhile, the Chemical Formula 2 can be preferably any one selected from the group consisting of the following Chemical Formulas 2-1 to 2-6. More preferably, the Chemical Formula 2 can be any one selected from the group consisting of the following Chemical Formulas 2-1 to 2-3:

<Chemical Formula 2-1>

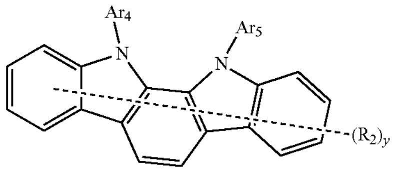

<Chemical Formula 2-2>

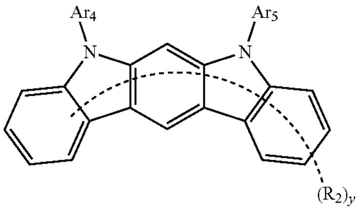

<Chemical Formula 2-3>

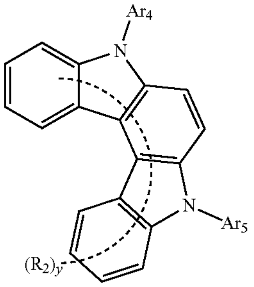

<Chemical Formula 2-4>

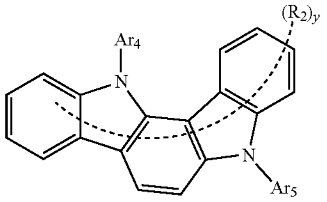

<Chemical Formula 2-5>

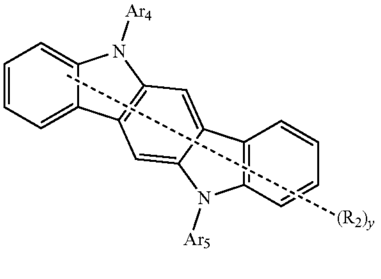

-continued

<Chemical Formula 2-6>

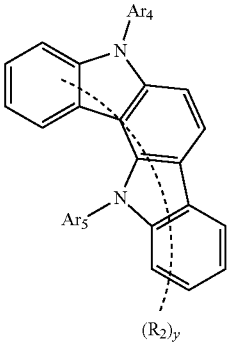

wherein in Chemical Formulas 2-1 to 2-6, $Ar_4$, $Ar_5$, $R_2$, and y are as defined above.

In Chemical Formulas 2, preferably $Ar_4$ and $Ar_5$ can be each independently an unsubstituted $C_{6-30}$ aryl, more preferably, $Ar_4$ and $Ar_5$ are each independently, phenyl, biphenyl, terphenyl, fluorenyl, 9,9-dimethylfluorenyl, or 9,9-diphenylfluorenyl, each of which is unsubstituted.

Further, in Chemical Formula 2, preferably $Ar_4$ is an unsubstituted $C_{6-30}$ aryl, and $Ar_5$ can be an unsubstituted $C_{5-60}$ heteroaryl containing one heteroatom selected from the group consisting of N, O and S. More preferably, $Ar_4$ can be phenyl, biphenyl or terphenyl, each of which is unsubstituted, and $Ar_5$ can be dibenzofuranyl, dibenzothiophenyl, carbazol-9-yl, or 9-phenyl-9H-carbazolyl, each of which is unsubstituted.

In Chemical Formula 2, preferably, all of $R_2$ can be hydrogen, and in this case, y can be an integer of 10.

Representative examples of the compound of Chemical Formula 2 are as follows:

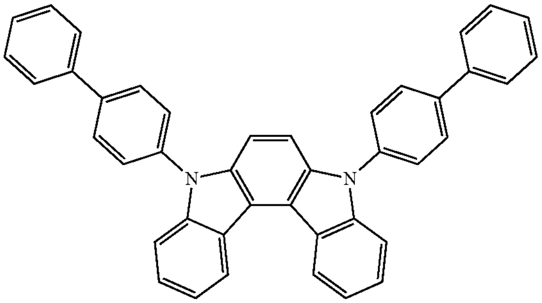

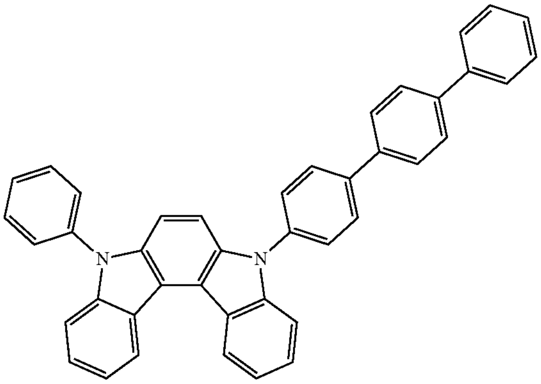

-continued
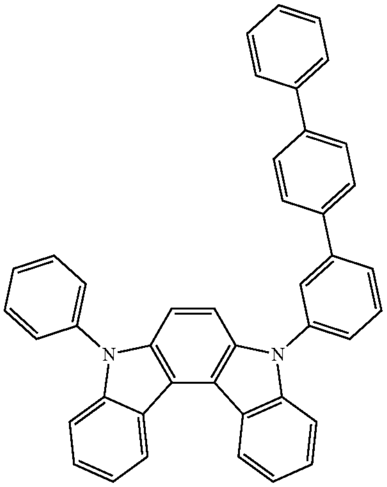
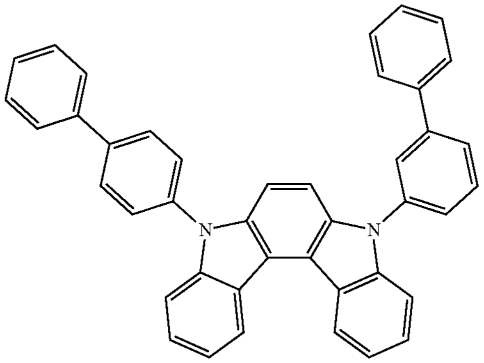
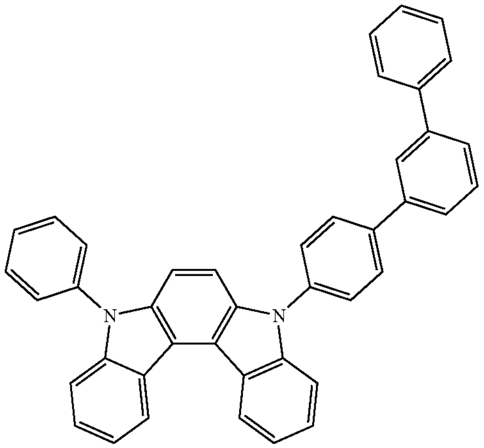
-continued
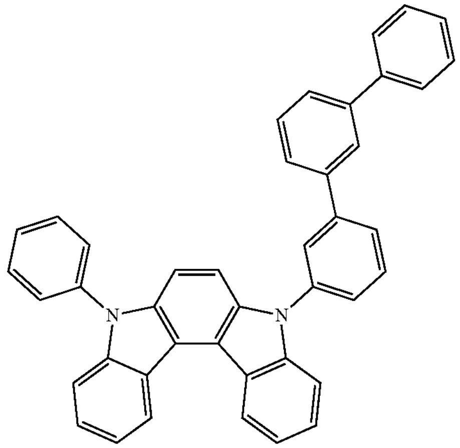
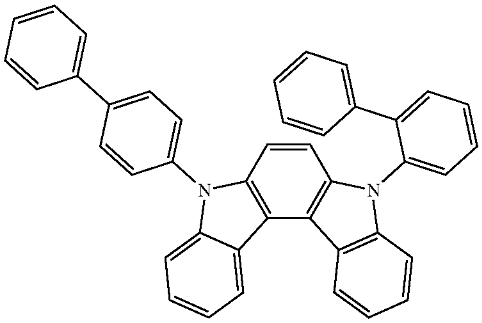
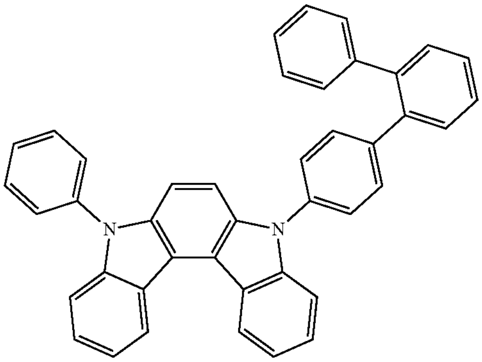
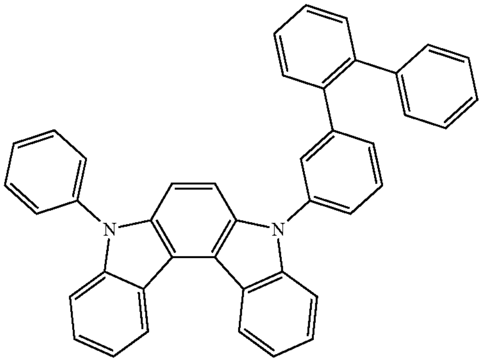

-continued
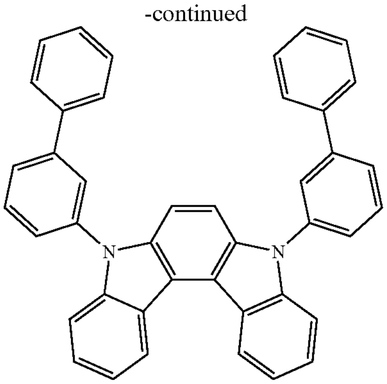
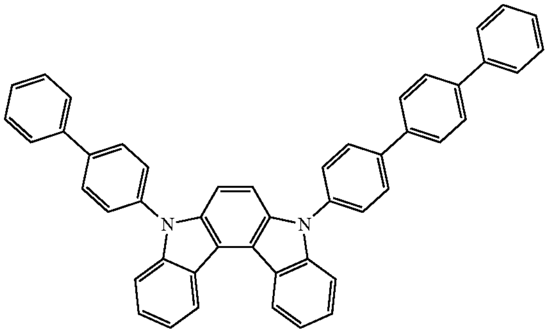
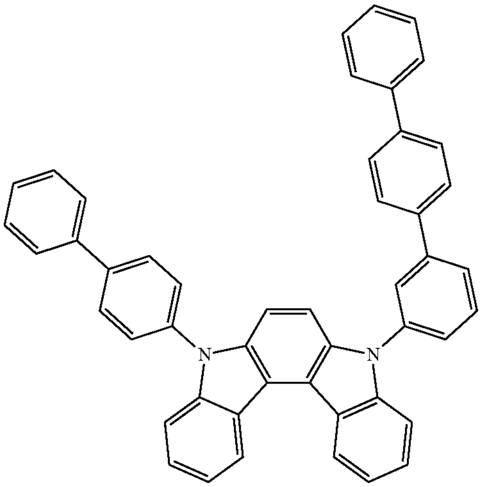
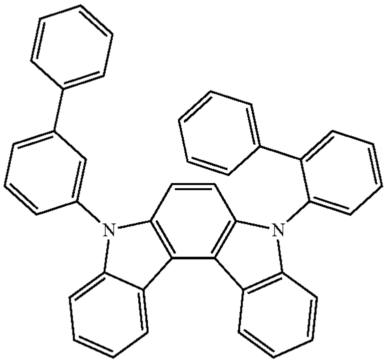
-continued
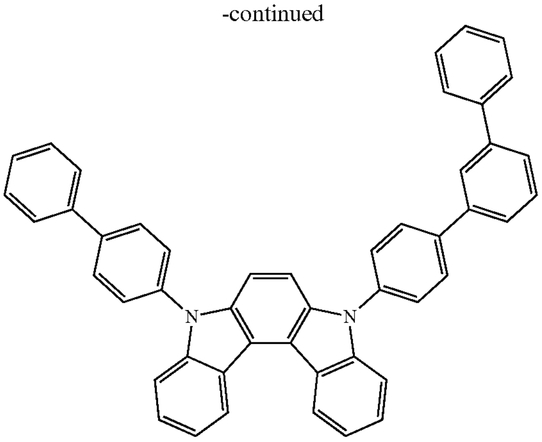
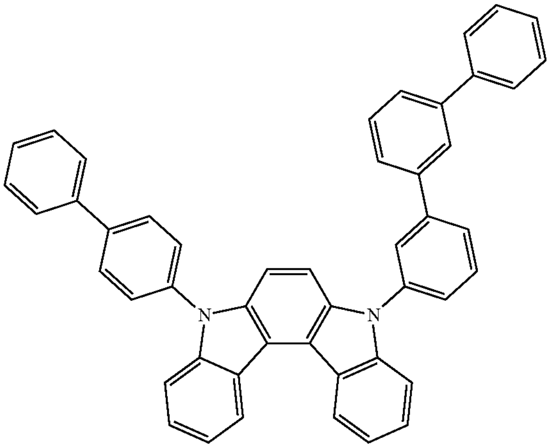
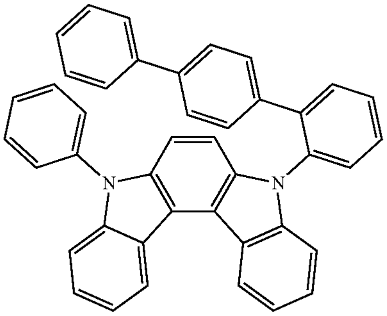
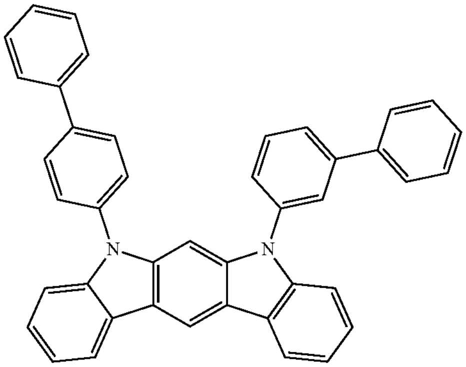

-continued
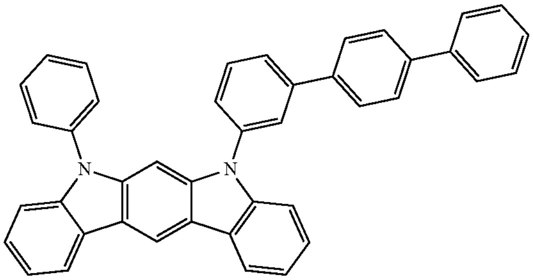
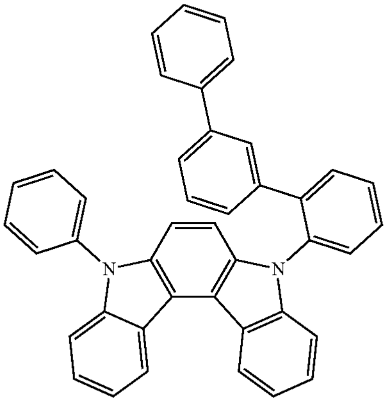
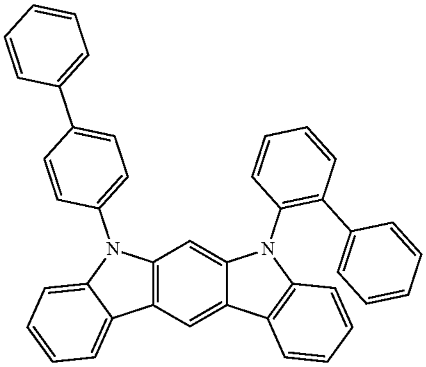
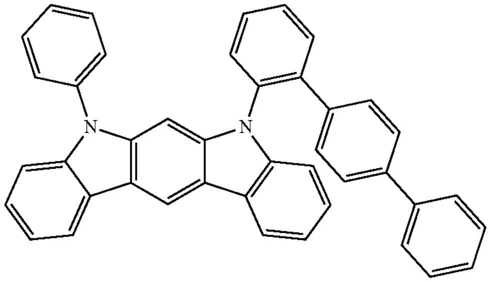
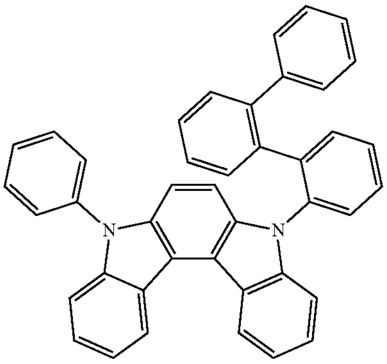
-continued
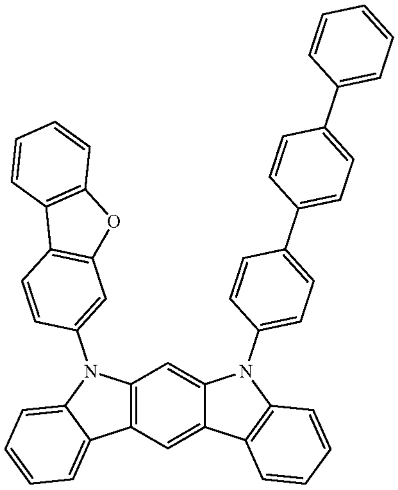
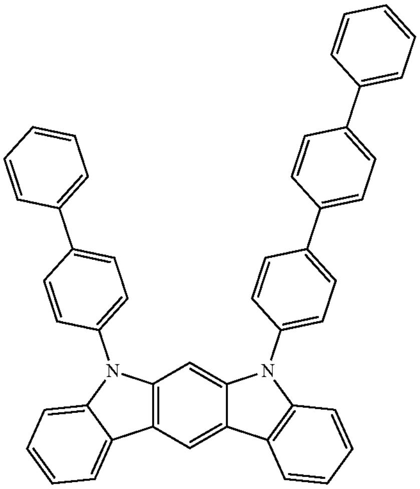
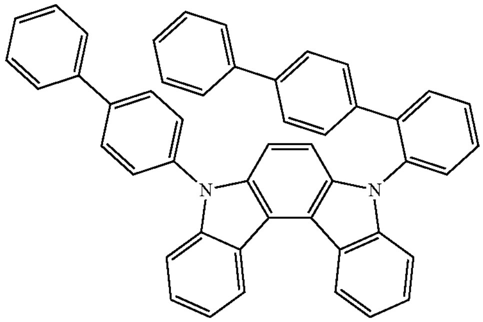
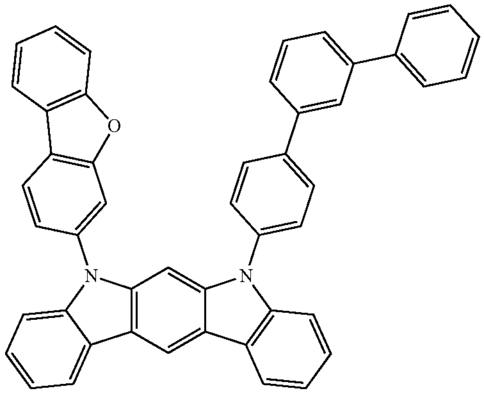

-continued
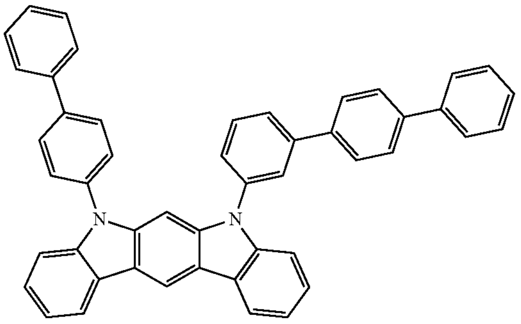 [SMILES: c1ccc(-c2ccc(-c3cccc(-n4c5ccccc5c5cc6c7ccccc7n(-c7ccc(-c8ccccc8)cc7)c6cc54)c3)cc2)cc1]
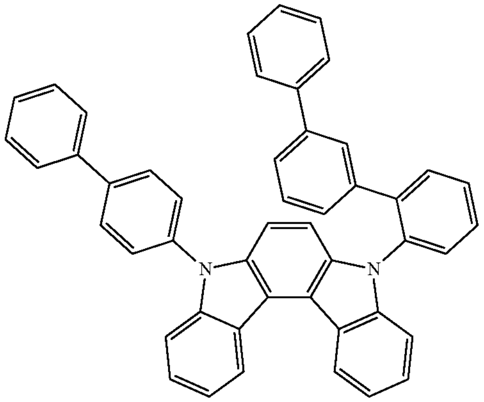 [SMILES: c1ccc(-c2ccc(-n3c4ccccc4c4c5c6ccccc6n(-c6ccccc6-c6cccc(-c7ccccc7)c6)c5ccc43)cc2)cc1]
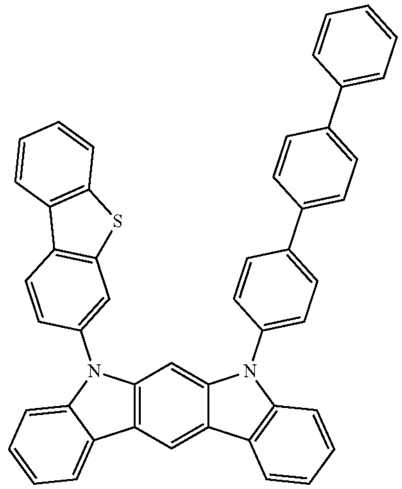
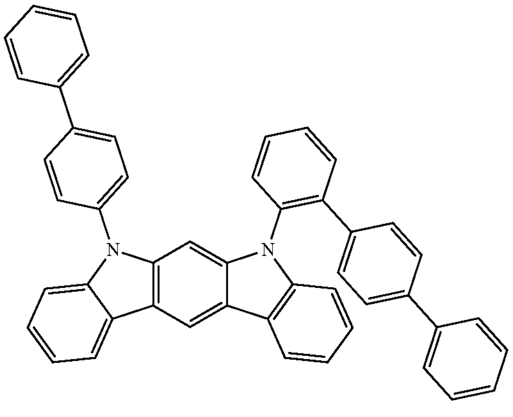
-continued
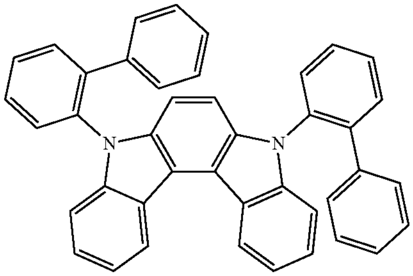
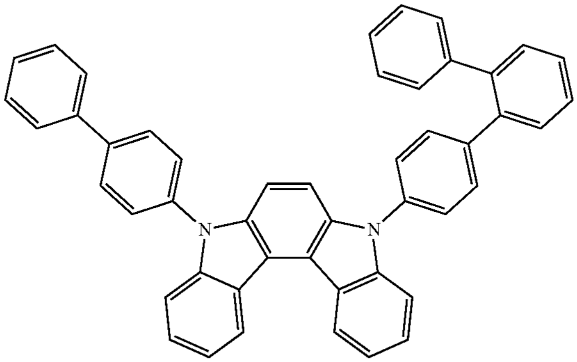
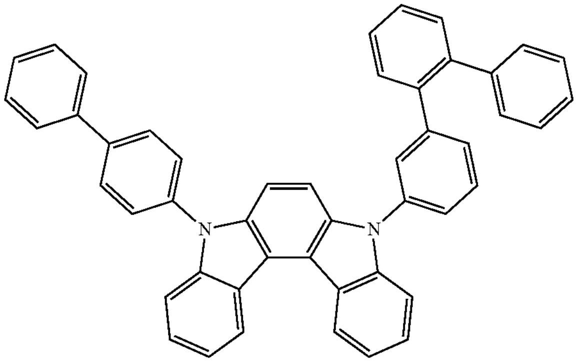
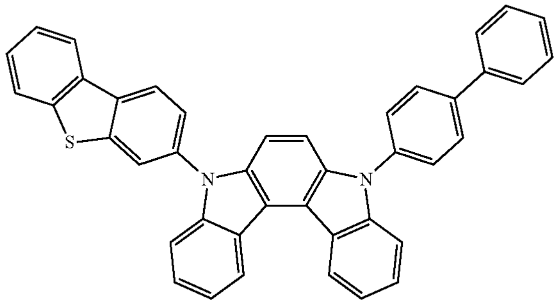
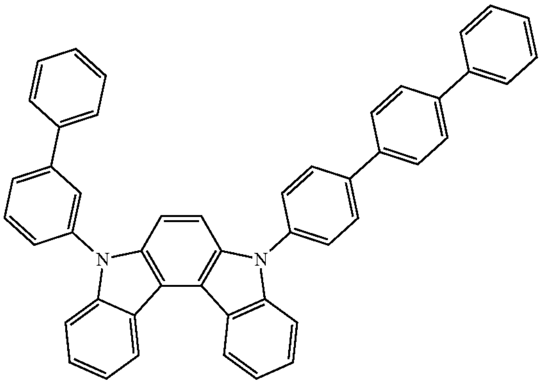

-continued
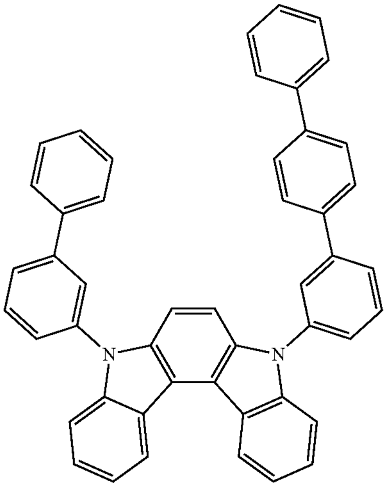
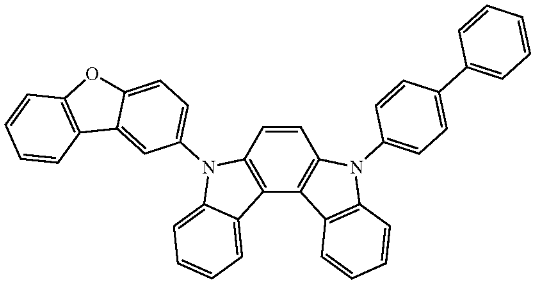
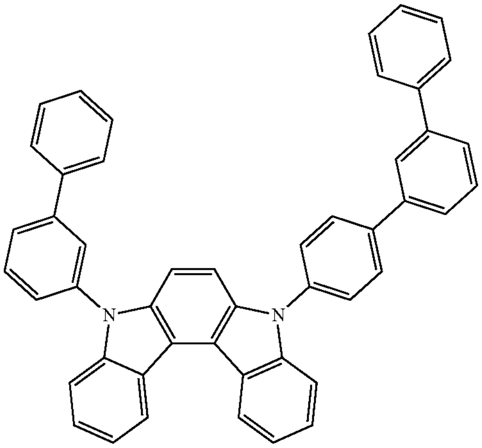
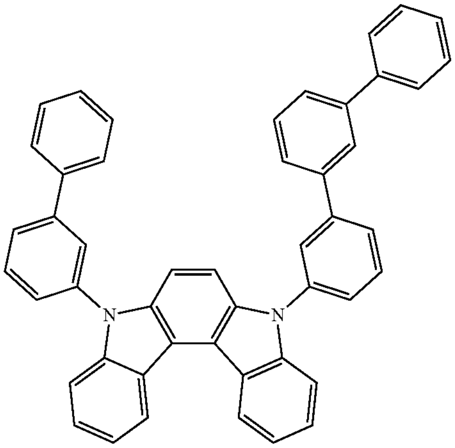
-continued
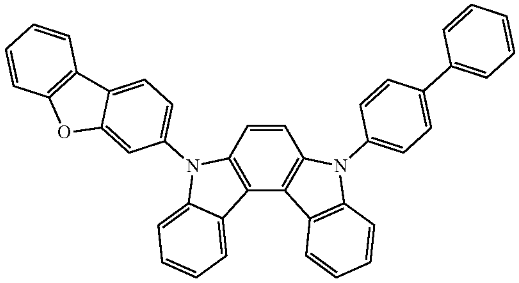
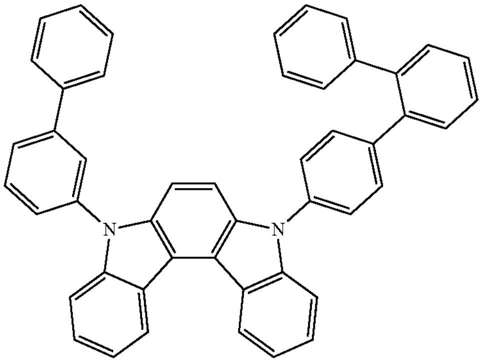
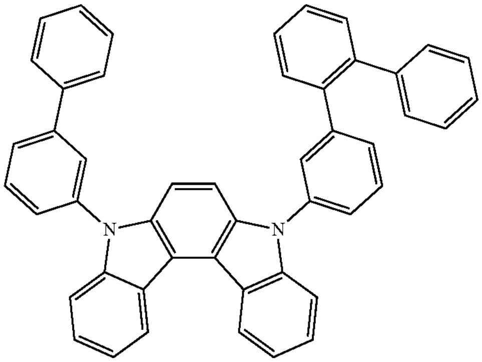
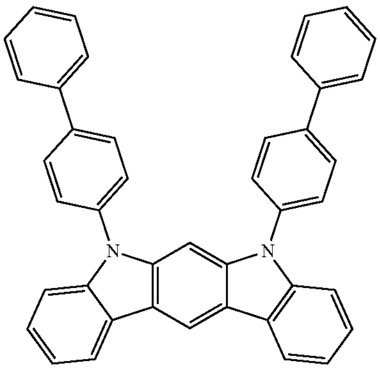

-continued
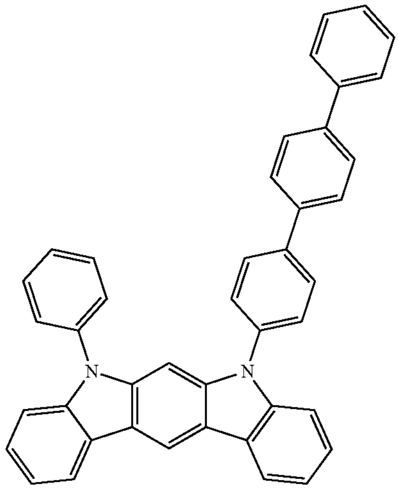
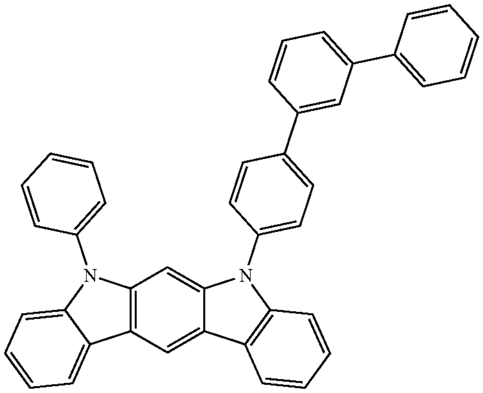
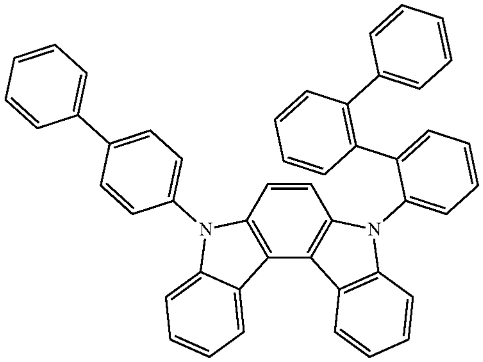
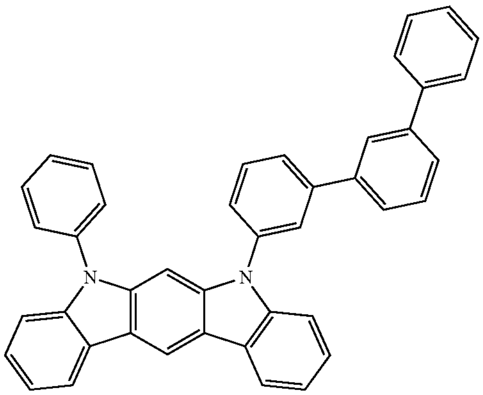
-continued
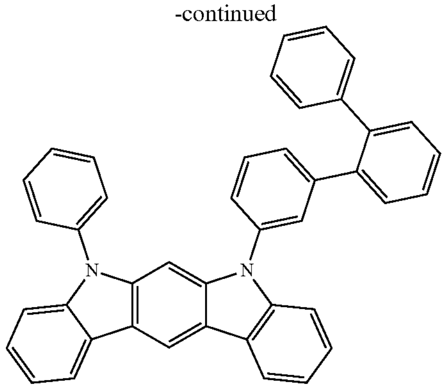
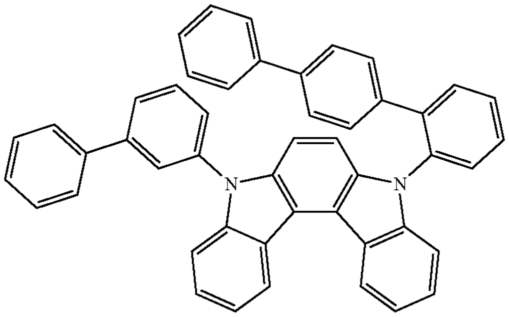
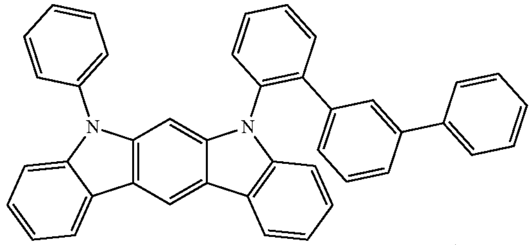
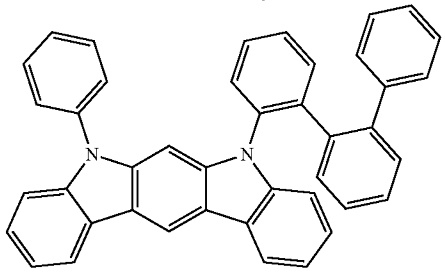
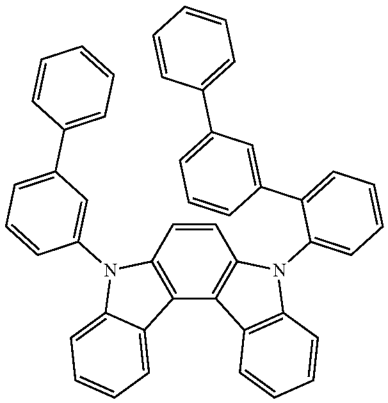

-continued
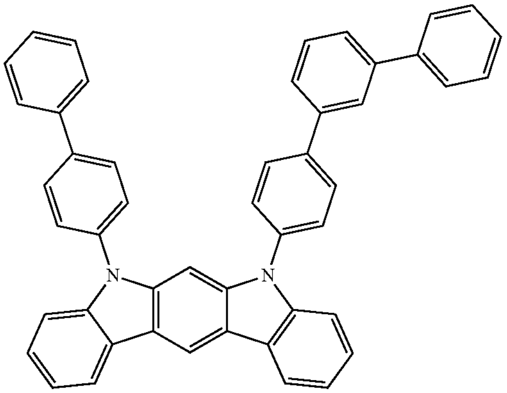
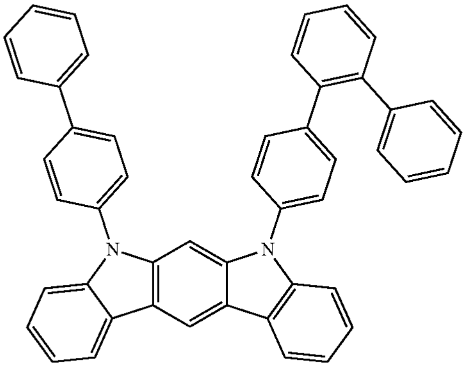
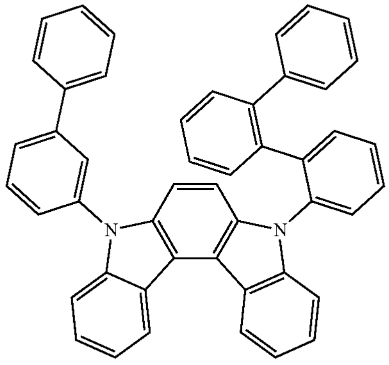
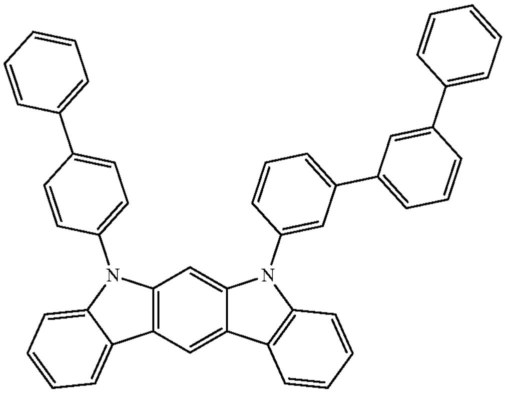
-continued
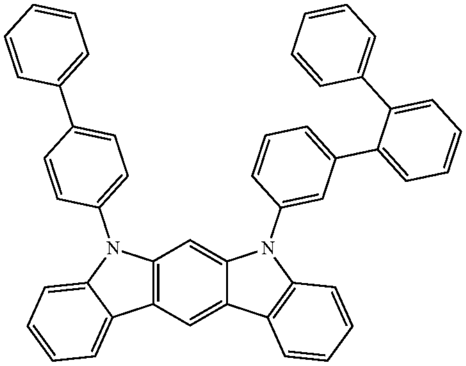
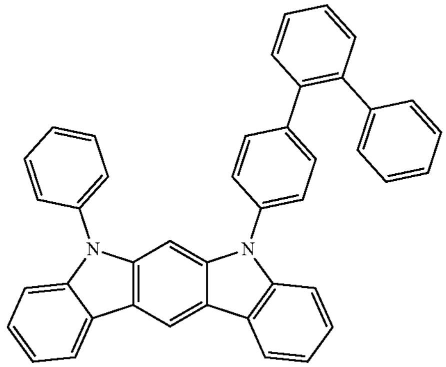
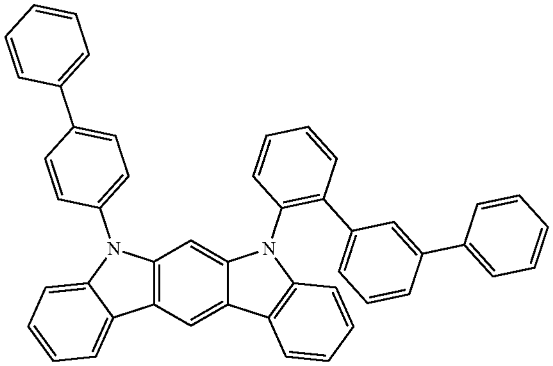
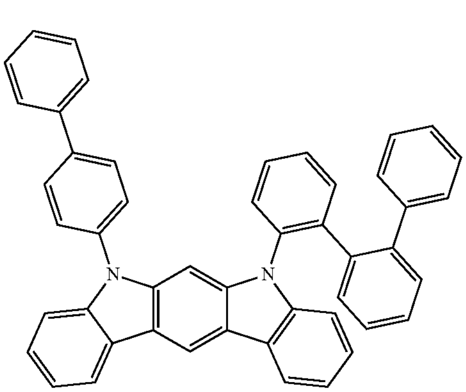

-continued
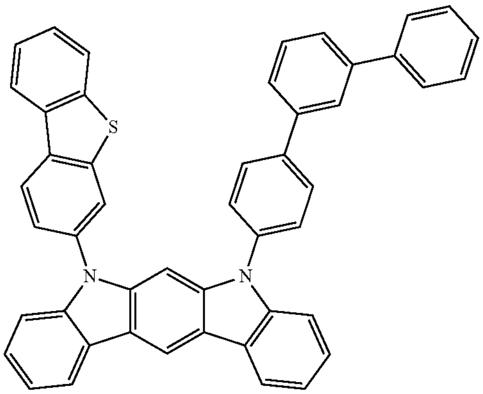
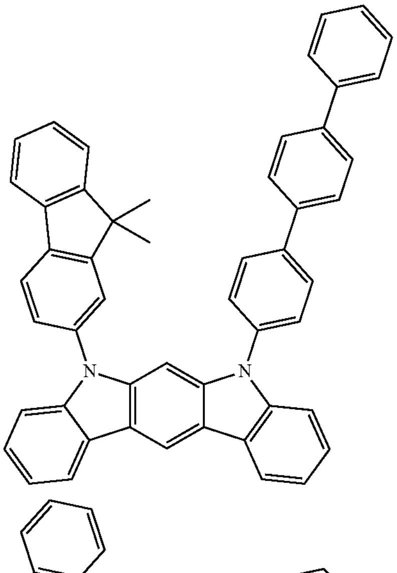
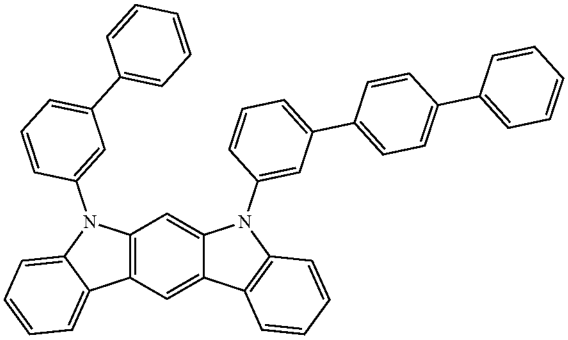
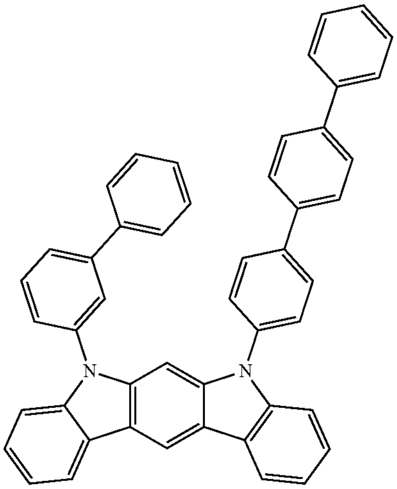
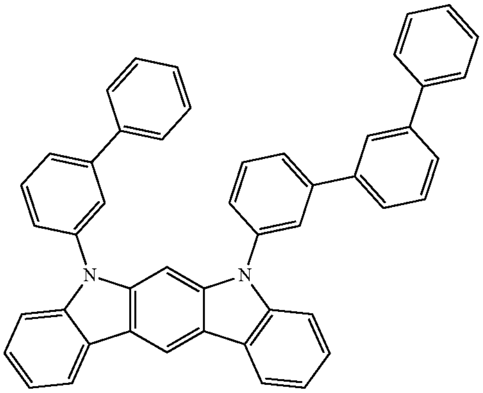
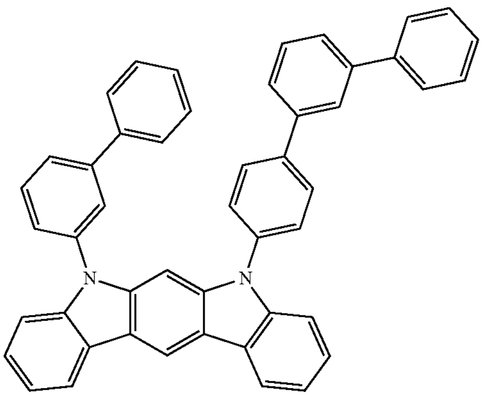
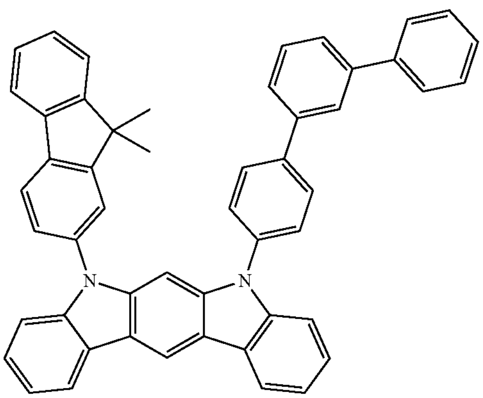
-continued -continued
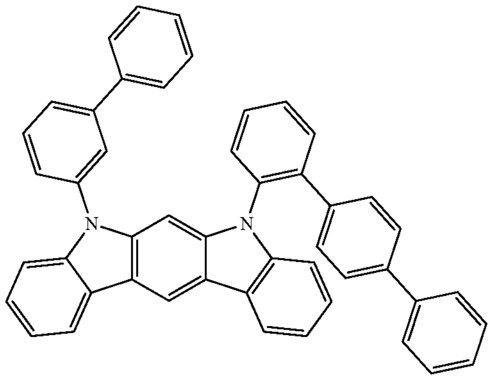
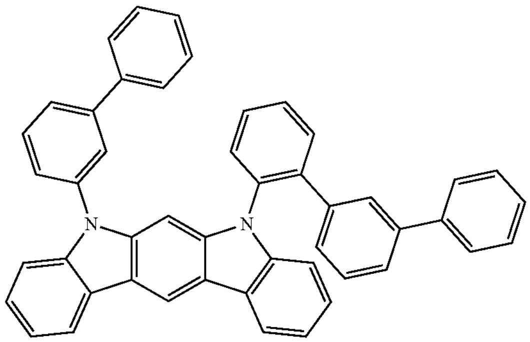
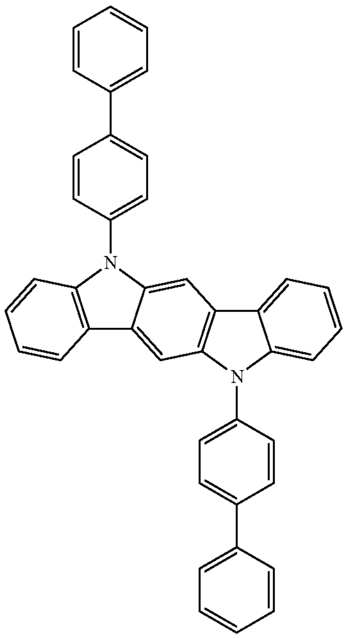
-continued
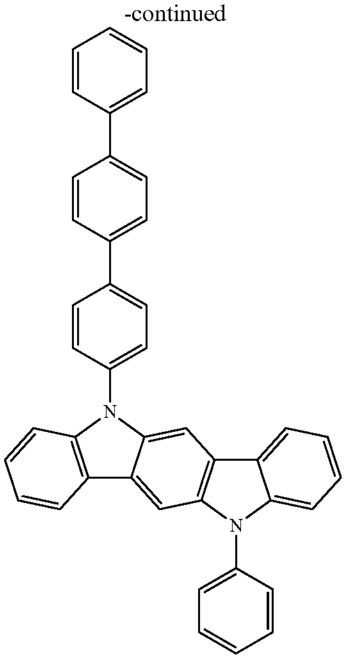
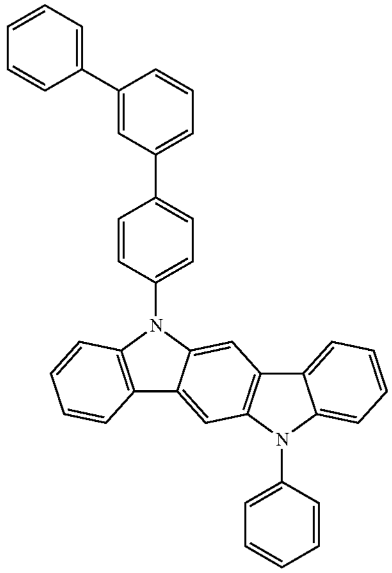
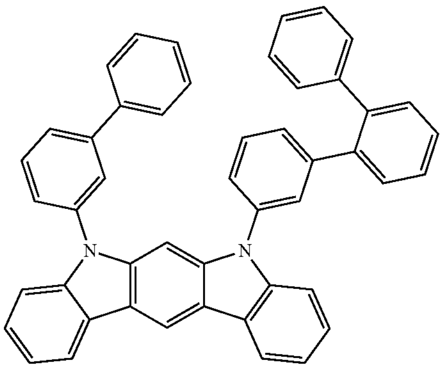

-continued
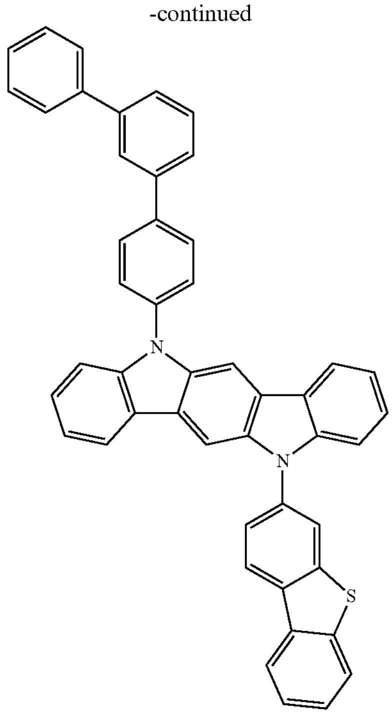
-continued
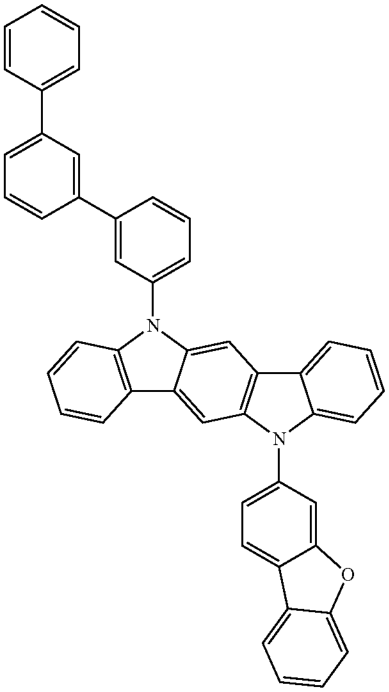
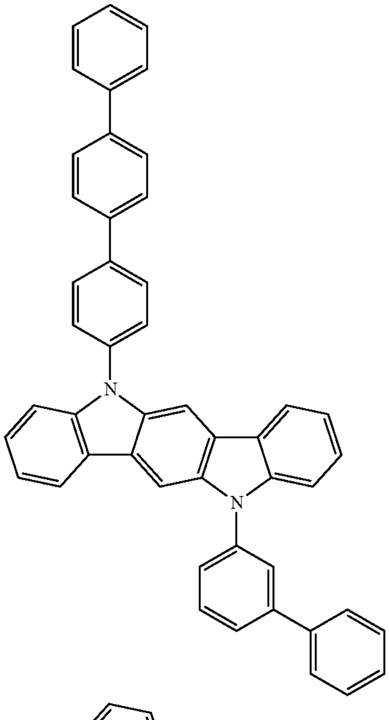
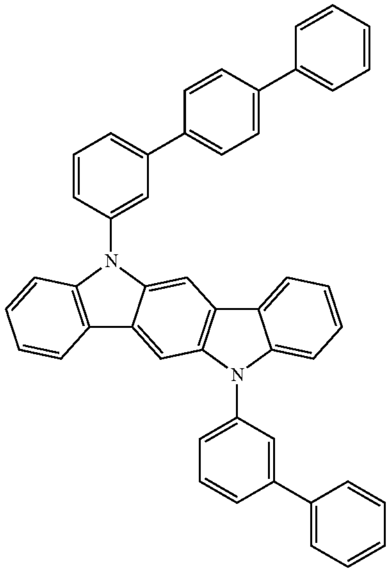
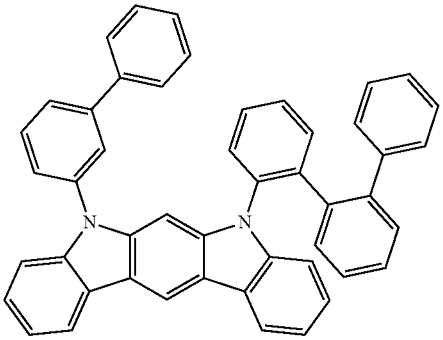

-continued
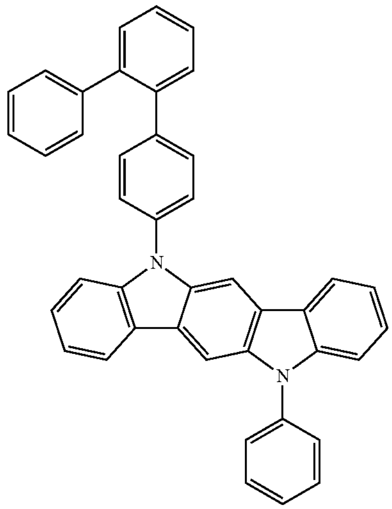
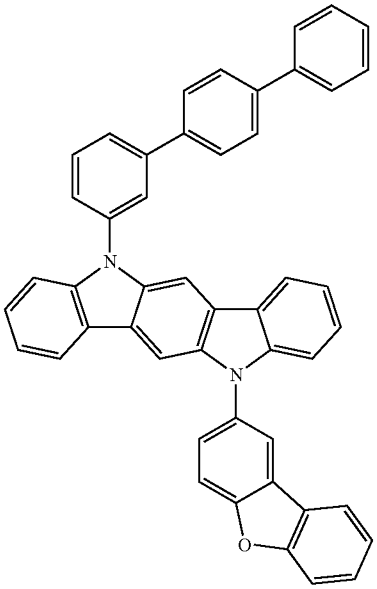
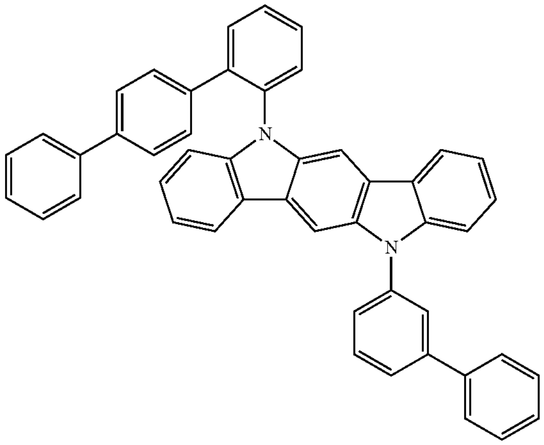
-continued
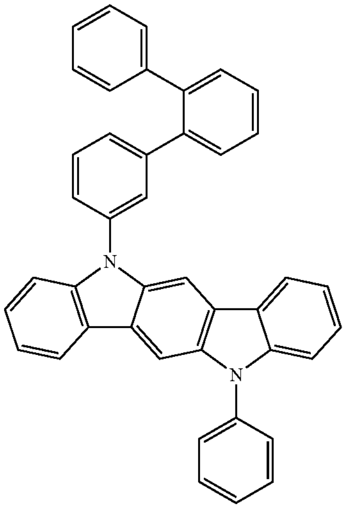
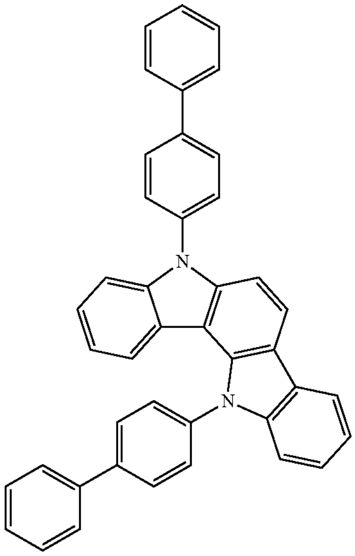
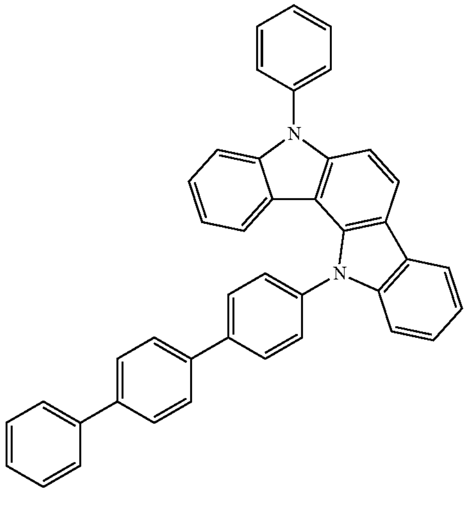

-continued
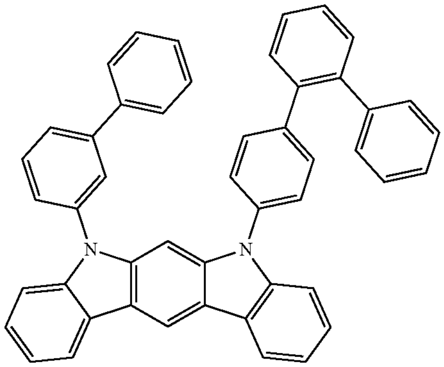
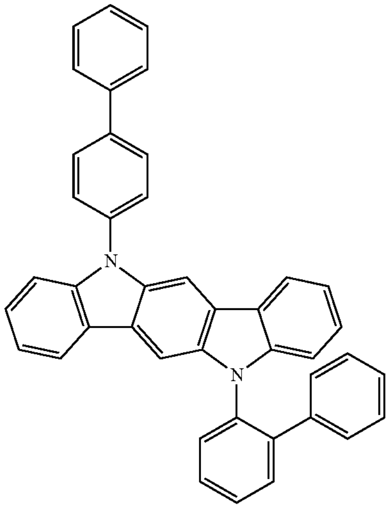
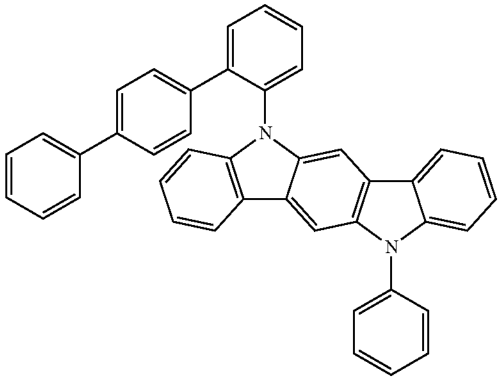
-continued
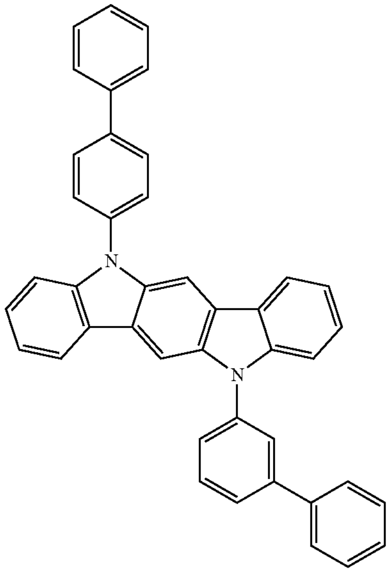
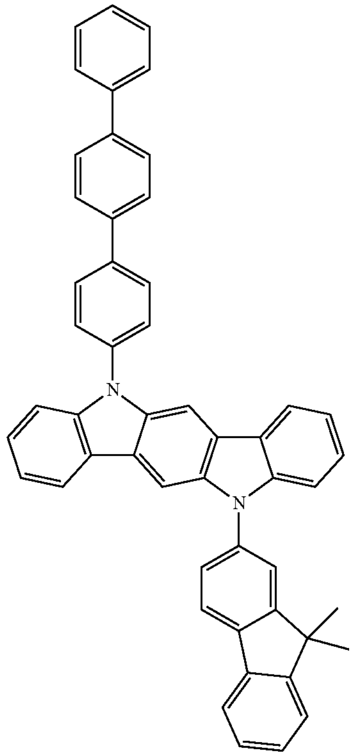

-continued
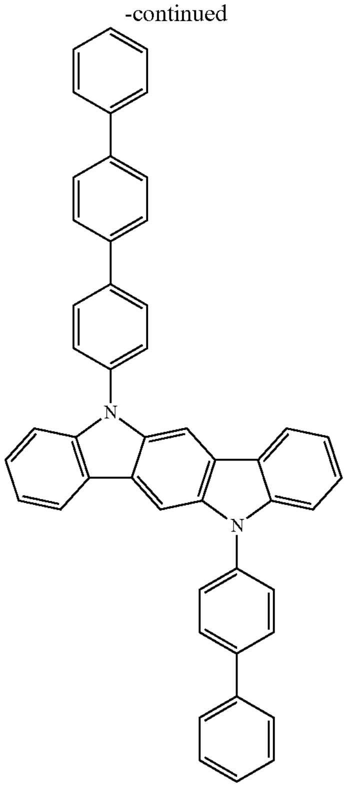
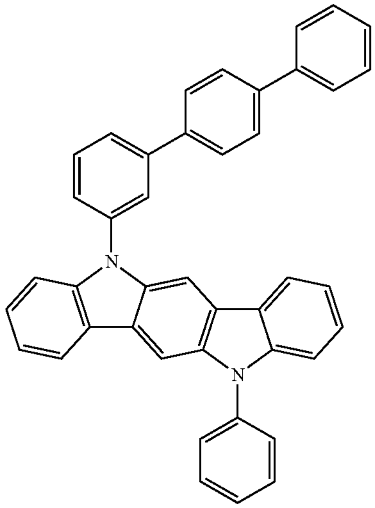
-continued
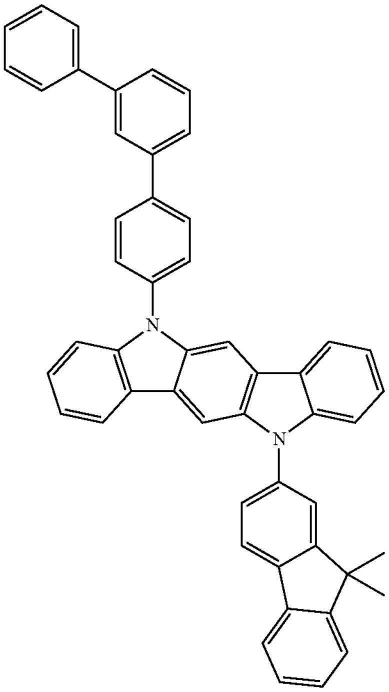
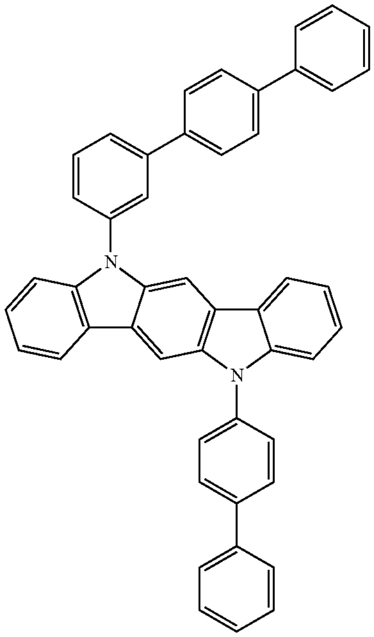

-continued
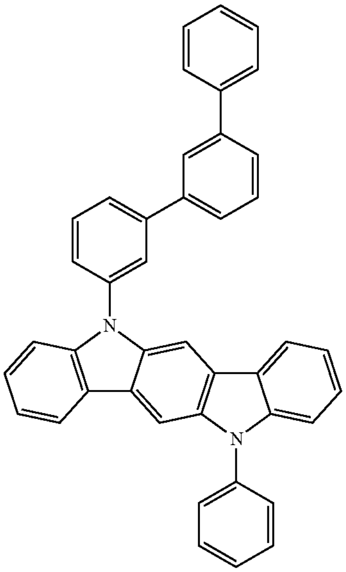
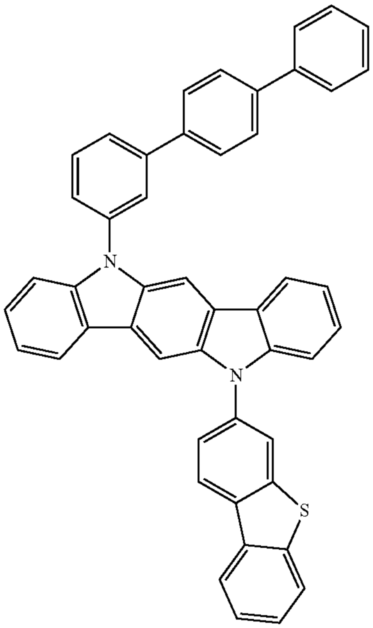
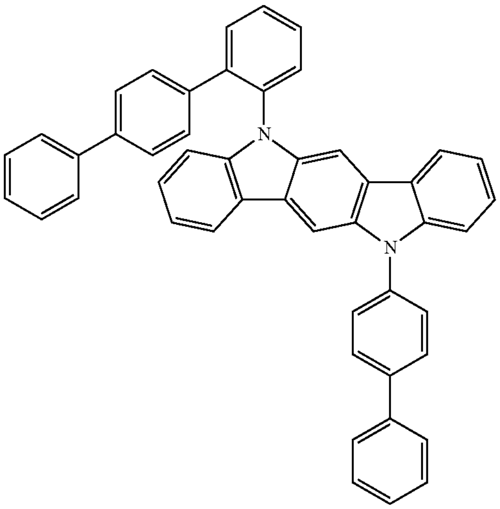
-continued
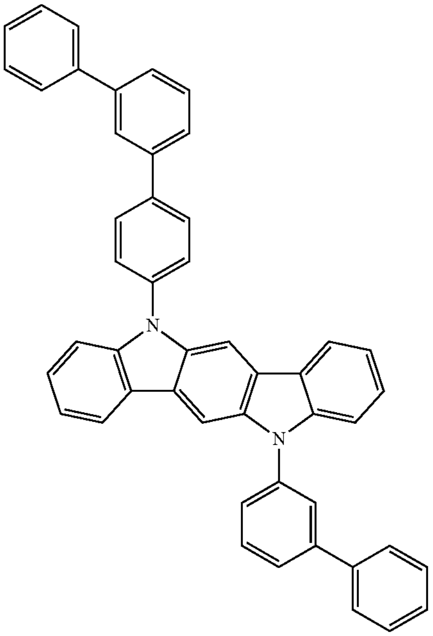
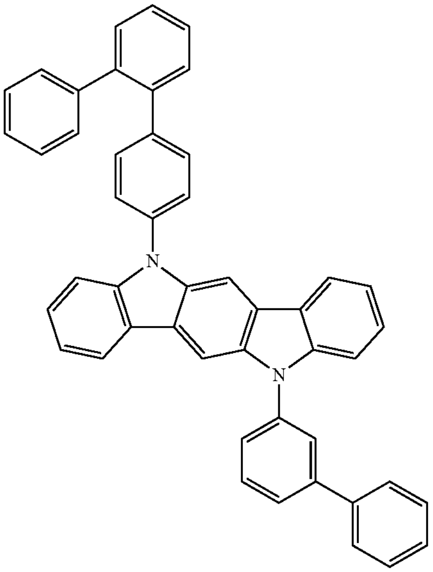

-continued
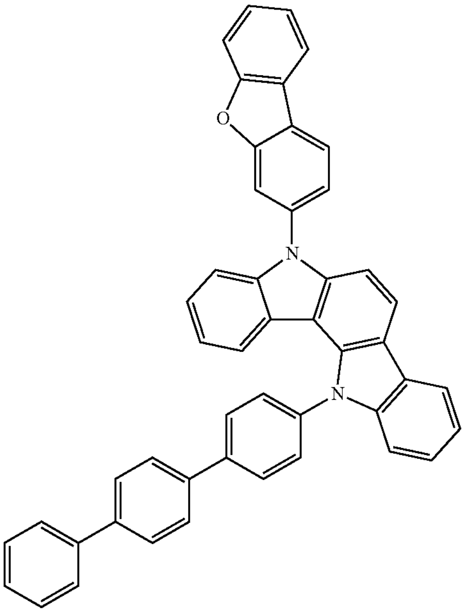
-continued
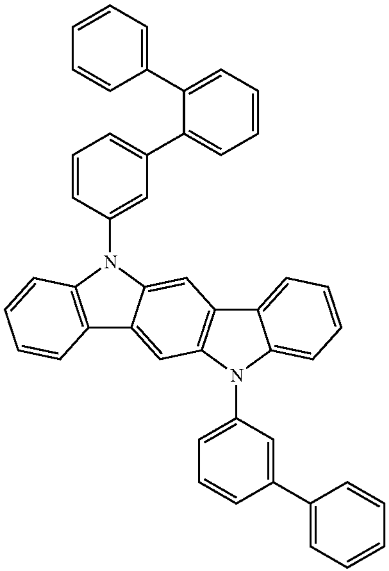
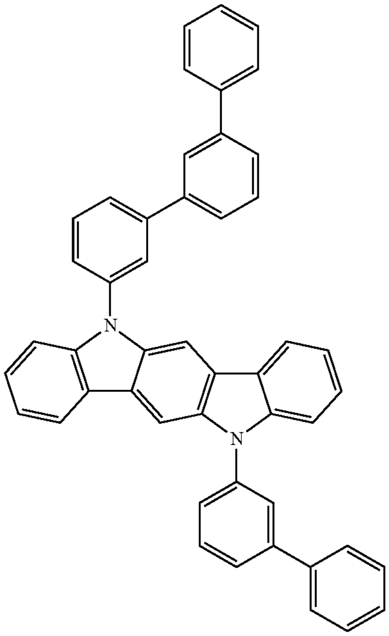
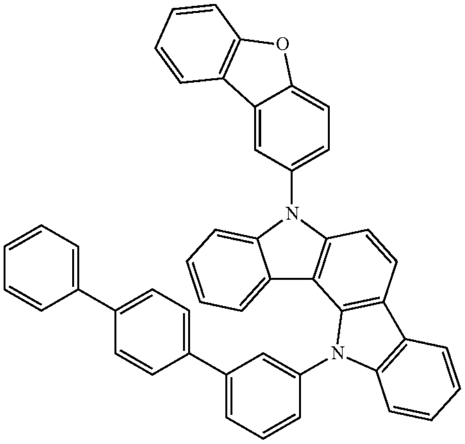
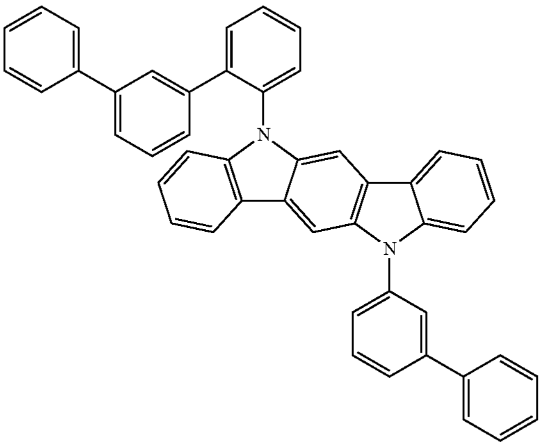

-continued
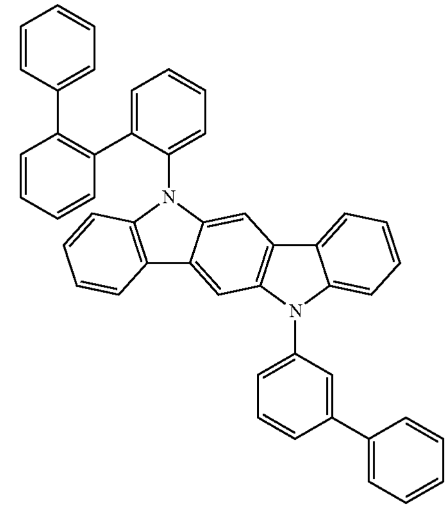
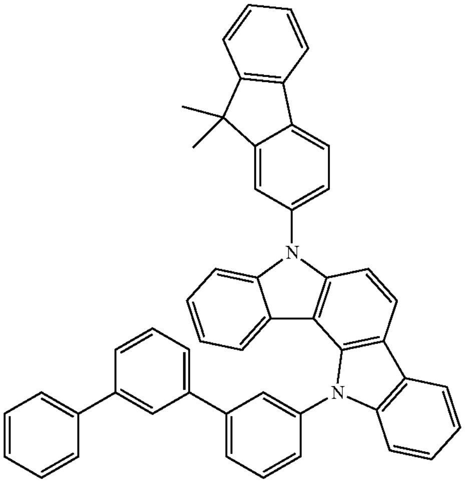
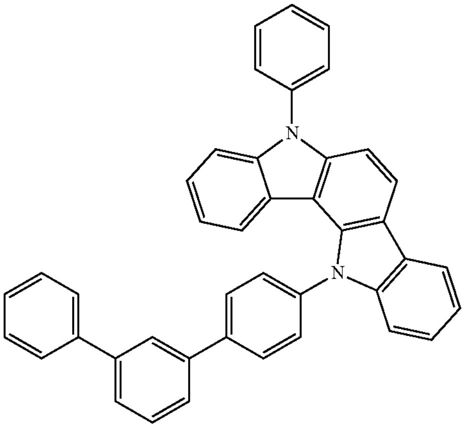
-continued
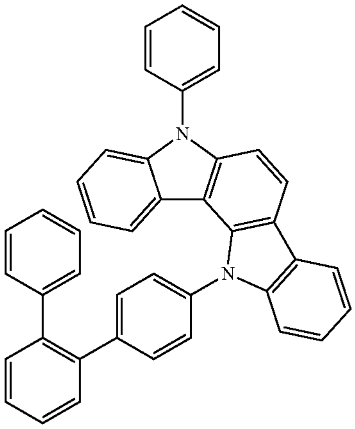
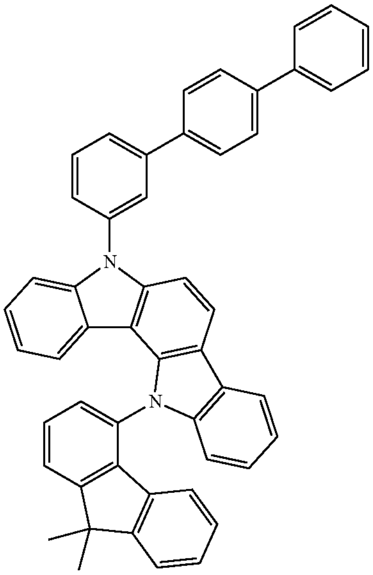
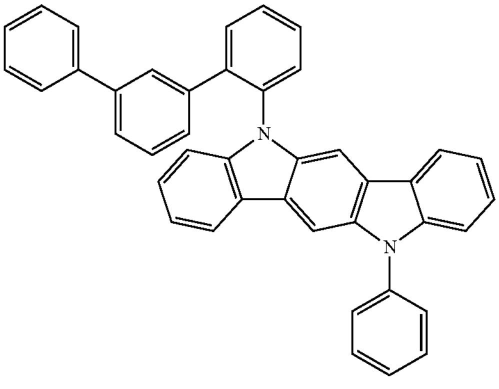

-continued
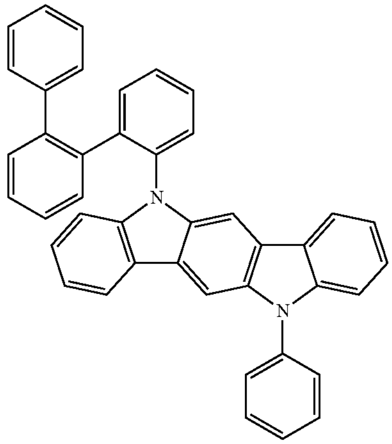
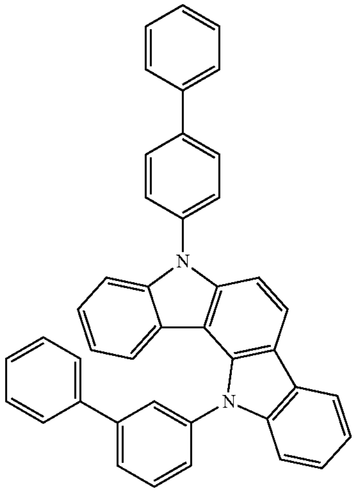
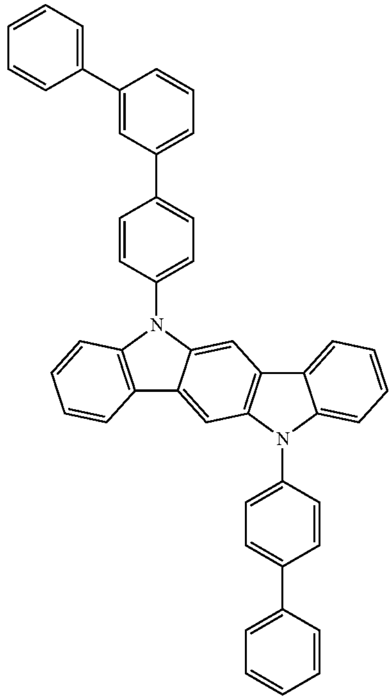
-continued
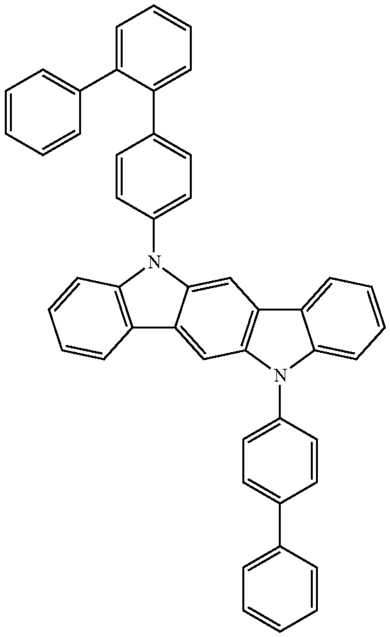
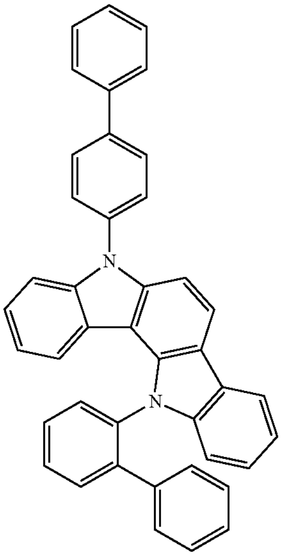

-continued
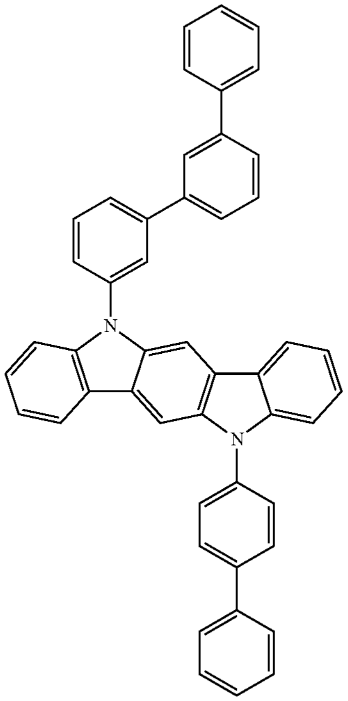
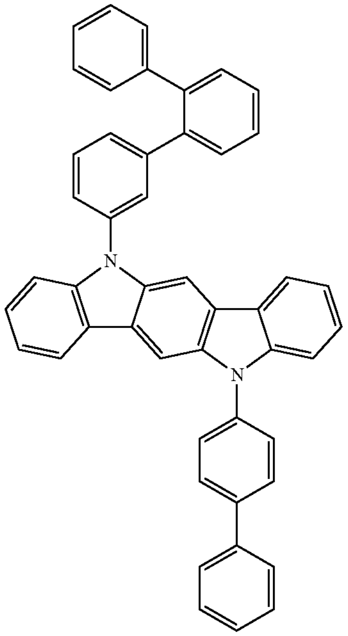
-continued
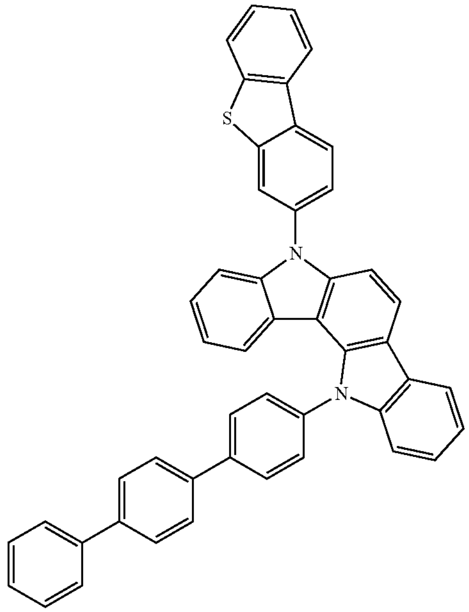
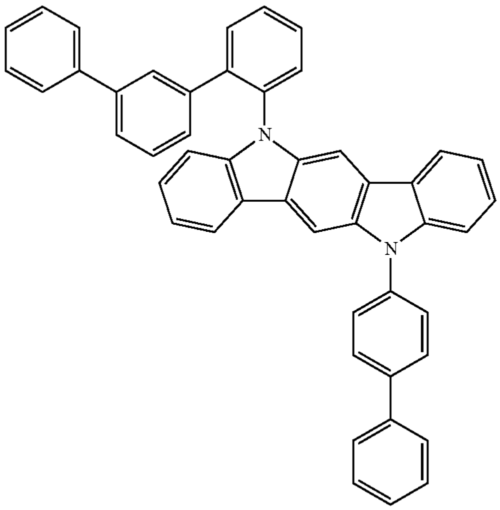
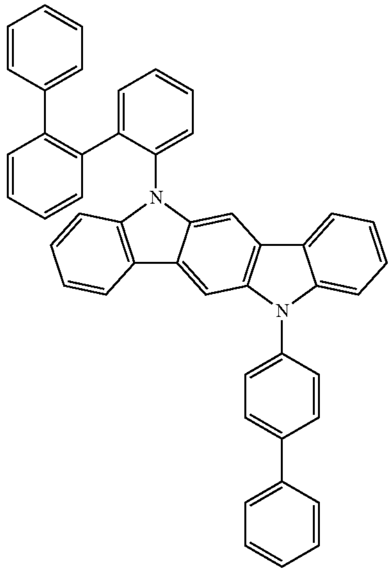

-continued
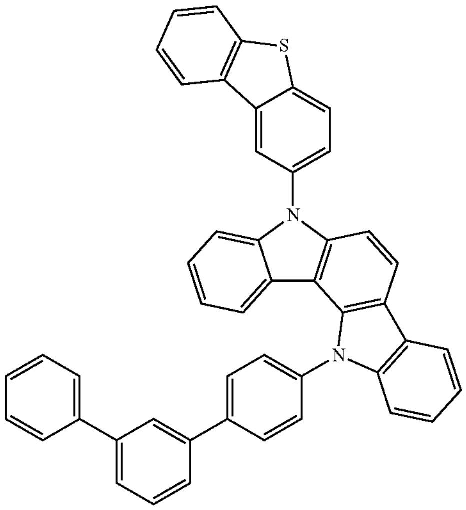
-continued
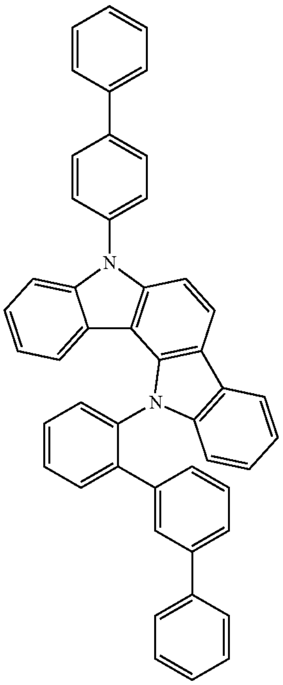
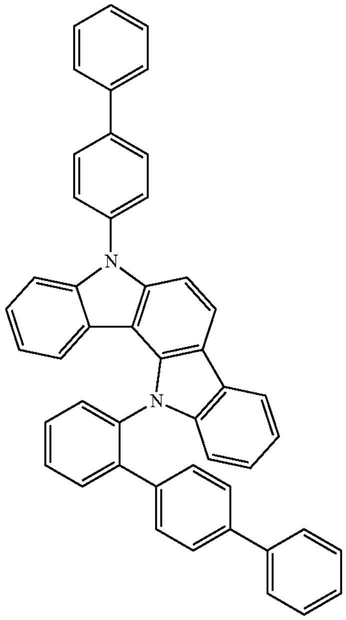
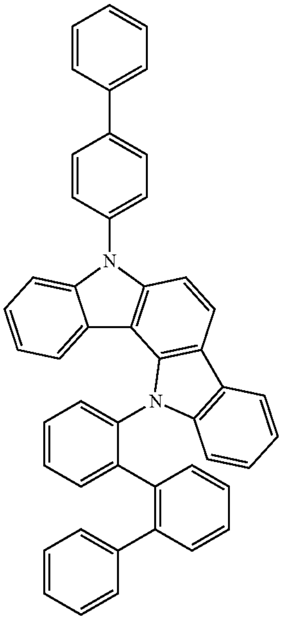

-continued
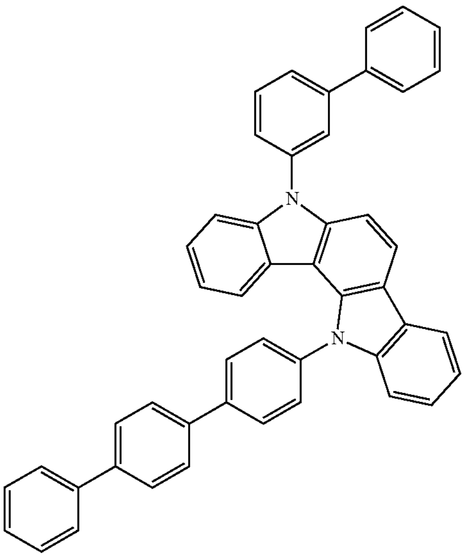
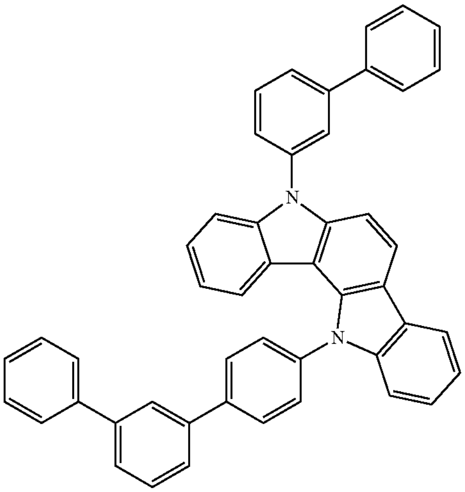
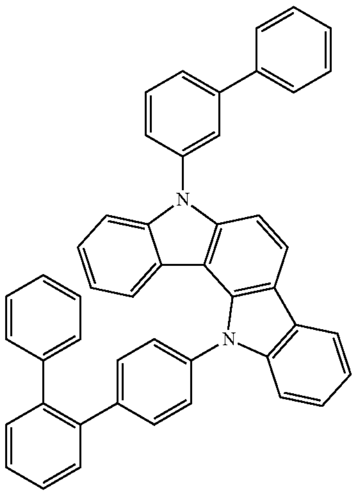
-continued
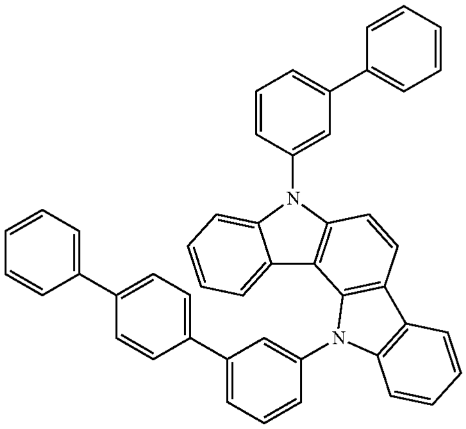
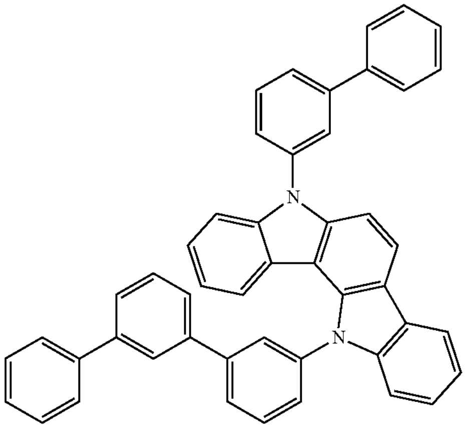
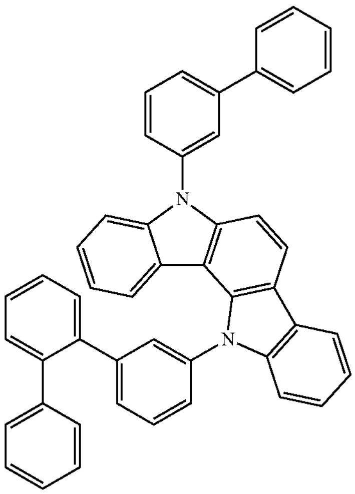

-continued
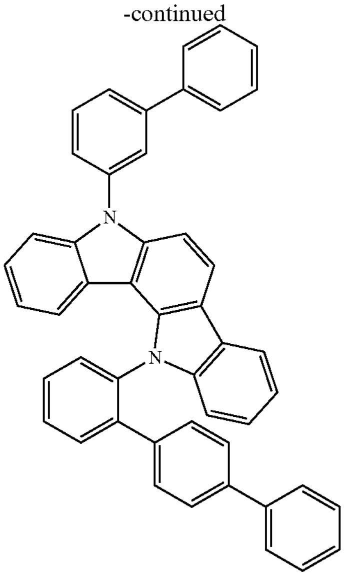
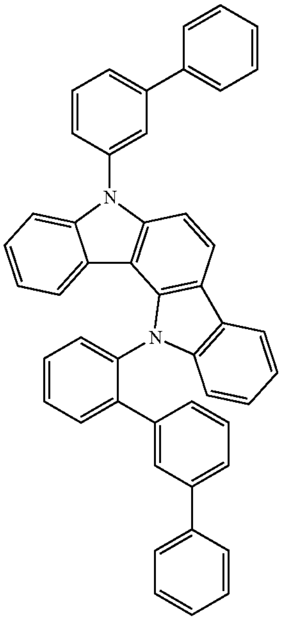
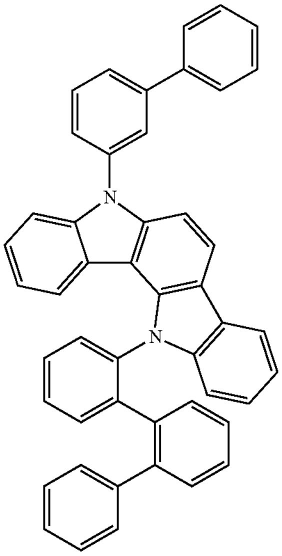
-continued
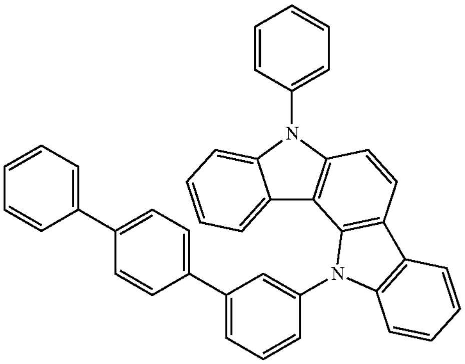
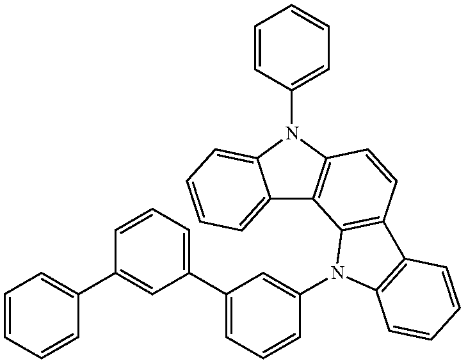
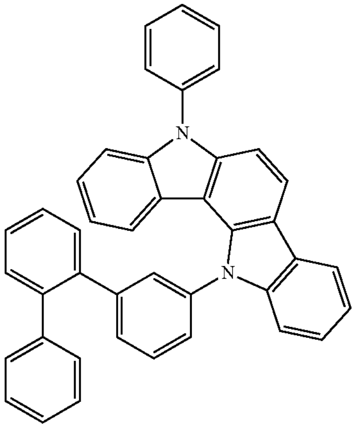
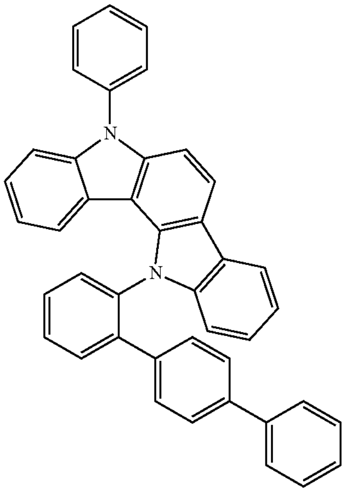

-continued
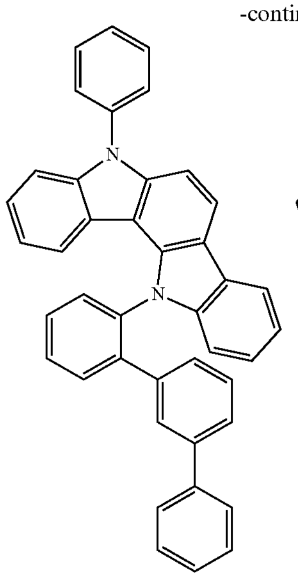
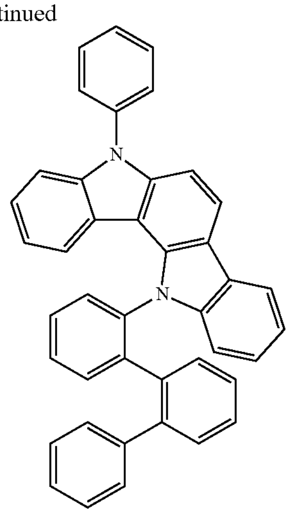
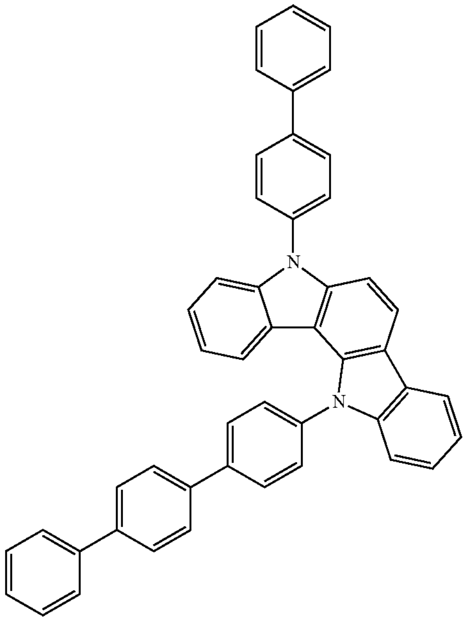
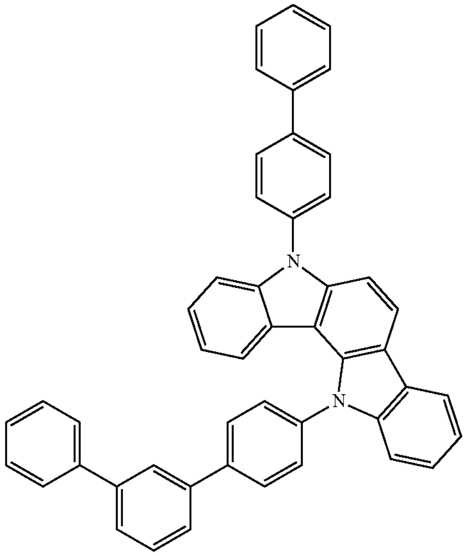
-continued
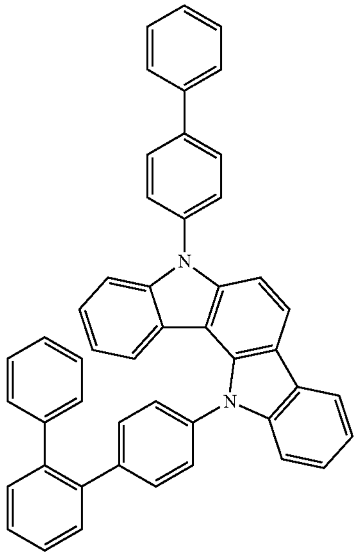
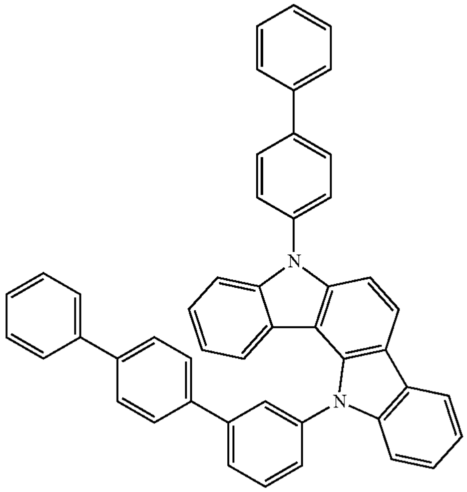
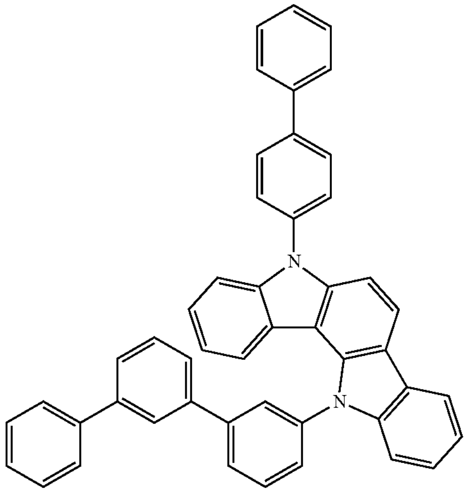

-continued

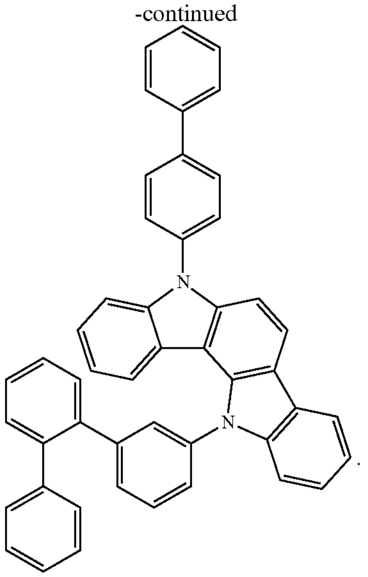

The compound of Chemical Formula 2 can be prepared, for example, by the preparation method as shown in the following Reaction Scheme 2.

<Reaction Scheme 2>

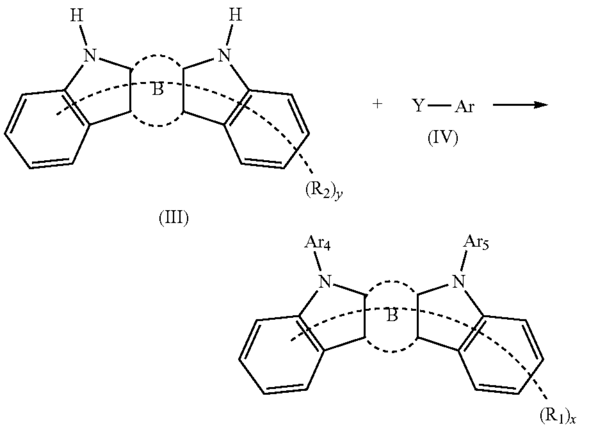

(III) (IV) (2)

wherein in Reaction Scheme 2, $Ar_4$, $Ar_5$, $R_2$, and y are as defined in Chemical Formula 2, and Y is halogen, preferably chloro or bromo. The Ar is as defined in $Ar_4$ or $Ar_5$.

The Reaction Scheme 2 is an amine substitution reaction, which is preferably carried out in the presence of a palladium catalyst and a base, and a reactive group for the amine substitution reaction can be modified as known in the art. The above preparation method can be further specified in the Preparation Examples described hereinafter.

In Reaction Scheme 2, the reaction of Compound (III) and Compound (IV) is shown in one step, but in Compound (2), when $Ar_4$ and $Ar_5$ are different from each other, it can be carried out in two steps by changing Ar in Compound (IV) to functional groups corresponding to $Ar_4$ and $Ar_5$, respectively. At this time, the order of the reaction steps is not particularly limited.

Preferably, in the light emitting layer, the weight ratio of the first compound of Chemical Formula 1 and the second compound of Chemical Formula 2 is 10:90 to 90:10, more preferably, 20:80 to 80:20, 30:70 to 70:30, 30:70 to 50:50, or 30:70 to 40:60.

Meanwhile, the light emitting layer can further include a dopant in addition to the host. The dopant material is not particularly limited as long as it is a material used for the organic light emitting device. As an example, an aromatic amine derivative, a styrylamine compound, a boron complex, a fluoranthene compound, a metal complex, and the like can be mentioned. Specific examples of the aromatic amine derivatives include substituted or unsubstituted fused aromatic ring derivatives having an arylamino group, examples thereof include pyrene, anthracene, chrysene, and periflanthene having the arylamino group, and the like. The styrylamine compound is a compound where at least one arylvinyl group is substituted in substituted or unsubstituted arylamine, in which one or two or more substituent groups selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, examples of the metal complex include an iridium complex, a platinum complex, and the like, but are not limited thereto.

Electron Transport Layer

The organic light emitting device according to the present disclosure can include an electron transport layer on the light emitting layer, if necessary.

The electron transport layer is a layer that receives the electrons from the electron injection layer formed on the cathode or the cathode and transports the electrons to the light emitting layer, and that suppress the transfer of holes from the light emitting layer, and an electron transport material is suitably a material which can receive electrons well from a cathode and transfer the electrons to a light emitting layer, and has a large mobility for electrons.

Specific examples of the electron transport material include: an Al complex of 8-hydroxyquinoline, a complex including $Alq_3$, an organic radical compound, a hydroxyflavone-metal complex, and the like, but are not limited thereto. The electron transport layer can be used with any desired cathode material, as used according to a conventional technique. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

Electron Injection Layer

The organic light emitting device according to the present disclosure can further include an electron injection layer on the light emitting layer (or on the electron transport layer, if the electron transport layer exists).

The electron injection layer is a layer which injects electrons from an electrode, and is preferably a compound which has a capability of transporting electrons, has an effect of injecting electrons from a cathode and an excellent effect of injecting electrons into a light emitting layer or a light emitting material, prevents excitons produced from the light emitting layer from moving to a hole injection layer, and is also excellent in the ability to form a thin film.

Specific examples of the electron injection layer include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto.

Examples of the metal complex compound include 8-hydroxy-quinolinato lithium, bis(8-hydroxyquinolinato)zinc, bis(8-hydroxy-quinolinato)copper, bis(8-hydroxyquinolinato)manganese, tris(8-hydroxyquinolinato)aluminum, tris(2-methyl-8-hydroxyquinolinato)-aluminum, tris(8-hydroxyquinolinato)gallium, bis(10-hydroxybenzo[h]-quinolinato)beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)(2-naphtholato)-gallium, and the like, but are not limited thereto.

Organic Light Emitting Device

The structure of the organic light emitting device according to the present disclosure is illustrated in FIGS. 1 and 2. FIG. 1 shows an example of an organic light emitting device comprising a substrate 1, an anode 2, a light emitting layer 3, and a cathode 4. FIG. 2 shows an example of an organic light emitting device comprising a substrate 1, an anode 2, a hole injection layer 5, a hole transport layer 6, an electron blocking layer 7, a light emitting layer 3, a hole blocking layer 8, an electron injection and transport layer 9, and a cathode 4.

The organic light emitting device according to the present disclosure can be manufactured by sequentially stacking the above-described structures. In this case, the organic light emitting device can be manufactured by depositing a metal, metal oxides having conductivity, or an alloy thereof on the substrate by using a PVD (physical vapor deposition) method such as a sputtering method or an e-beam evaporation method to form the anode, forming the respective layers described above thereon, and then depositing a material that can be used as the cathode thereon. In addition to such a method, the organic light emitting device can be manufactured by sequentially depositing from the cathode material to the anode material on a substrate in the reverse order of the above-mentioned configuration (WO 2003/012890). Further, the light emitting layer can be formed by subjecting hosts and dopants to a vacuum deposition method and a solution coating method. Herein, the solution coating method means a spin coating, a dip coating, a doctor blading, an inkjet printing, a screen printing, a spray method, a roll coating, or the like, but is not limited thereto.

On the other hand, the organic light emitting device according to the present disclosure can be a front side emission type, a back side emission type, or a double side emission type according to the used material.

Hereinafter, preferred examples of the present disclosure will be provided for a better understanding of the invention. However, these examples are presented for illustrative purposes only, and the scope of the present disclosure is not limited thereto.

Synthesis Example 1-1: Synthesis of Compound 1-1

Step 1) Preparation of Intermediate A

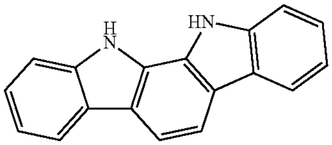

+

-continued

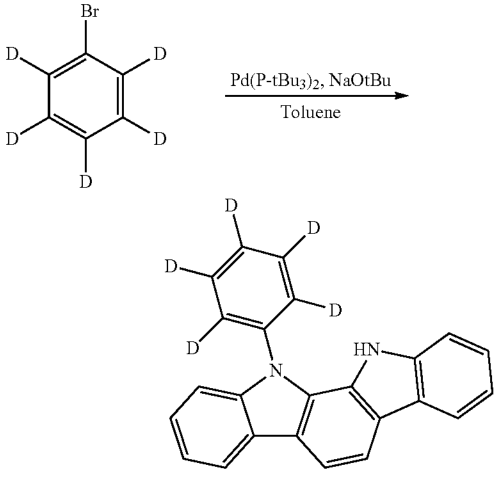

A 11,12-dihydroindolo[2,3-a]carbazole (15.0 g, 58.5 mmol), 1-bromobenzene-2,3,4,5,6-d5 (10.4 g, 64.4 mmol), bis(tri-tert-butyl-phosphine)palladium(0) ($Pd(P-t-Bu_3)_2$) (0.6 g, 1.2 mmol), sodium tert-butoxide (NaOtBu)(8.4 g, 87.8 mmol), and toluene 500 ml were added to a three-necked flask, and the mixture was stirred at reflux under an argon atmosphere for 8 hours. After completion of the reaction, the reaction temperature was cooled to room temperature, then $H_2O$ was added, and the reaction solution was transferred to a separatory funnel, and extracted. The extract was dried over $MgSO_4$ and concentrated, and then the sample was purified by silica gel column chromatography to give 13.2 g of Intermediate A. (Yield: 67%, MS [M+H]+=337)

Step 2) Synthesis of Compound 1-1

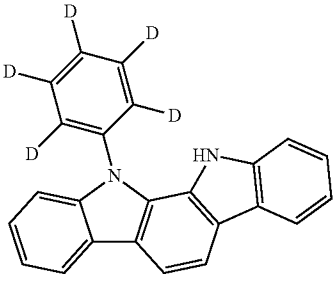

A

+

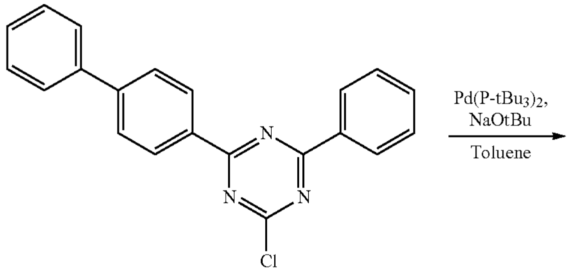

a

-continued

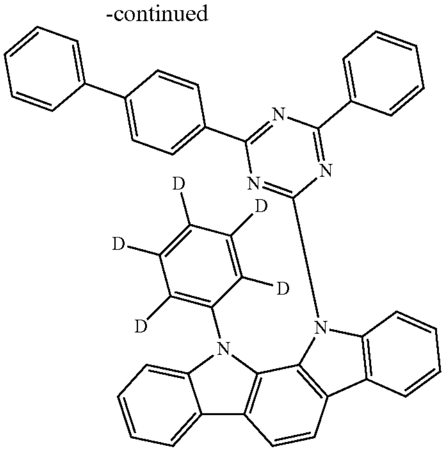

1-1

Intermediate A (13.0 g, 38.5 mmol), Compound a (14.6 g, 42.4 mmol), bis(tri-tert-butylphosphine)palladium(0) (0.4 g, 0.8 mmol), sodium tert-butoxide (5.6 g, 57.8 mmol) and xylene 400 ml were added to a three-necked flask, and the mixture was stirred at room temperature under an argon atmosphere for 8 hours. After completion of the reaction, the reaction temperature was cooled to room temperature, then $H_2O$ was added, and the reaction solution was transferred to a separatory funnel, and extracted. The extract was dried over $MgSO_4$ and concentrated, and then the sample was purified by silica gel column chromatography and then purified by sublimation to give 7.9 g of Compound 1-1. (Yield: 32%, MS [M+H]+=644)

Synthesis Example 1-2: Synthesis of Compound 1-2

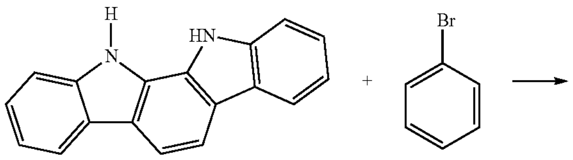

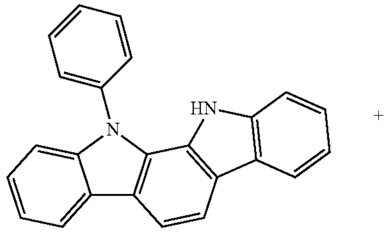

B

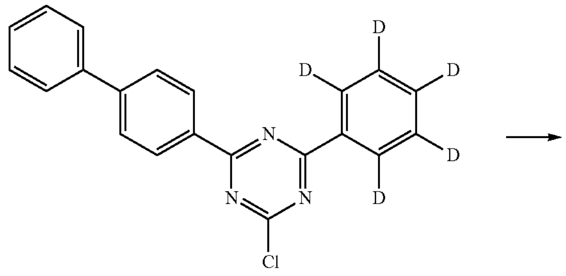

b

-continued

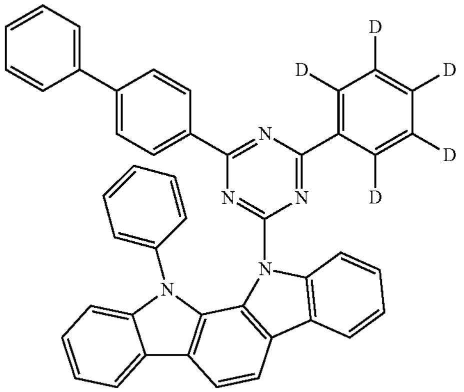

1-2

Compound 1-2 was prepared in the same manner as in the Preparation of Compound 1-1, except that in step 1 of Synthesis Example 1-1, bromobenzene was used instead of 1-bromobenzene-2,3,4,5,6-d5 to prepare Intermediate B, and in step 2, Compound b was used instead of Compound a. (MS$[M+H]^+$=644)

Synthesis Example 1-3: Synthesis of Compound 1-3

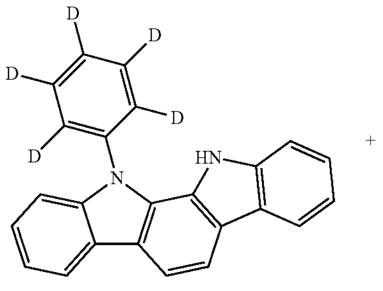

A

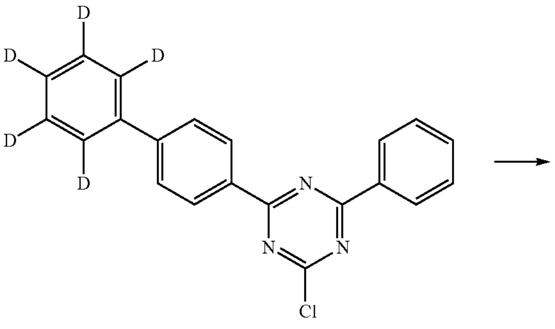

C

-continued

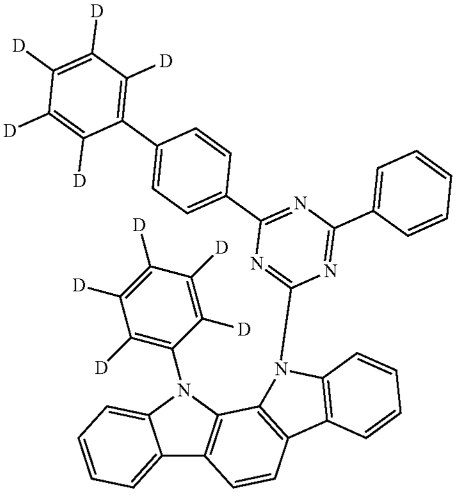

1-3

Compound 1-3 was prepared in the same manner as in the Preparation of Compound 1-1, except that in step 2 of Synthesis Example 1-1, Compound c was used instead of Compound a. (MS[M+H]$^+$=649)

Synthesis Example 1-4: Synthesis of Compound 1-4

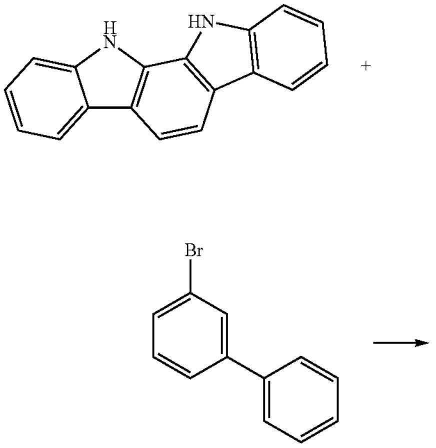

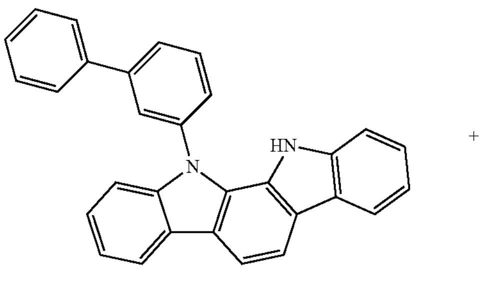

C

-continued

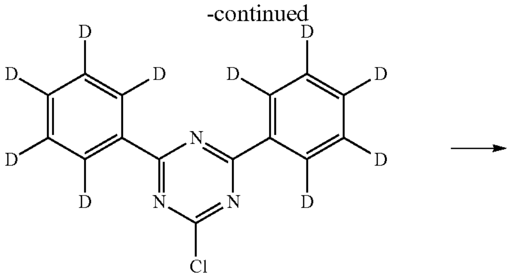

d

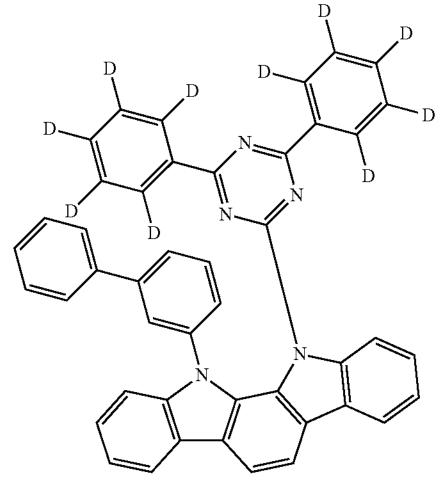

1-4

Compound 1-4 was prepared in the same manner as in the Preparation of Compound 1-1, except that in step 1 of Synthesis Example 1-1, 3-bromo-1,1'-biphenyl was used instead of 1-bromobenzene-2,3,4,5,6-d5 to prepare Intermediate C, and in step 2, Compound d was used instead of Compound a. (MS[M+H]*=649)

Synthesis Example 1-5: Synthesis of Compound 1-5

Step 1) Synthesis of Intermediate 1-5-1

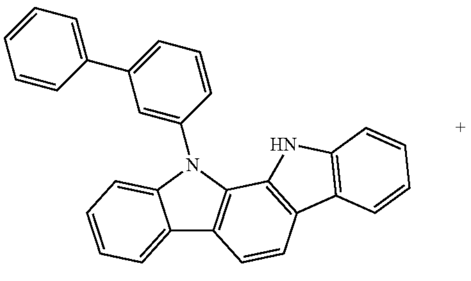

C

-continued

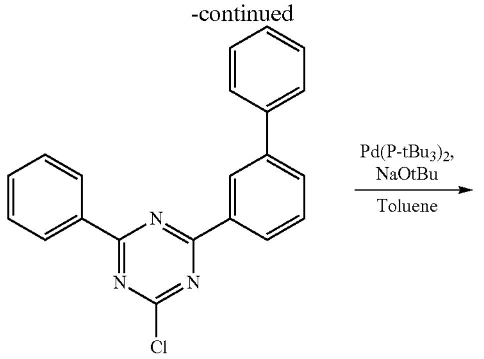

e

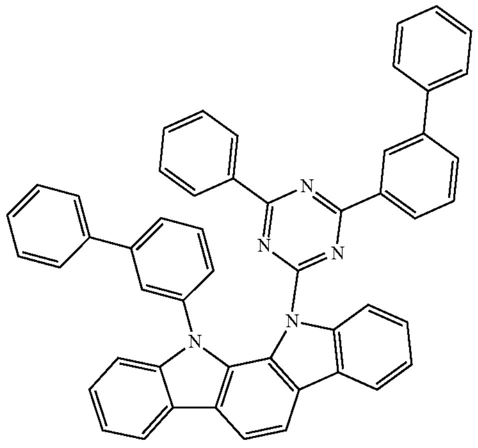

1-5-1

Intermediate C (15.0 g, 36.7 mmol), Compound e (13.9 g, 40.4 mmol), bis(tri-tert-butylphosphine)palladium(0) (0.4 g, 0.7 mmol), sodium tert-butoxide (5.3 g, 55.1 mmol) and xylene 400 ml were added to a three-necked flask, and the mixture was stirred at room temperature under an argon atmosphere for 8 hours. After completion of the reaction, the reaction temperature was cooled to room temperature, then $H_2O$ was added, and the reaction solution was transferred to a separatory funnel, and extracted. The extract was dried over $MgSO_4$ and concentrated, and then the sample was purified by silica gel column chromatography to give 17.1 g of Compound 1-5-1. (Yield: 65%, MS $[M+H]^+$=715)

Step 2) Synthesis of Compound 1-5

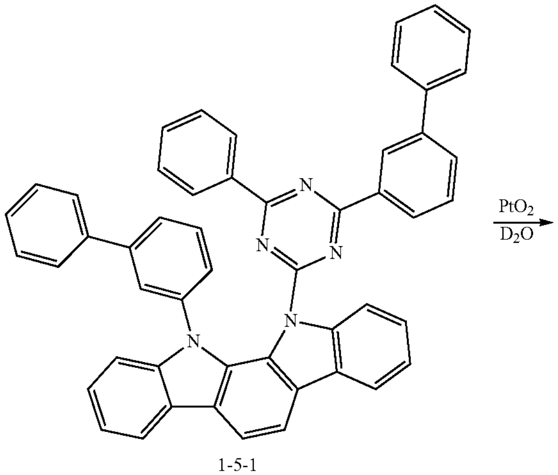

1-5-1

-continued

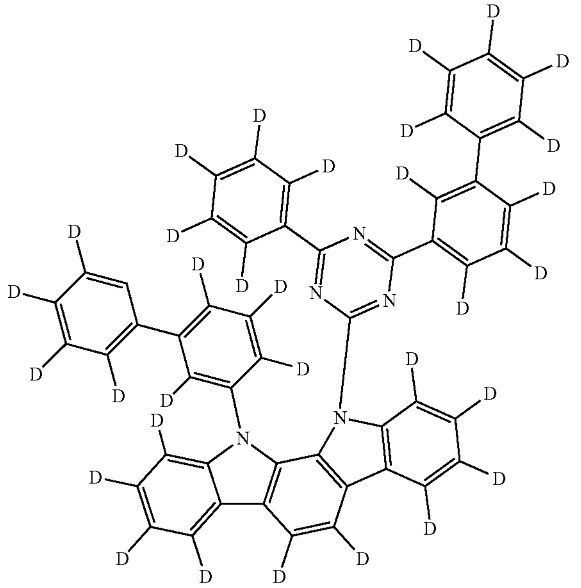

1-5

Compound 1-5-1 (10.0 g, 14.0 mmol), $PtO_2$ (1.0 g, 4.2 mmol), and 70 ml of D2O were added to a shaker tube, and then the tube was sealed and heated at 250° C. and 600 psi for 12 hours. After completion of the reaction, chloroform was added, and the reaction solution was transferred to a separatory funnel, and extracted. The extract was dried over $MgSO_4$ and concentrated, and then the sample was purified by silica gel column chromatography and purified by sublimation to give 4.4 g of Compound 1-5. (Yield: 42%, deuterium substitution rate: 82%, $MS[M+H]^+$=749).

Synthesis Example 1-6: Synthesis of Compound 1-6

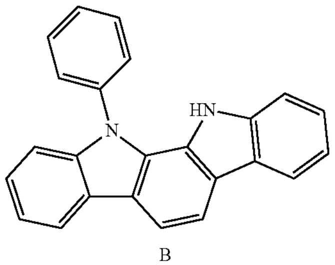

+

B

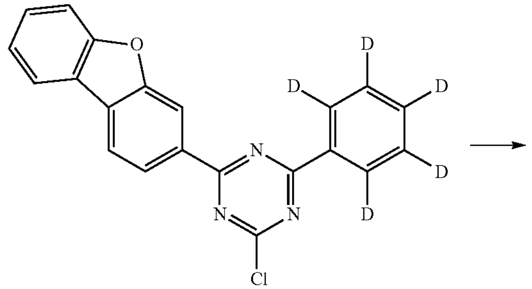

f

-continued

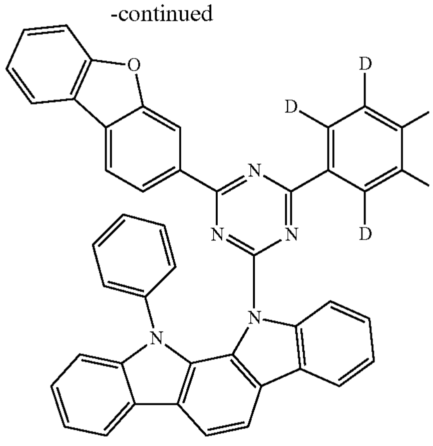

1-6

Compound 1-6 was prepared in the same manner as in the Preparation of Compound 1-1, except that in step 2 of Synthesis Example 1-1, Intermediate B was used instead of Intermediate A, and Compound f was used instead of Compound a. (MS[M+H]$^+$=658)

Synthesis Example 1-7: Synthesis of Compound 1-7

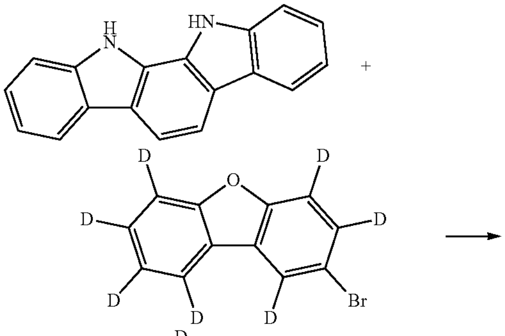

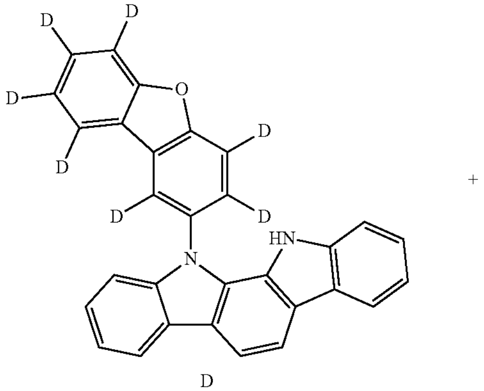

D

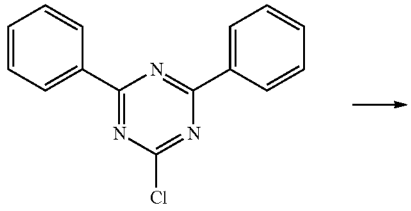

g

-continued

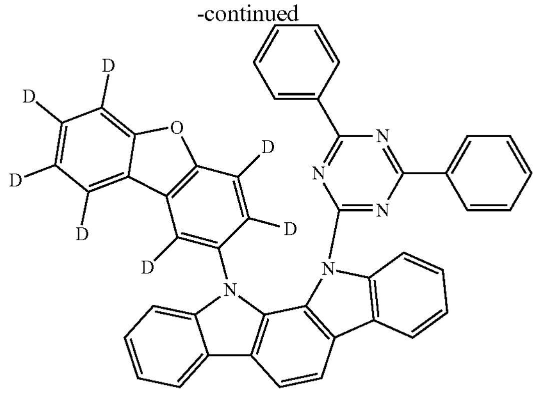

1-7

Compound 1-7 was prepared in the same manner as in the Preparation of Compound 1-1, except that in step 1 of Synthesis Example 1-1, 2-bromodibenzo[b,d] furan-1,3,4,6,7,8,9-d7 was used instead of 1-bromobenzene-2,3,4,5,6-d5 to prepare intermediate D, and in step 2, Compound g was instead of Compound a. (MS[M+H]$^+$=660)

Synthesis Example 1-8: Synthesis of Compound 1-8

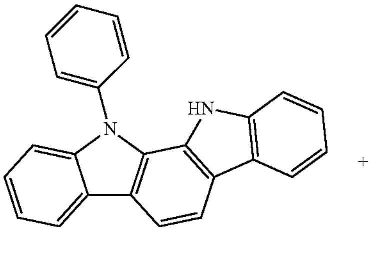

B

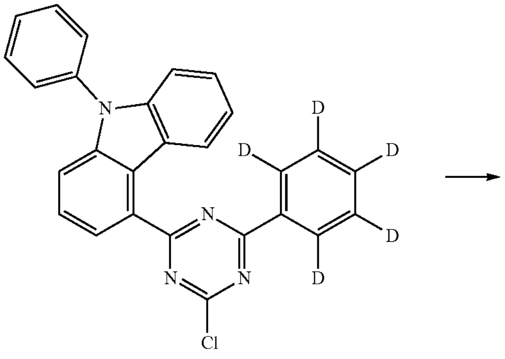

h

-continued

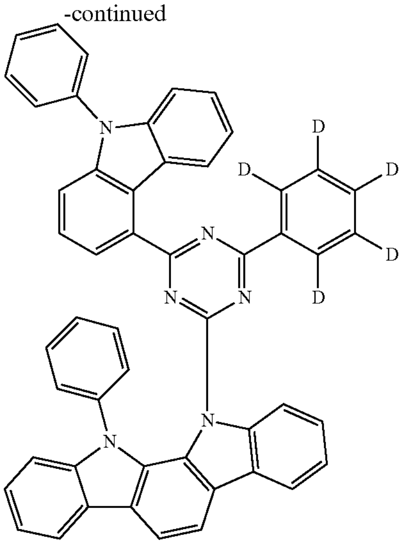

1-8

Compound 1-8 was prepared in the same manner as in the Preparation of Compound 1-1, except that in step 2 of Synthesis Example 1-1, Intermediate B was used instead of Intermediate A and Compound h was used instead of Compound a. (MS[M+H]+=733)

Synthesis Example 1-9: Synthesis of Compound 1-9

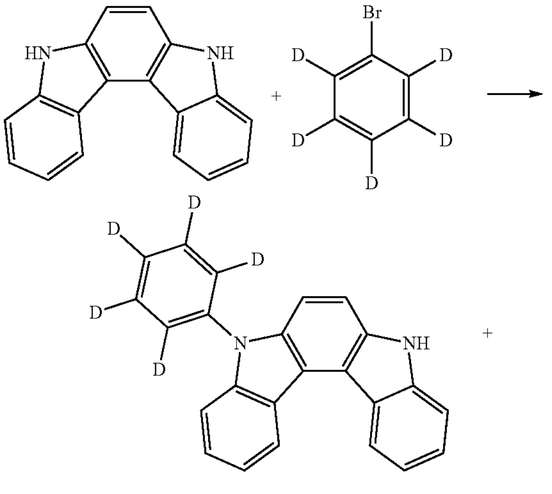

E

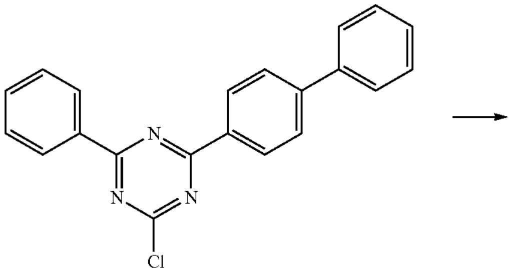

a

-continued

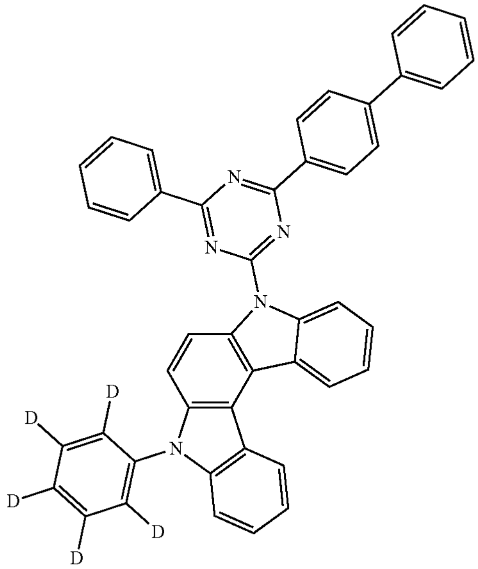

1-9

Compound 1-9 was prepared in the same manner as in the Preparation of Compound 1-1, except that in step 1 of Synthesis Example 1-1, 5,8-dihydroindolo[2,3-c]carbazole was used instead of 11,12-dihydroindolo[2,3-a]carbazole. (MS[M+H]+=644)

Synthesis Example 1-10: Synthesis of Compound 1-10

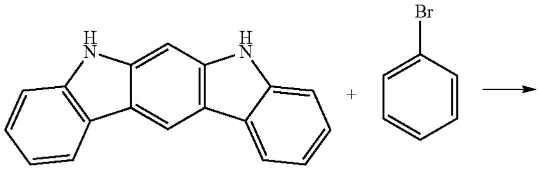

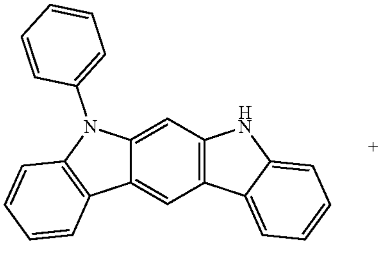

F

-continued

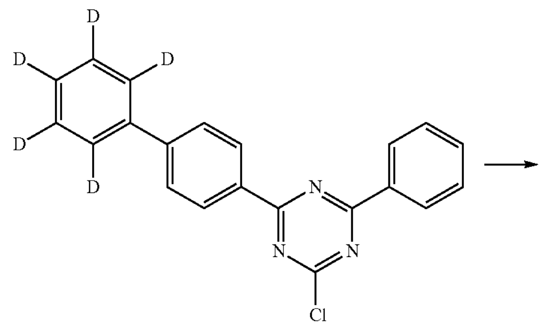

C

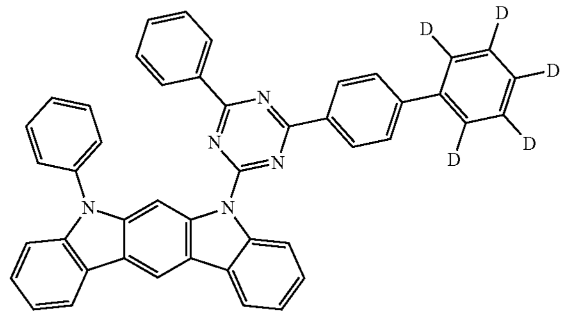

1-10

Compound 1-10 was prepared in the same manner as in the Preparation of Compound 1-1, except that in step 1 of Synthesis Example 1-1, 5,7-dihydroindolo[2,3-b]carbazole was used instead of 11,12-dihydroindolo[2,3-a]carbazole and bromobenzene was used instead of 1-bromobenzene-2,3,4,5,6-d5 to prepare intermediate F, and in step 2, Compound c was used instead of Compound a. (MS[M+H]$^+$=644)

Synthesis Example 1-11: Synthesis of Compound 1-11

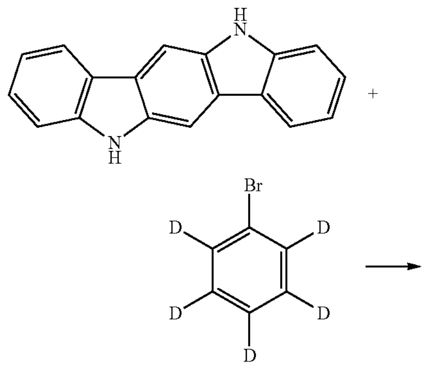

-continued

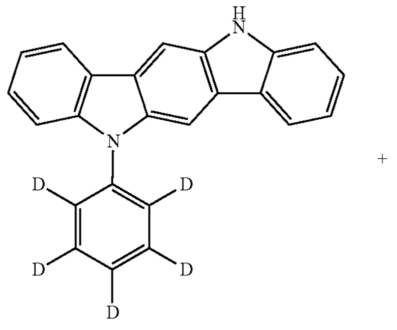

G

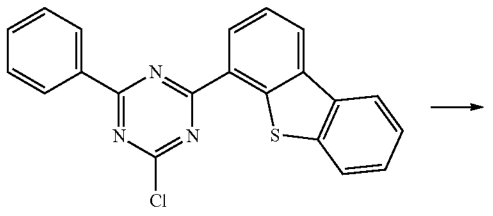

i

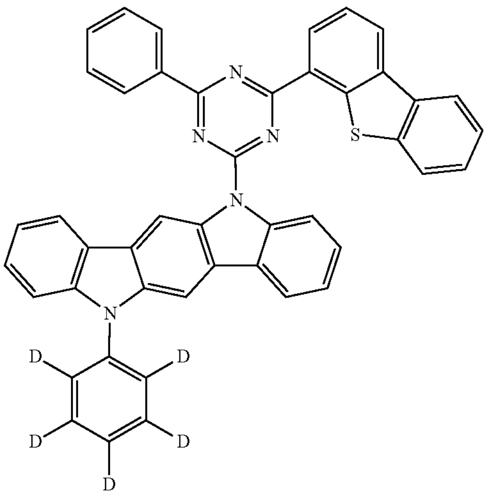

1-11

Compound 1-11 was prepared in the same manner as in the Preparation of Compound 1-1, except that in step 1 of Synthesis Example 1-1, 5,11-dihydroindolo[3,2-b]carbazole was used instead of 11,12-dihydroindolo[2,3-a]carbazole to prepare Intermediate G, and in step 2, Compound i was used instead of Compound a. (MS[M+H]$^+$=674)

Synthesis Example 1-12: Synthesis of Compound 1-12

Step 1) Synthesis of Intermediate H

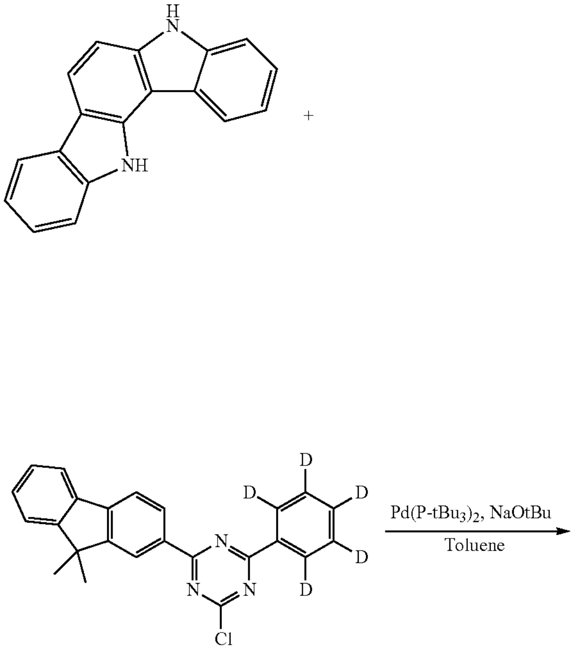

j

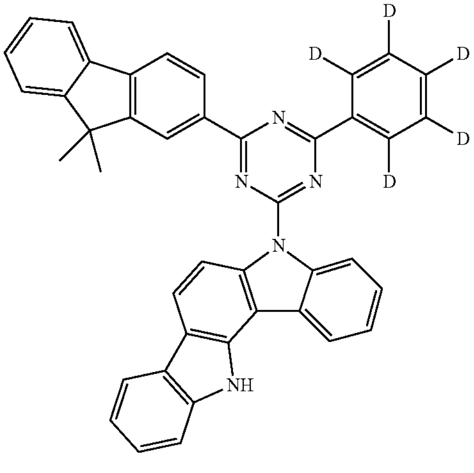

H 5,12-Dihydroindolo[3,2-a]carbazole (10.0 g, 39.0 mmol), Compound j (16.7 g, 42.9 mmol), bis(tri-tert-butylphosphine)palladium(0) (0.4 g, 0.8 mmol), sodium tert-butoxide (5.6 g, 58.5 mmol) and toluene 400 ml were added to a three-necked flask, and the mixture was stirred at room temperature under an argon atmosphere for 8 hours. After completion of the reaction, the reaction temperature was cooled to room temperature, then $H_2O$ was added, and the reaction solution was transferred to a separatory funnel, and extracted. The extract was dried over $MgSO_4$ and concentrated, and then the sample was purified by silica gel column chromatography to give 16.9 g of Intermediate H. (Yield: 71%, MS $[M+H]^+=608$)

Step 2) Synthesis of Compound 1-12

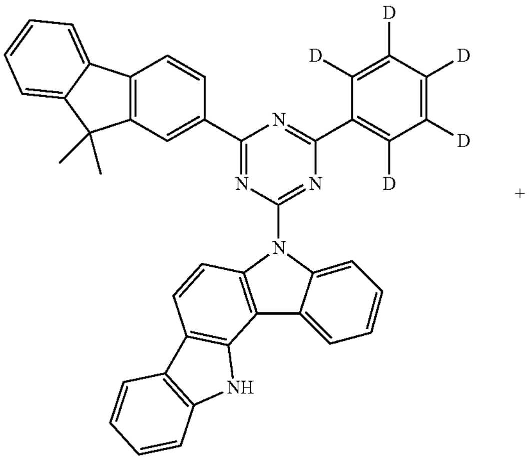

H

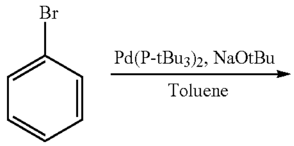

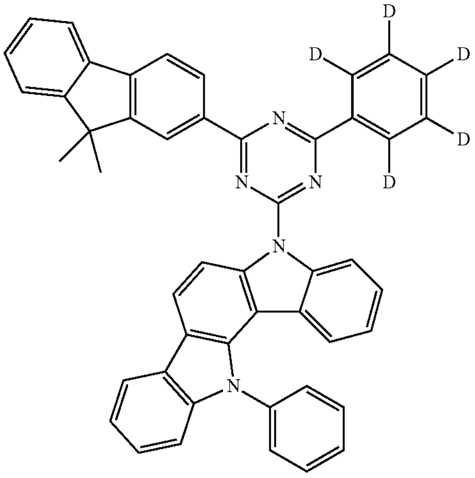

1-12

Intermediate H (15.0 g, 24.6 mmol), bromobenzene (4.3 g, 27.1 mmol), bis(tri-tert-butylphosphine)palladium(0) (0.3 g, 0.5 mmol), sodium tert-butoxide (3.6 g, 37.0 mmol) and xylene 250 ml were added to a three-necked flask, and the mixture was stirred at room temperature under an argon atmosphere for 8 hours. After completion of the reaction, the reaction temperature was cooled to room temperature, then $H_2O$ was added, and the reaction solution was transferred to a separatory funnel, and extracted. The extract was dried over $MgSO_4$ and concentrated, and then the sample was purified by silica gel column chromatography and purified by sublimation to give 5.4 g g of Compound 1-12. (Yield: 32%, MS $[M+H]^+=684$)

Synthesis Example 1-13: Synthesis of Compound 1-13

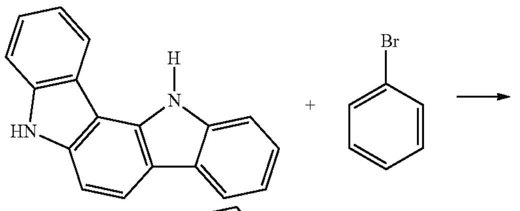

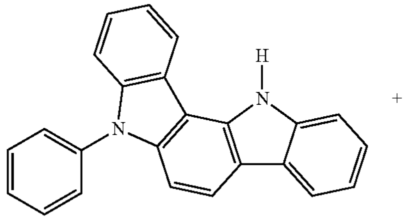

l

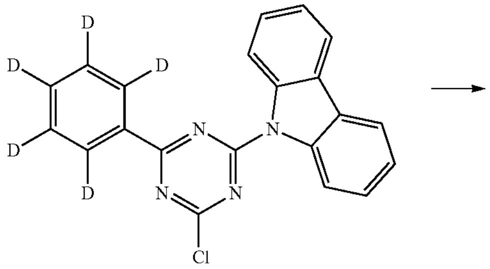

k

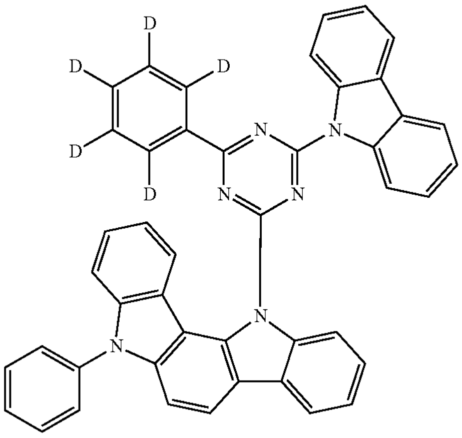

1-13

Compound 1-13 was prepared in the same manner as in the Preparation of Compound 1-1, except that in step 1 of Synthesis Example 1-1, 5,12-dihydroindolo[3,2-a]carbazole was used instead of 11,12-dihydroindolo[2,3-a]carbazole and bromobenzene was used instead of 1-bromobenzene-2,3,4,5,6-d5 to prepare Intermediate I, and in step 2, Compound k was used instead of Compound a. (MS[M+H]$^+$=657)

Synthesis Example 1-14: Synthesis of Compound 1-14

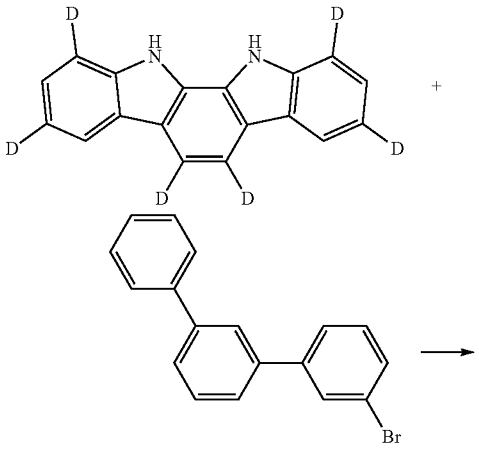

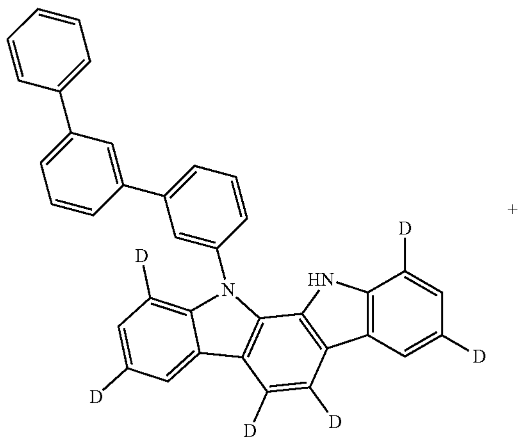

J

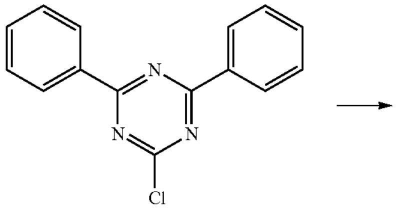

l

-continued

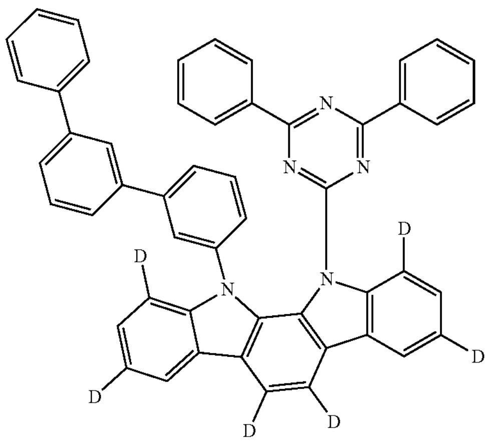

1-14

Compound 1-14 was prepared in the same manner as in the Preparation of Compound 1-1, except that in step 1 of Synthesis Example 1-1, 11,12-dihydroindolo[2,3-a]carbazole-1,3,5,6,8,10-d6 was used instead of 11,12-dihydroindolo[2,3-a]carbazole and 3-bromo-1,1':3',1"-terphenyl was used instead of 1-bromobenzene-2,3,4,5,6-d5 to prepare Intermediate J, and in step 2, Compound 1 was used instead of Compound a. (MS[M+H]$^+$=723)

Synthesis Example 1-15: Synthesis of Compound 1-15

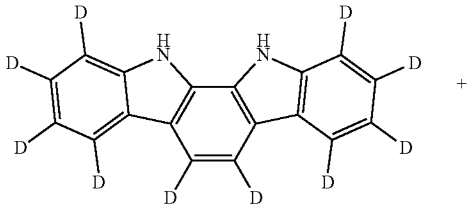

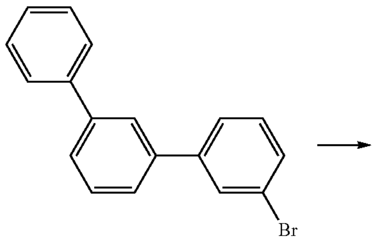

-continued

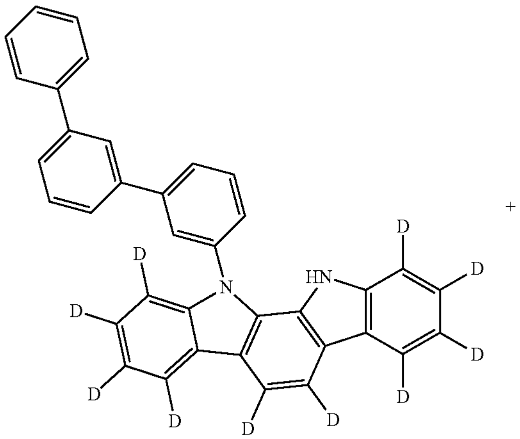

K

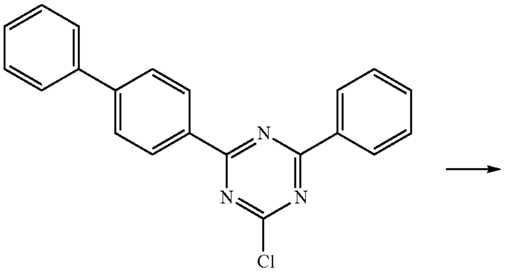

m

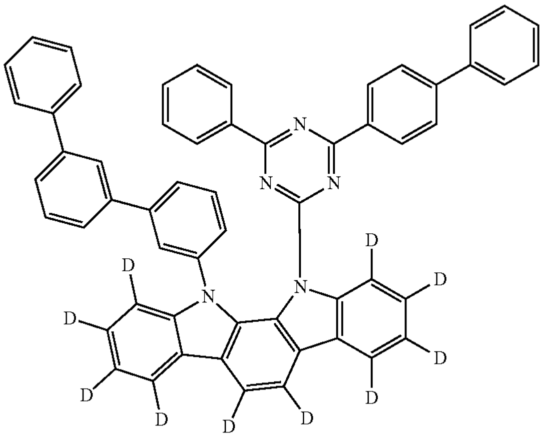

1-15

Compound 1-15 was prepared in the same manner as in the Preparation of Compound 1-1, except that in step 1 of Synthesis Example 1-1, 11,12-dihydroindolo[2,3-a]carbazole-1,2,3,4,5,6,7,8,9,10-d10 was used instead of 11,12-dihydroindolo[2,3-a]carbazole and 3-bromo-1,1':3',1"-terphenyl used instead of 1-bromobenzene-2,3,4,5,6-d5 to prepare Intermediate K, and in step 2, Compound m was used instead of Compound a. (MS[M+H]*=803)

Synthesis Example 2-1: Synthesis of Compound 2-1

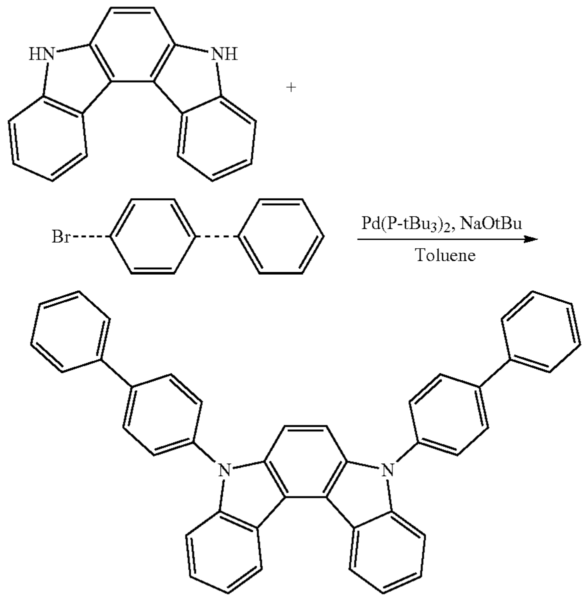

2-1

5,8-dihydroindolo[2,3-c]carbazole (15.0 g, 58.5 mmol) and 4-bromo-1,1'-biphenyl (30.0 g, 128.8 mmol) were added to 300 ml of toluene under a nitrogen atmosphere, and the mixture was stirred and refluxed. Then, sodium tert-butoxide (16.9 g, 175.6 mmol) and bis(tri-tert-butylphosphine) palladium(0) (0.9 g, 1.8 mmol) were added thereto. After the reaction for 12 hours, the mixture was cooled to room temperature, and the organic layer was separated using chloroform and water, and the organic layer was distilled. This was again dissolved in chloroform, washed twice with water, and then the organic layer was separated, anhydrous magnesium sulfate was added thereto, stirred, filtered, and the filtrate was distilled under reduced pressure. The concentrated compound was purified by silica gel column chromatography and then purified by sublimation to give 9.8 g of Compound 2-1. (Yield: 30%, MS: $[M+H]^+=562$)

Synthesis Example 2-2: Synthesis of Compound 2-2

Step 1) Synthesis of Intermediate 2-1-1

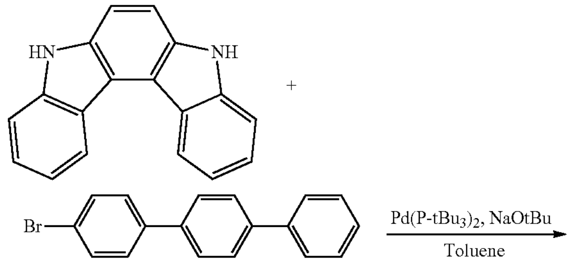

-continued

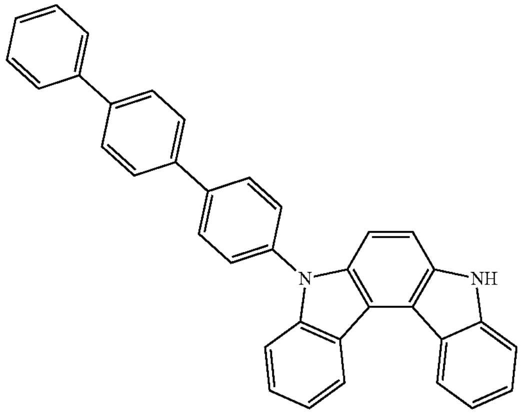

2-2-1

5,8-Dihydroindolo[2,3-c]carbazole (15.0 g, 58.5 mmol) and 4-bromo-1,1':4',1"-terphenyl (19.9 g, 64.4 mmol) were added to 300 ml of toluene under nitrogen atmosphere, and the mixture was stirred and refluxed. Then, sodium tert-butoxide (8.4 g, 87.8 mmol) and bis(tri-tert-butylphosphine) palladium(0) (0.9 g, 1.8 mmol) were added thereto. After the reaction for 11 hours, the mixture was cooled to room temperature, and the organic layer was separated using chloroform and water, and the organic layer was distilled. This was again dissolved in chloroform, washed twice with water, and then the organic layer was separated, anhydrous magnesium sulfate was added thereto, stirred, filtered, and the filtrate was distilled under reduced pressure. The concentrated compound was purified by silica gel column chromatography to give 19.3 g of Intermediate 2-2-1. (Yield: 68%, MS: $[M+H]^+=486$)

Step 2) Synthesis of Compound 2-2

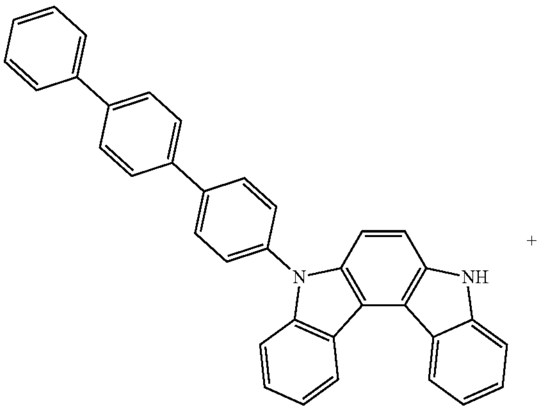

2-2-1

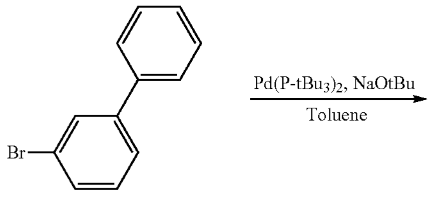

-continued

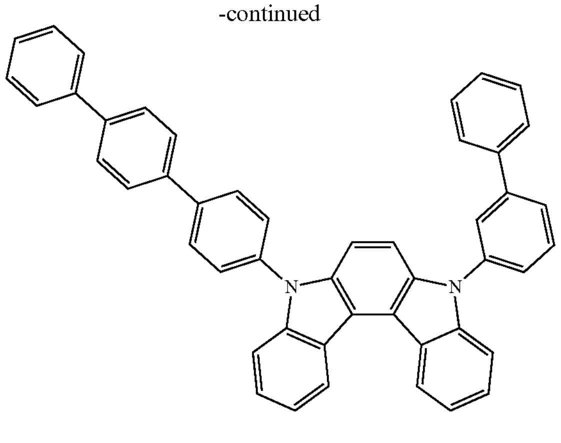

2-2

Intermediate 2-2-1 (15.0 g, 31.0 mmol) and 3-bromo-1,1'-biphenyl (7.9 g, 34.0 mmol) were added to 300 ml of toluene under a nitrogen atmosphere, and the mixture was stirred and refluxed. Then, sodium tert-butoxide (4.5 g, 46.4 mmol) and bis(tri-tert-butylphosphine) palladium(0) (0.5 g, 0.9 mmol) were added thereto. After the reaction for 7 hours, the mixture was cooled to room temperature, and the organic layer was separated using chloroform and water, and the organic layer was distilled. This was again dissolved in chloroform, washed twice with water, and then the organic layer was separated, anhydrous magnesium sulfate was added thereto, stirred, filtered, and the filtrate was distilled under reduced pressure. The concentrated compound was purified by silica gel column chromatography and then purified by sublimation to give 9.5 g of Compound 2-2. (Yield: 48%, MS: $[M+H]^+=638$)

Synthesis Example 2-3: Synthesis of Compound 2-3

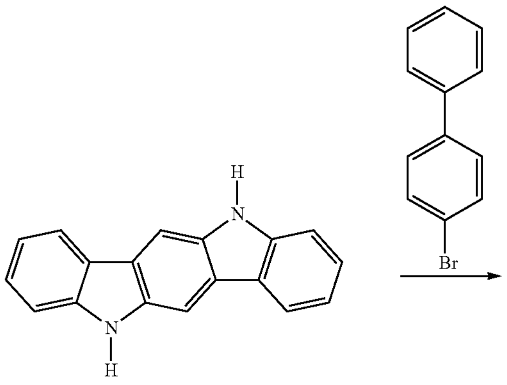

-continued

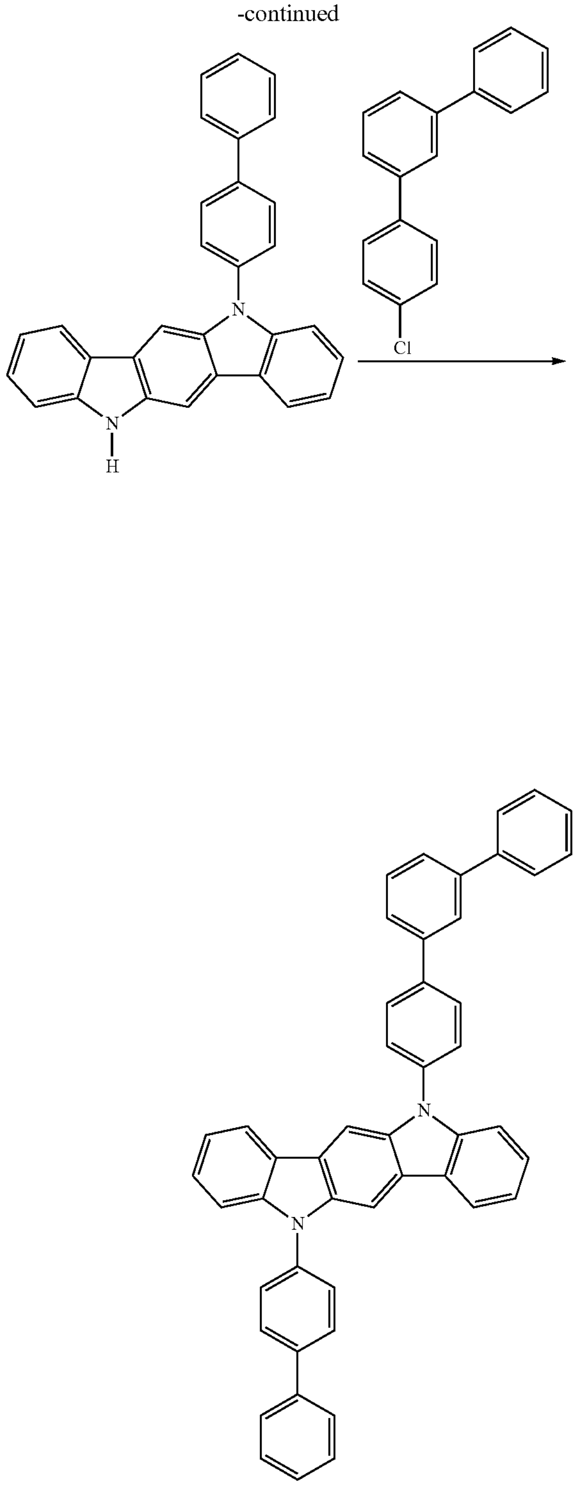

2-3

Compound 2-3 was prepared in the same manner as in the Preparation of Compound 2-2, except that in step 1 of Synthesis Example 2-2, 5,11-dihydroindolo[3,2-b]carbazole was used instead of 5,8-dihydroindolo[2,3-c]carbazole and 4-bromo-1,1'-biphenyl was used instead of 4-bromo-1,1':4',1"-terphenyl, and in step 2, 4-chloro-1,1':3',1"-terphenyl was used instead of 3-bromo-1,1'-biphenyl. ($MS[M+H]^+=638$)

Synthesis Example 2-4: Synthesis of Compound 2-4

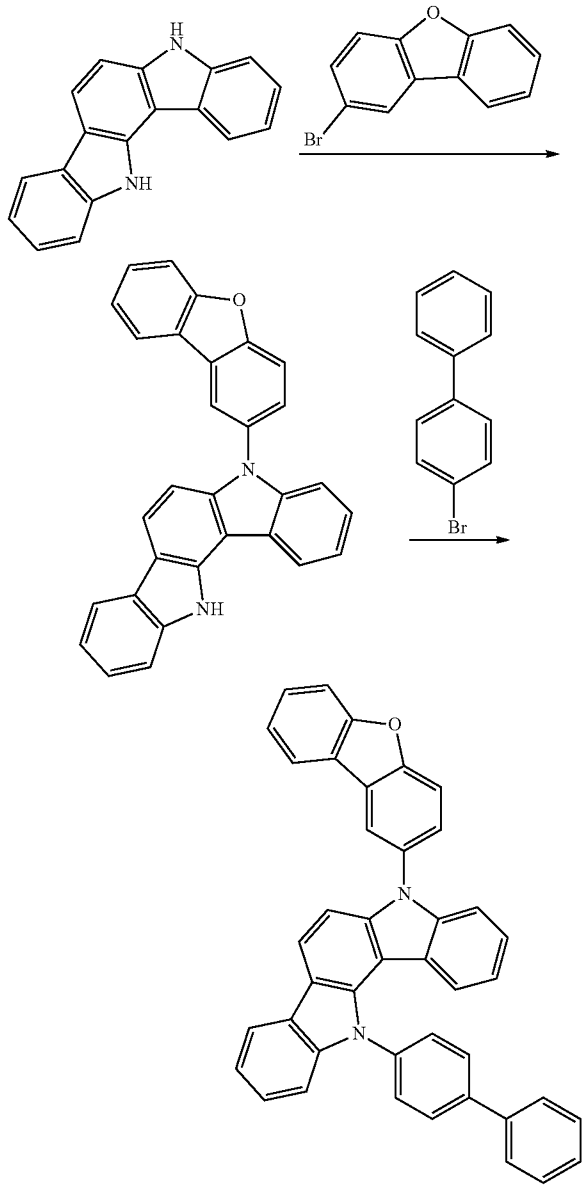

2-4

Compound 2-4 was prepared in the same manner as in the Preparation of Compound 2-2, except that in step 1 of Synthesis Example 2-2, 5,12-dihydroindolo[3,2-a]carbazole was used instead of 5,8-dihydroindolo[2,3-c]carbazole and 2-bromodibenzo[b,d]furan was used instead of 4-bromo-1,1':4',1''-terphenyl, and in step 2, 4-bromo-1,1'-biphenyl was used instead of 3-bromo-1,1'-biphenyl. (MS[M+H]$^+$=576)

Example 1

A glass substrate on which a thin film of ITO (indium tin oxide) was coated in a thickness of 1,400 Å was put into distilled water containing the detergent dissolved therein and ultrasonically washed. In this case, the detergent used was a product commercially available from Fisher Co. and the distilled water was one which had been twice filtered by using a filter commercially available from Millipore Co. The ITO was washed for 30 minutes, and ultrasonic washing was then repeated twice for 10 minutes by using distilled water. After the washing with distilled water was completed, the substrate was ultrasonically washed with isopropyl alcohol, acetone, and methanol solvent, and dried, after which it was transported to a plasma cleaner. Then, the substrate was cleaned with oxygen plasma for 5 minutes, and then transferred to a vacuum evaporator.

On the ITO transparent electrode thus prepared, the following compound HT-A and 5 wt. % of the following compound PD were thermally vacuum deposited to a thickness of 100 Å to form a hole injection layer, and then only the compound HT-A was deposited to a thickness of 1150 Å to form a hole transport layer. The following compound HT-B was thermally vacuum deposited thereon to a thickness of 450 Å as an electron blocking layer. Then, vacuum deposition was performed to a thickness of 400 Å by using Compound 1-1 and Compound 2-1 in a weight ratio of 40:60 as the host of the light emitting layer, and 8 wt. % of the following compound GD of the host as a dopant. Then, the following compound ET-A was vacuum-deposited to a thickness of 50 Å as a hole blocking layer. Then, the following compounds ET-B and Liq were thermally vacuum-deposited in a ratio of 2:1 to a thickness of 250 Å on the hole blocking layer, and LiF and magnesium were then vacuum deposited in a ratio of 1:1 to a thickness of 30 Å to sequentially form an electron transport layer and an electron injection layer. Magnesium and silver were deposited in a ratio of 1:4 to a thickness of 160 Å on the electron injection layer to form a cathode, thereby completing the manufacture of an organic light emitting device.

HT-A

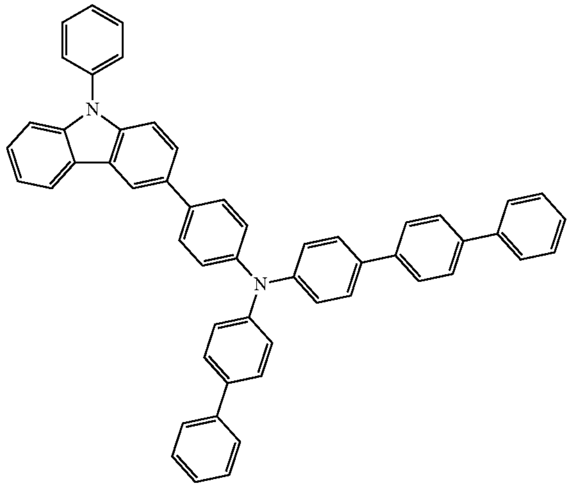

-continued

PD

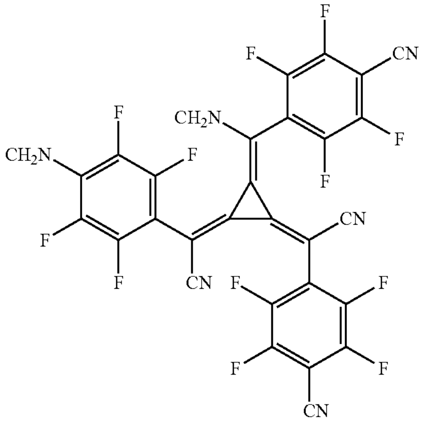

HT-B

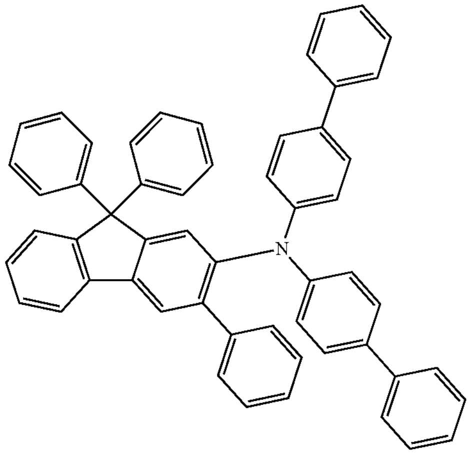

GD

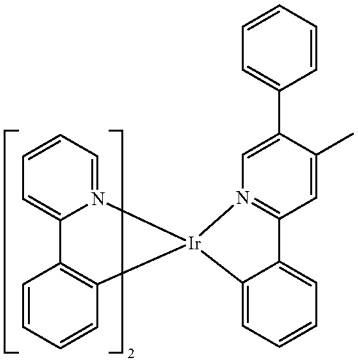

-continued

ET-A

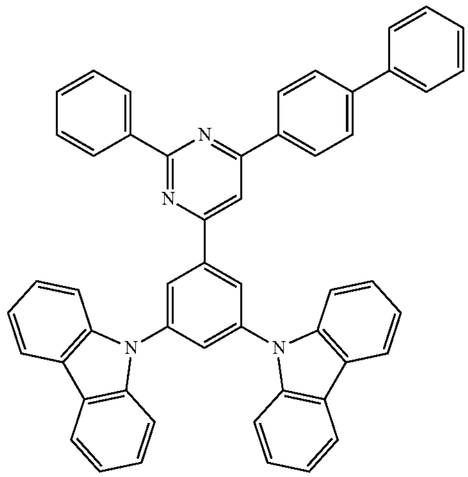

ET-B

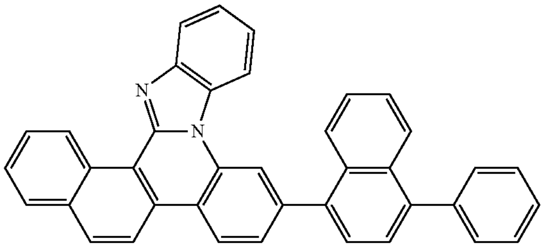

Liq

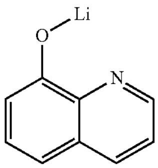

Examples 2 to 23, and Comparative Examples 1 to 20

The organic light emitting devices of Examples 2 to 23 and Comparative Examples 1 to 20 were respectively manufactured in the same manner as in Example 1, except that the host material was changed as shown in Table 1 below. In this case, when a mixture of two kinds of compounds was used as the host, the parenthesis means the weight ratio between the host compounds.

-continued
GH-1-A
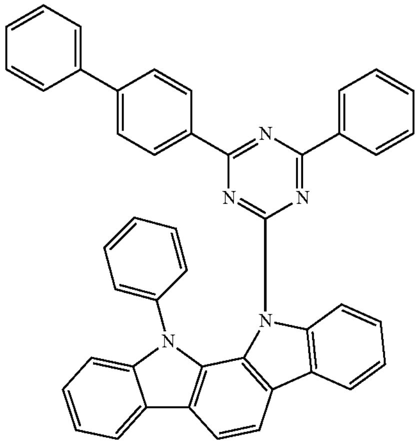
GH-1-B
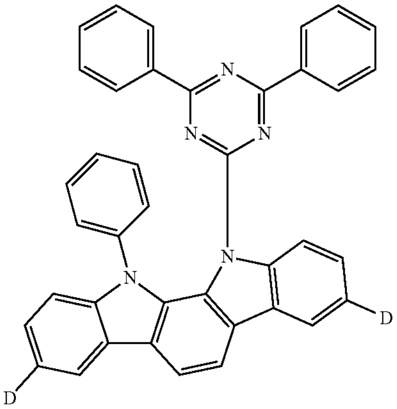
GH-1-C
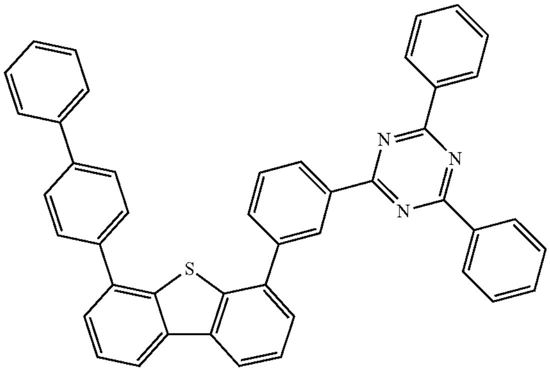
GH-2-A
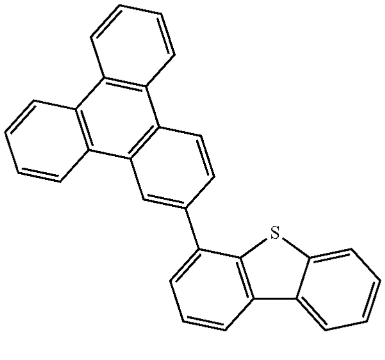
GH-2-B
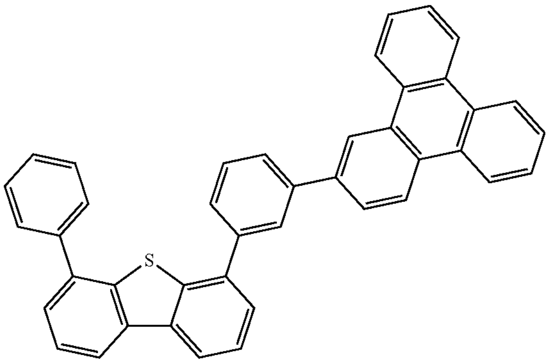
GH-2-C
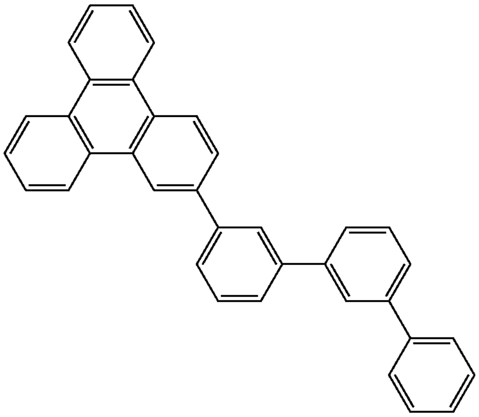
GH-2-D
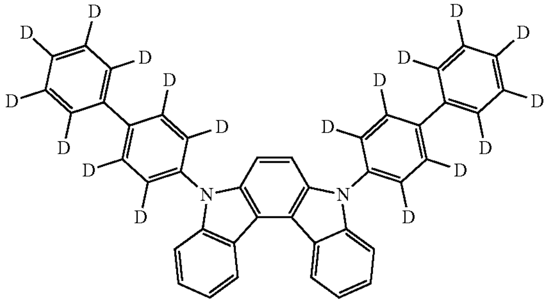
GH-2-E
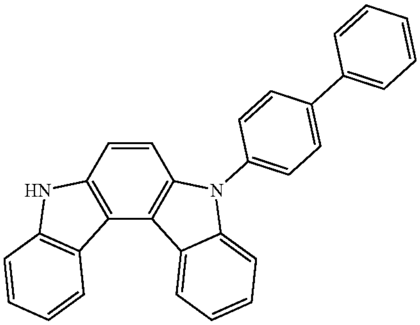

-continued

GH-2-F

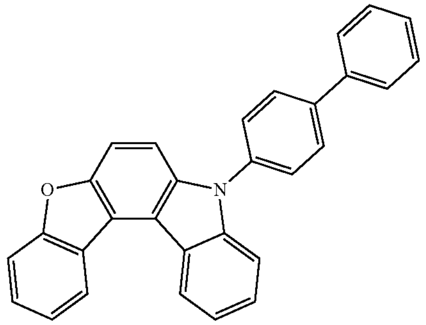

GH-2-G

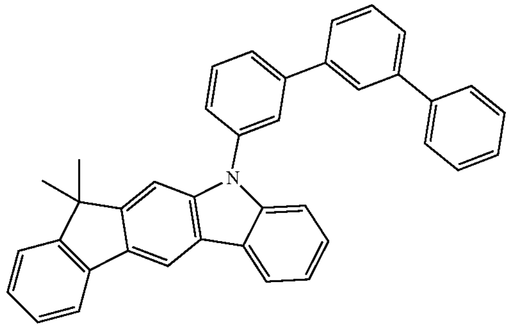

Experimental Example: Evaluation of Device Characteristics

The voltage, efficiency and lifetime (T95) were measured by applying a current to the organic light emitting devices manufactured in Examples and Comparative Examples, and the results are shown in Table 1 below. At this time, the voltage and efficiency were measured at a current density of 10 mA/$cm^2$, and T95 means the time (hr) required for the luminance to be reduced to 95% of the initial luminance at a current density of 20 mA/$cm^2$.

TABLE 1

| | | @ 10 mA/$cm^2$ | | @20 mA/$cm^2$ |
|---|---|---|---|---|
| | Host material | Voltage (V) | Efficiency (cd/A) | Lifetime (T95, hr) |
| Example 1 | Compound 1-1: Compound 2-1 (40:60) | 4.01 | 64.1 | 132 |
| Example 2 | Compound 1-2: Compound 2-1 (40:60) | 4.00 | 64.1 | 135 |
| Example 3 | Compound 1-3: Compound 2-1 (40:60) | 4.01 | 64.2 | 143 |
| Example 4 | Compound 1-4: Compound 2-1 (40:60) | 4.08 | 62.2 | 138 |
| Example 5 | Compound 1-5: Compound 2-1 (40:60) | 4.02 | 64.3 | 152 |
| Example 6 | Compound 1-6: Compound 2-1 (40:60) | 4.07 | 64.7 | 145 |
| Example 7 | Compound 1-7: Compound 2-1 (40:60) | 4.08 | 64.2 | 130 |
| Example 8 | Compound 1-8: Compound 2-1 (40:60) | 4.05 | 64.1 | 128 |
| Example 9 | Compound 1-9: Compound 2-1 (40:60) | 4.17 | 63.7 | 133 |
| Example 10 | Compound 1-10: Compound 2-1 (40:60) | 4.16 | 64.2 | 130 |
| Example 11 | Compound 1-11: Compound 2-1 (40:60) | 4.13 | 63.8 | 131 |
| Example 12 | Compound 1-12: Compound 2-1 (40:60) | 4.19 | 64.7 | 127 |
| Example 13 | Compound 1-13: Compound 2-1 (40:60) | 4.21 | 62.9 | 137 |
| Example 14 | Compound 1-14: Compound 2-1 (40:60) | 4.03 | 65.1 | 138 |
| Example 15 | Compound 1-15: Compound 2-1 (40:60) | 4.07 | 64.9 | 141 |
| Example 16 | Compound 1-1: Compound 2-1 (40:60) | 4.03 | 64.6 | 135 |
| Example 17 | Compound 1-2: Compound 2-2 (40:60) | 4.02 | 64.5 | 130 |
| Example 18 | Compound 1-2: Compound 2-3 (40:60) | 4.07 | 63.1 | 122 |
| Example 19 | Compound 1-3: Compound 2-3 (40:60) | 4.08 | 63.2 | 128 |
| Example 20 | Compound 1-4: Compound 2-3 (40:60) | 4.09 | 63.3 | 125 |
| Example 21 | Compound 1-5: Compound 2-4 (40:60) | 4.11 | 64.1 | 141 |
| Example 22 | Compound 1-6: Compound 2-4 (40:60) | 4.18 | 64.0 | 130 |
| Example 23 | Compound 1-10: Compound 2-4 (30:70) | 4.21 | 63.1 | 119 |
| Comparative Example 1 | Compound 1-1 | 4.71 | 54.1 | 91 |
| Comparative Example 2 | Compound 1-6 | 4.67 | 52.7 | 84 |
| Comparative Example 3 | Compound 2-1 | 7.62 | 7.5 | 5 |
| Comparative Example 4 | Compound 2-3 | 7.82 | 5.8 | 3 |
| Comparative Example 5 | Compound GH-1-A: Compound 2-1 (40:60) | 4.02 | 62.5 | 82 |
| Comparative Example 6 | Compound GH-1-B: Compound 2-1 (40:60) | 4.23 | 61.7 | 71 |
| Comparative Example 7 | Compound GH-1-C: Compound 2-1 (40:60) | 4.65 | 56.6 | 85 |
| Comparative Example 8 | Compound GH-1-A: Compound 2-2 (40:60) | 4.07 | 62.3 | 86 |
| Comparative Example 9 | Compound GH-1-B: Compound 2-3 (40:60) | 4.35 | 58.2 | 65 |
| Comparative Example 10 | Compound 1-1: Compound GH-2-A (40:60) | 4.51 | 56.6 | 90 |

TABLE 1-continued

| | Host material | @ 10 mA/cm² Voltage (V) | Efficiency (cd/A) | @20 mA/cm² Lifetime (T95, hr) |
|---|---|---|---|---|
| Comparative Example 11 | Compound 1-1: Compound GH-2-B (40:60) | 4.57 | 57.7 | 92 |
| Comparative Example 12 | Compound 1-1: Compound GH-2-C (40:60) | 4.48 | 55.7 | 93 |
| Comparative Example 13 | Compound 1-6: Compound GH-2-B (40:60) | 4.51 | 56.5 | 103 |
| Comparative Example 14 | Compound GH-1-A: Compound GH-2-D (40:60) | 4.02 | 62.5 | 82 |
| Comparative Example 15 | Compound 1-1: Compound GH-2-E (40:60) | 5.51 | 31.0 | 21 |
| Comparative Example 16 | Compound 1-1: Compound GH-2-F (40:60) | 5.23 | 42.3 | 40 |
| Comparative Example 17 | Compound 1-1: Compound GH-2-G (40:60) | 5.07 | 44.5 | 51 |
| Comparative Example 18 | Compound GH-1-A | 4.71 | 54.2 | 60 |
| Comparative Example 19 | Compound GH-1-B | 4.83 | 50.3 | 53 |
| Comparative Example 20 | Compound GH-2-A | 7.76 | 6.7 | 8 |

In the present disclosure, both the first compound of Chemical Formula 1 and the second compound of Chemical Formula 2 have an indolocarbazole skeleton. Here, the first compound has a strong ability to transport electrons by containing a triazine group, and the second compound has a strong ability to transport holes, and thus has properties suitable for using a mixture of two materials as a host. In particular, since both materials have an indolocarbazole structure, they are well mixed with each other and are advantageous for the formation of exciplex, and are advantageous in effectively transferring energy to a dopant. At this time, the first compound becomes an anion and the second compound becomes a cation to form an exciplex, and the first compound, which becomes an anion state, has a more unstable state. By substituting five or more deuteriums therein, the first compound has a reduced vibration energy even in an anion state and a more stable energy.

Consequently, as can be seen in Table 1, Examples 1 to 23 in which the first compound of Chemical Formula 1 and the second compound of Chemical Formula 2 were used together as a light emitting layer of an organic light emitting device in the present disclosure exhibited significantly improved low voltage, high efficiency, and long life characteristics.

The invention claimed is:

1. An organic light emitting device, comprising:

an anode;

a cathode; and a light emitting layer interposed between the anode and the cathode, wherein the light emitting layer comprises a first compound of the following Chemical Formula 1 and a second compound of the following Chemical Formula 2-3:

<Chemical Formula 1>

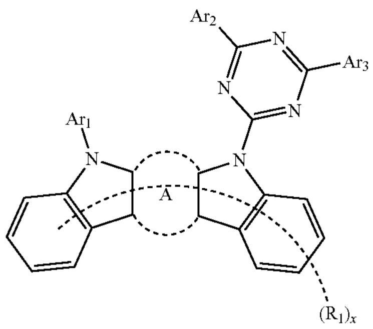

wherein in the Chemical Formula 1:

A is a benzene ring fused with two adjacent pentagonal rings, respectively;

$Ar_1$ and $Ar_2$ are each independently a phenyl, biphenyl, terphenyl, dibenzofuranyl, dibenzothiophenyl, fluorenyl, 9,9-dimethylfluorenyl, 9,9-diphenylfluorenyl, carbazol-9-yl, or 9-phenyl-9H-carbazolyl, wherein the phenyl, biphenyl, terphenyl, dibenzofuranyl, dibenzothiophenyl, fluorenyl, 9,9-dimethylfluorenyl, 9,9-diphenylfluorenyl, carbazol-9-yl, or 9-phenyl-9H-carbazolyl is unsubstituted or substituted with deuterium;

$Ar_3$ is phenyl, wherein the phenyl is unsubstituted or substituted with deuterium;

each $R_1$ is independently hydrogen or deuterium; and x is an integer of 10;

provided that at least one of $Ar_1$ to $Ar_3$, and $R_1$ is substituted with at least one deuterium, or at least one of $R_1$ is deuterium, and the first compound comprises at least 5 deuteriums;

<Chemical Formula 2-3>

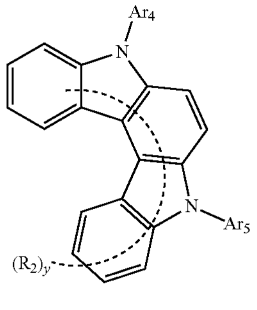

wherein in the Chemical Formula 2-3:

$Ar_4$ and $Ar_5$ are each independently phenyl, biphenyl, or terphenyl, each of which is unsubstituted;

each $R_2$ is independently hydrogen or deuterium; and y is an integer of 10.

2. The organic light emitting device according to claim 1, wherein the Chemical Formula 1 is any one selected from the group consisting of the following Chemical Formulas 1-1 to 1-6:

<Chemical Formula 1-1>

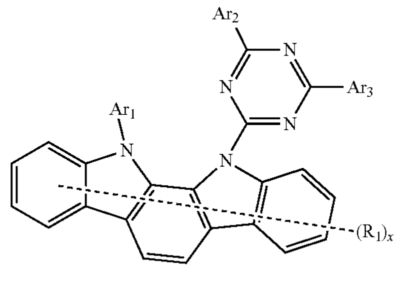

<Chemical Formula 1-2>

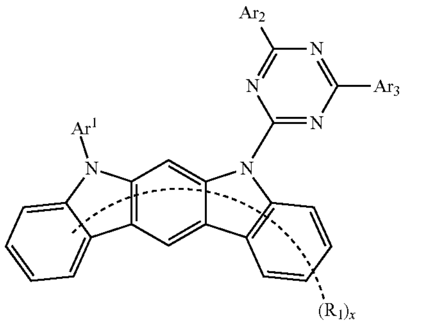

<Chemical Formula 1-3>

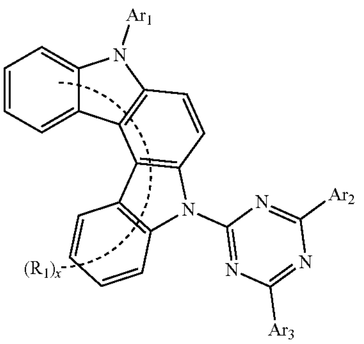

<Chemical Formula 1-4>

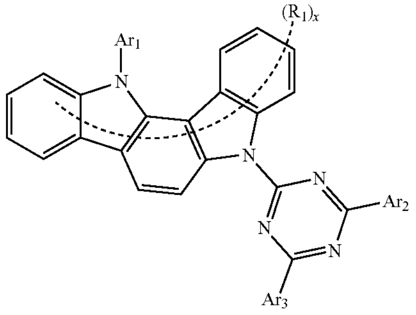

-continued

<Chemical Formula 1-5>

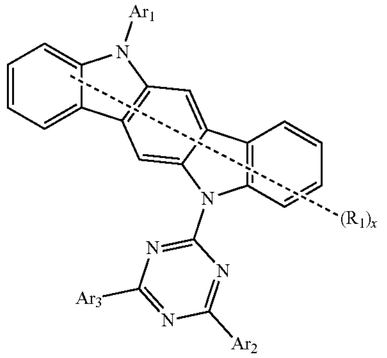

<Chemical Formula 1-6>

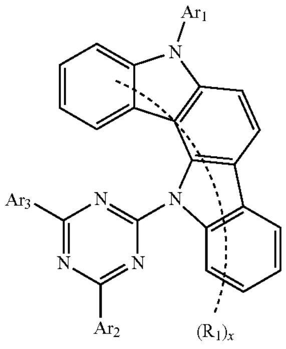

wherein in the Chemical Formulas 1-1 to 1-6, $Ar_1$ to $Ar_3$, $R_1$, and x are as defined in claim 1.

3. The organic light emitting device according to claim 1, wherein at least one of $Ar_1$ and $Ar_2$ is phenyl, and any remaining are each independently phenyl, biphenyl, terphenyl, dibenzofuranyl, dibenzothiophenyl, fluorenyl, 9,9-dimethylfluorenyl, 9,9-diphenylfluorenyl, carbazol-9-yl, or 9-phenyl-9H-carbazolyl.

4. The organic light emitting device according to claim 1, wherein at least one of $Ar_1$ and $Ar_2$ is phenyl substituted with 5 deuteriums, and any remaining are phenyl, biphenyl, terphenyl, dibenzofuranyl, dibenzothiophenyl, fluorenyl, 9,9-dimethylfluorenyl, 9,9-diphenylfluorenyl, carbazol-9-yl, or 9-phenyl-9H-carbazolyl, each of which is unsubstituted.

5. The organic light emitting device according to claim 1, wherein one of $Ar_1$ and $Ar_2$ is biphenyl, terphenyl, dibenzofuranyl, dibenzothiophenyl, fluorenyl, 9,9-dimethylfluorenyl, 9,9-diphenylfluorenyl, carbazol-9-yl, or 9-phenyl-9H-carbazolyl, each of which is substituted with 5 or more deuteriums, and the remaining are independently unsubstituted phenyl or unsubstituted biphenyl.

6. The organic light emitting device according to claim 1, wherein one of $Ar_1$ and $Ar_2$ is phenyl, biphenyl, terphenyl, dibenzofuranyl, dibenzothiophenyl, fluorenyl, 9,9-dimethylfluorenyl, 9,9-diphenylfluorenyl, carbazol-9-yl, or 9-phenyl-9H-carbazolyl, $Ar_3$ is phenyl, and the $Ar_1$ to $Ar_3$ are completely substituted with deuterium.

7. The organic light emitting device according to claim 1, wherein all of the $R_1$ are hydrogen.

8. The organic light emitting device according to claim 1, wherein at least 5 of the $R_1$ are deuterium, and any remaining is hydrogen.

9. The organic light emitting device according to claim 1, wherein the first compound is any one compound selected from the group consisting of the following compounds:
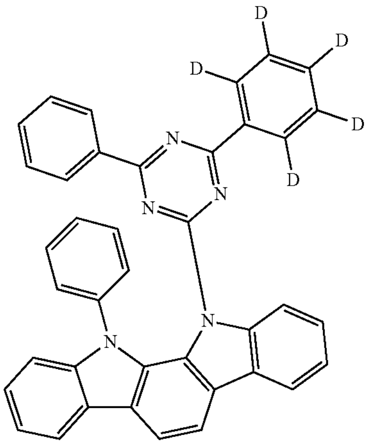
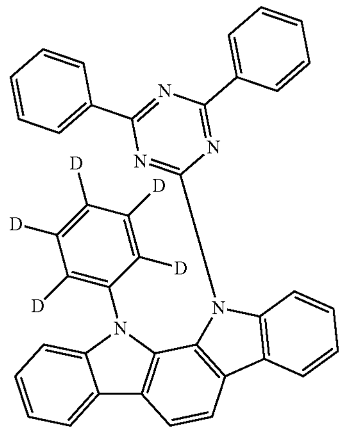
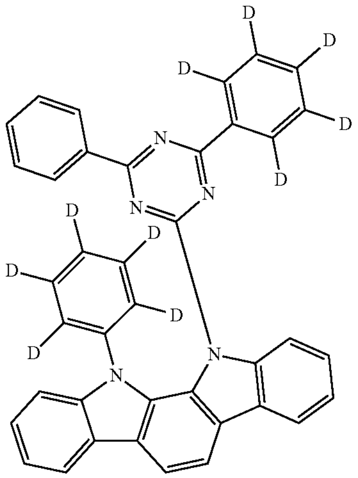
-continued
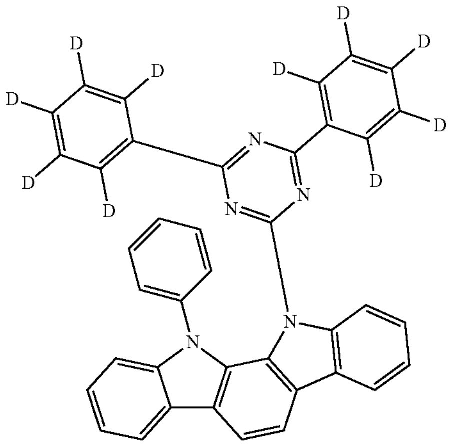
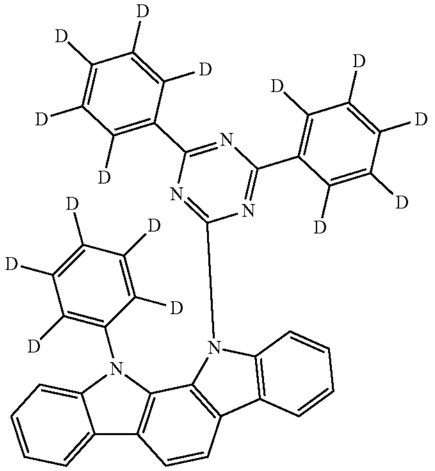
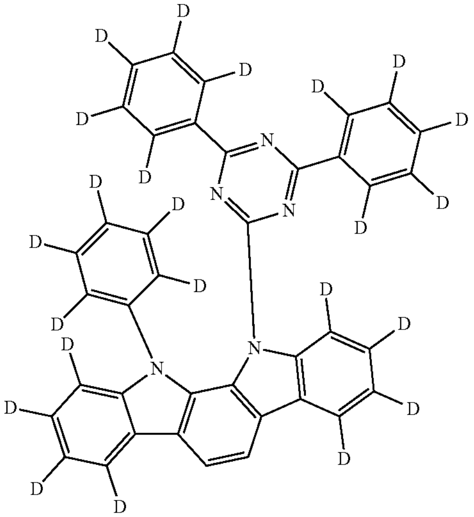

-continued
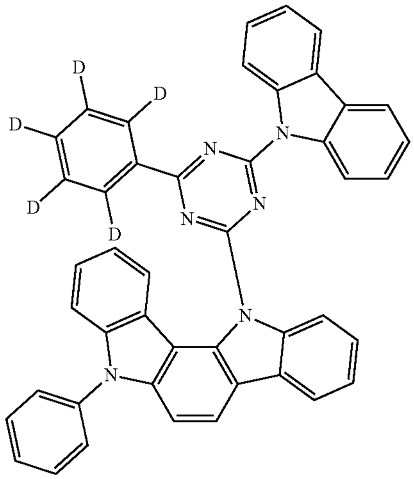
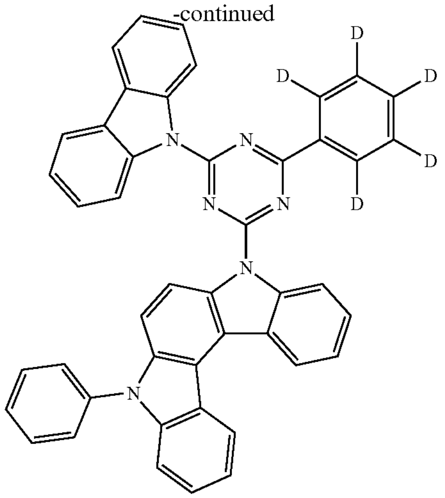
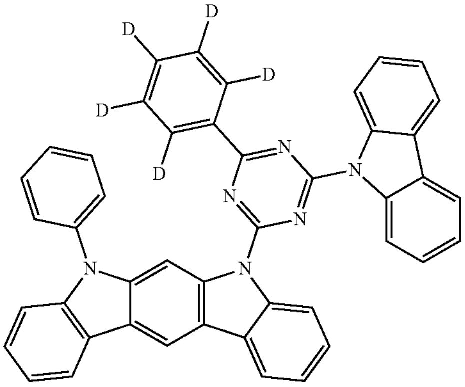
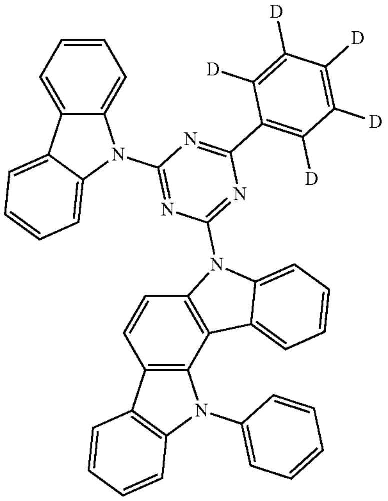
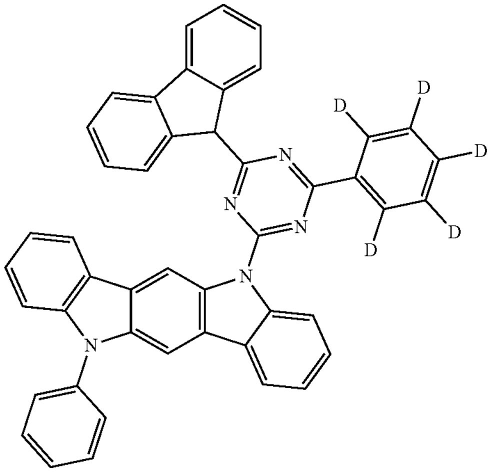
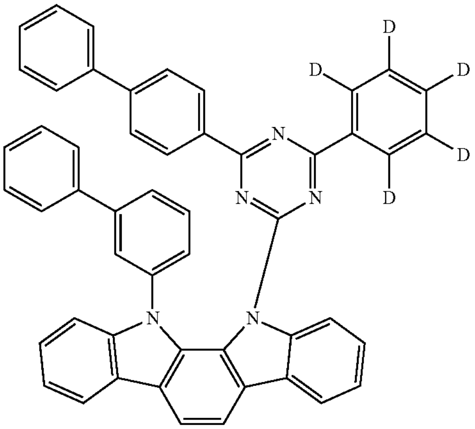

-continued
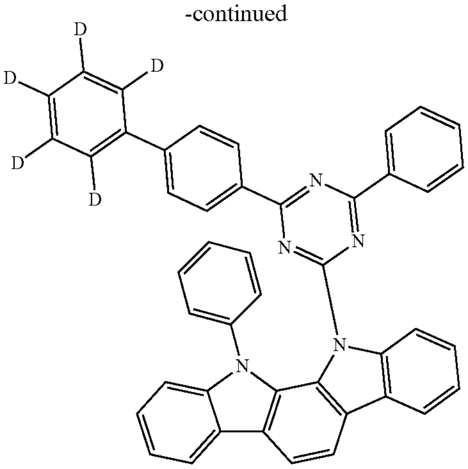
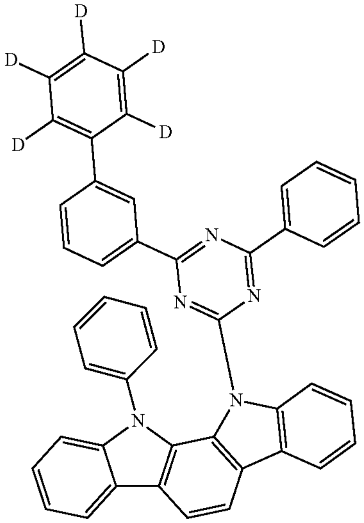
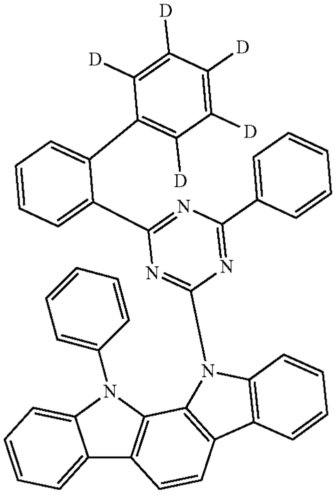
-continued
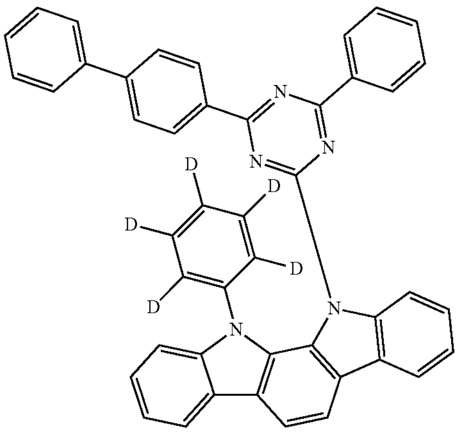
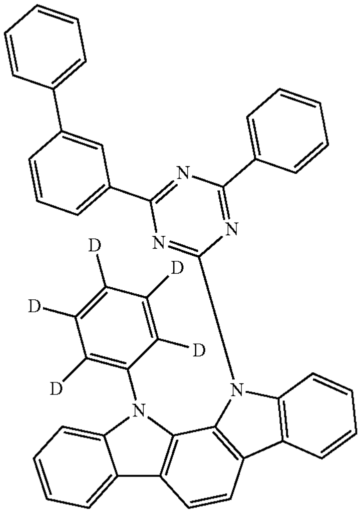
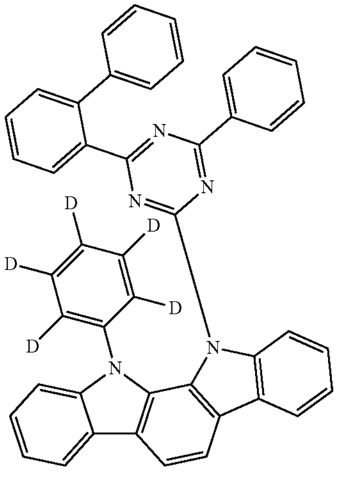

-continued
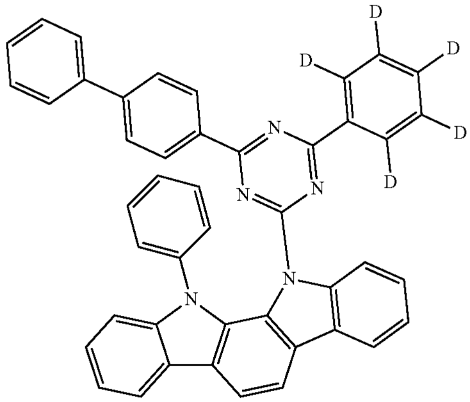
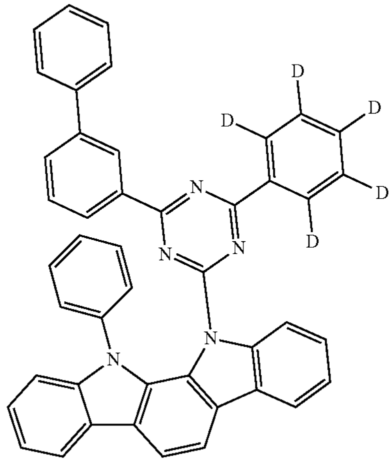
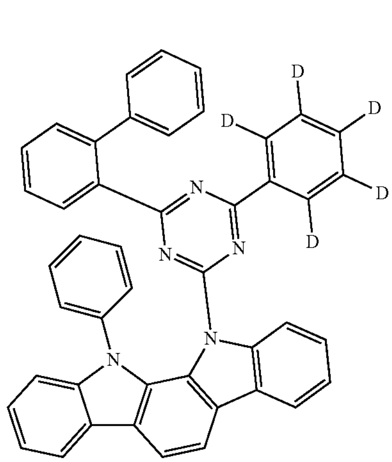
-continued
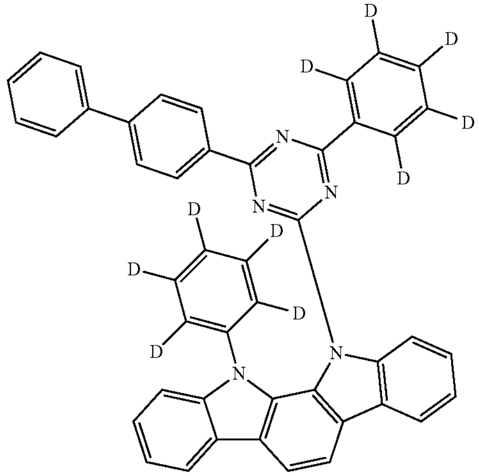
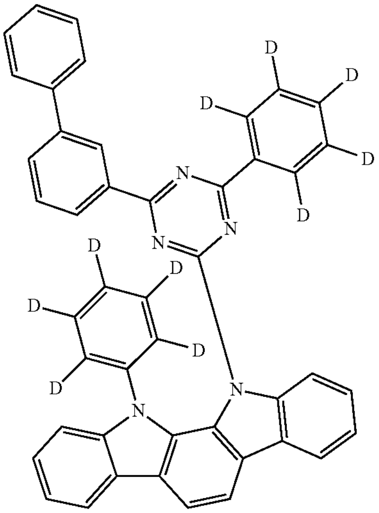
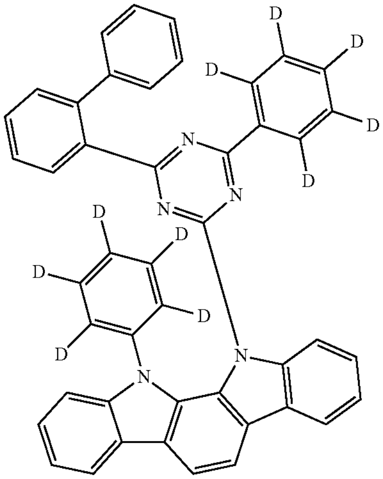

-continued
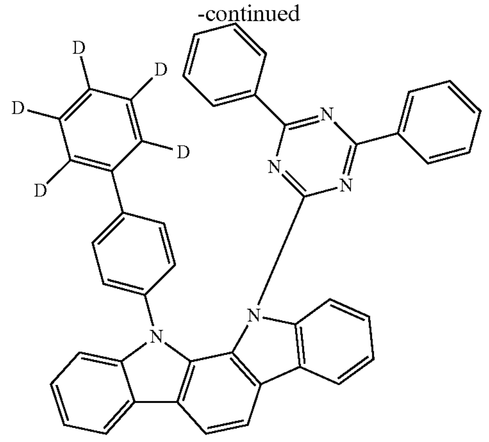
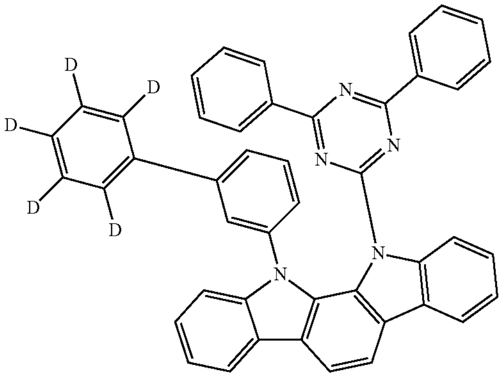
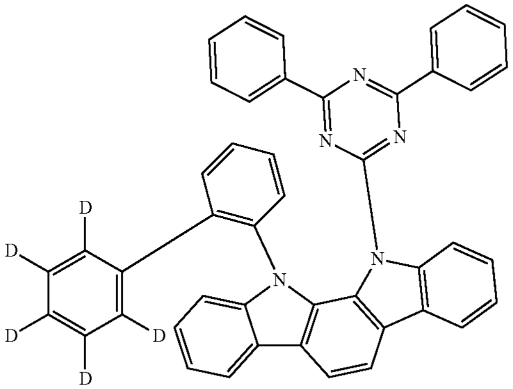
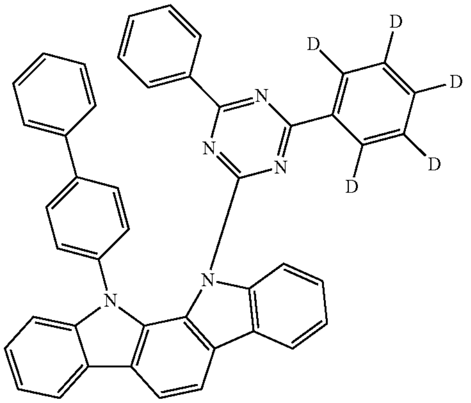
-continued
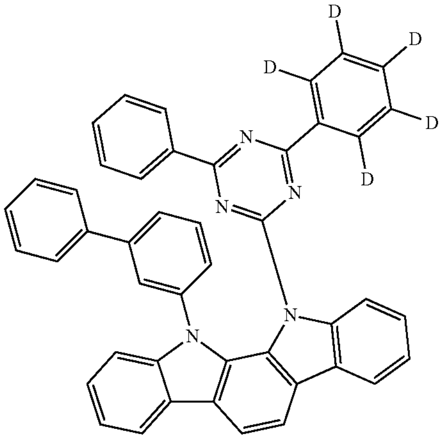
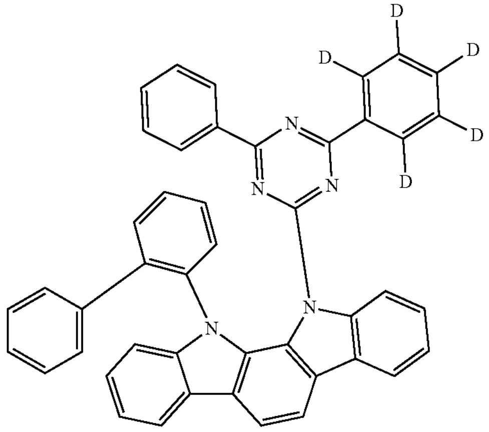
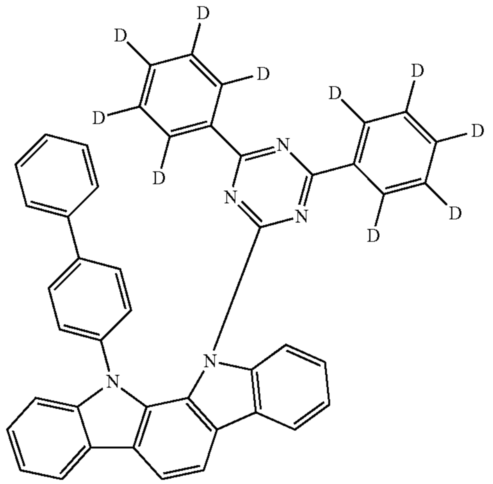

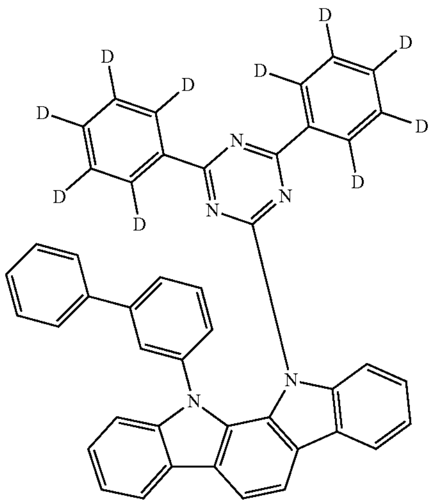
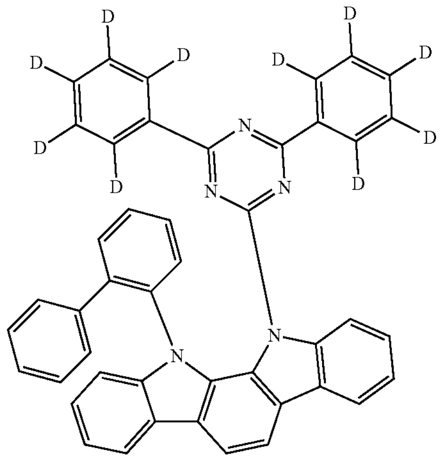
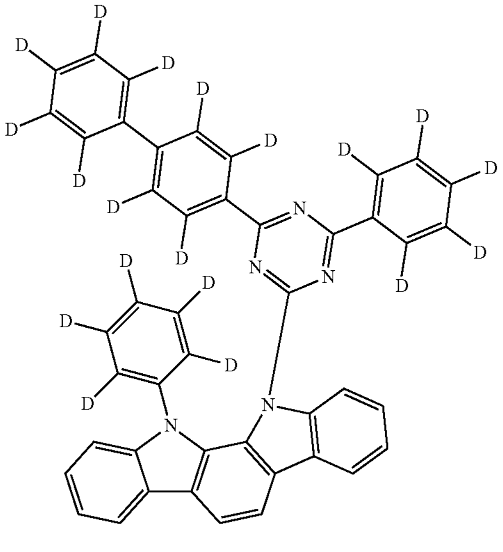
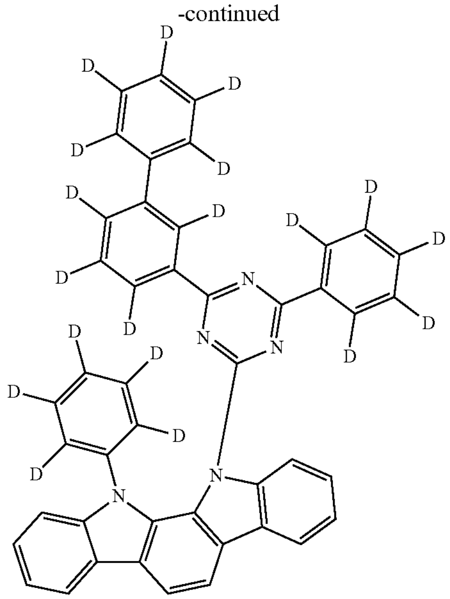
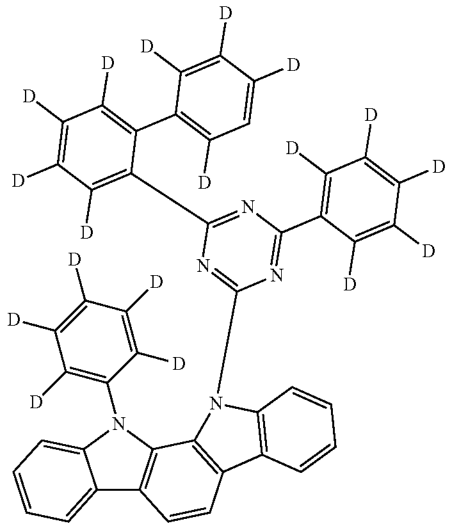
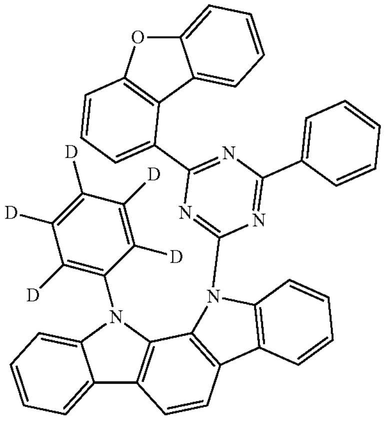

-continued
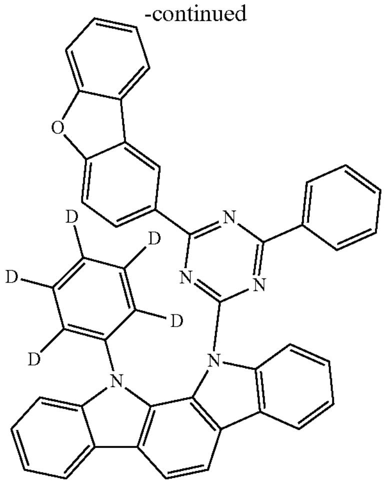
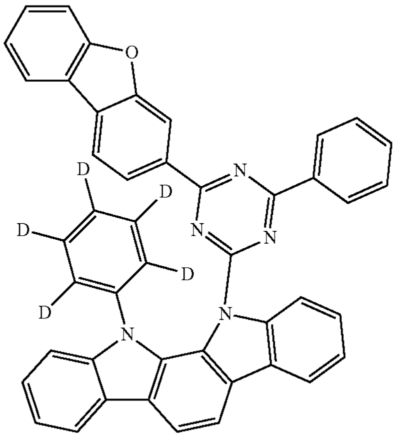
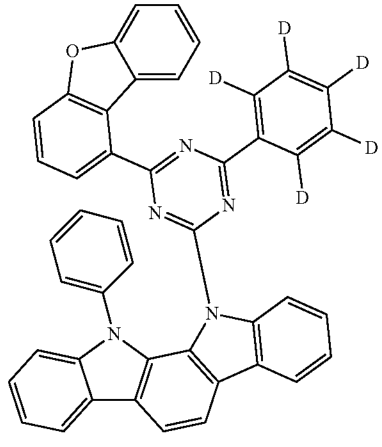
-continued
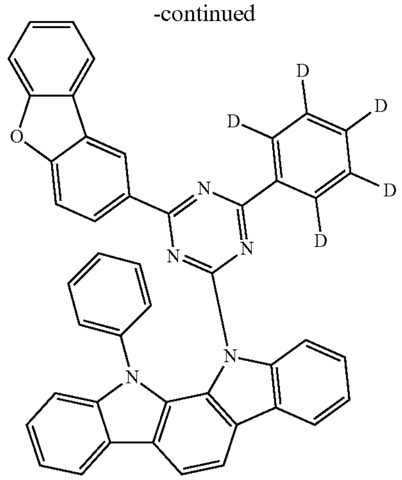
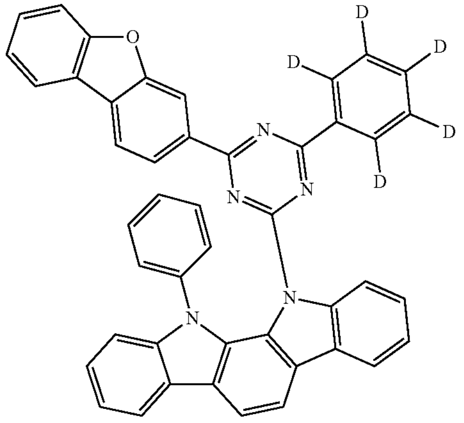
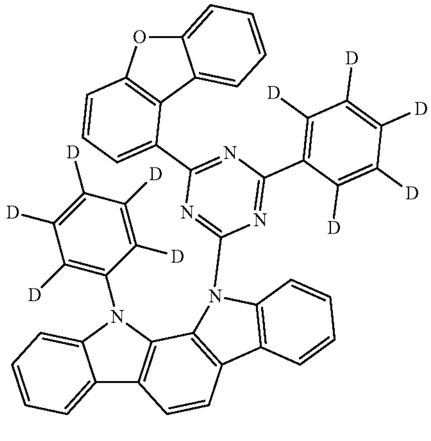

-continued
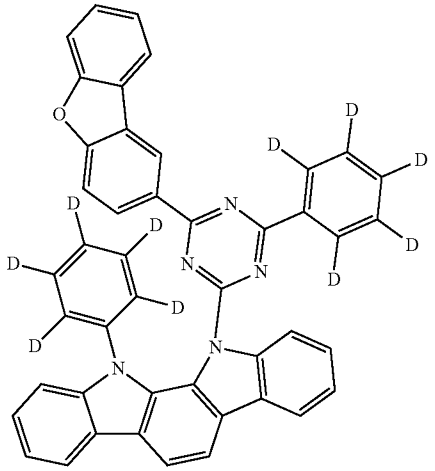
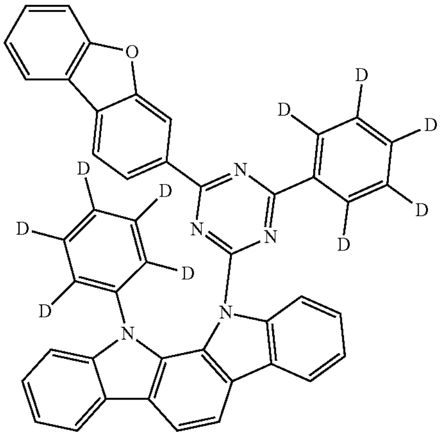
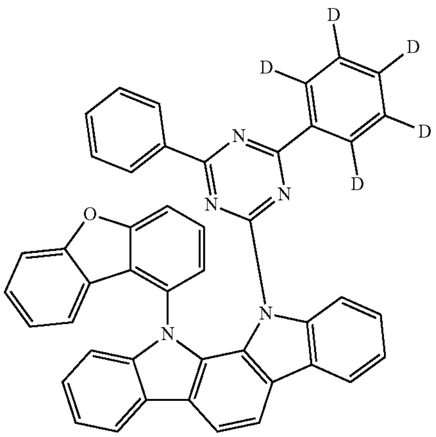
-continued
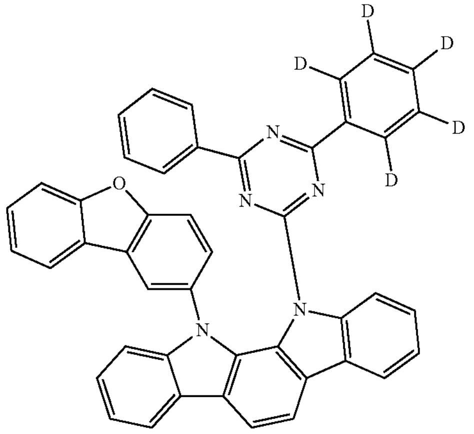
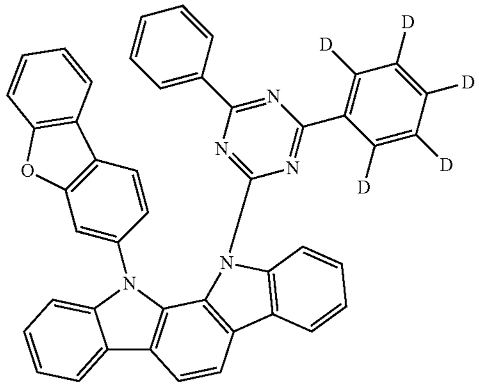
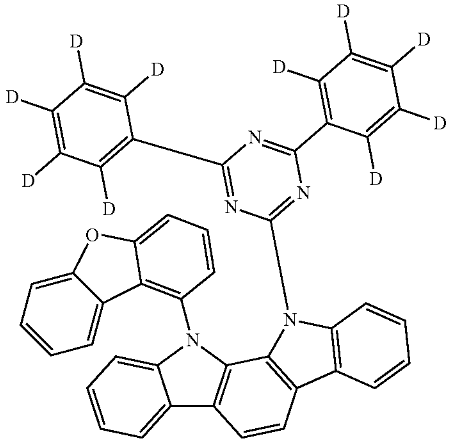
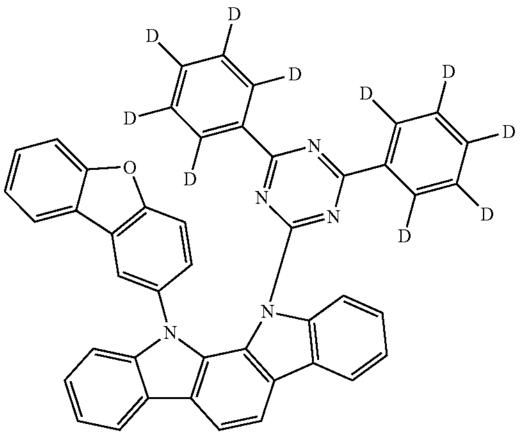

-continued
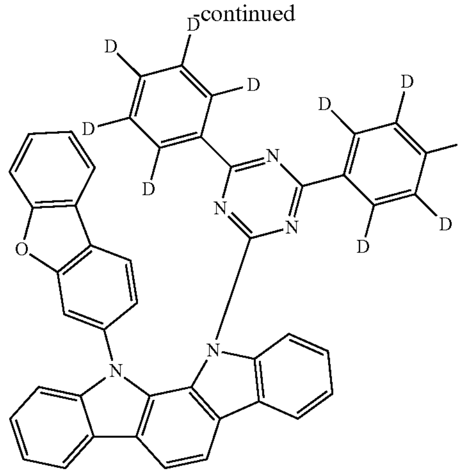
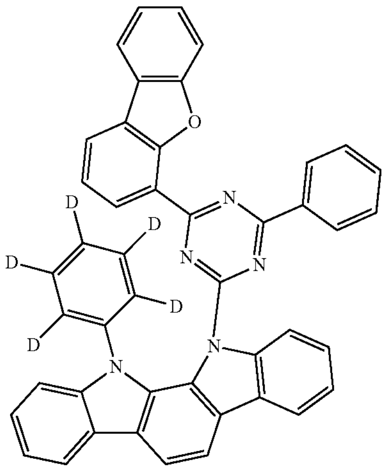
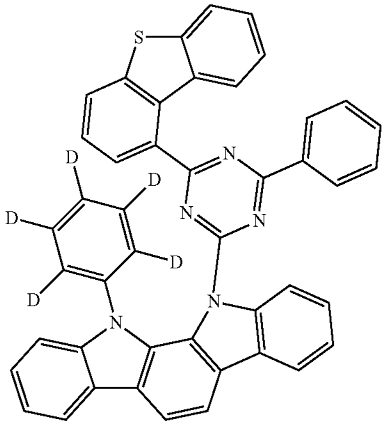
-continued
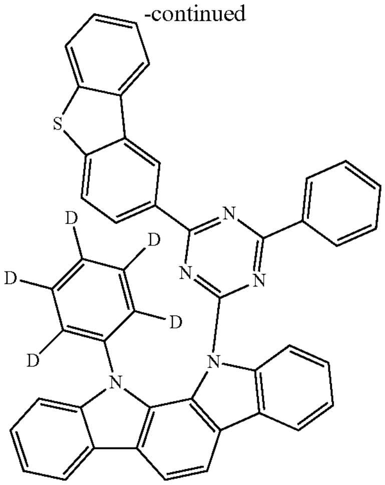
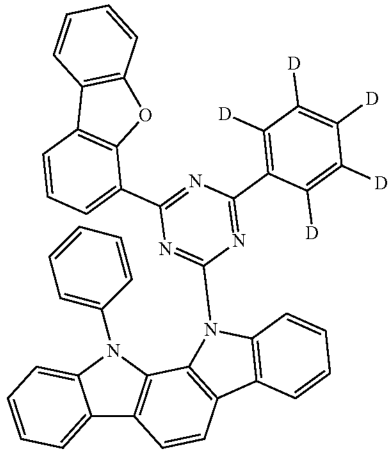
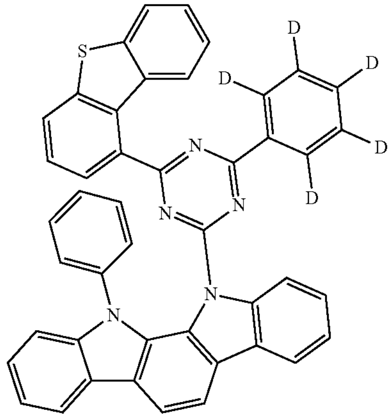

-continued
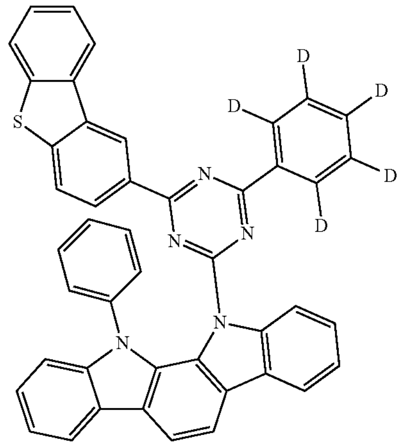
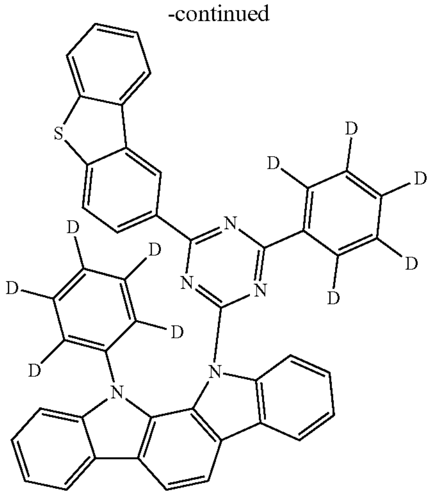
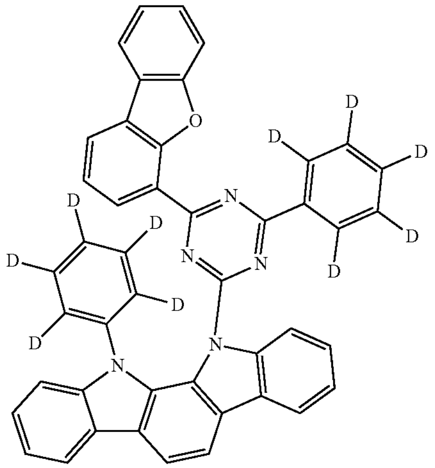
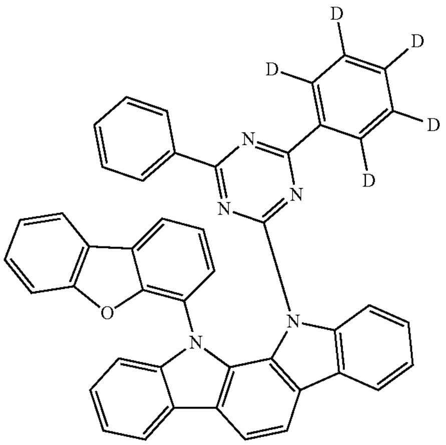
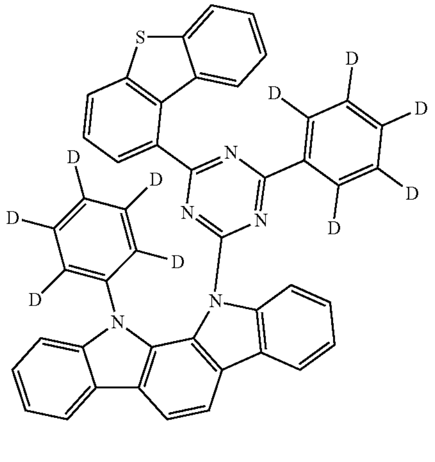
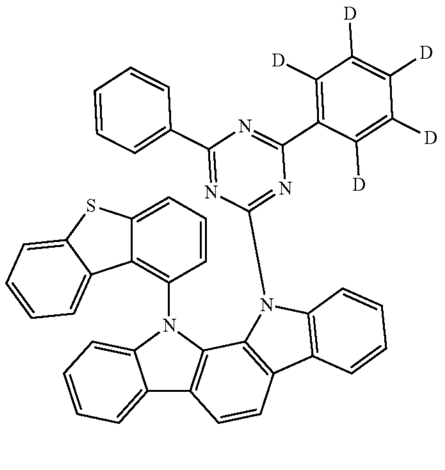

-continued
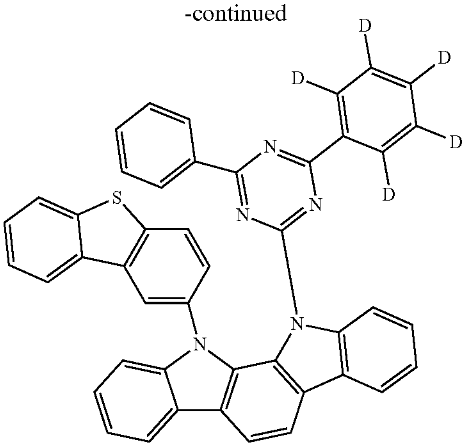
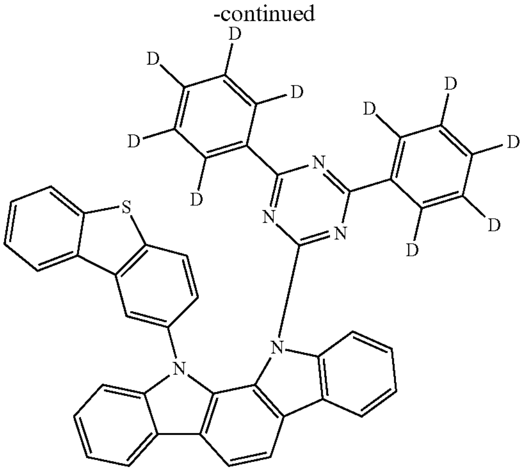
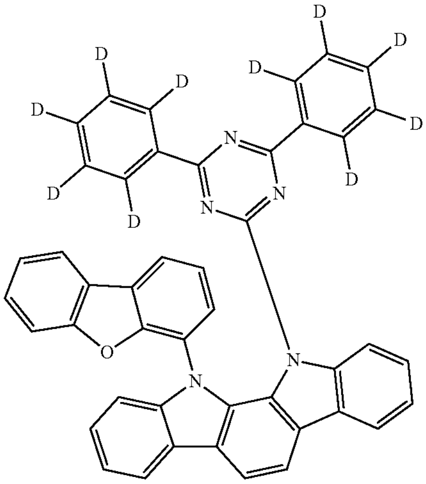
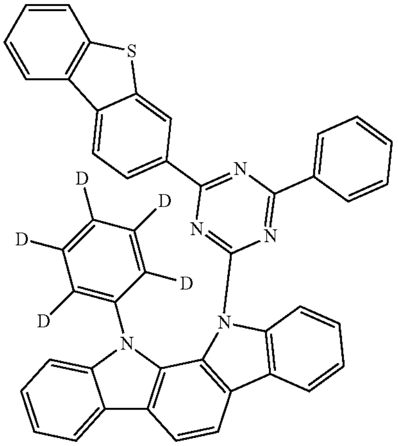
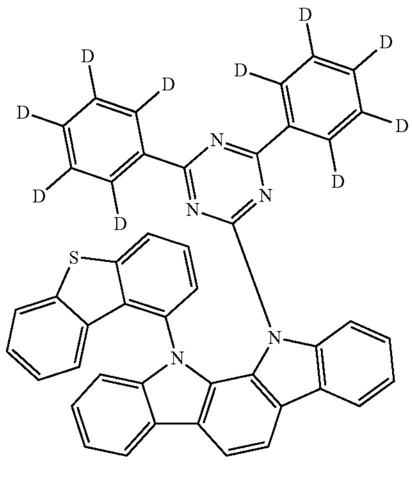
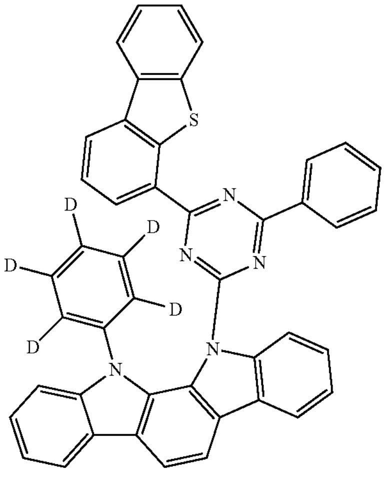
-continued -continued
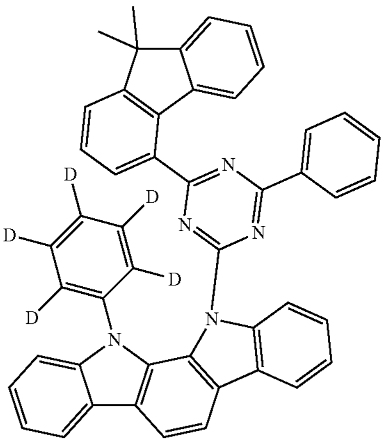
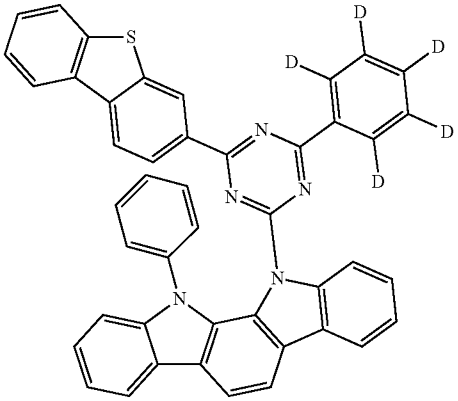
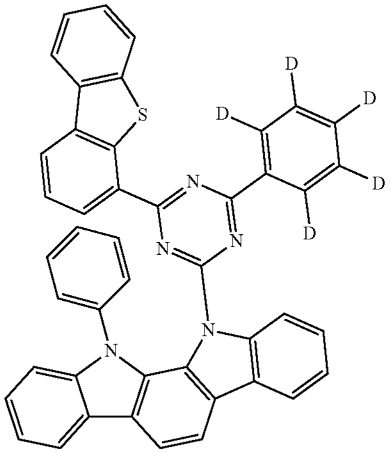
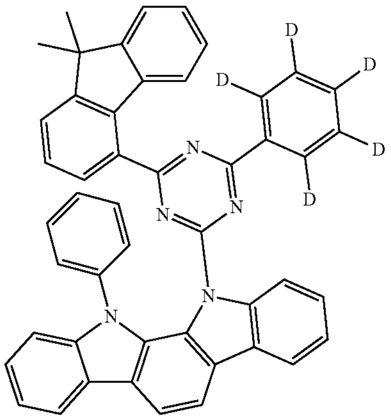
-continued
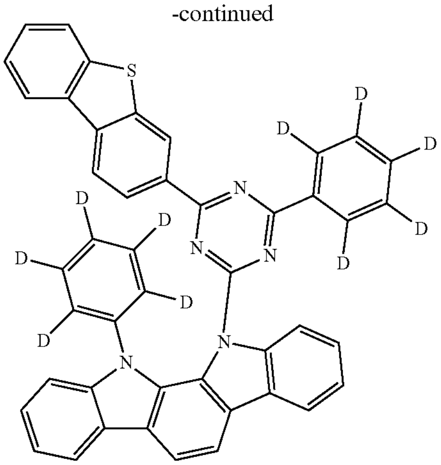
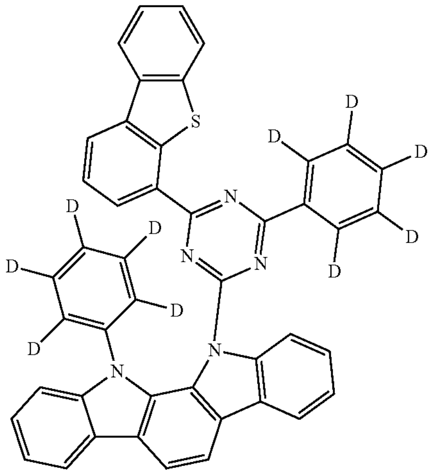
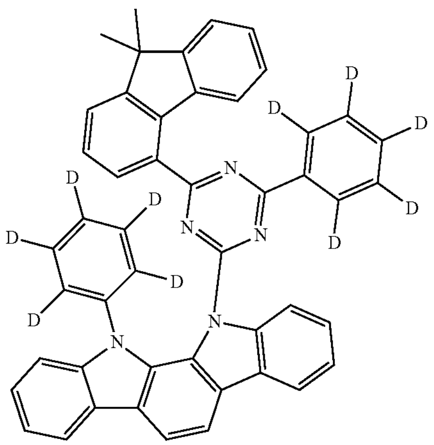

-continued
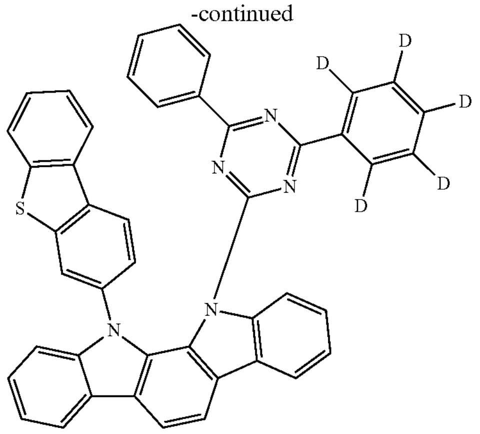
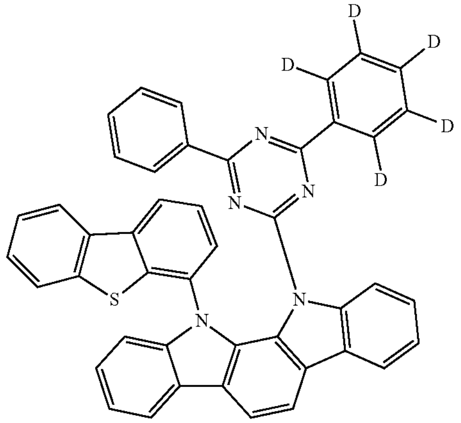
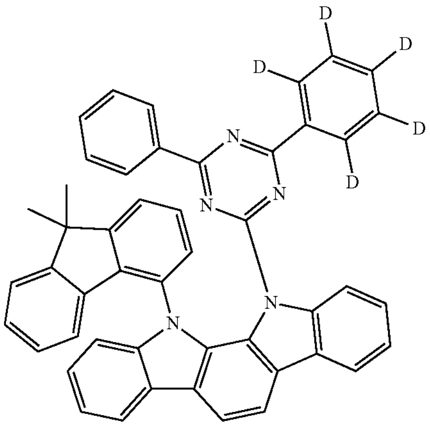
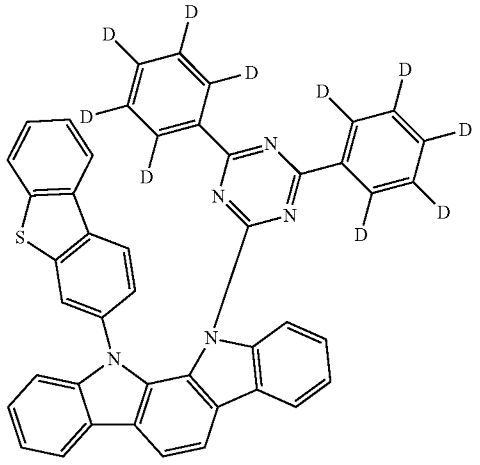
-continued
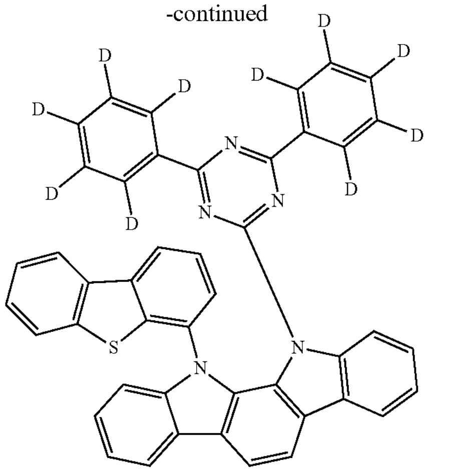
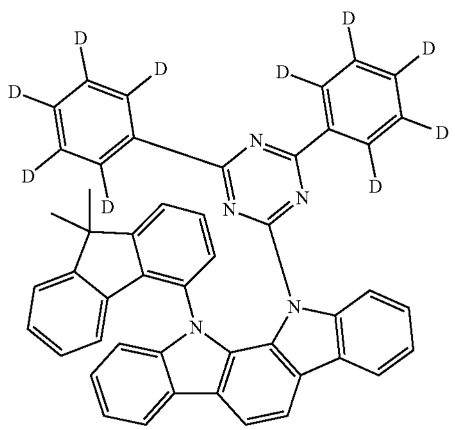
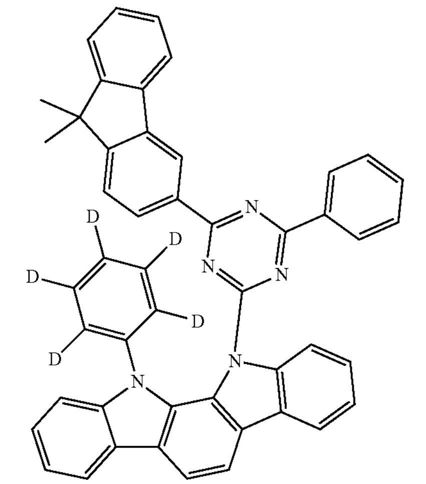

-continued
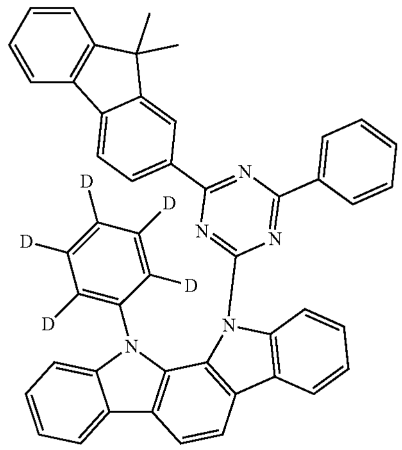
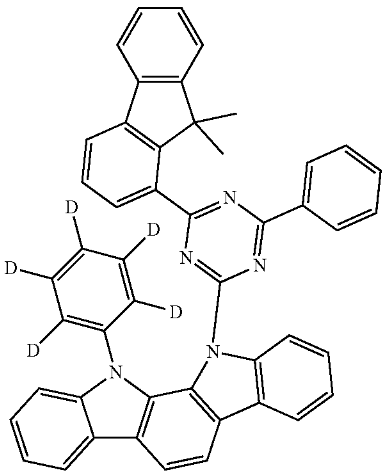
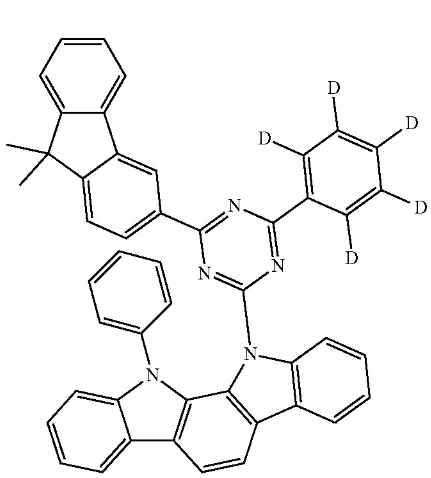
-continued
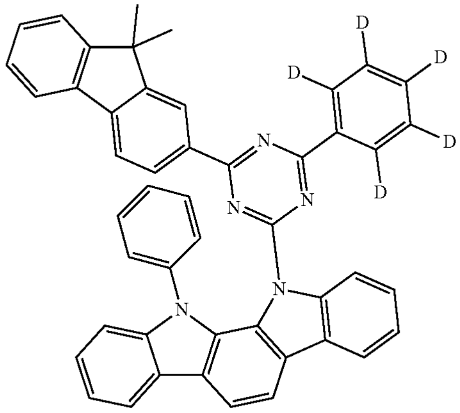
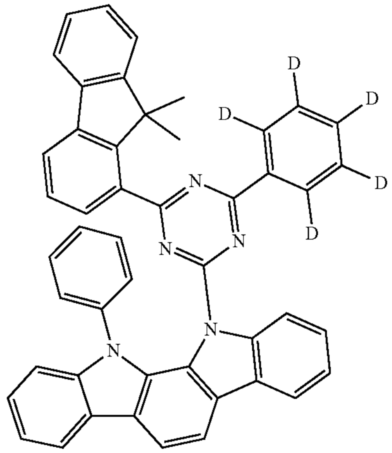
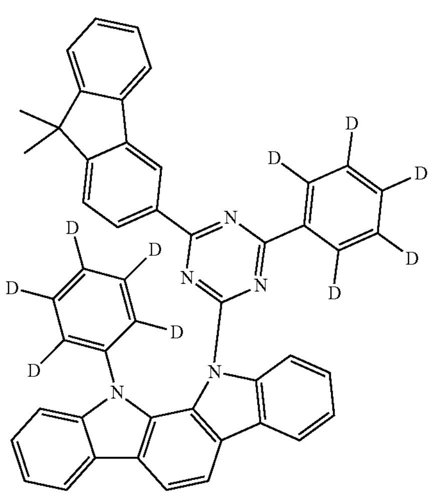

-continued
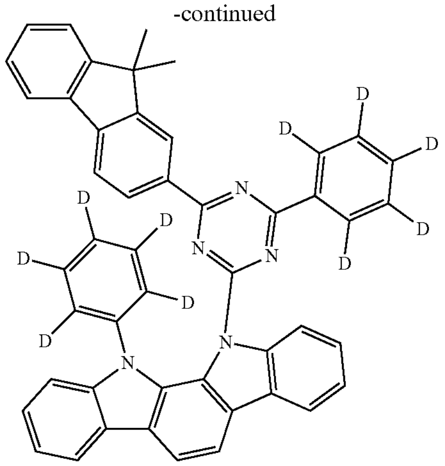
-continued
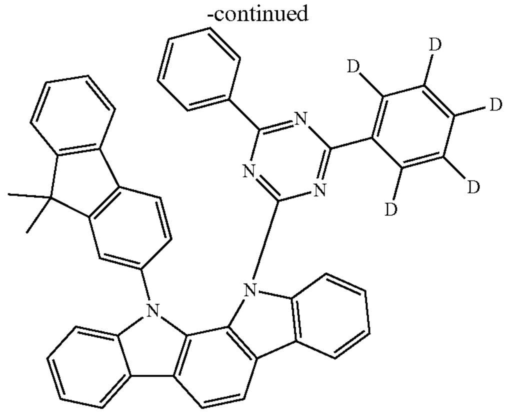
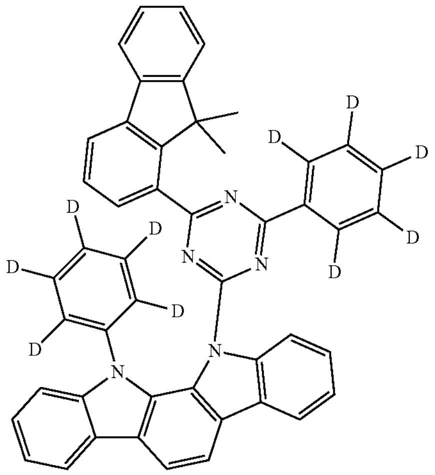
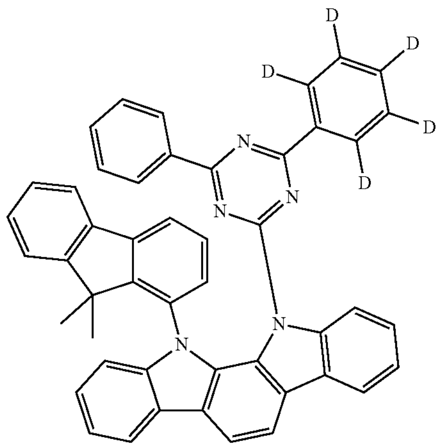
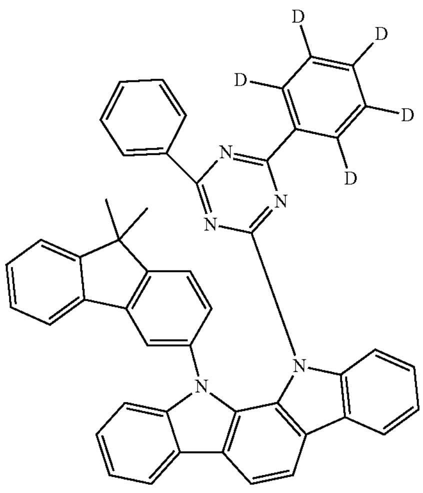
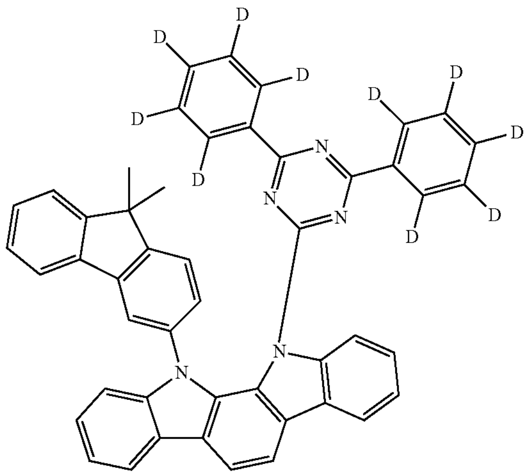

-continued
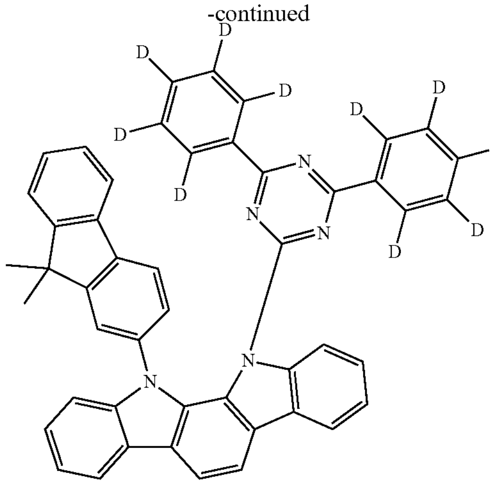
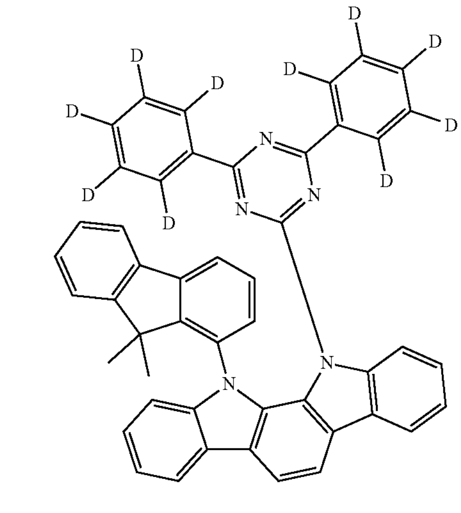
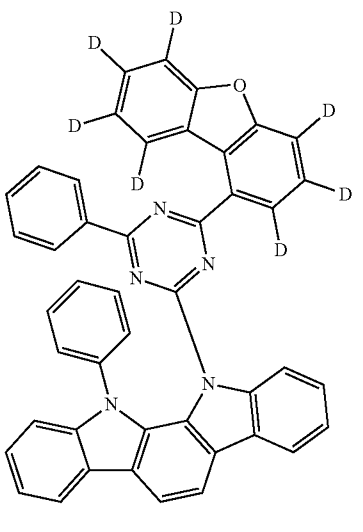
-continued
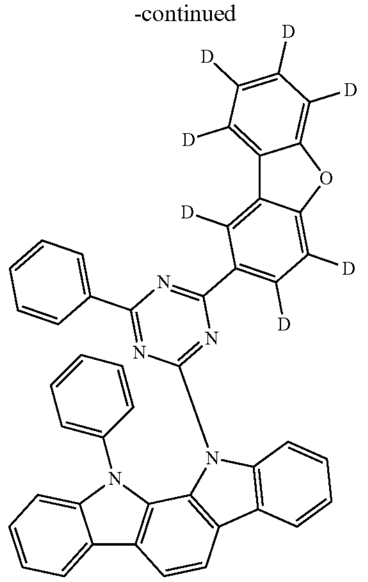
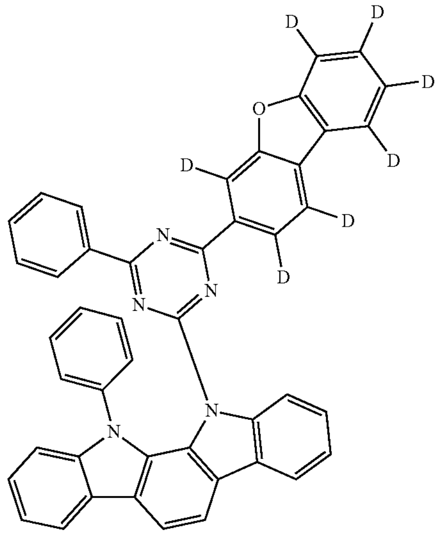
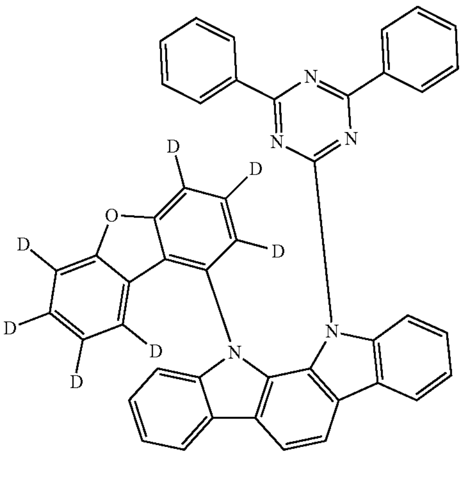

-continued
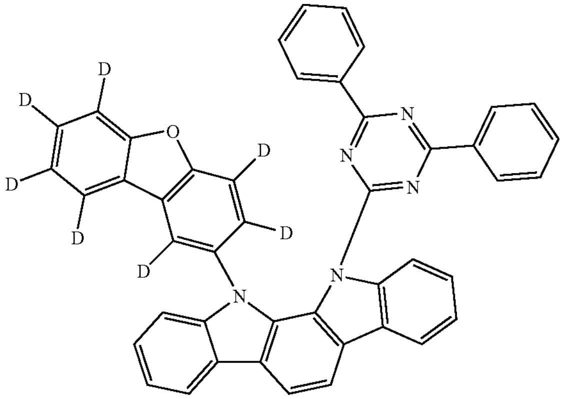
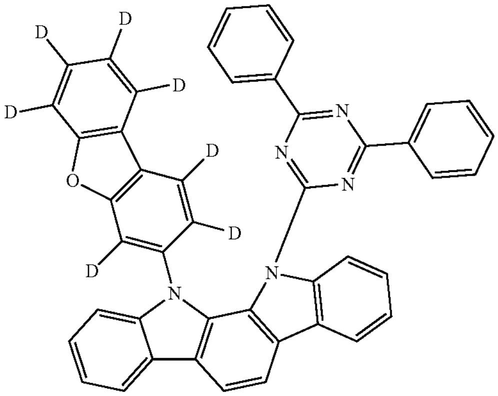
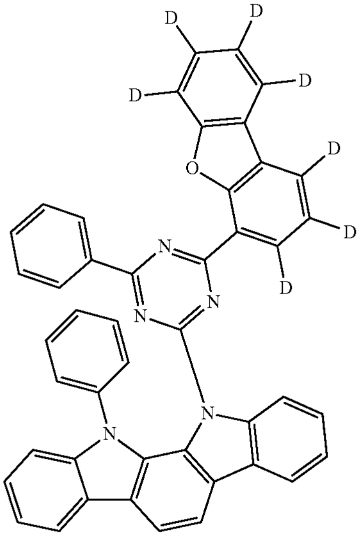
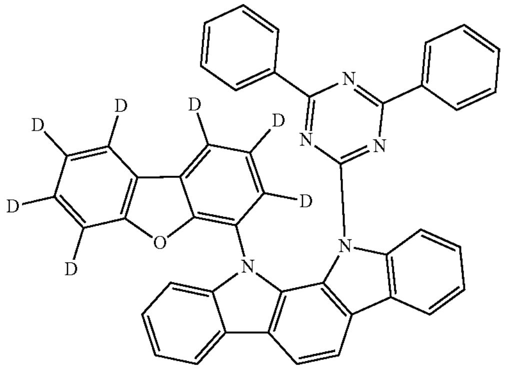
-continued
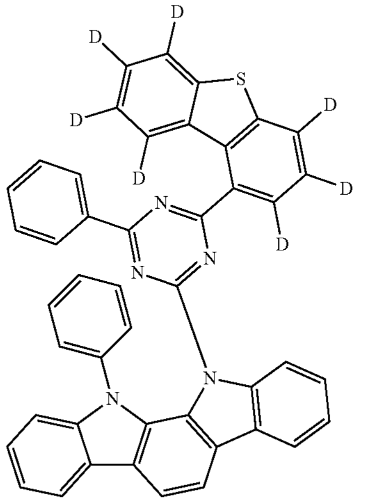
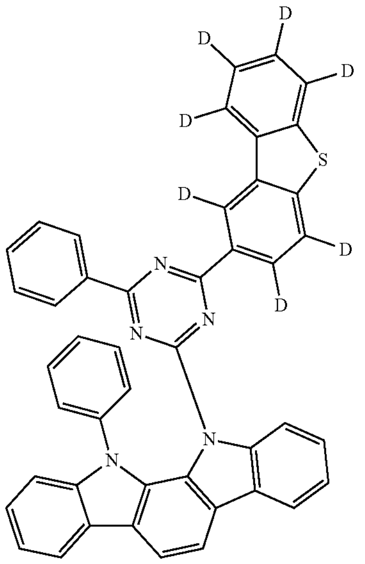
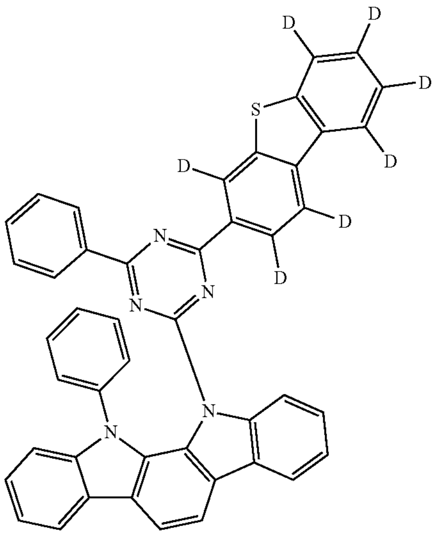

-continued
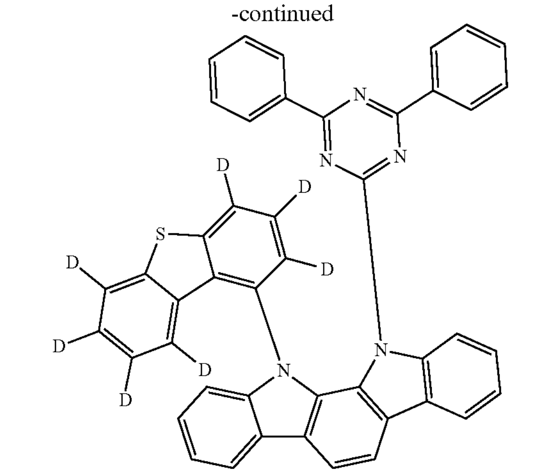
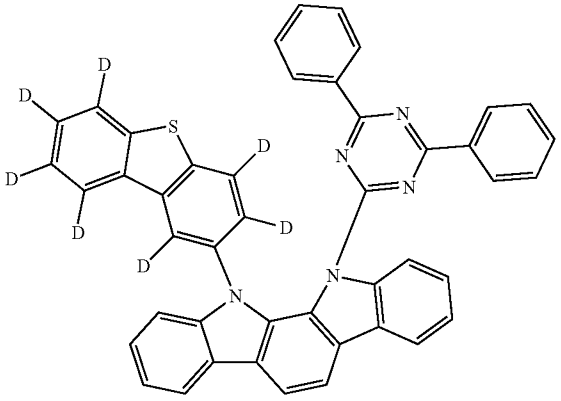
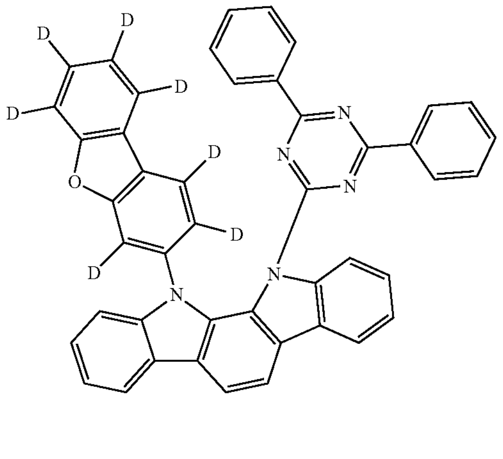
-continued
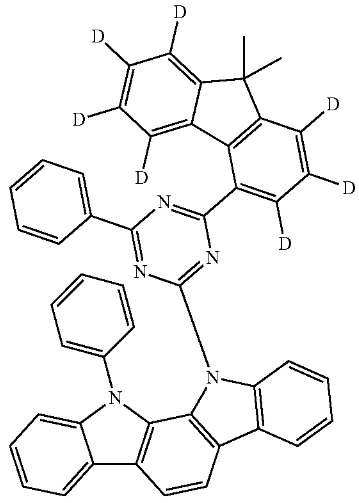
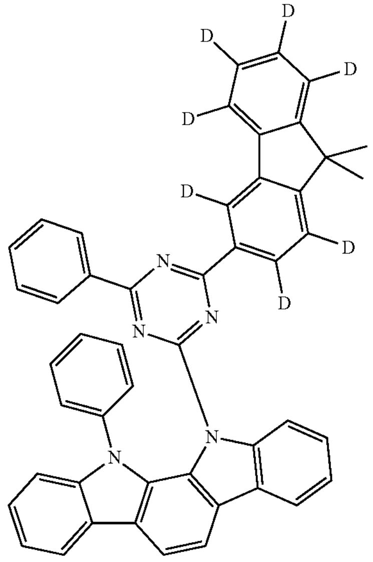
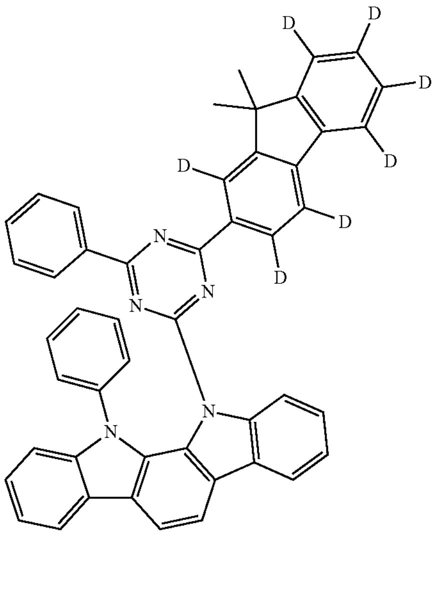

-continued
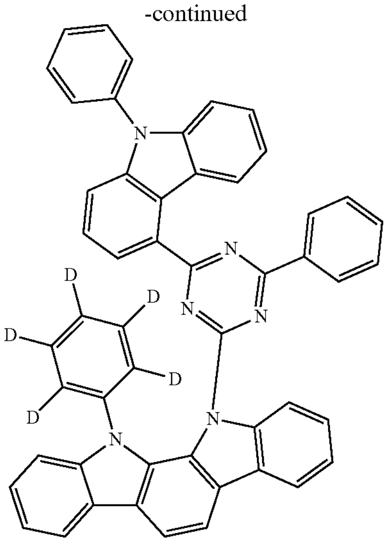
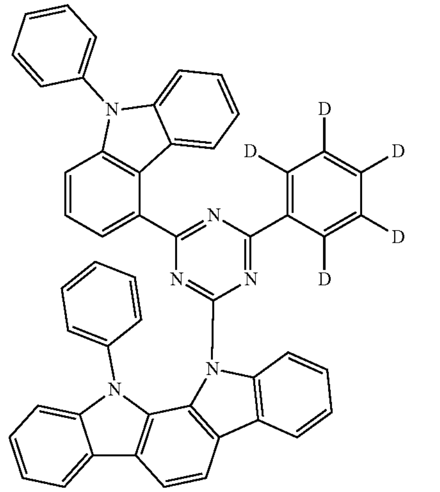
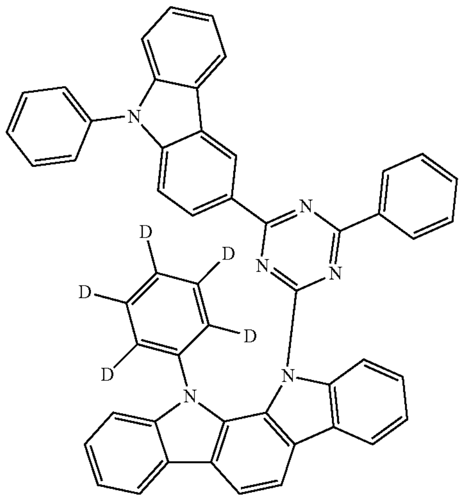
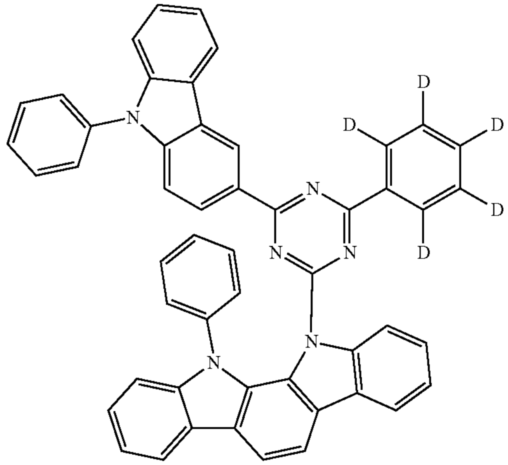
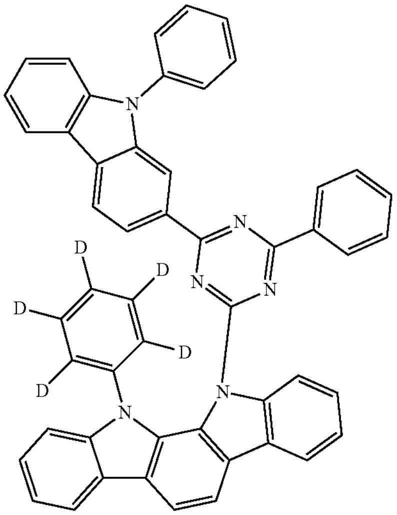
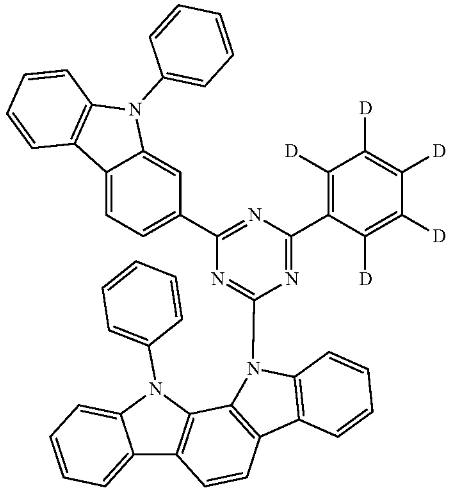

-continued
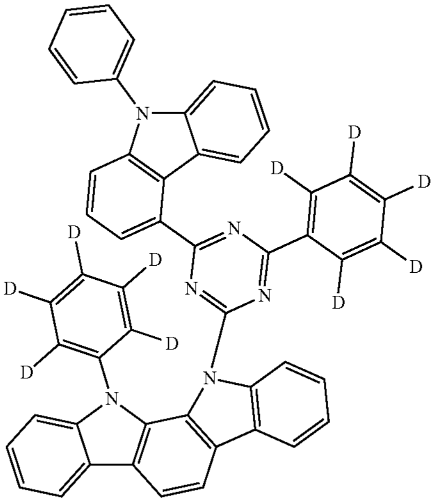
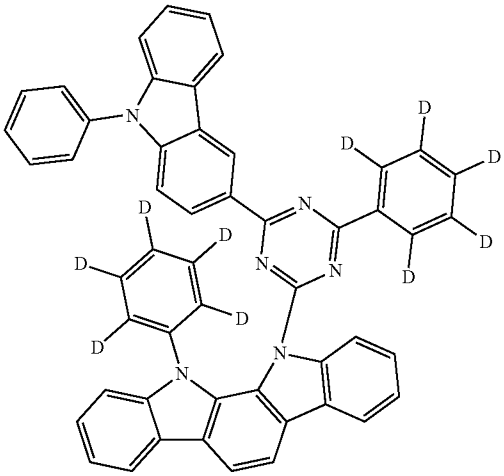
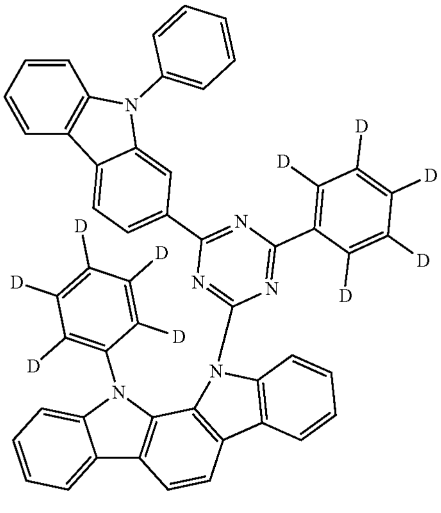
-continued
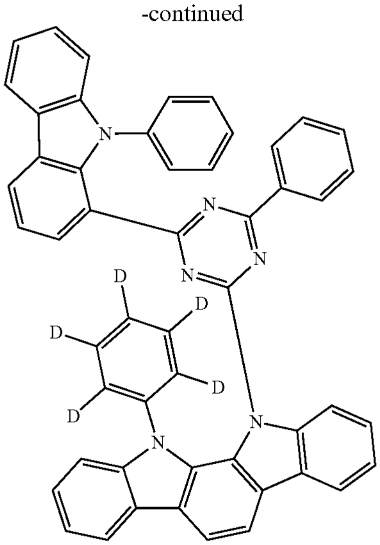
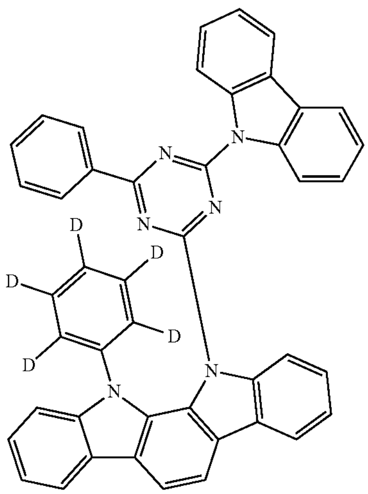
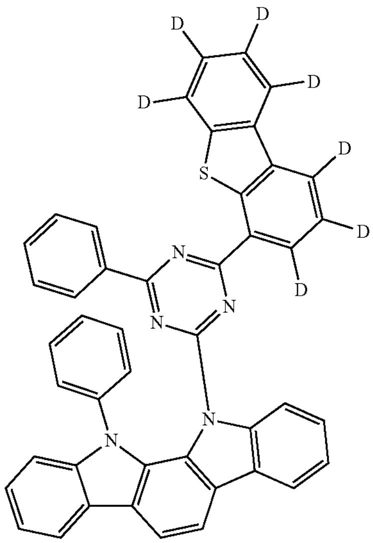

-continued
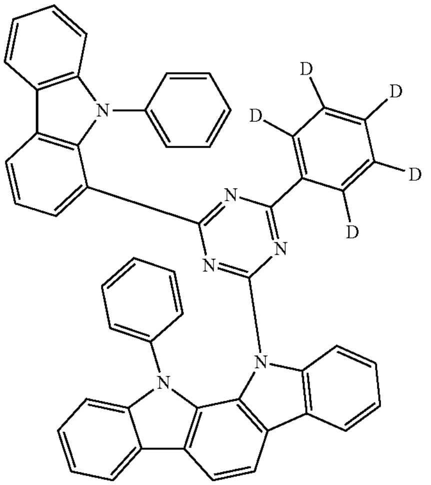
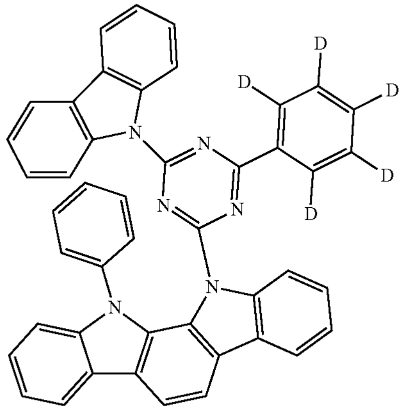
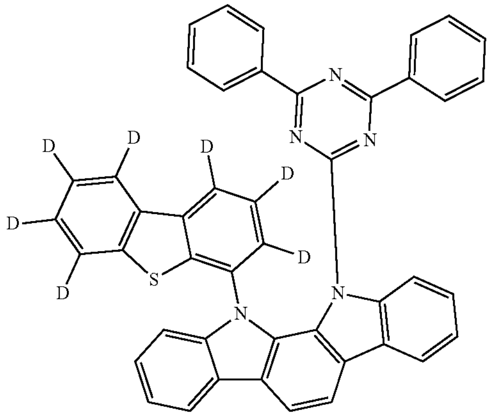
-continued
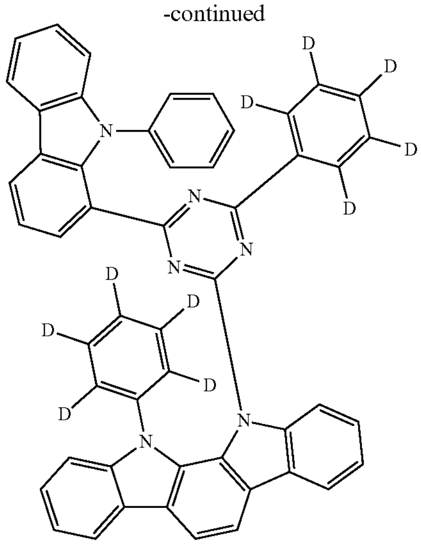
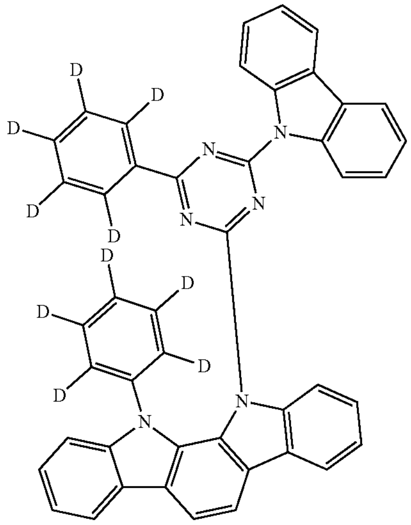
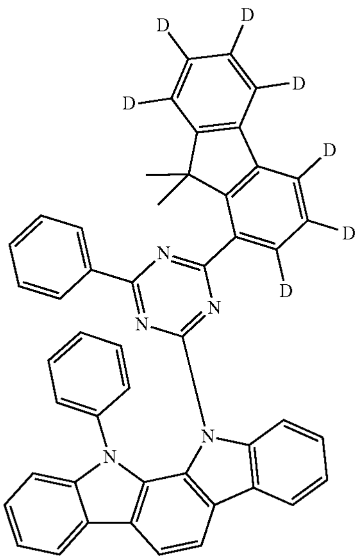

-continued
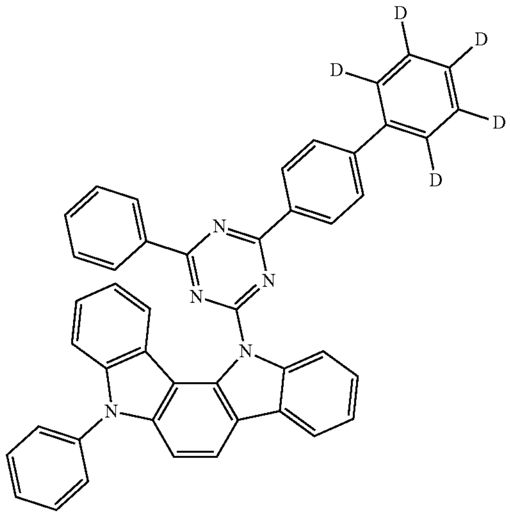
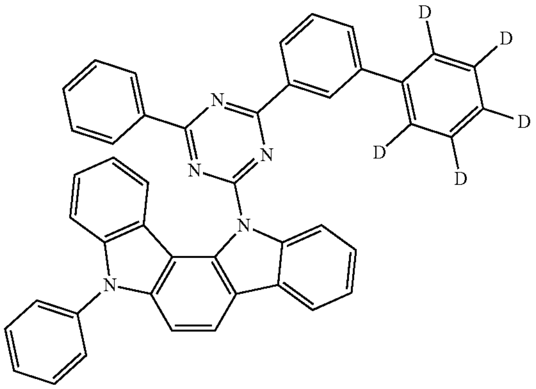
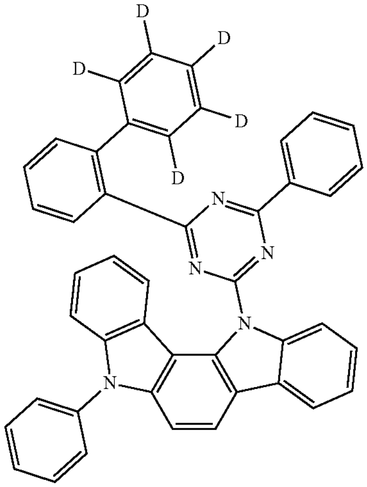
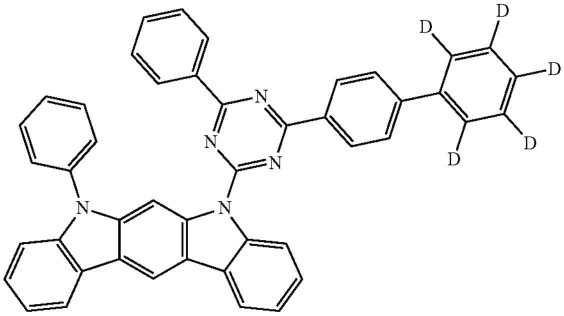
-continued
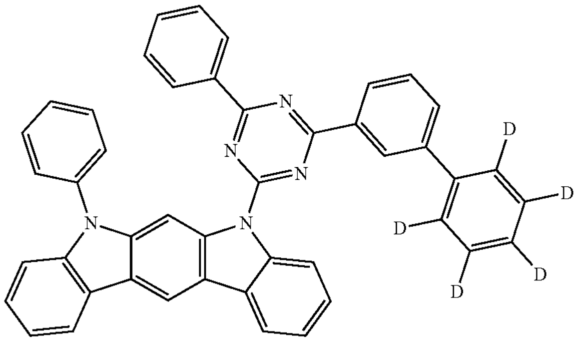
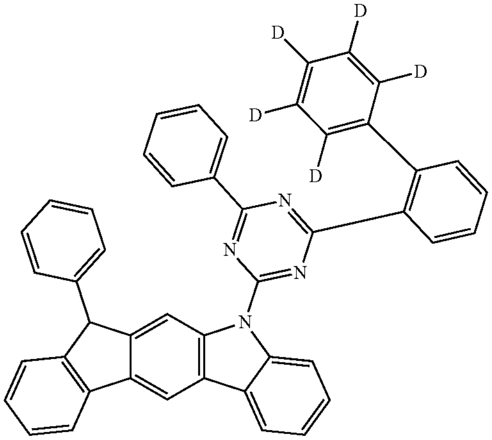
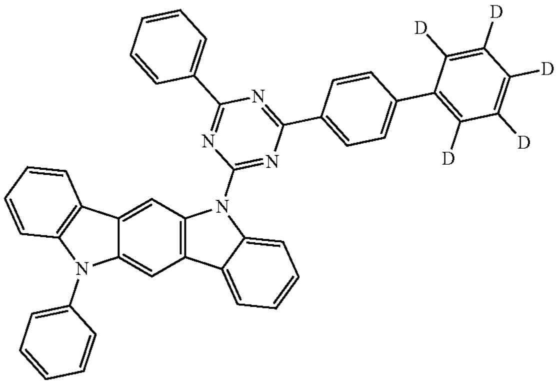
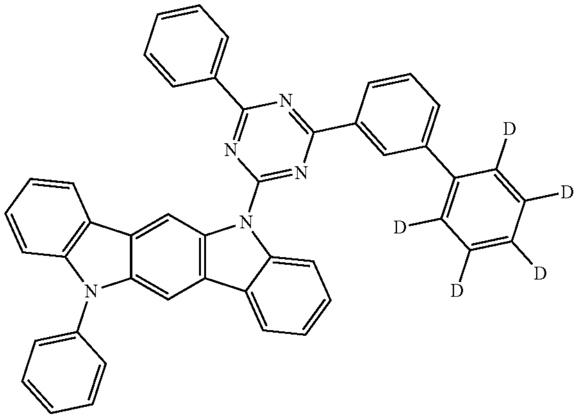

-continued
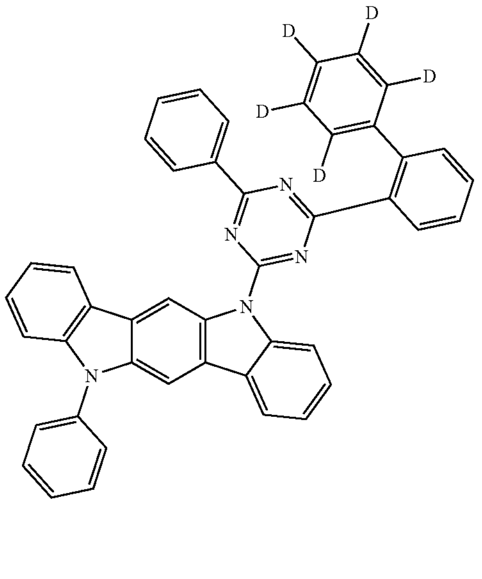
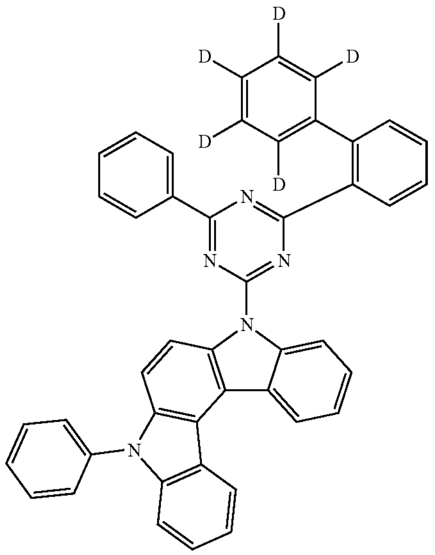
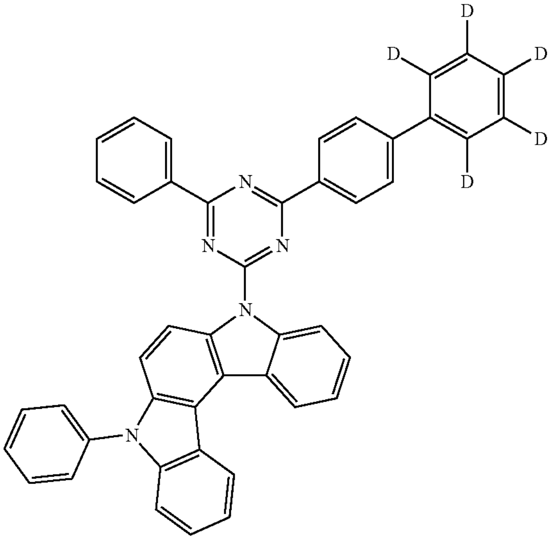
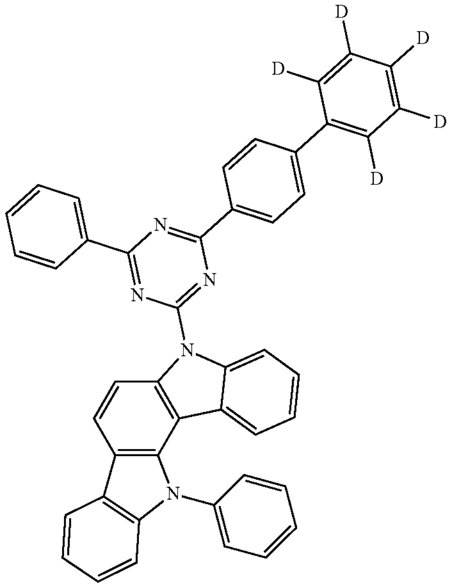
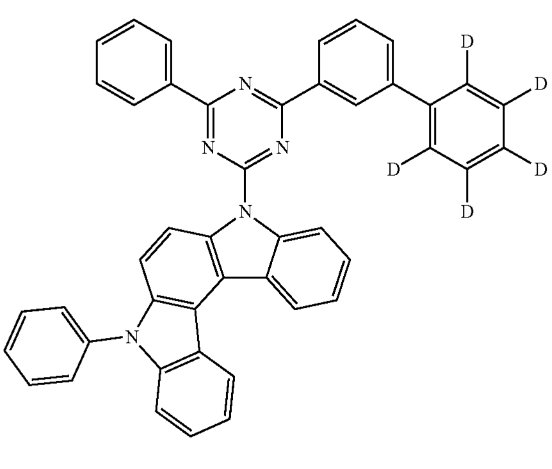
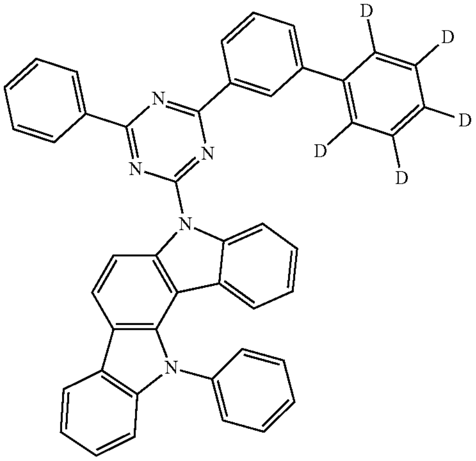
-continued -continued
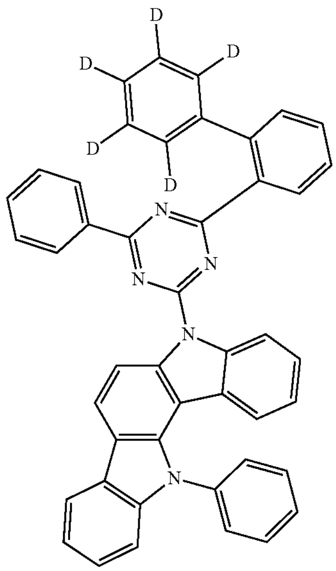
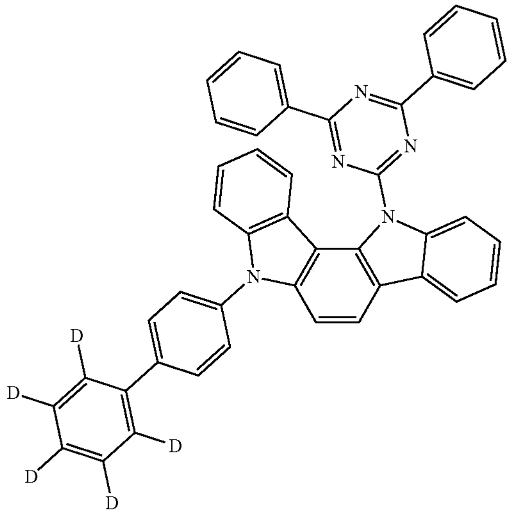
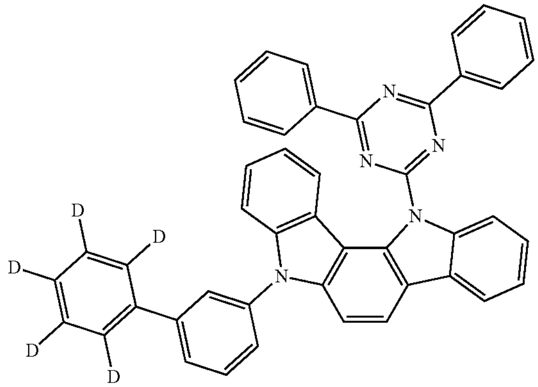
-continued
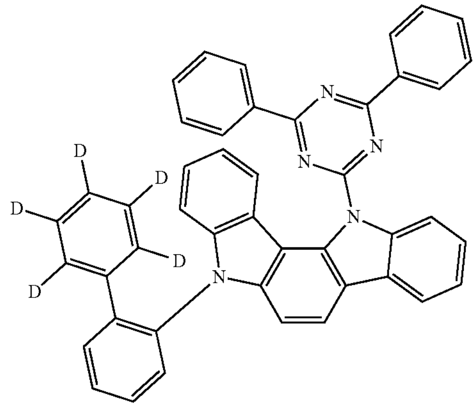
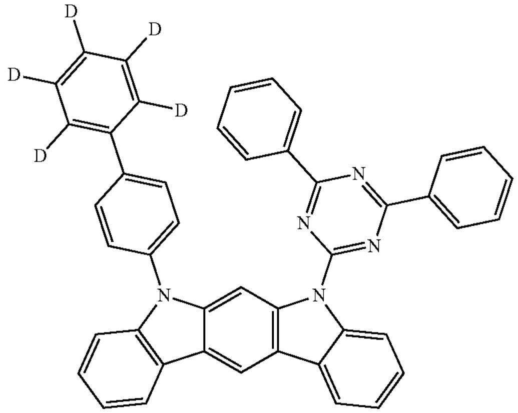
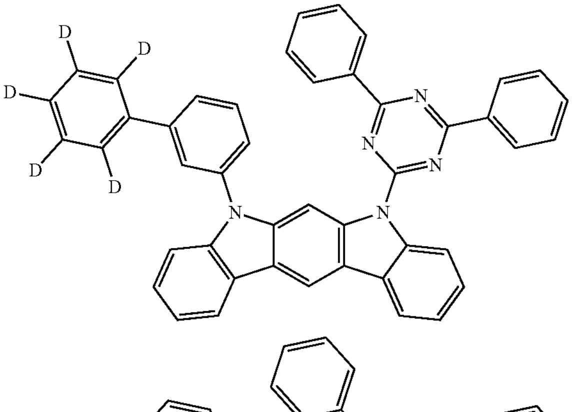
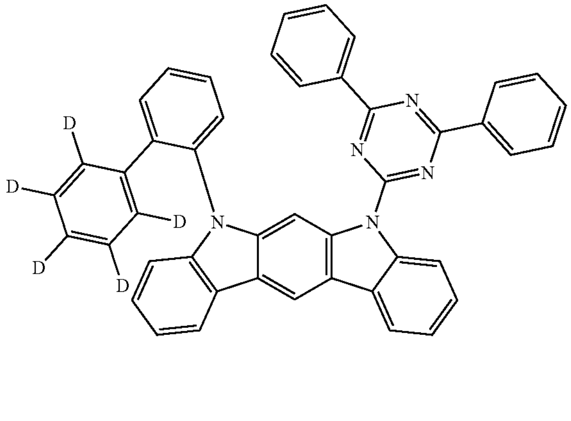

-continued
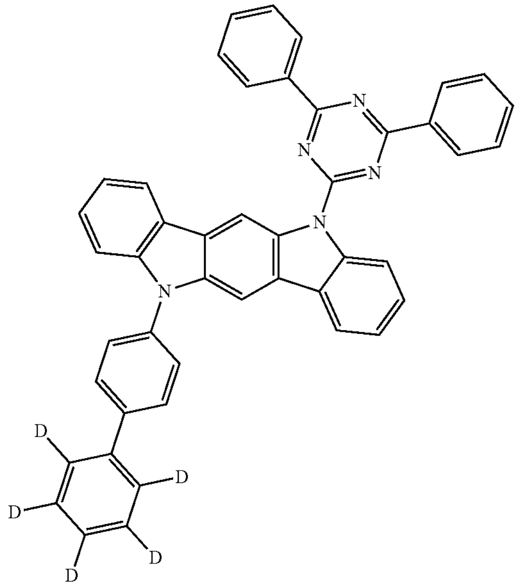
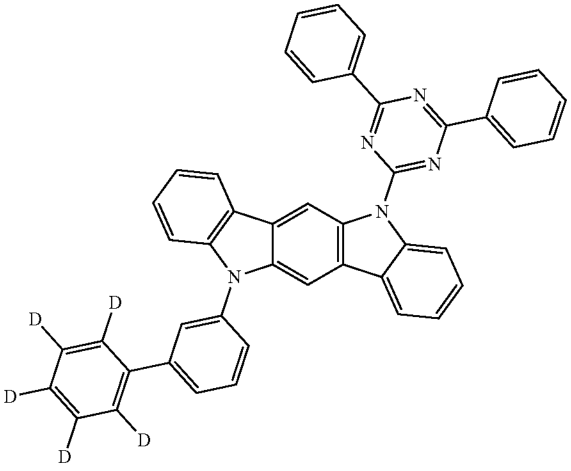
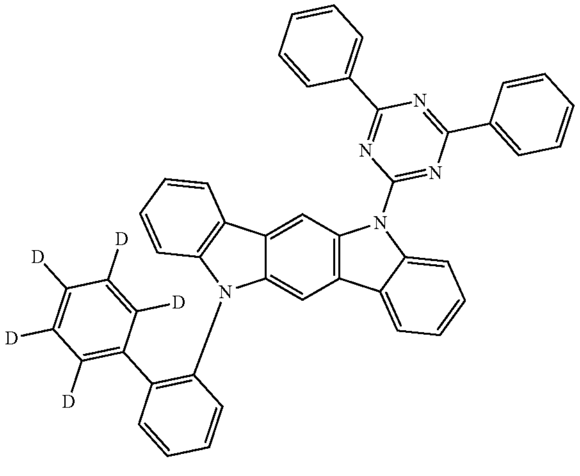
-continued
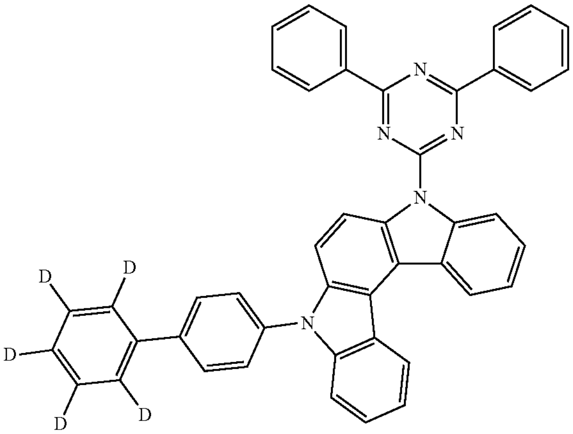
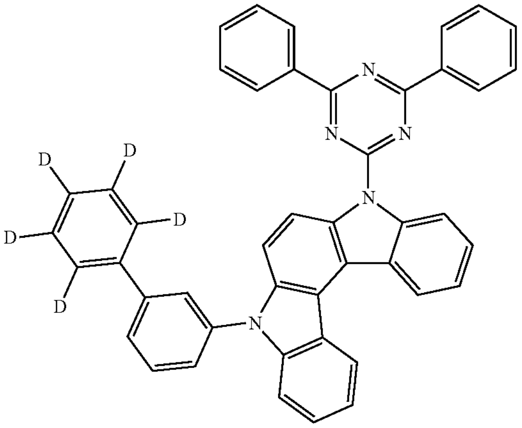
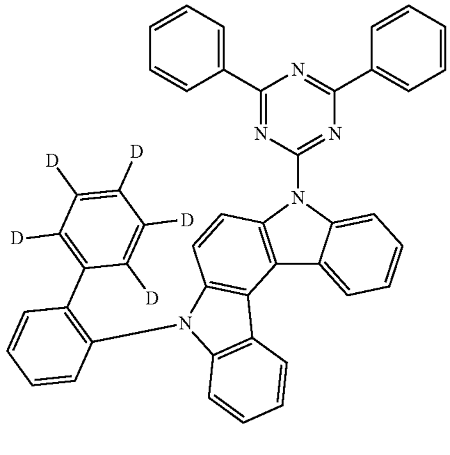

-continued
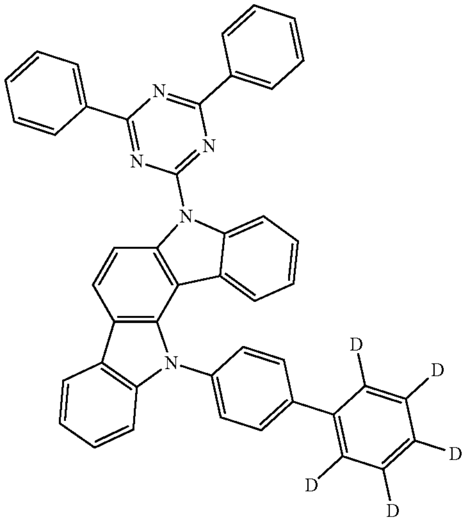
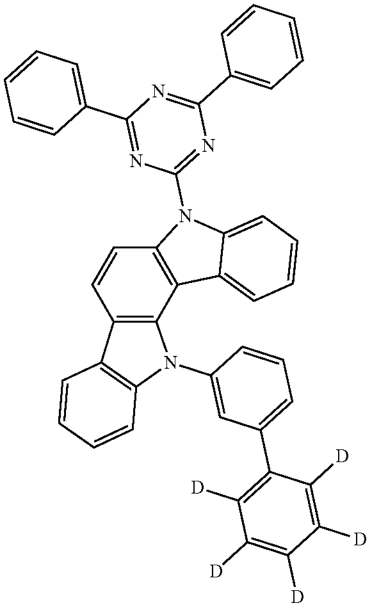
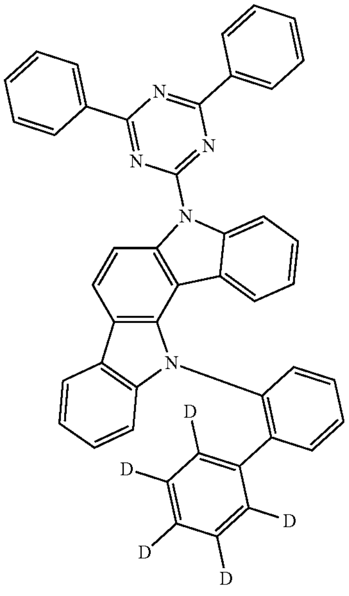
-continued
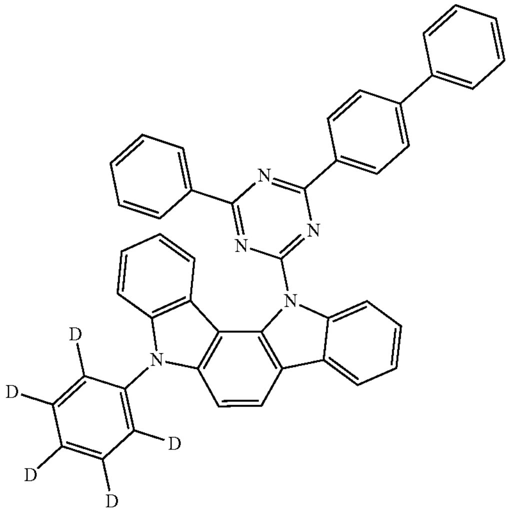
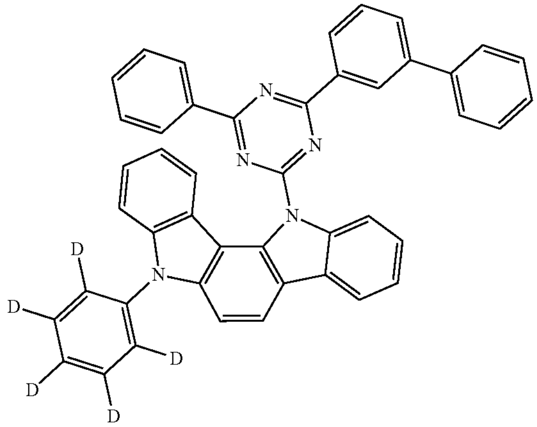
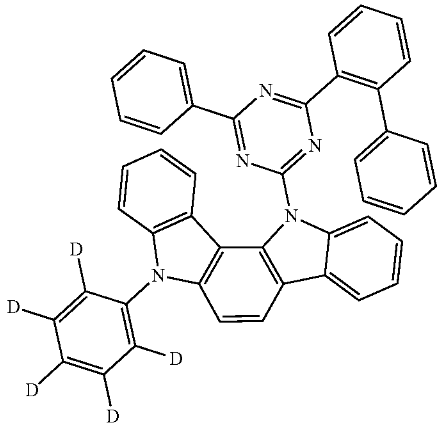
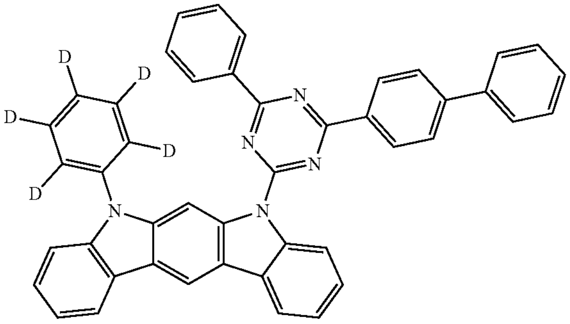

-continued
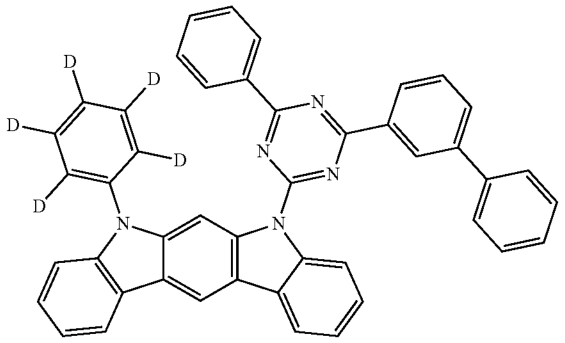
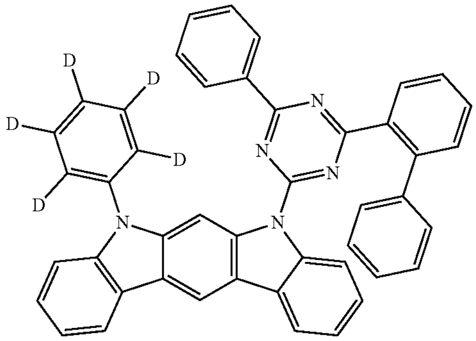
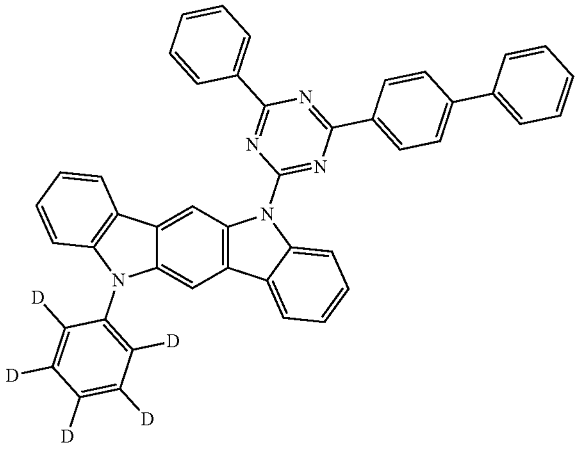
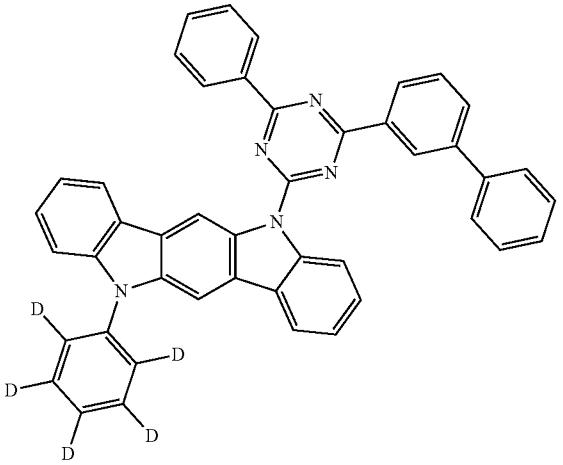
-continued
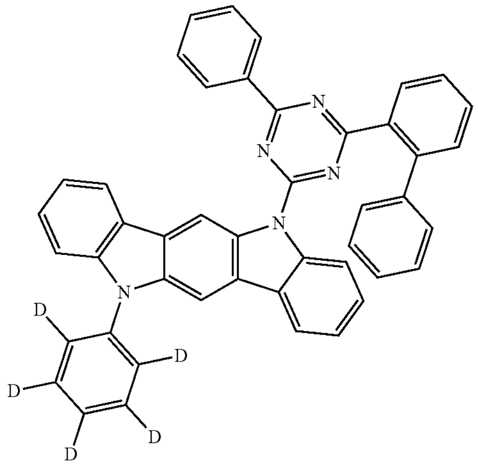
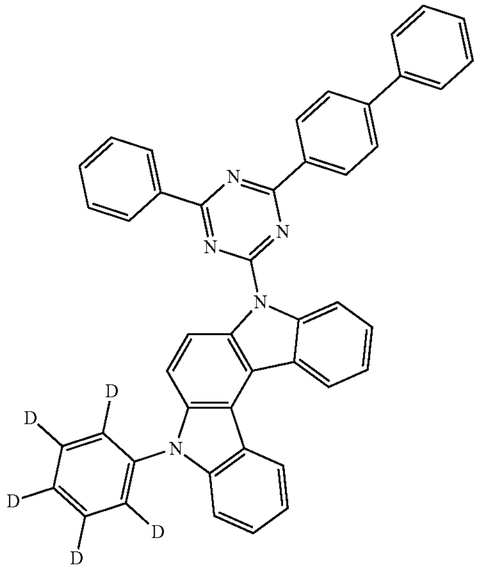
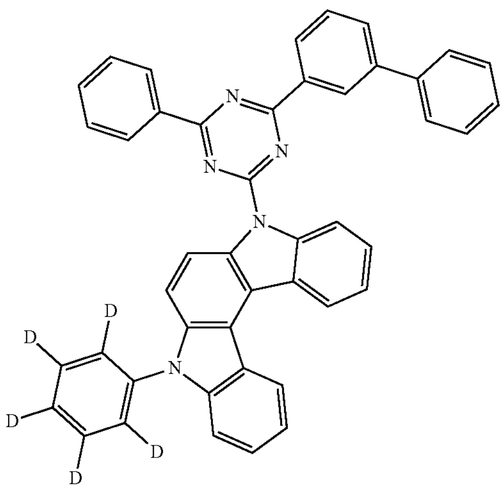

-continued
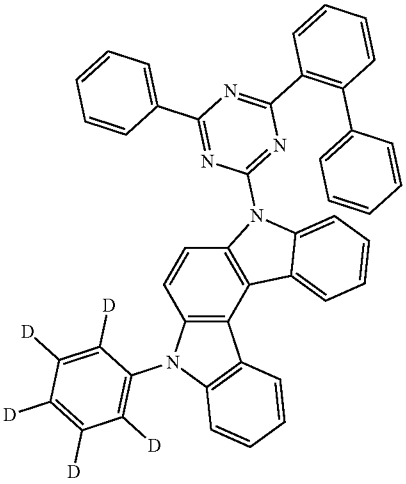
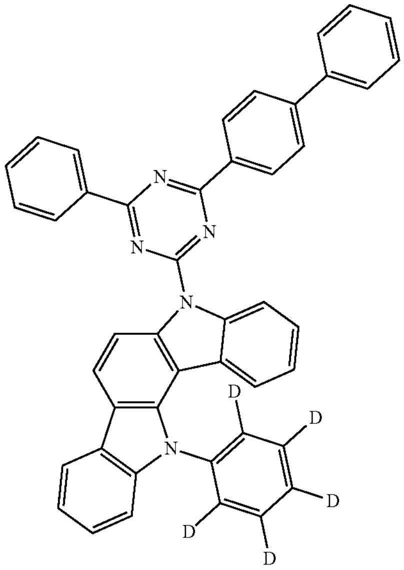
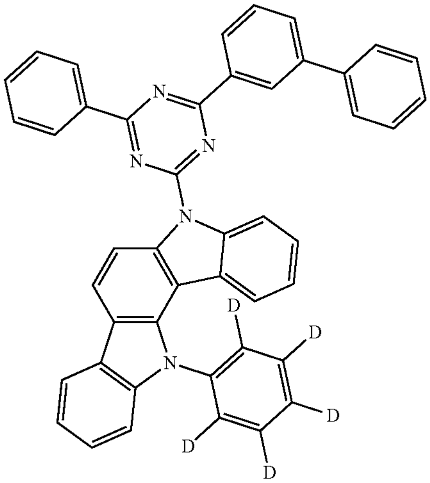
-continued
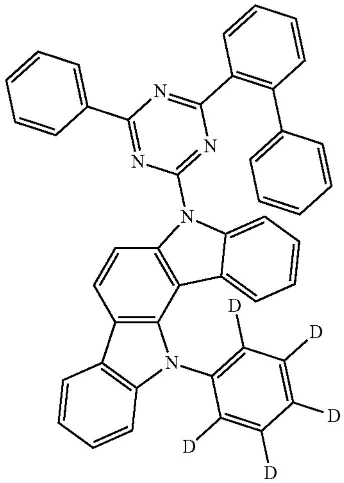
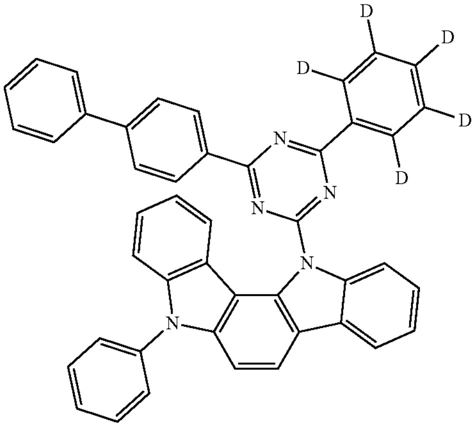
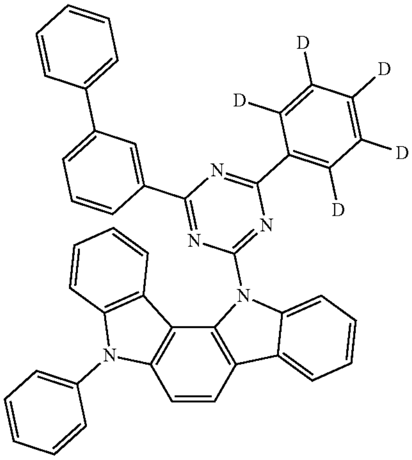

-continued
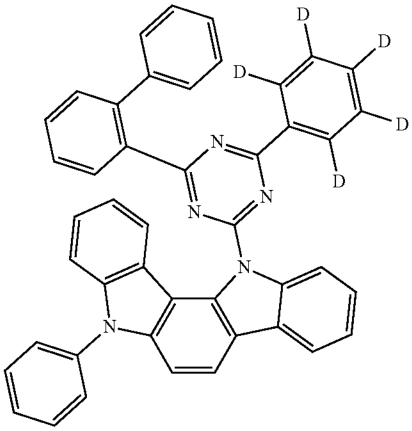
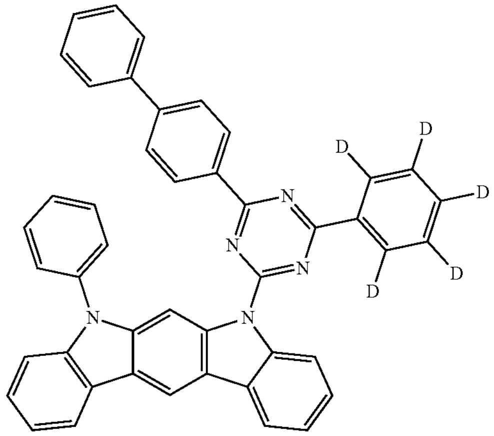
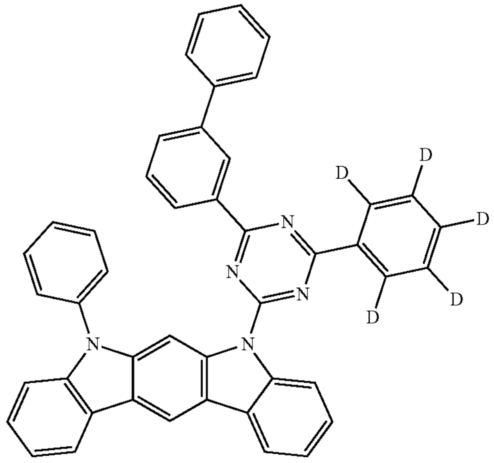
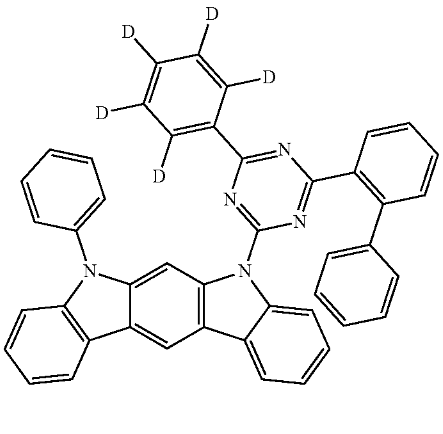
-continued
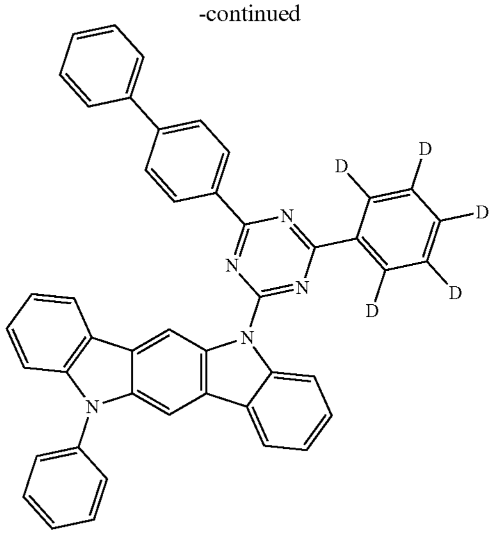
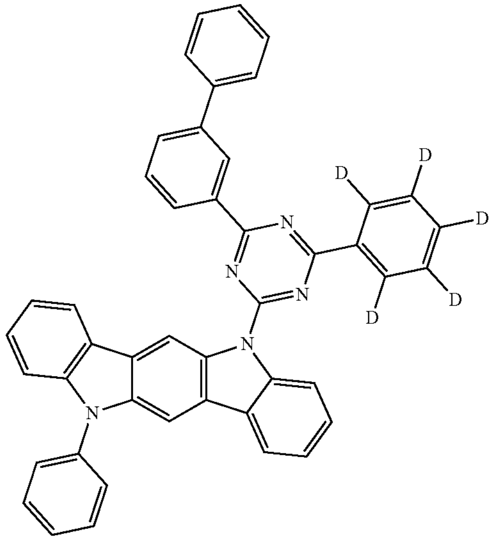
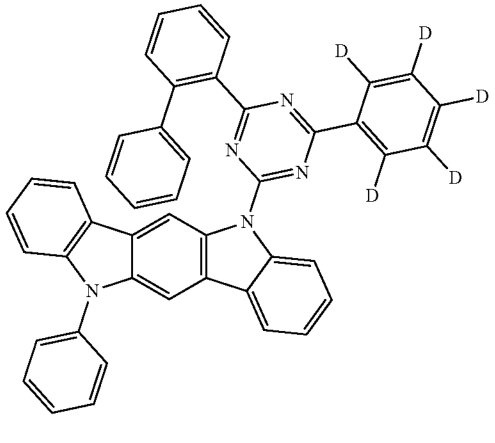

-continued
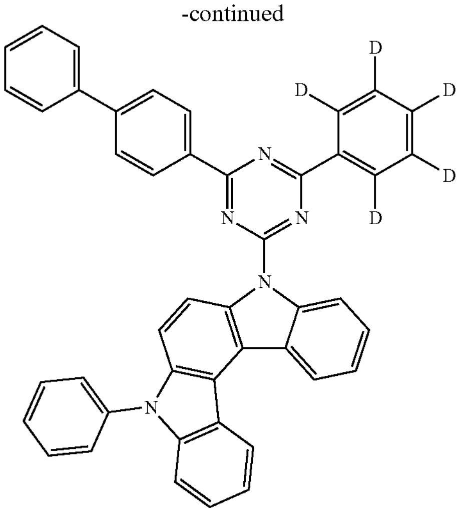
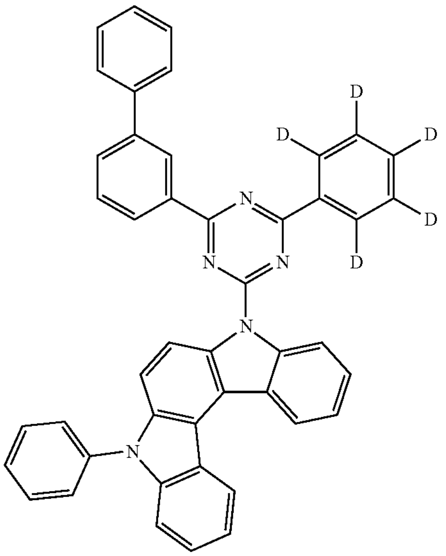
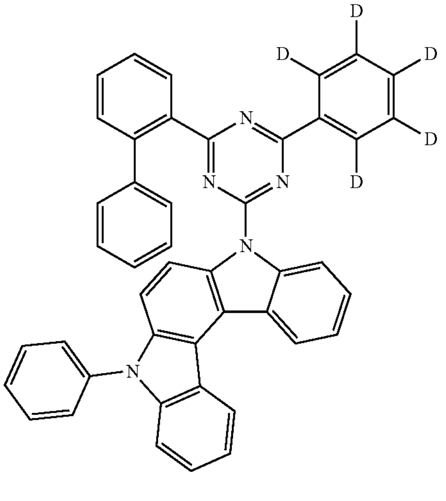
-continued
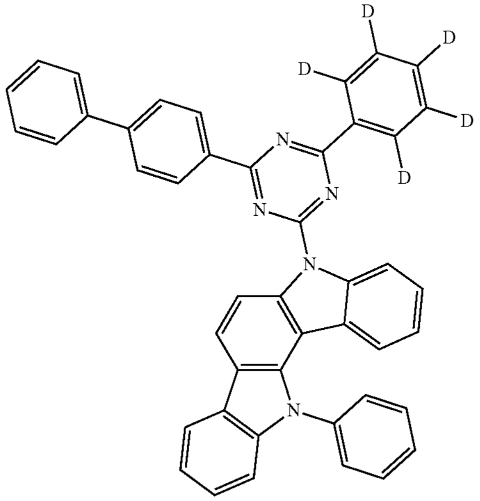
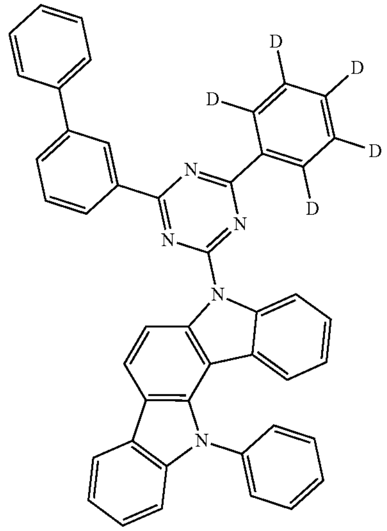
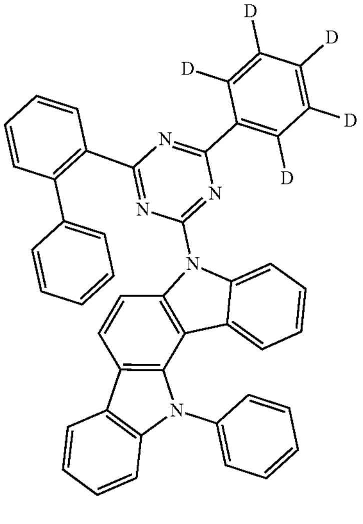

-continued
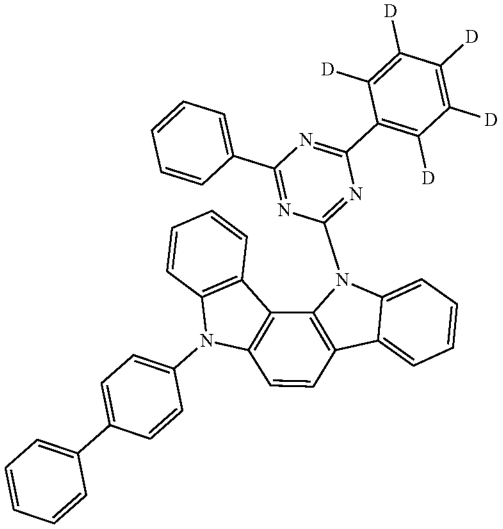
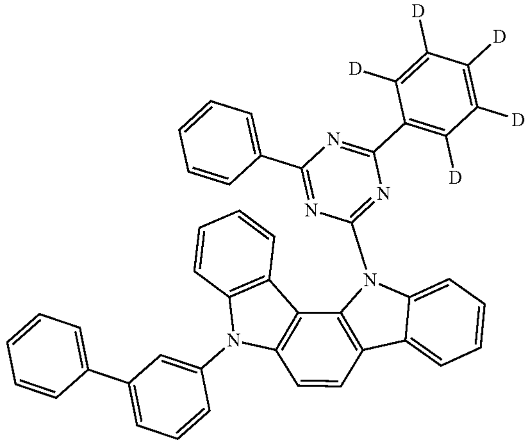
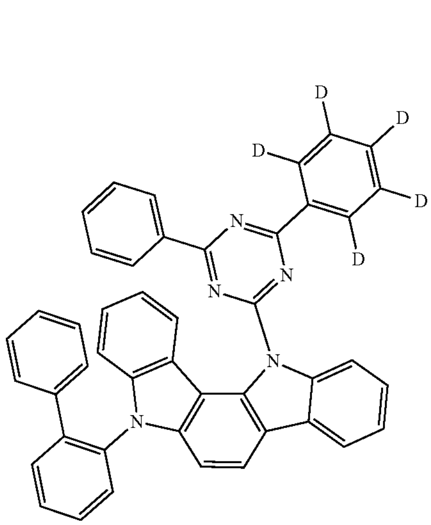
-continued
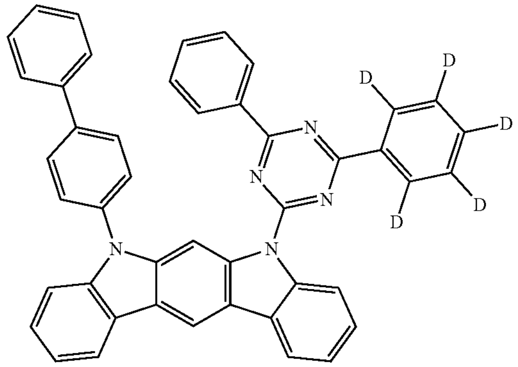
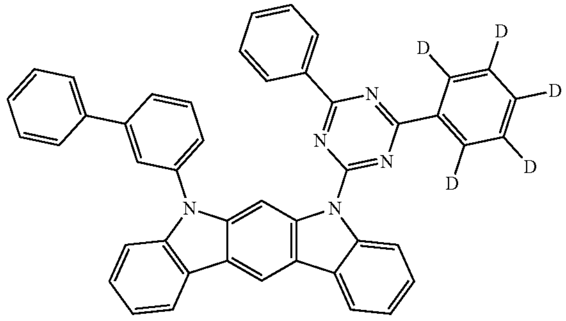
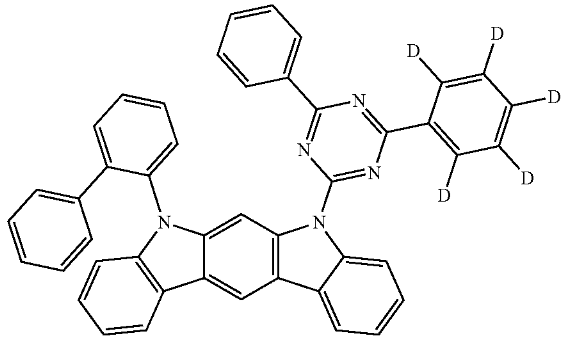
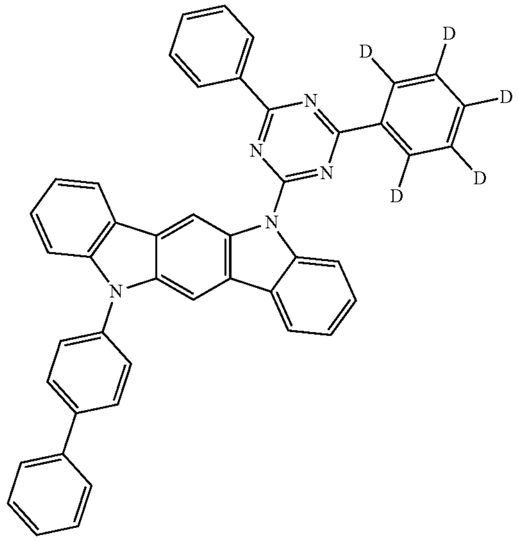

-continued
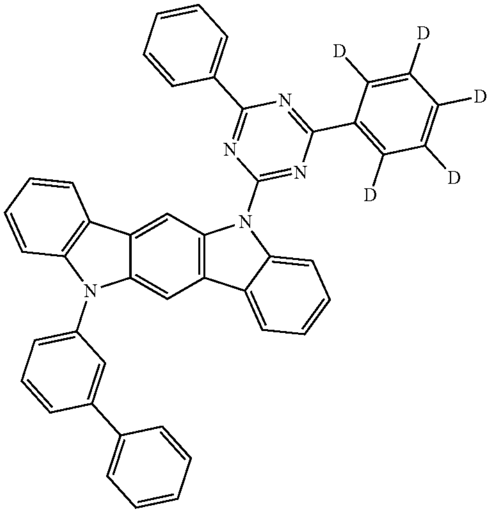
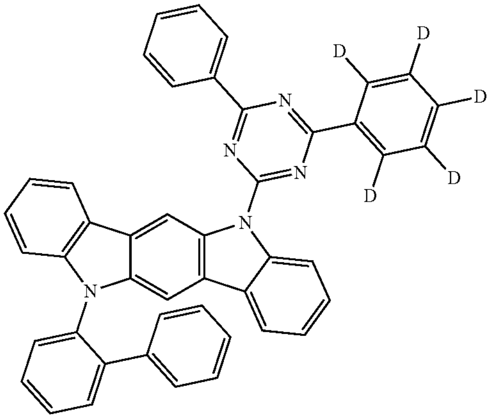
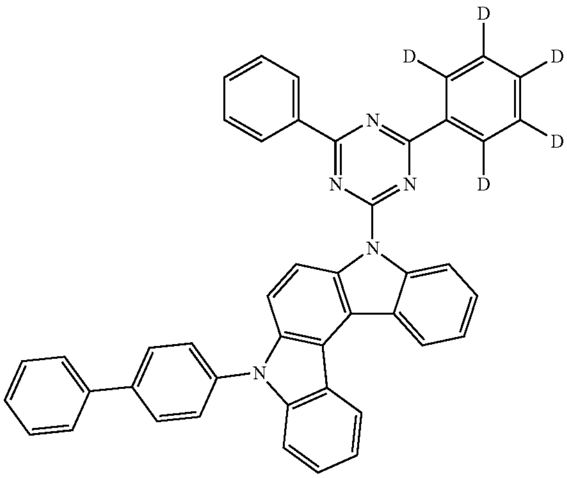
-continued
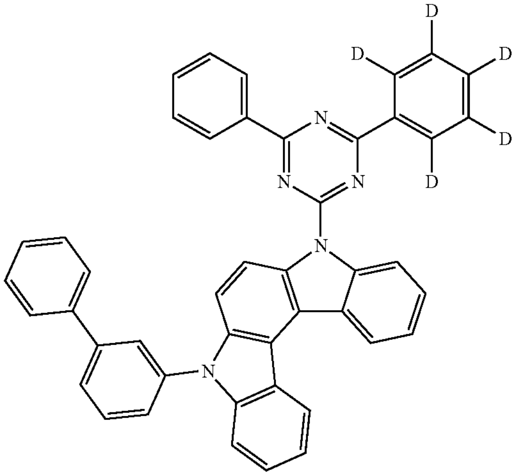
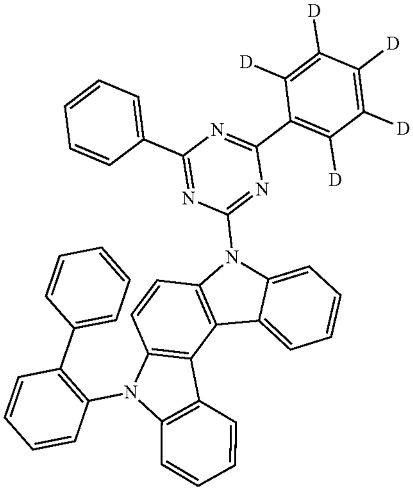
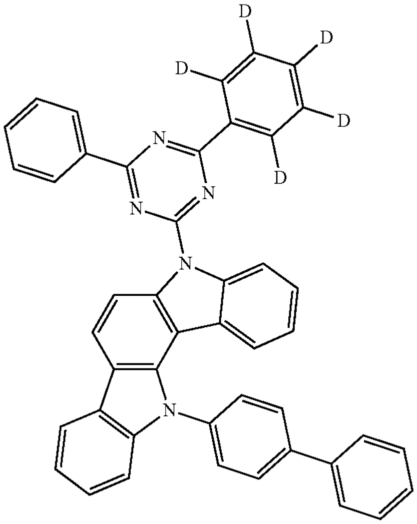

-continued
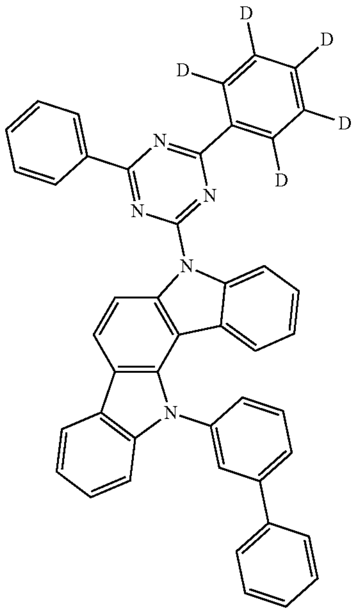
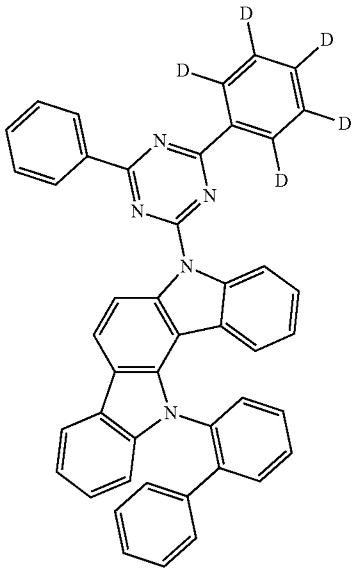
-continued
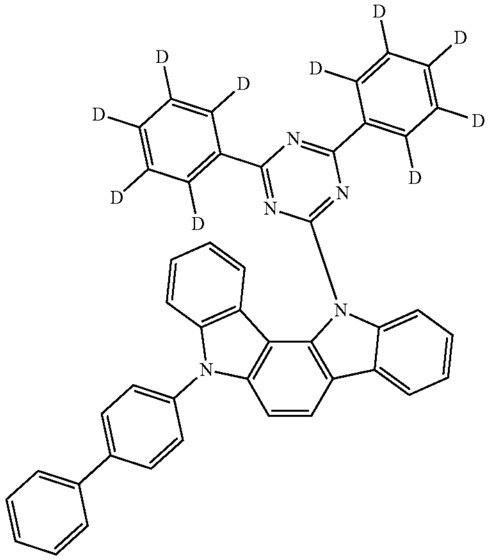
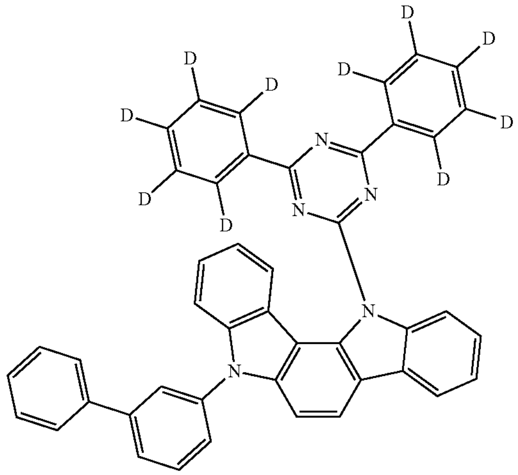
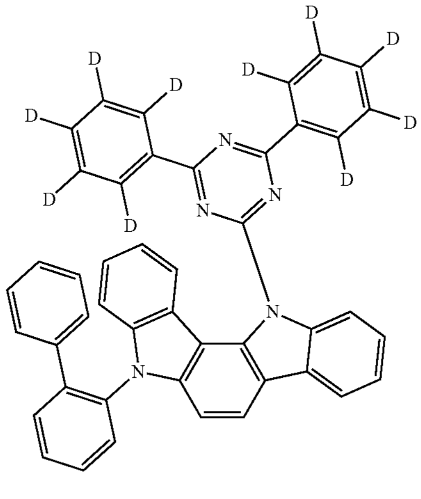

-continued
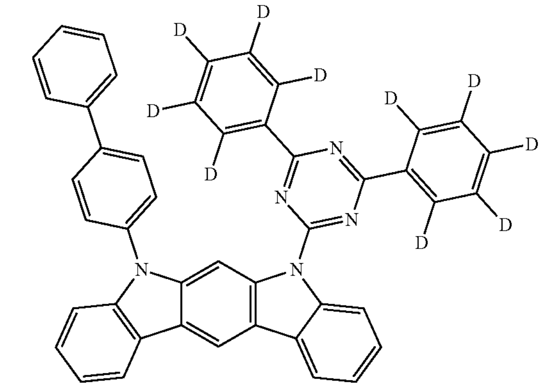
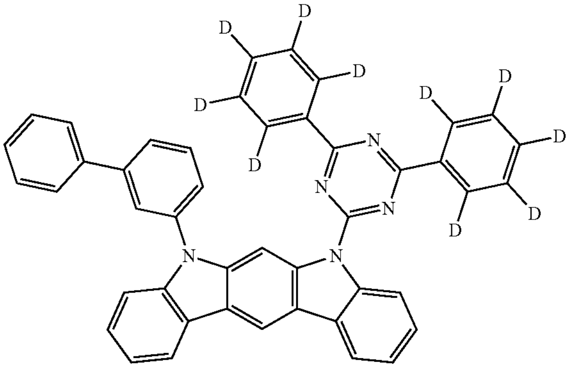
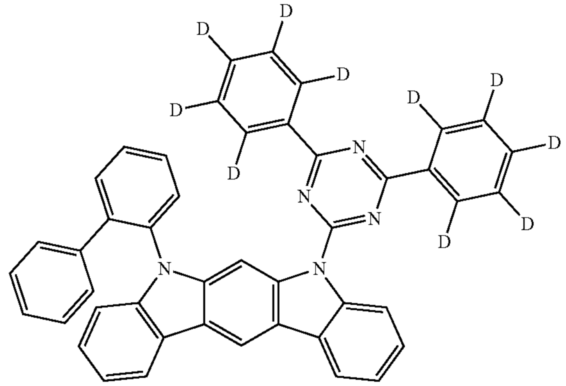
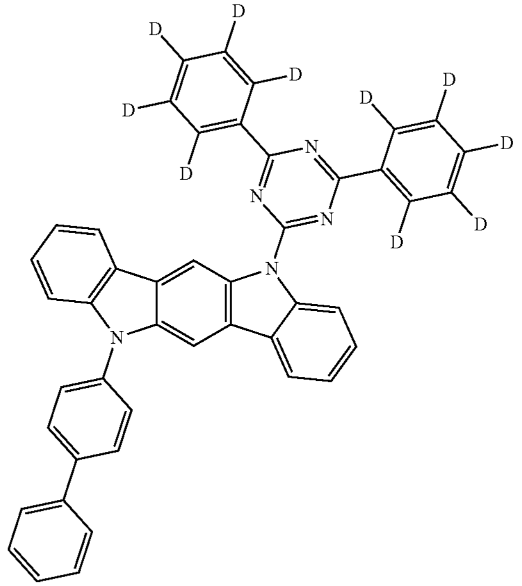
-continued
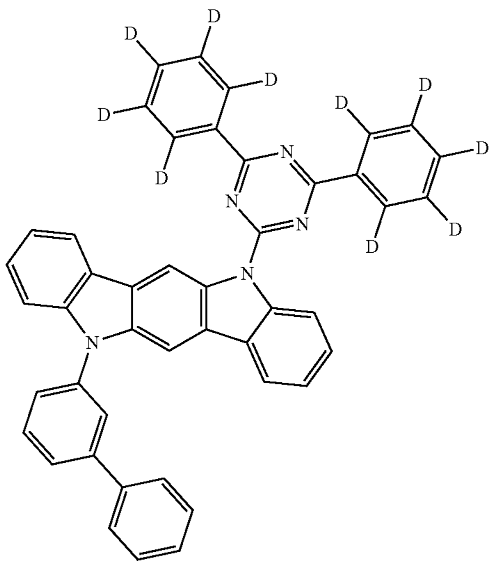
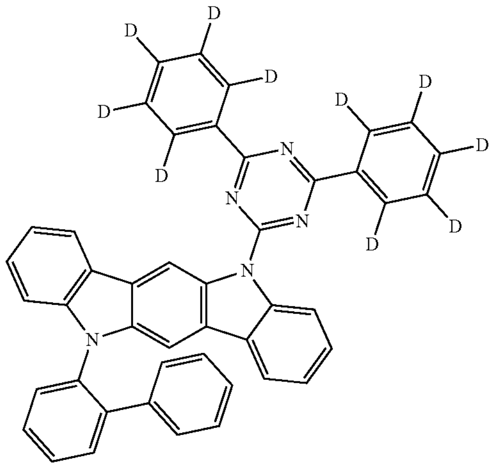
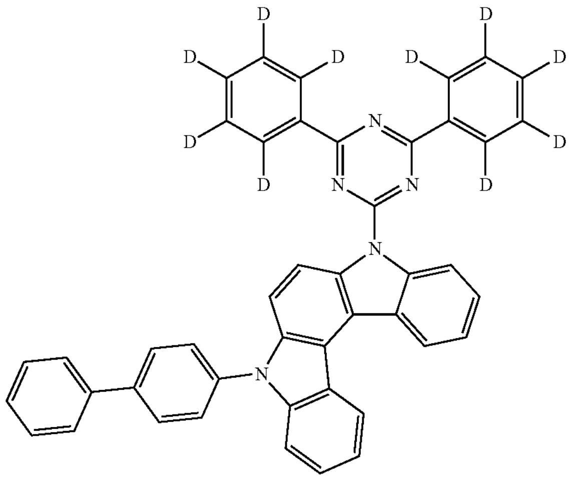

-continued
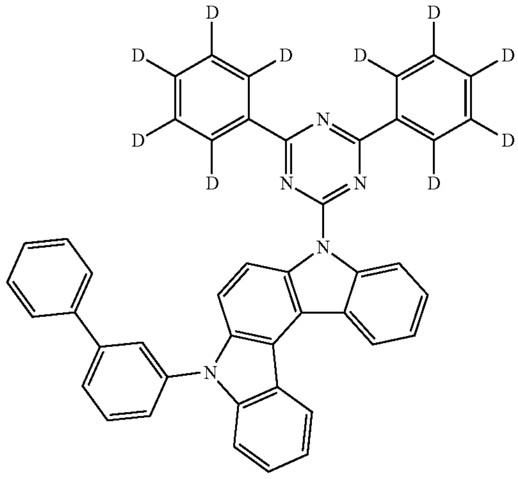
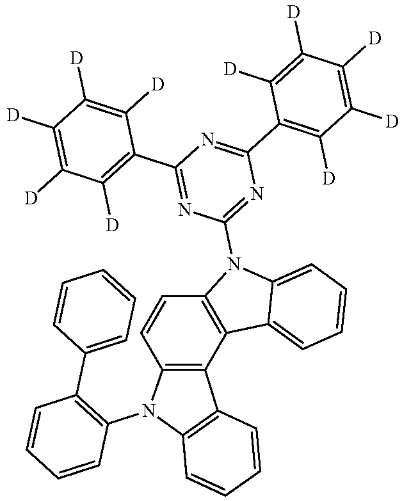
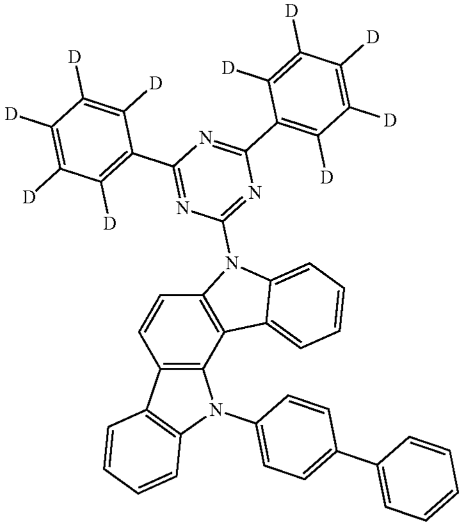
-continued
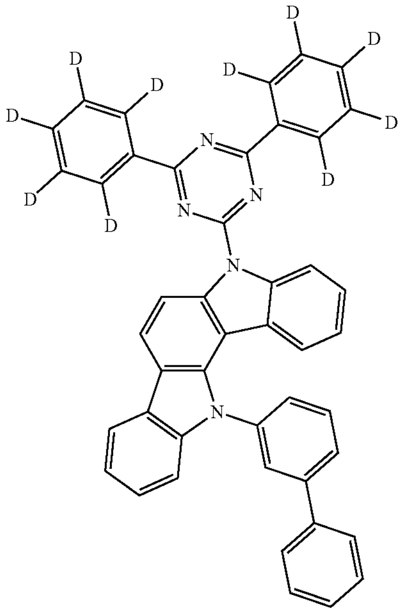
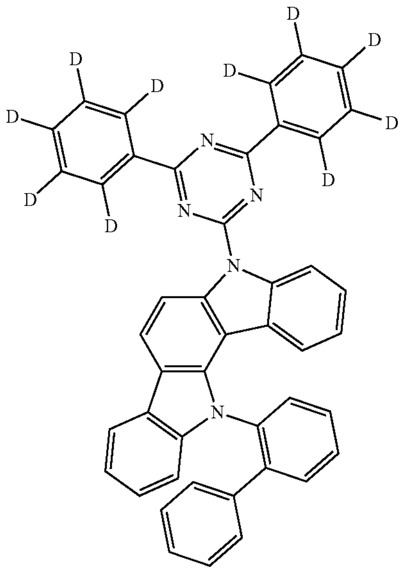
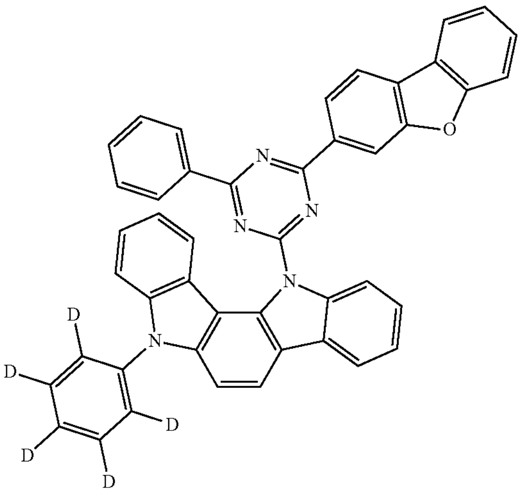

-continued
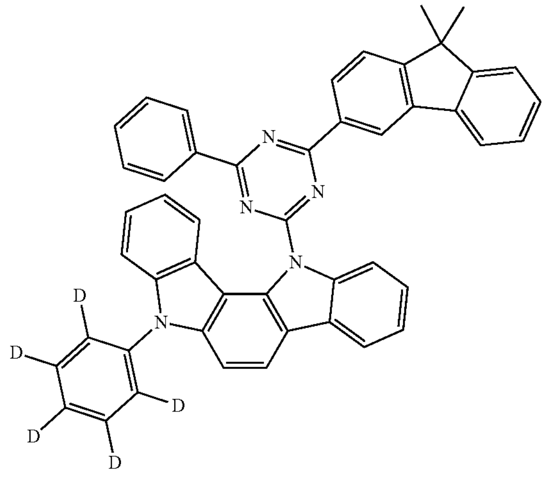
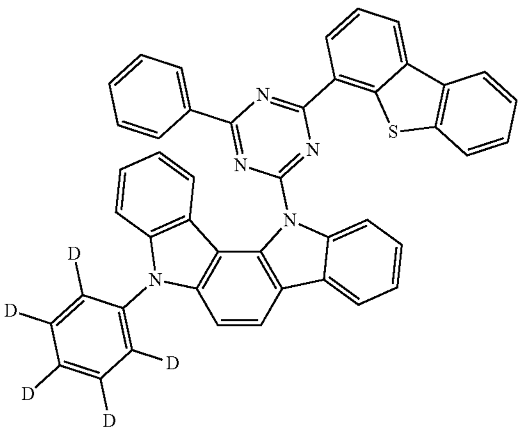
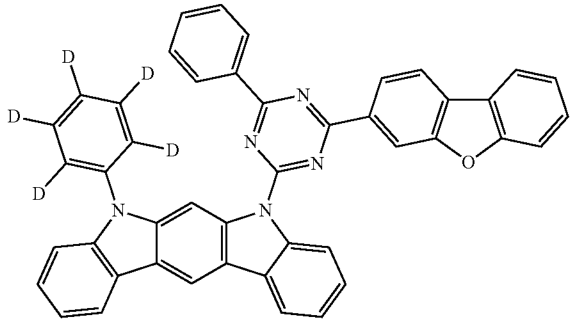
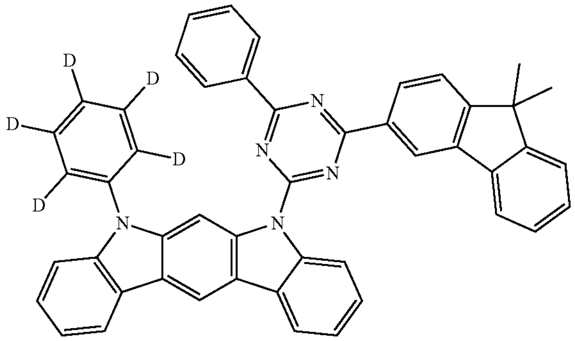
-continued
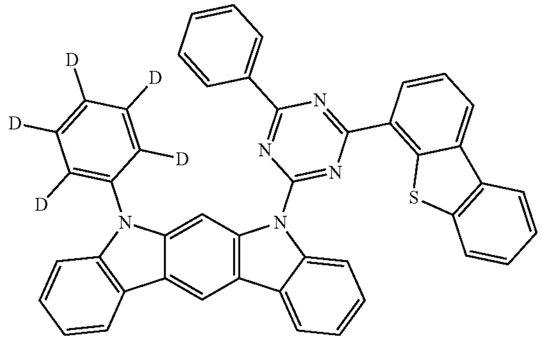
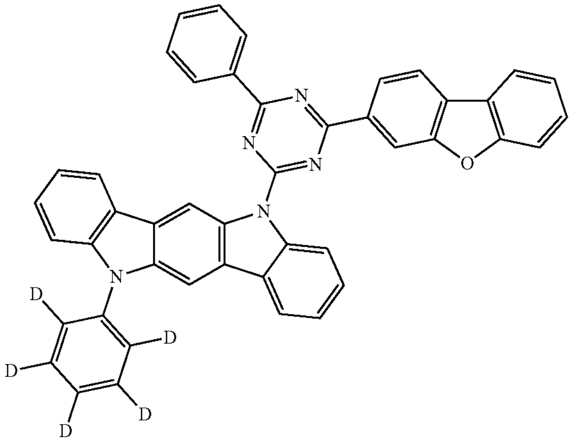
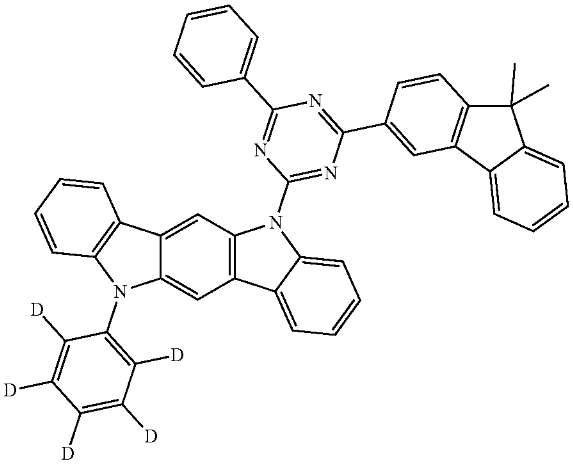
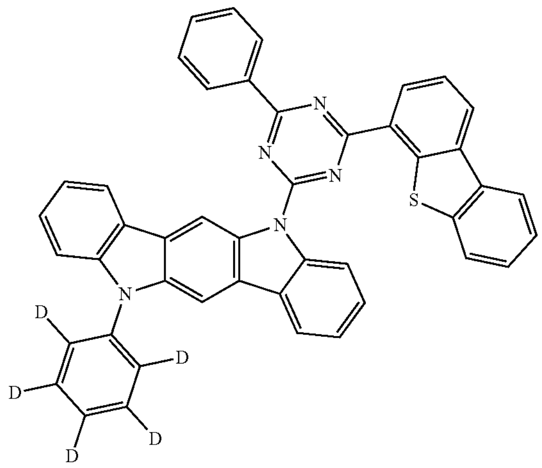

-continued
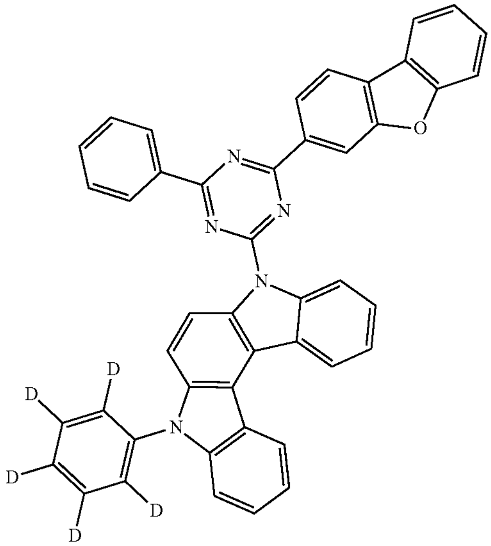
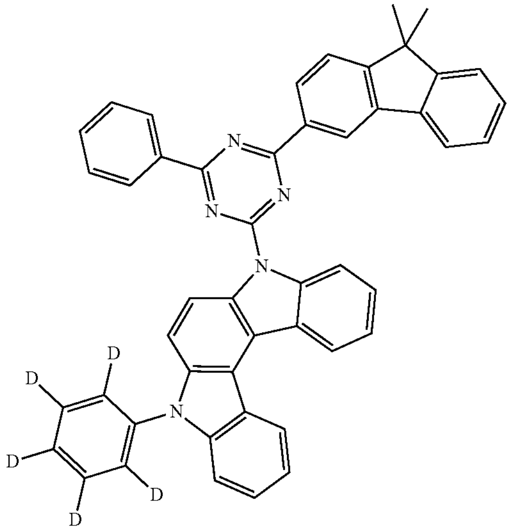
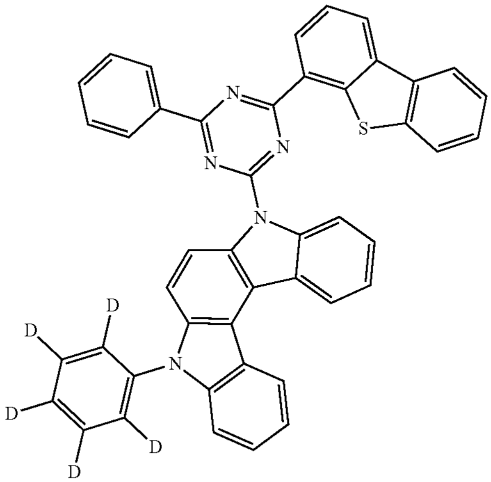
-continued
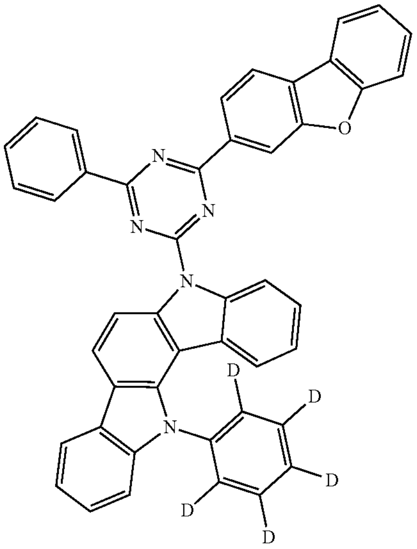
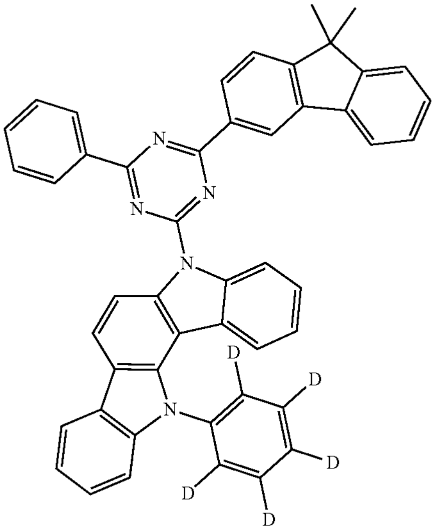
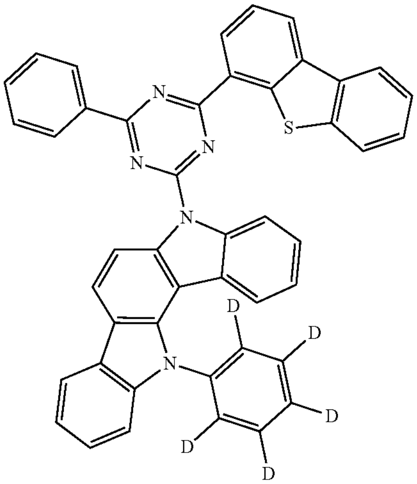

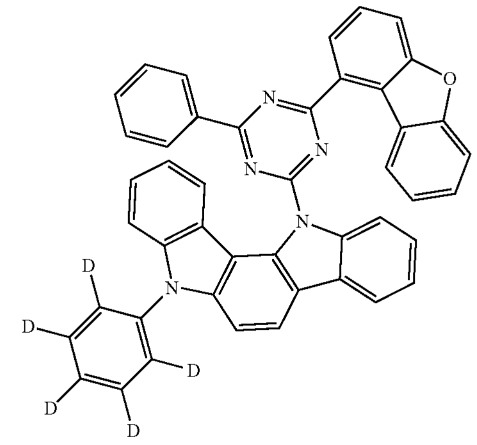
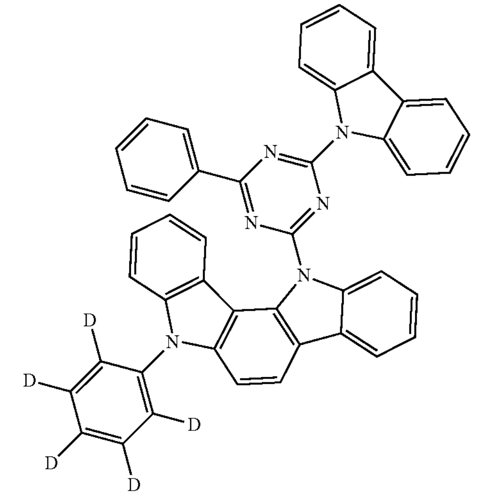
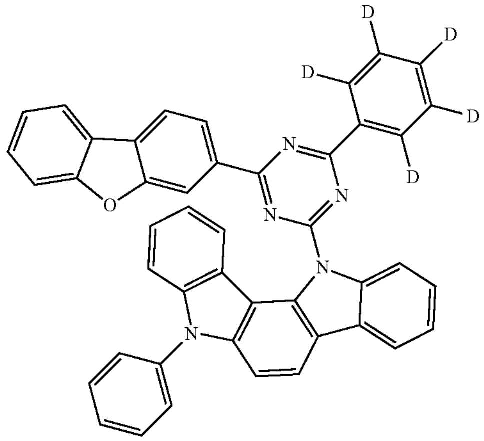
-continued
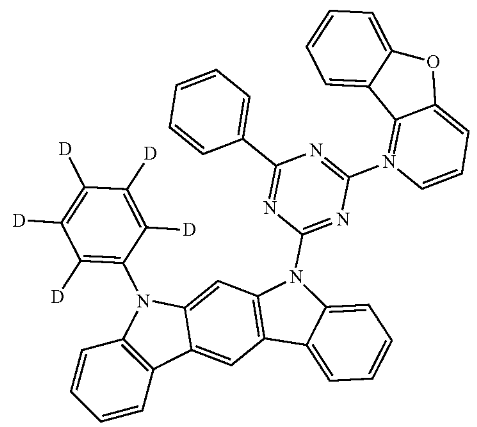
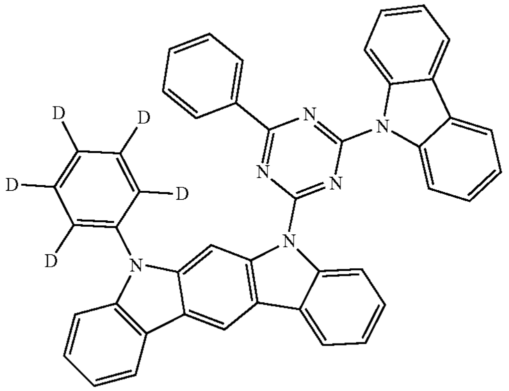
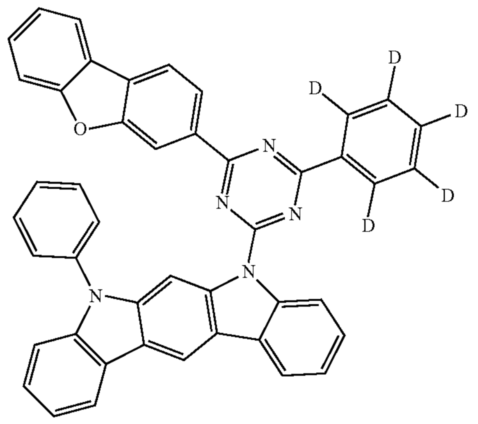

-continued
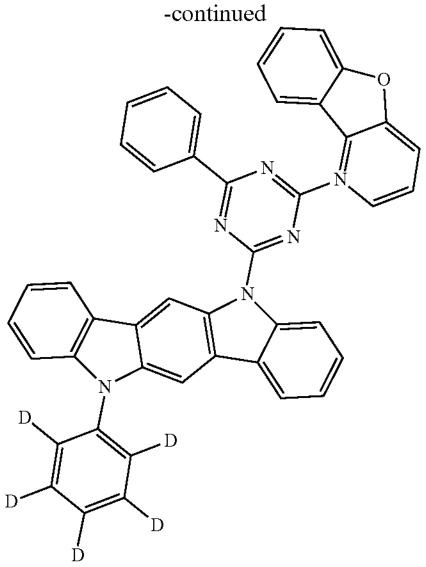
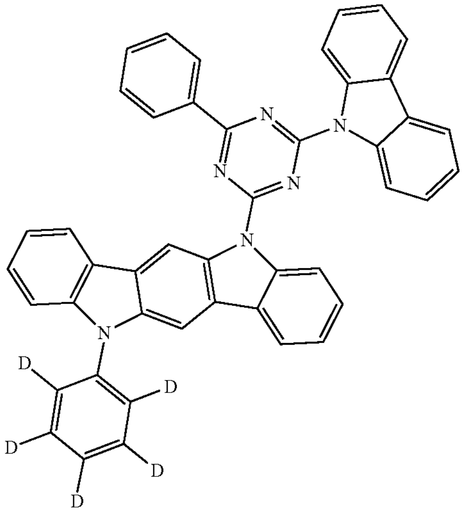
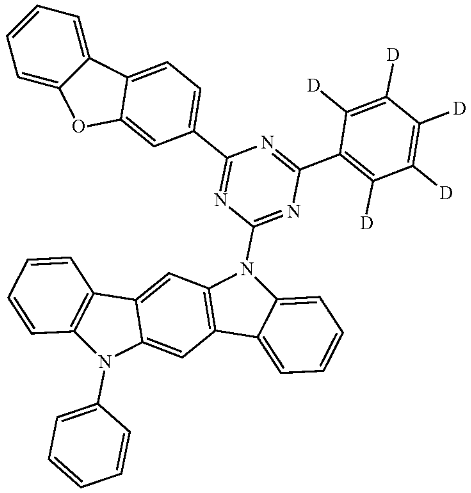
-continued
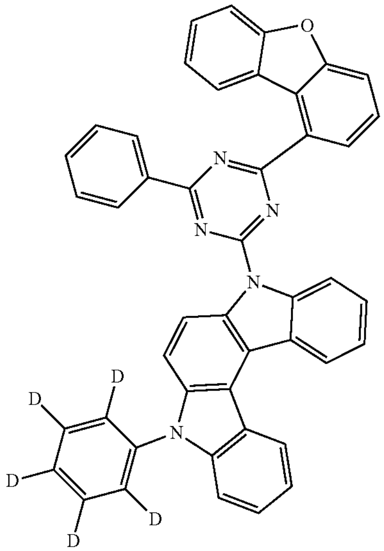
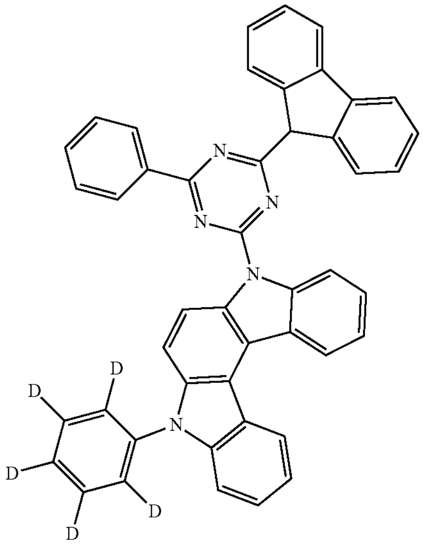
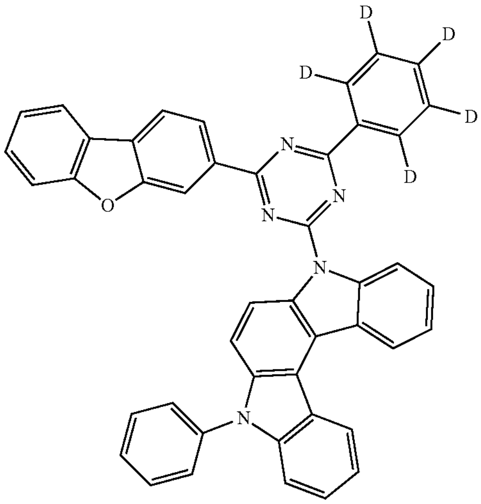

-continued
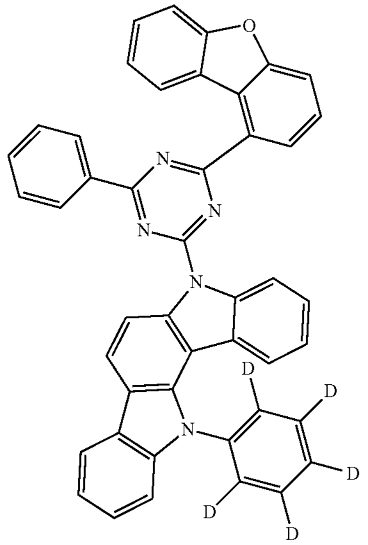
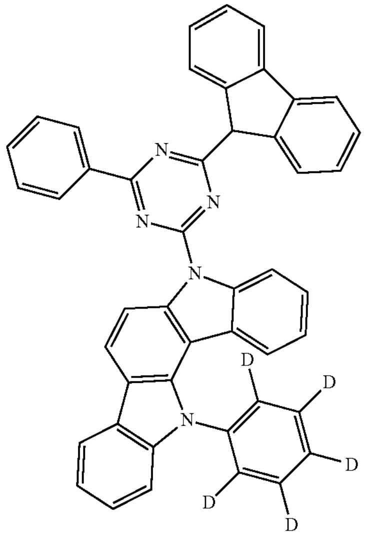
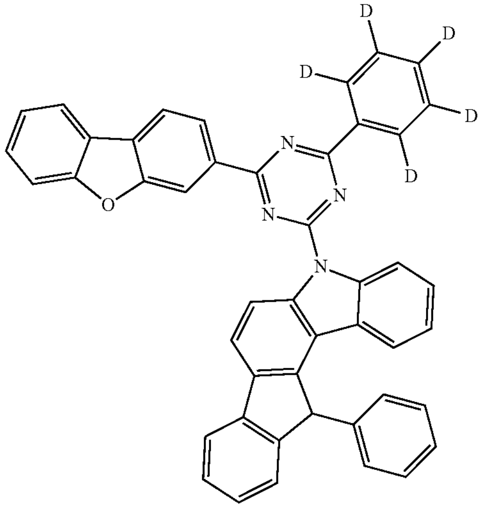
-continued
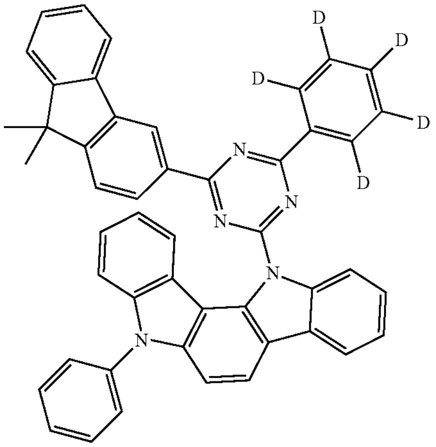
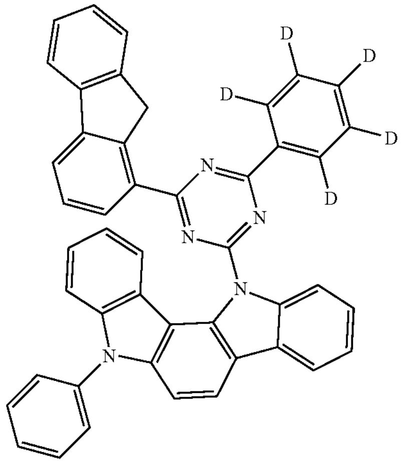
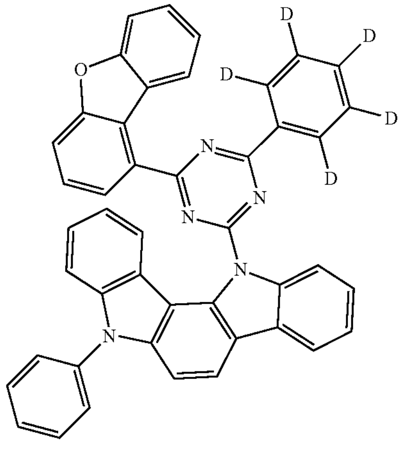

-continued
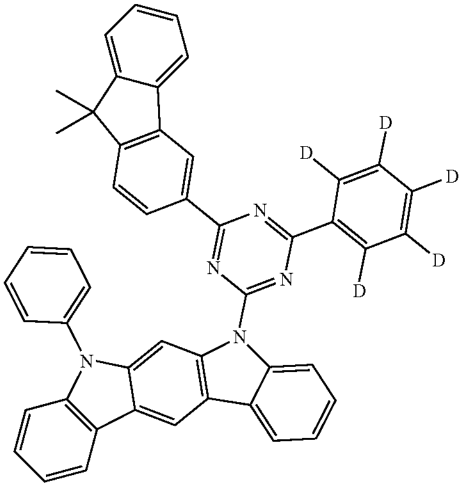
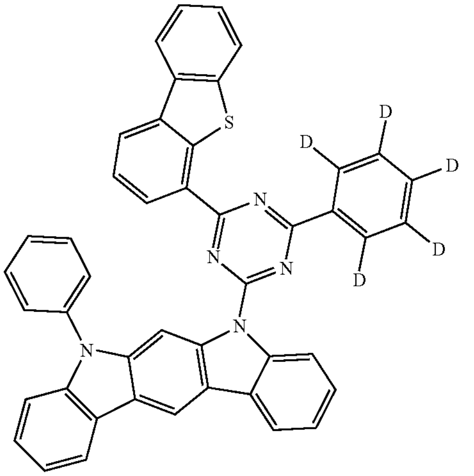
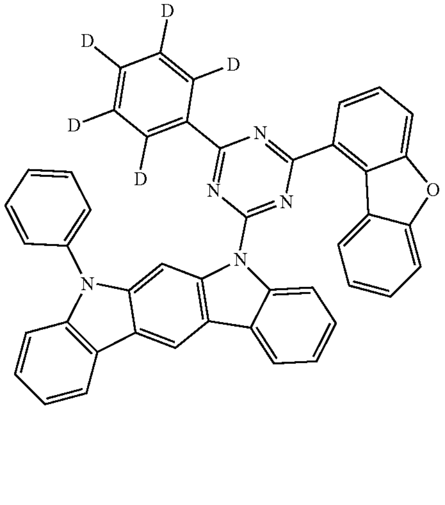
-continued
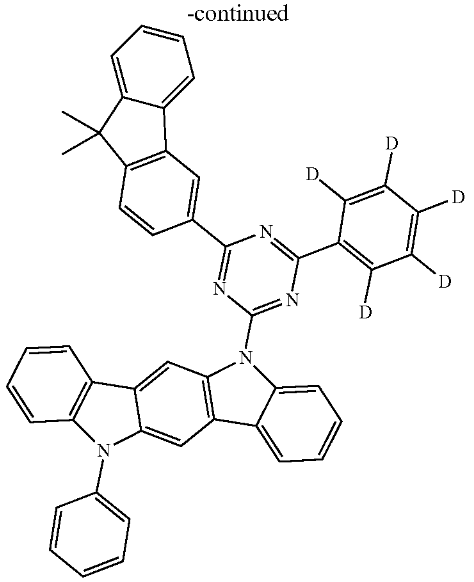
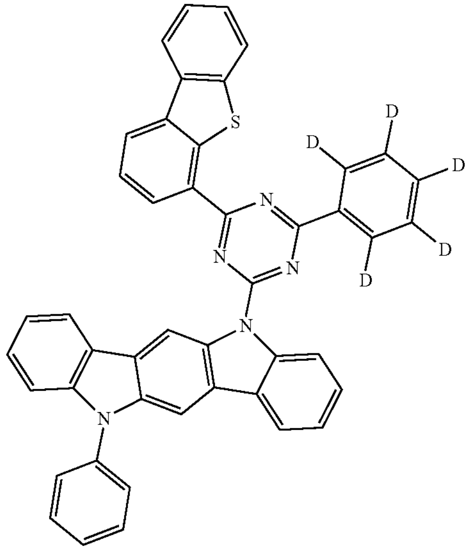
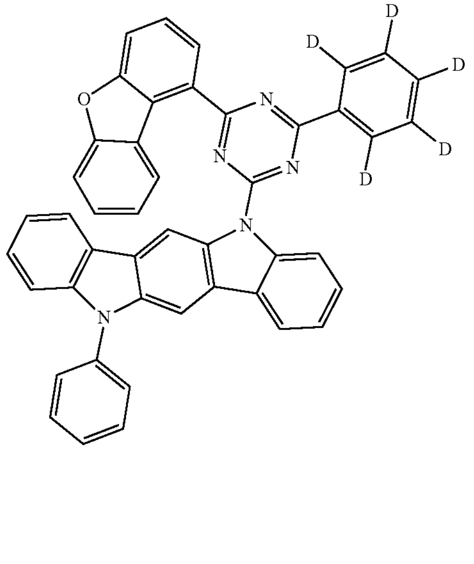

-continued
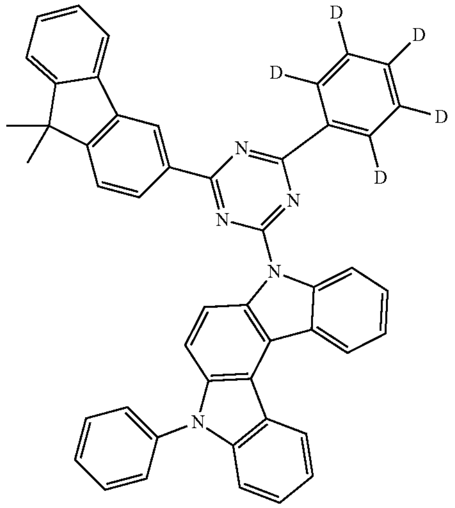
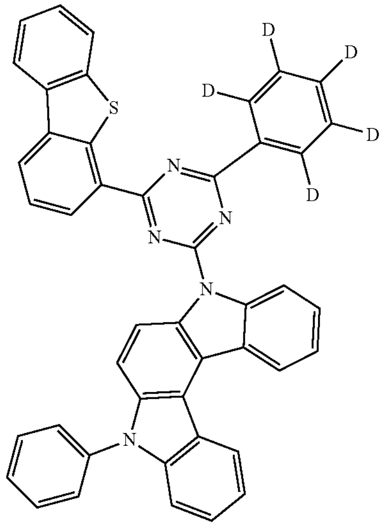
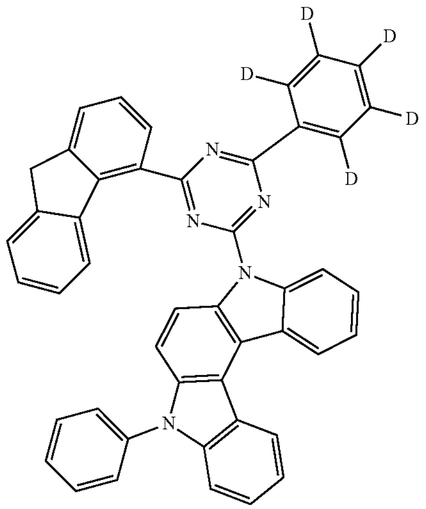
-continued
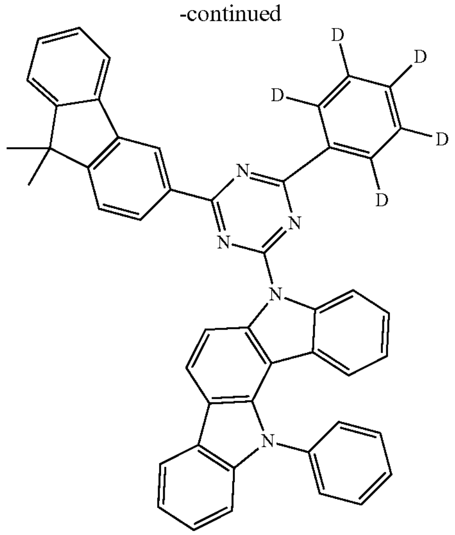
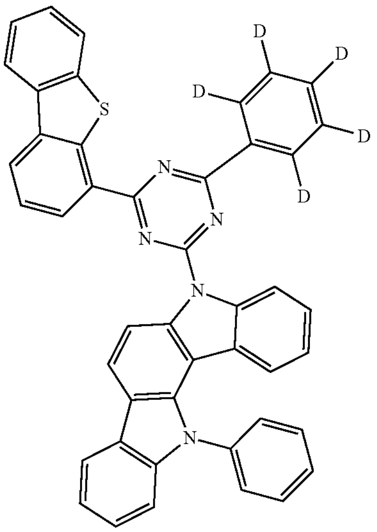
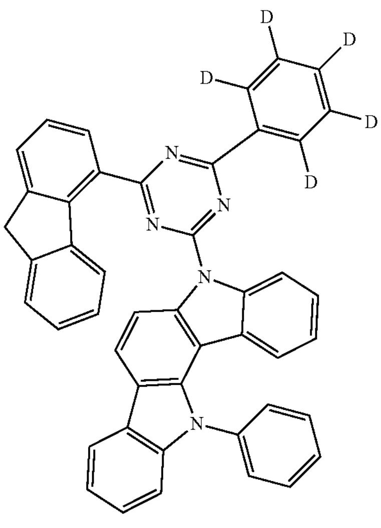

-continued
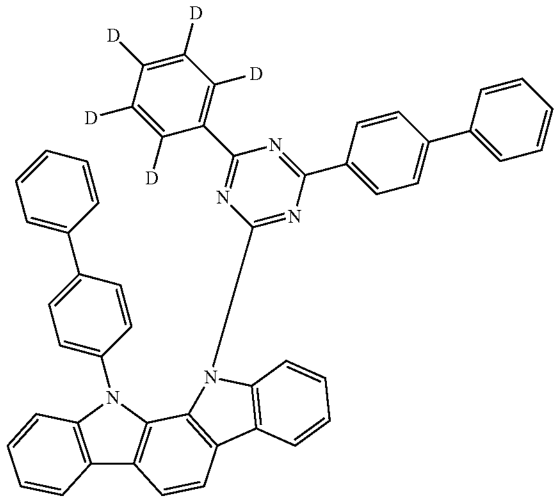
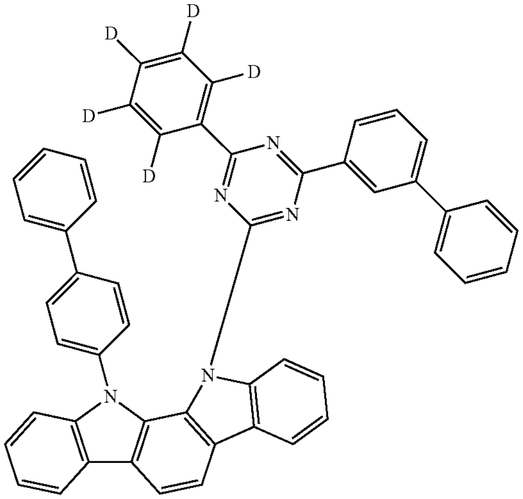
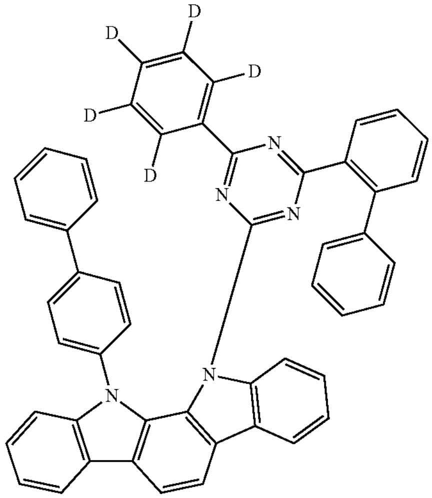
-continued
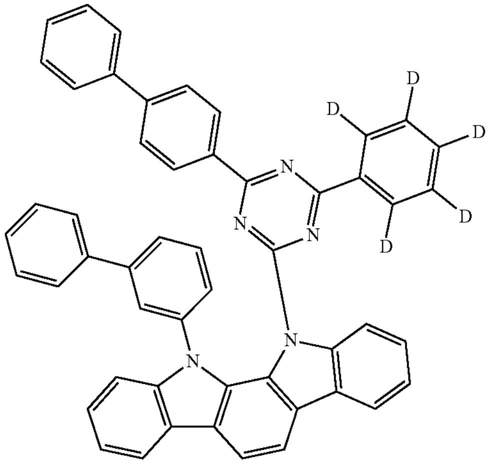
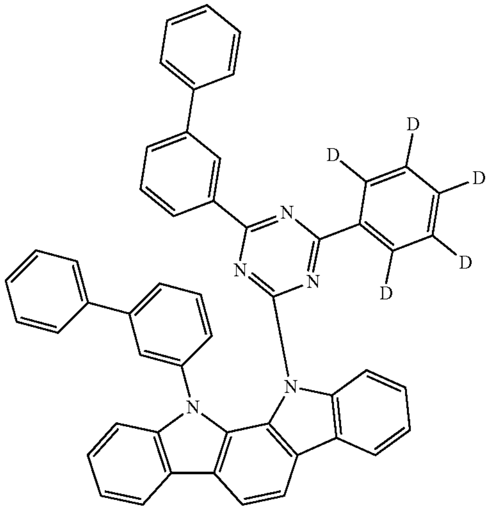
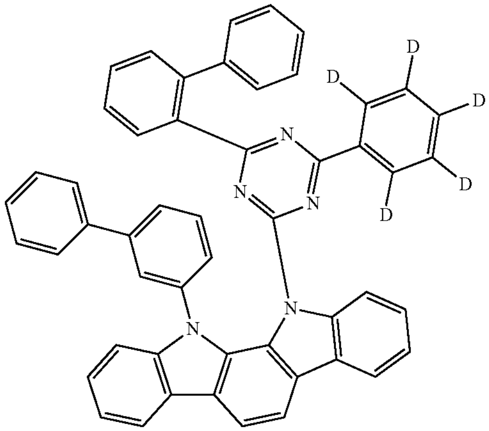

-continued
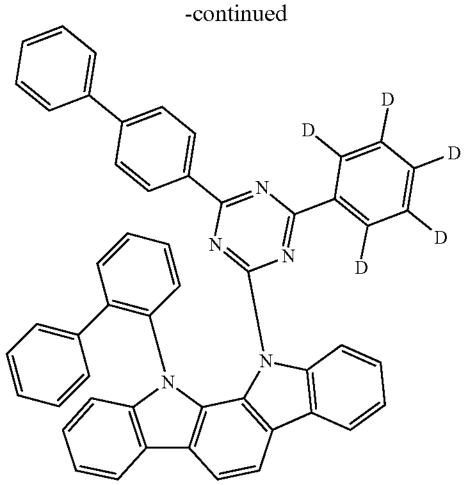
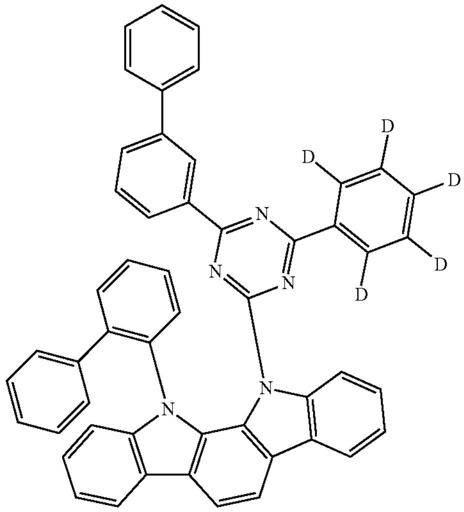
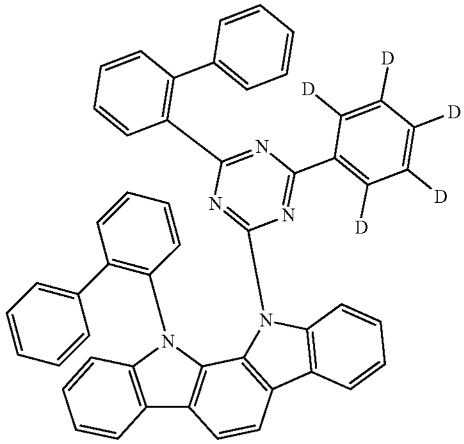
-continued
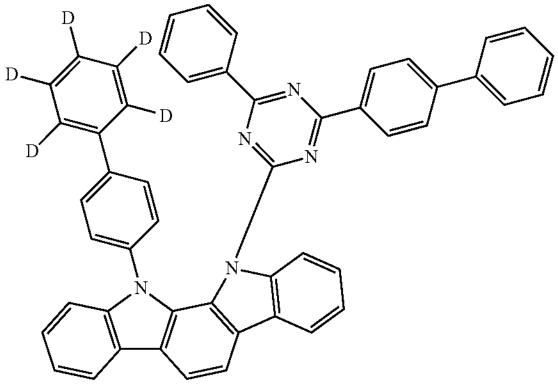
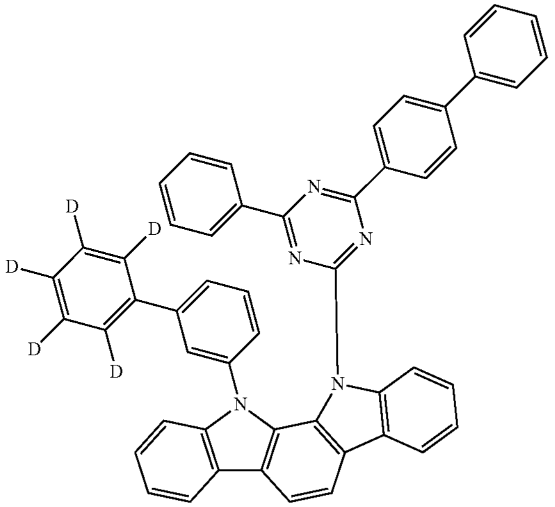
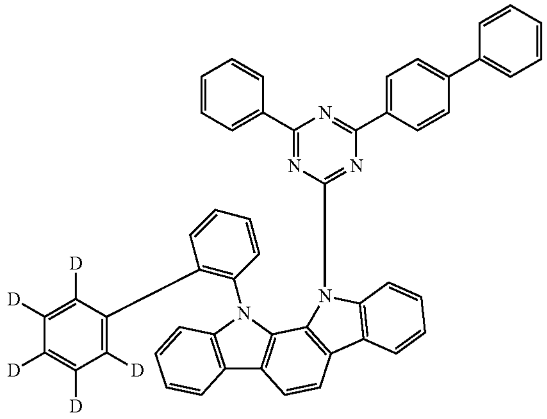
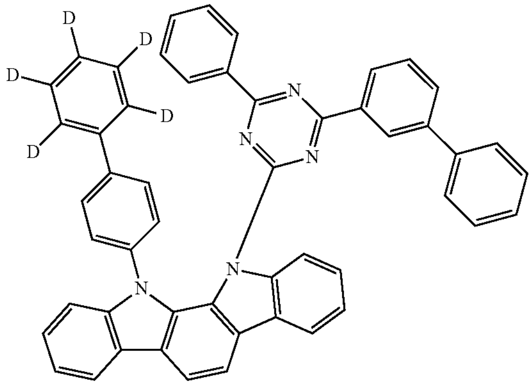

-continued
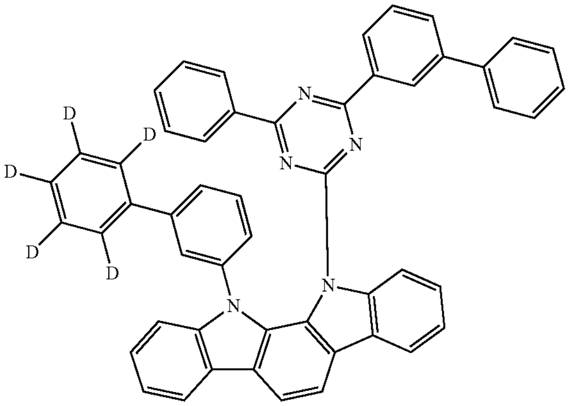
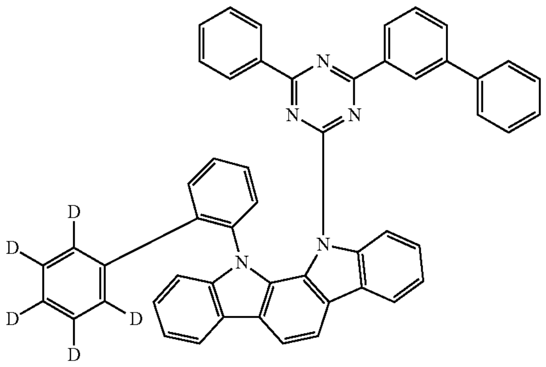
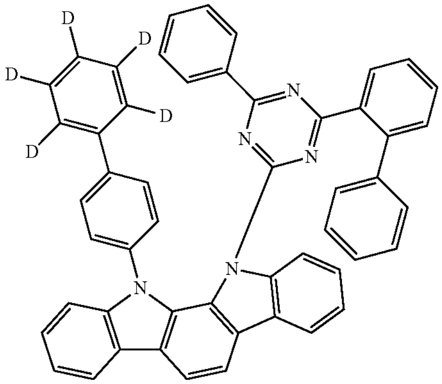
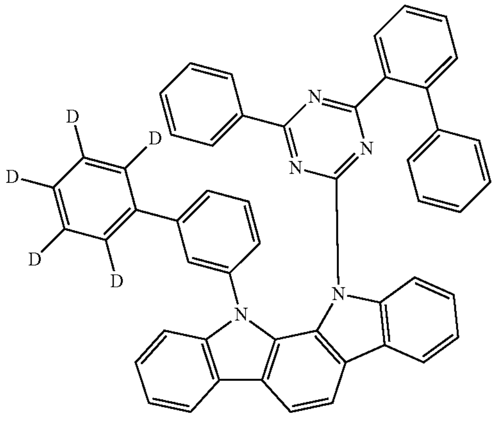
-continued
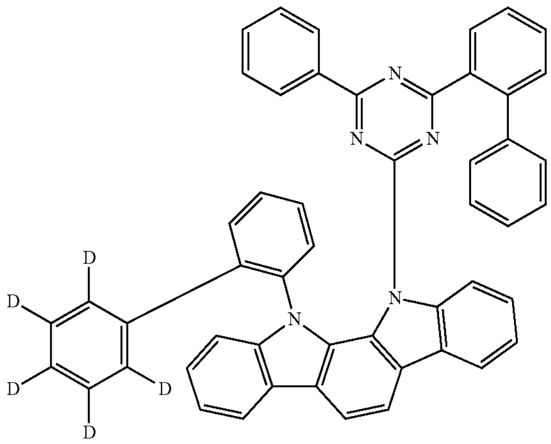
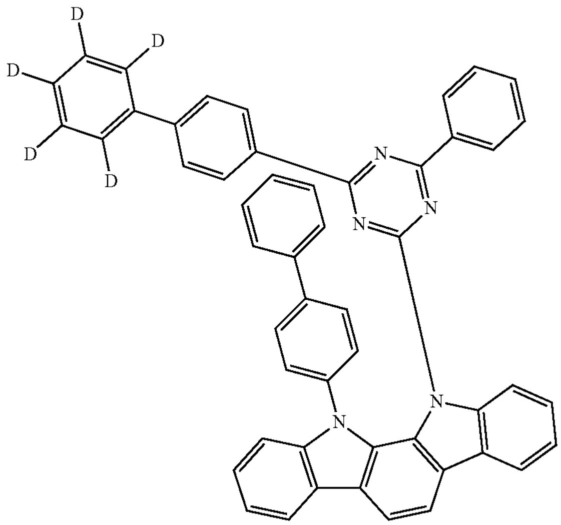
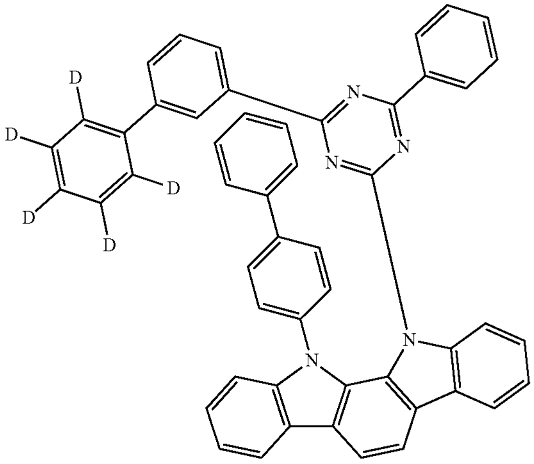

-continued
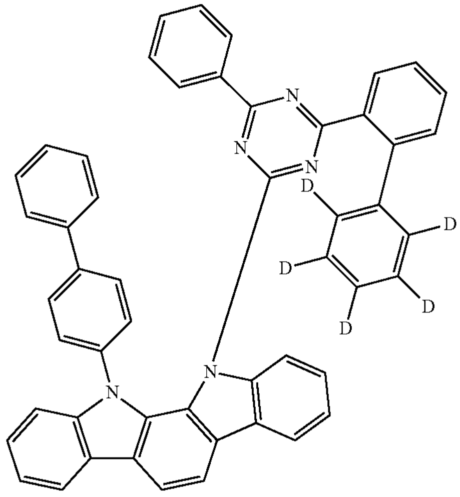
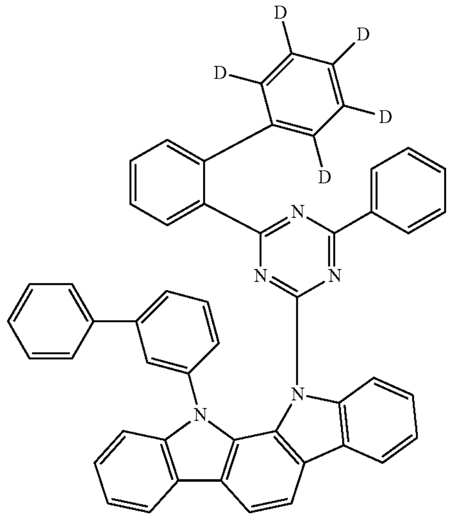
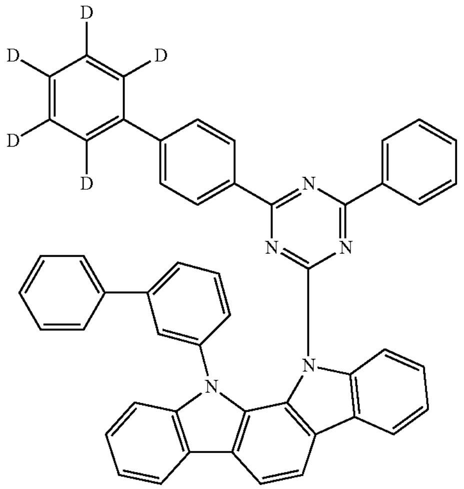
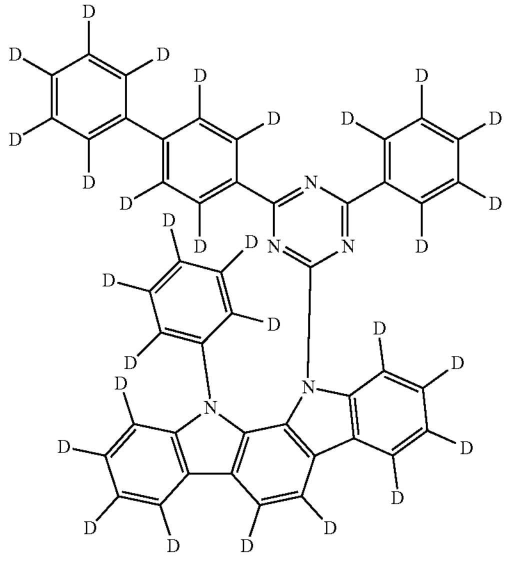
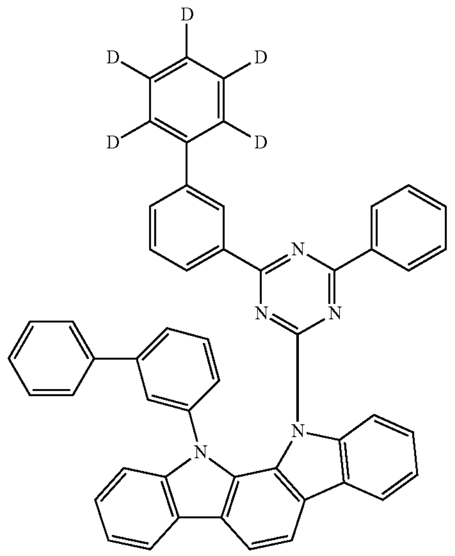
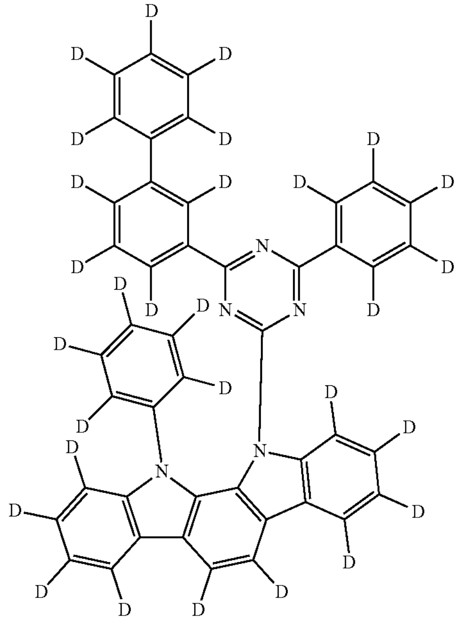
-continued -continued
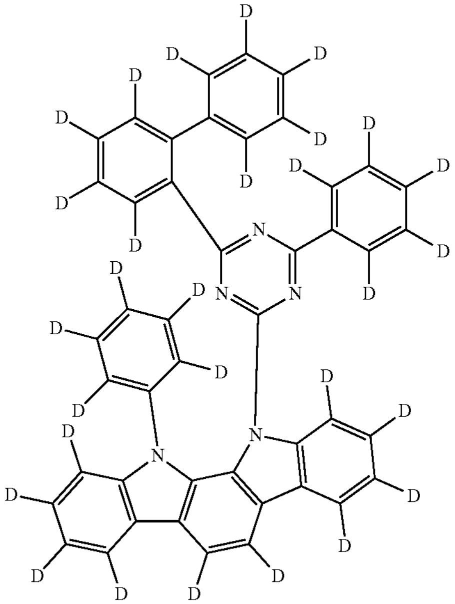
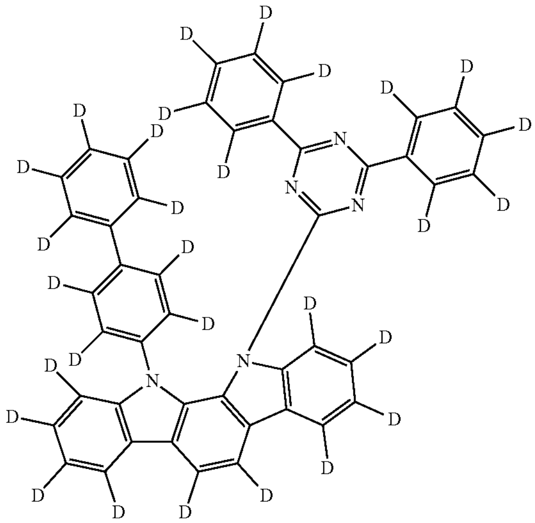
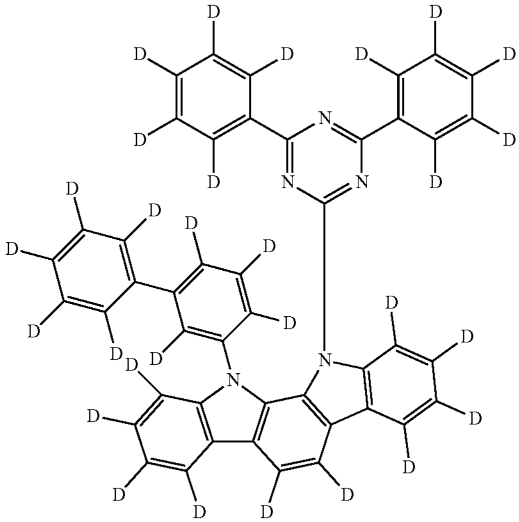
-continued
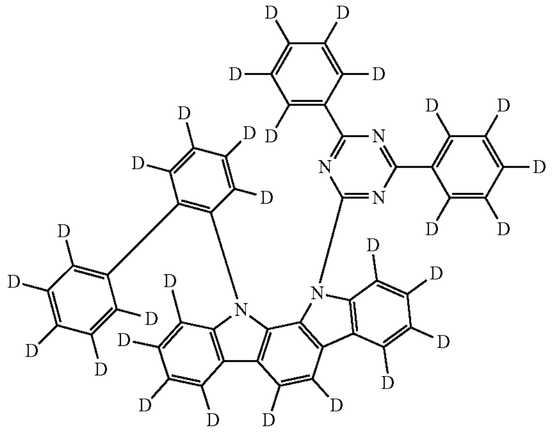
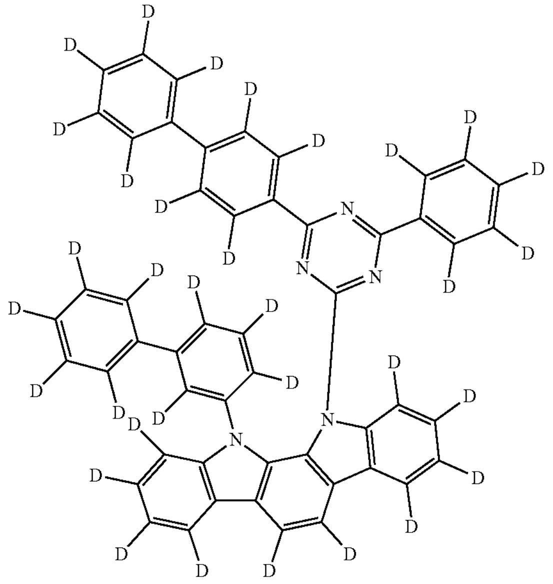
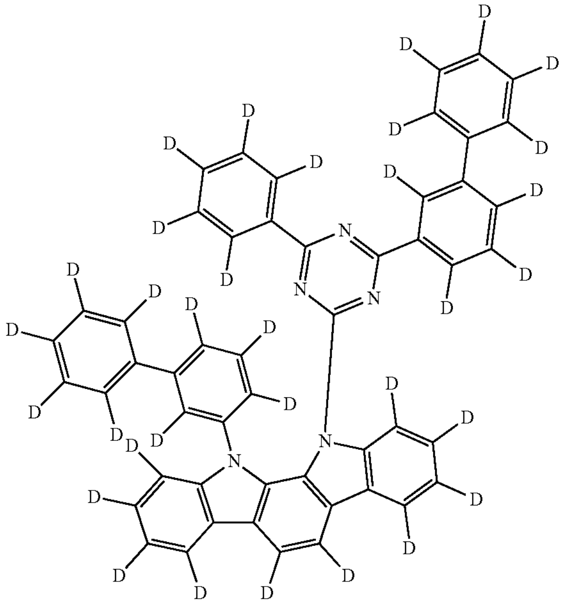

-continued
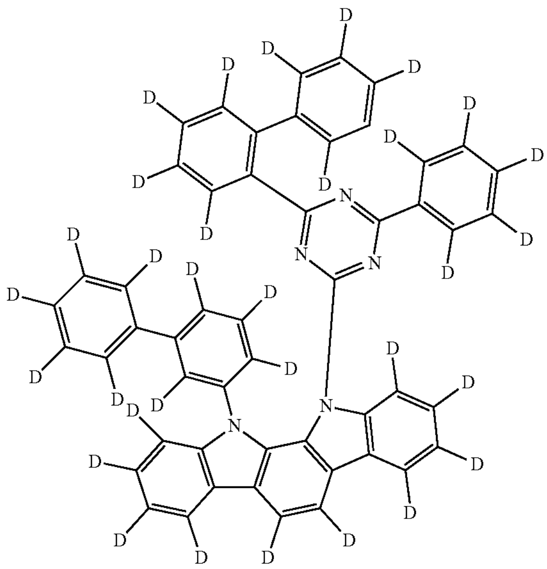
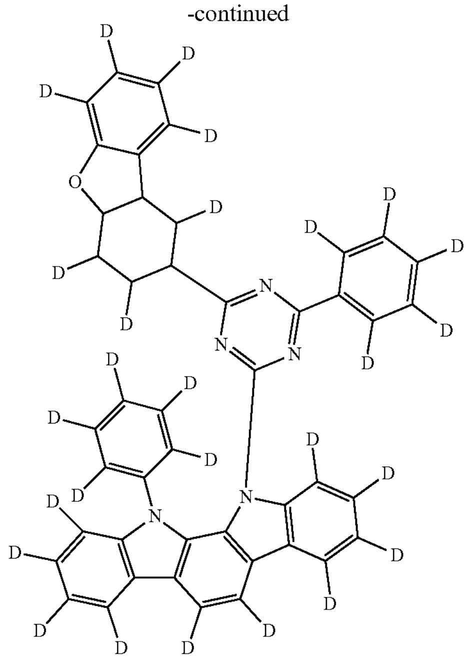
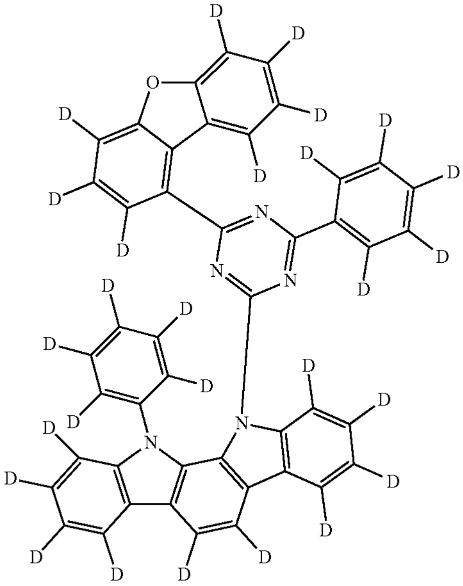
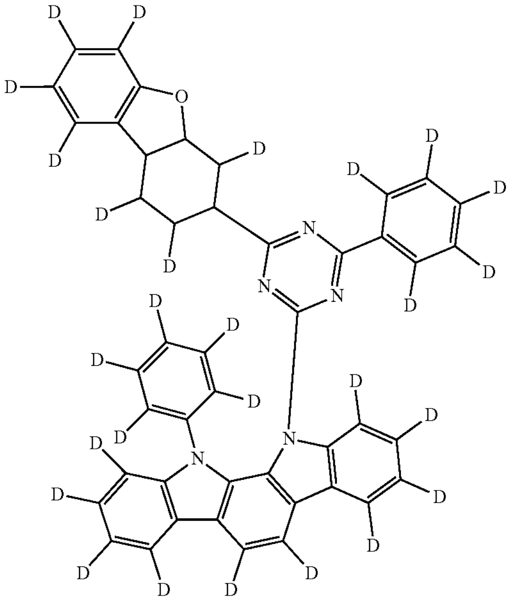
-continued

-continued
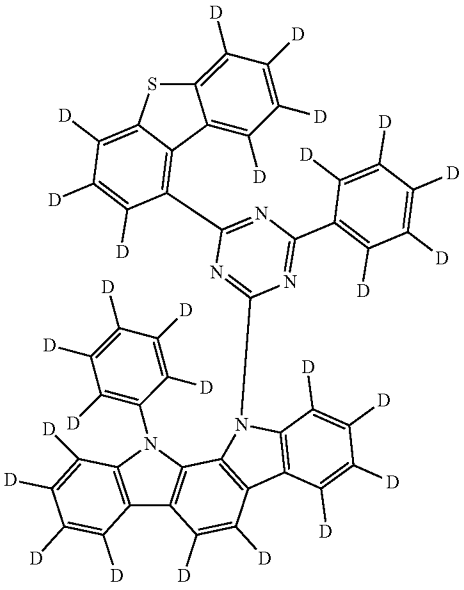
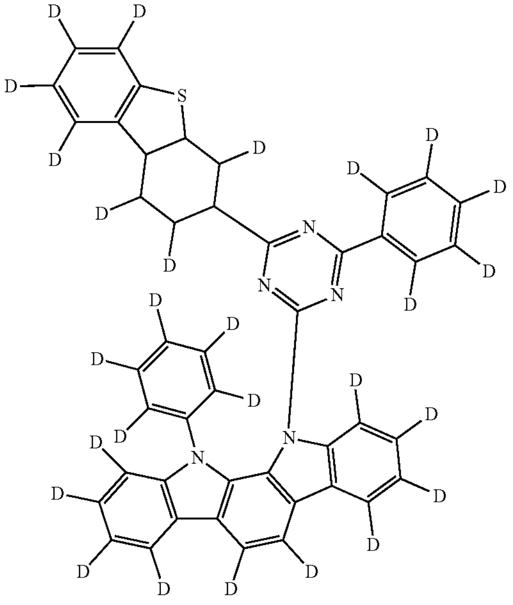
-continued
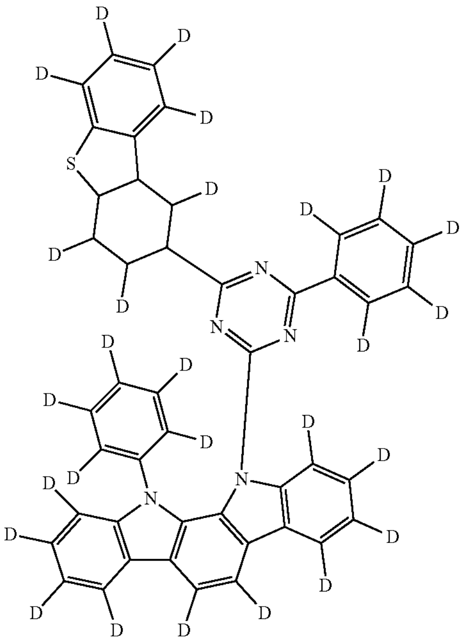
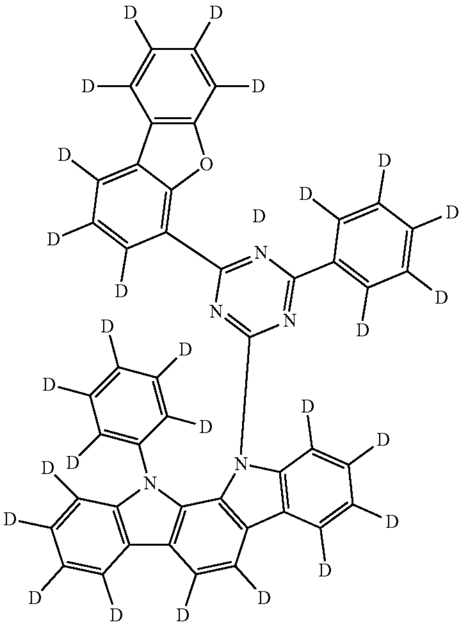

-continued
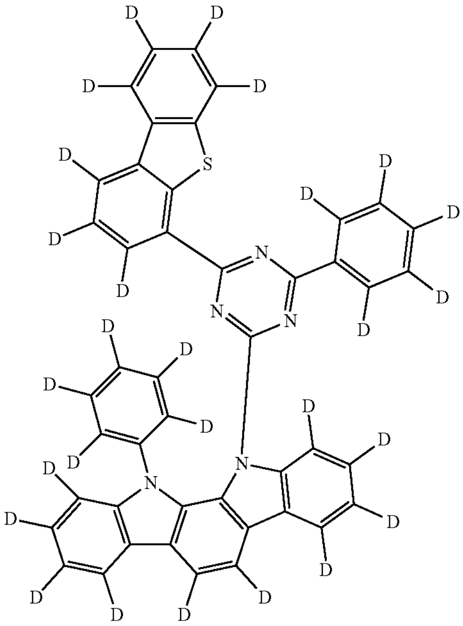
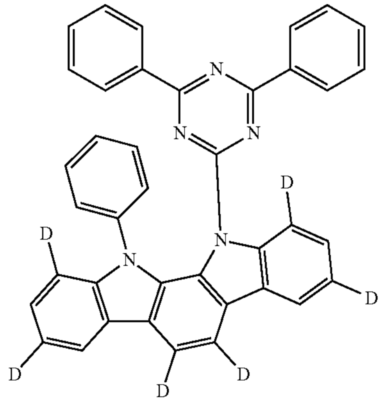
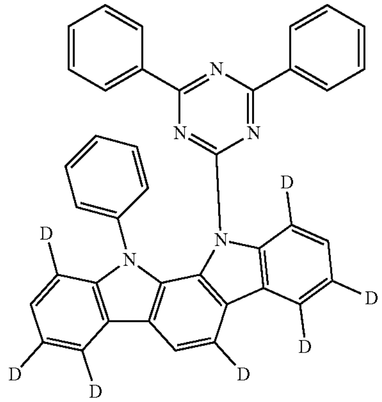
-continued
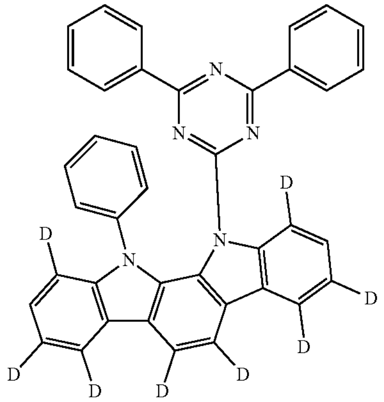
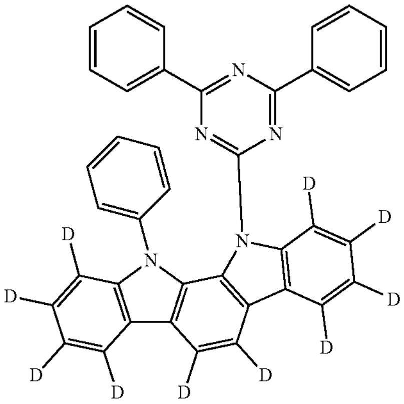
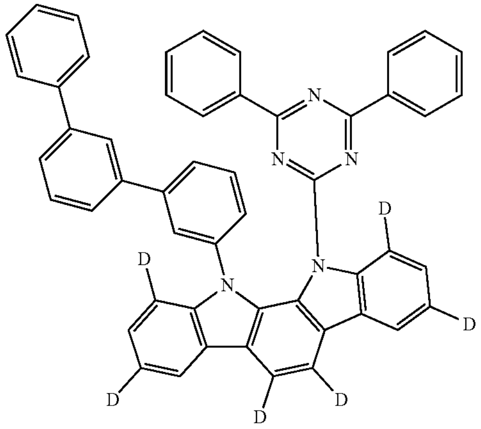
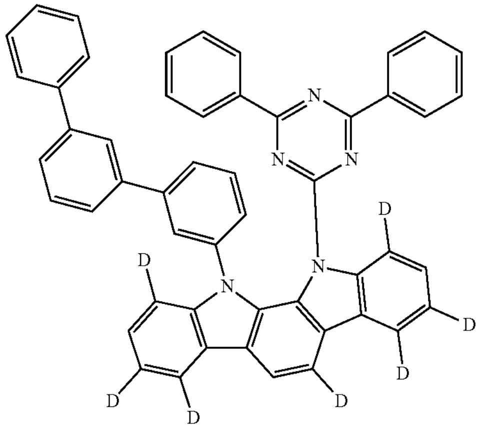

-continued
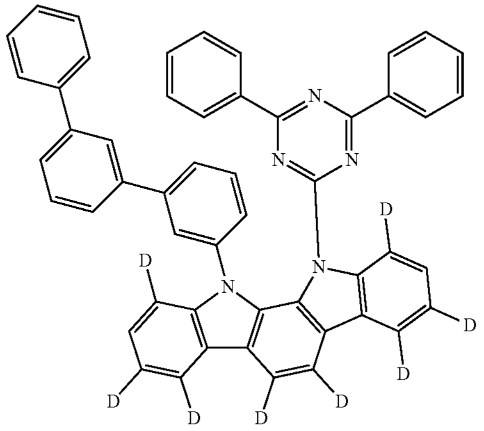
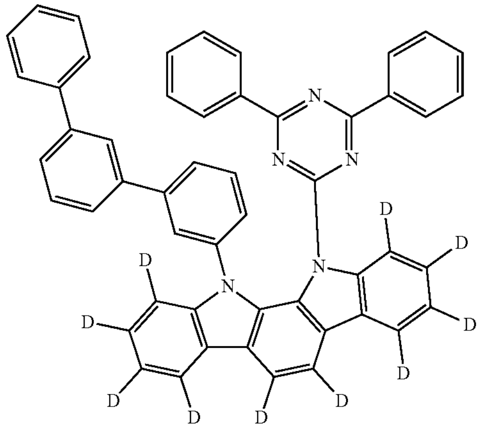
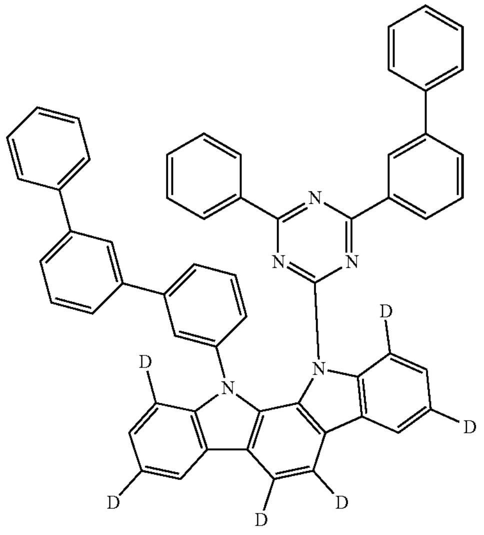
-continued
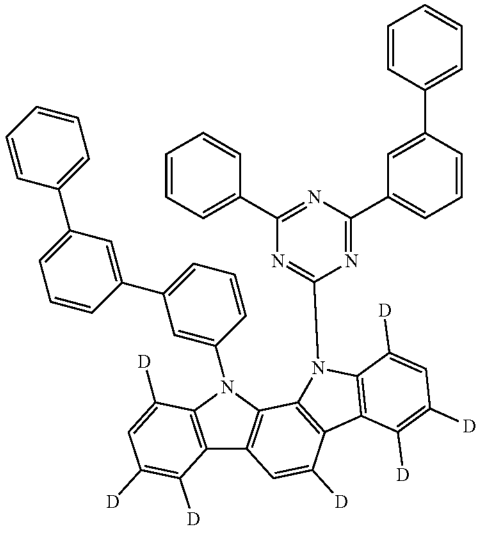
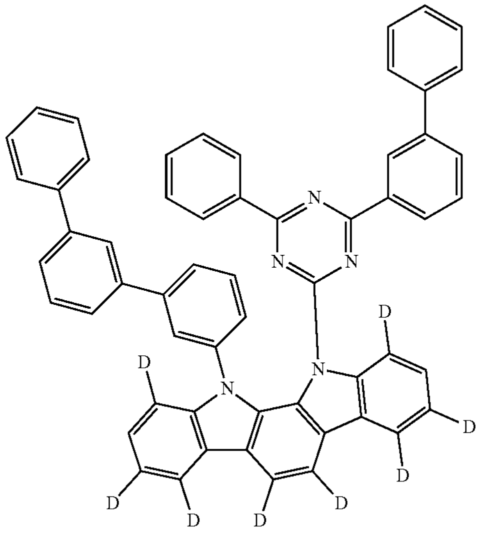
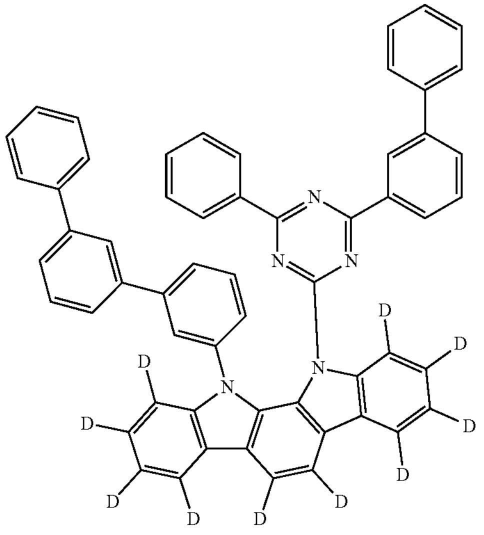

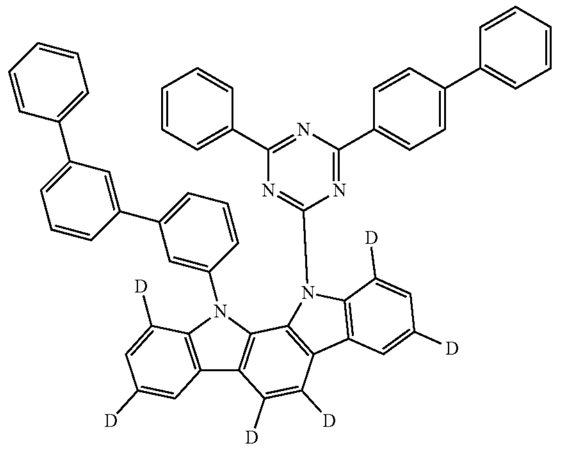
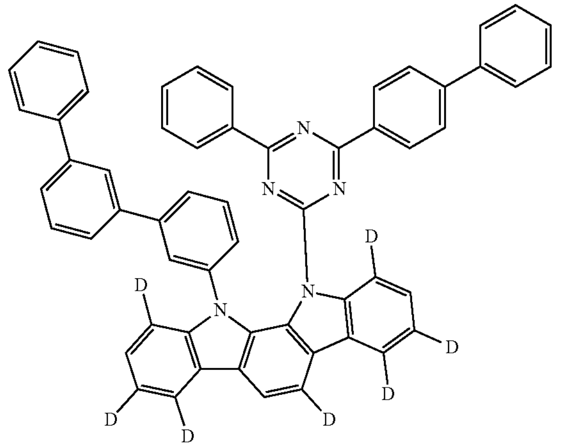
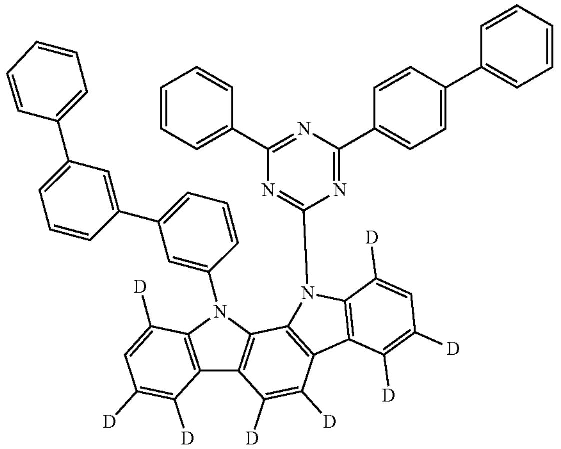
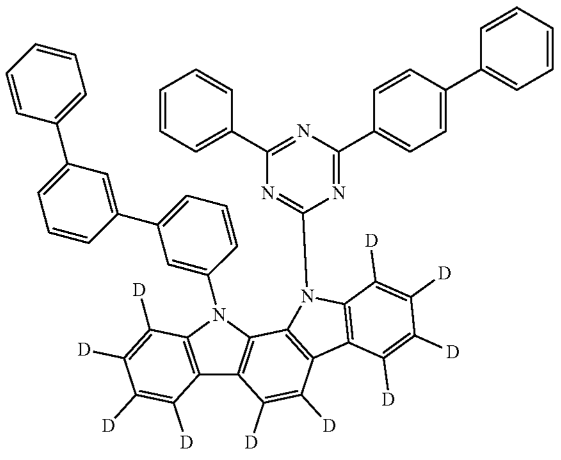
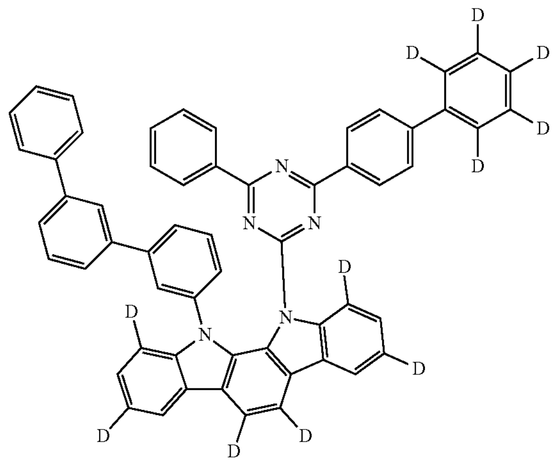
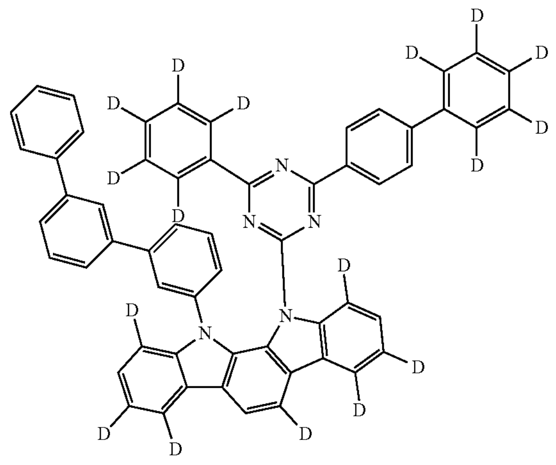

-continued
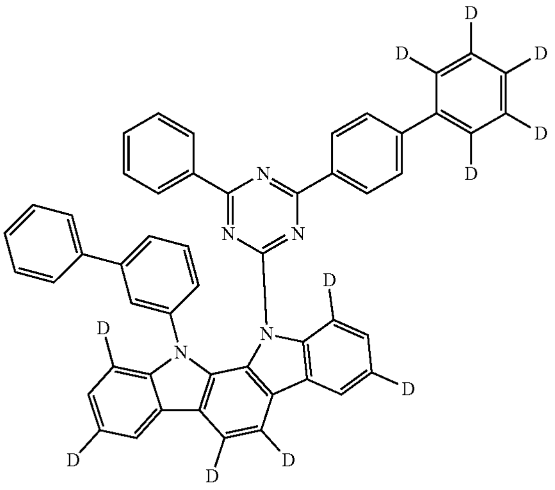
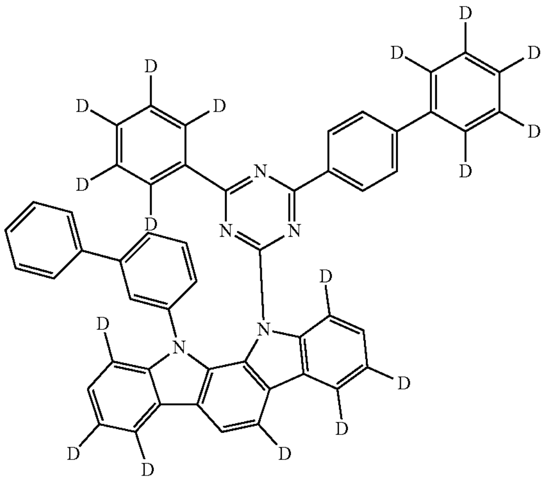
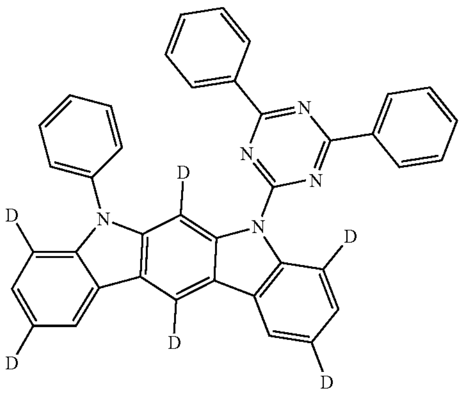
-continued
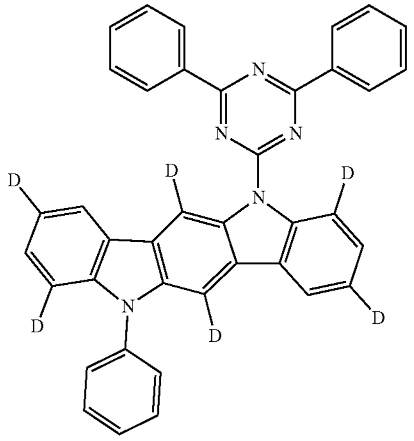
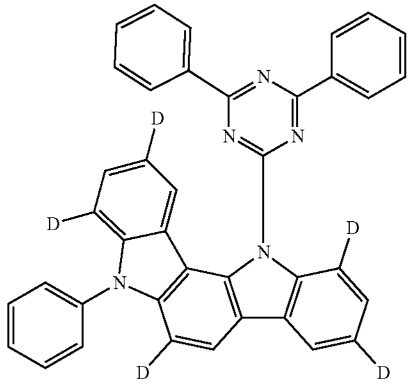
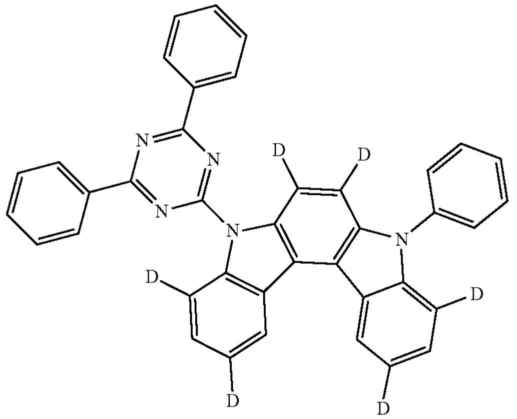
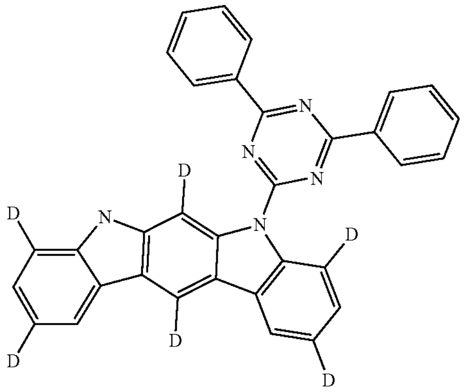

-continued
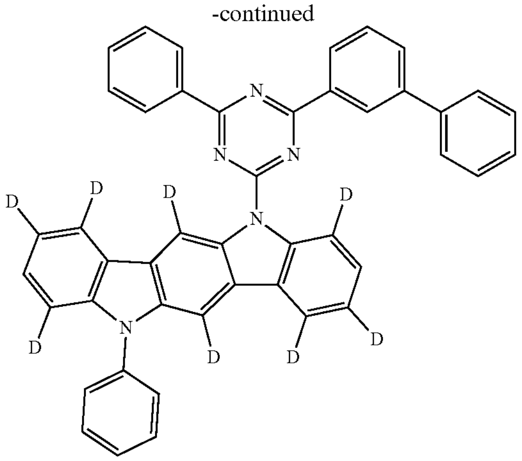
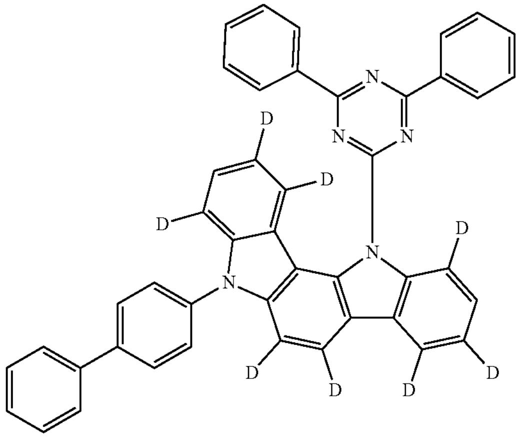
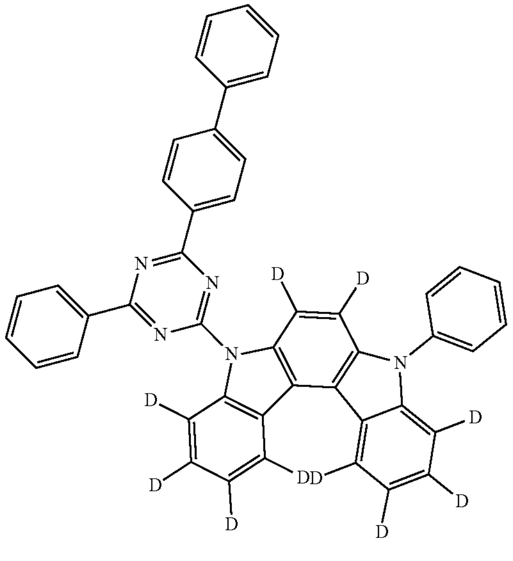
-continued
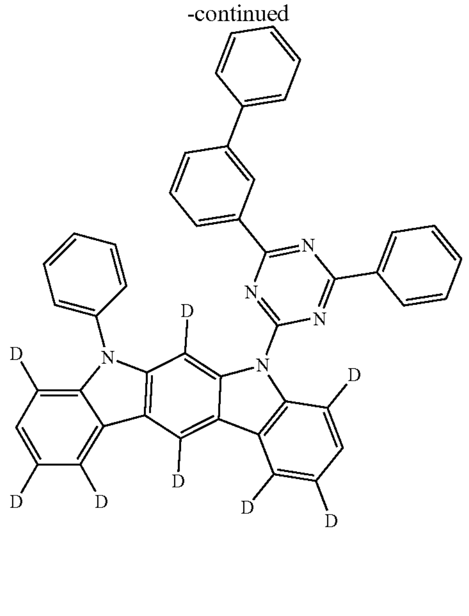
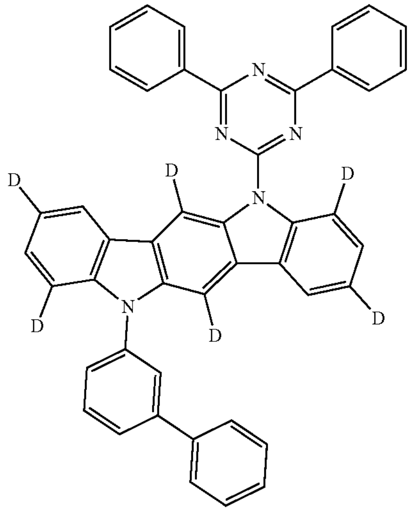
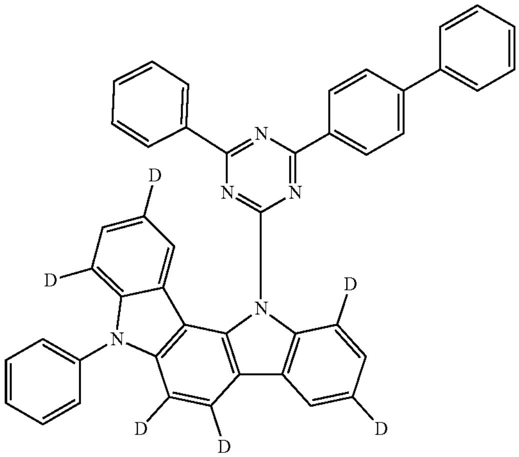

-continued
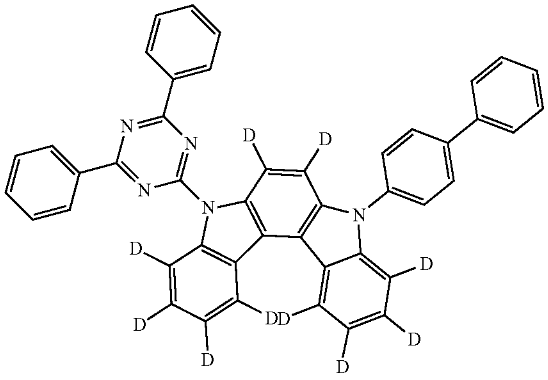
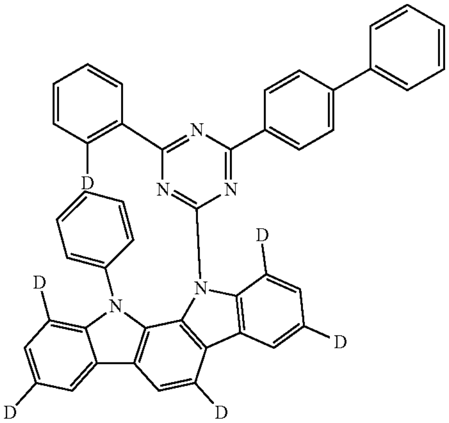
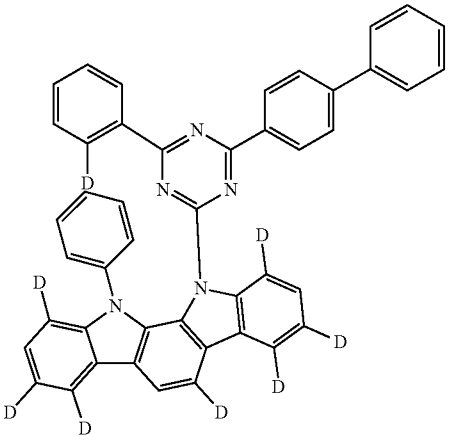
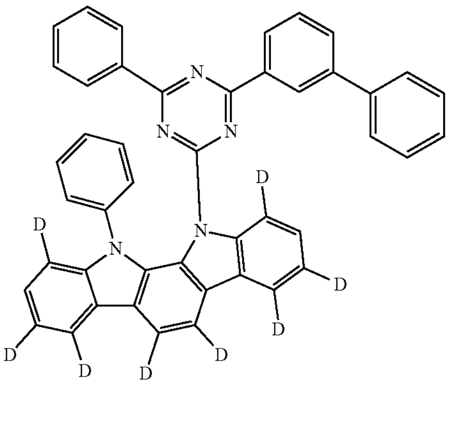
-continued
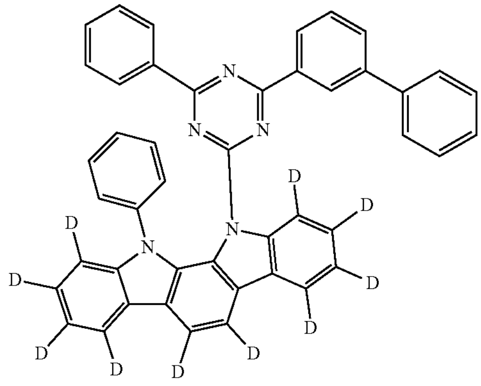
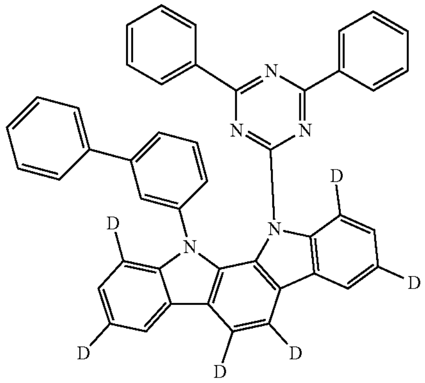
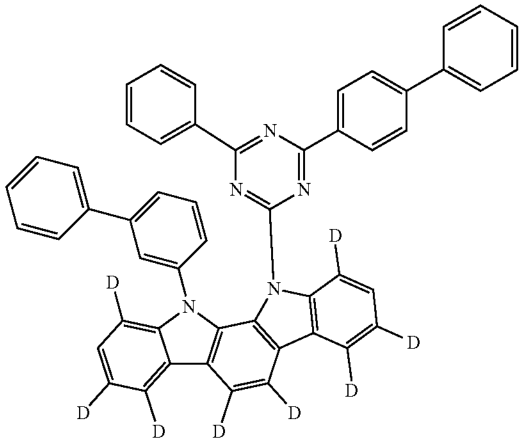
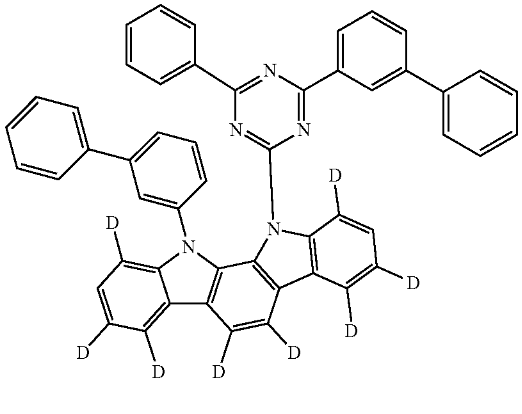

-continued
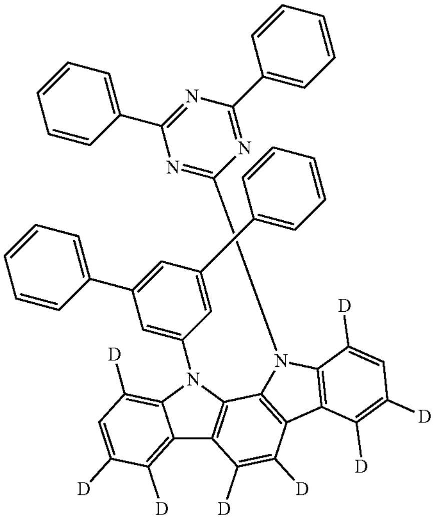
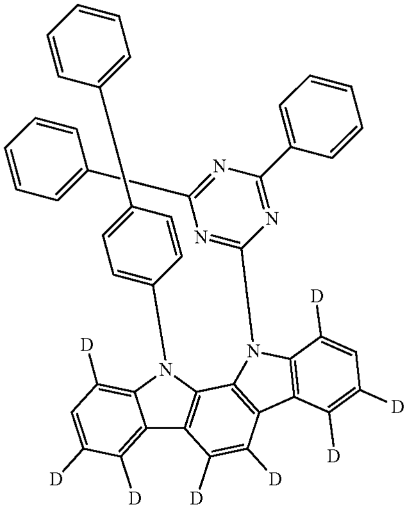
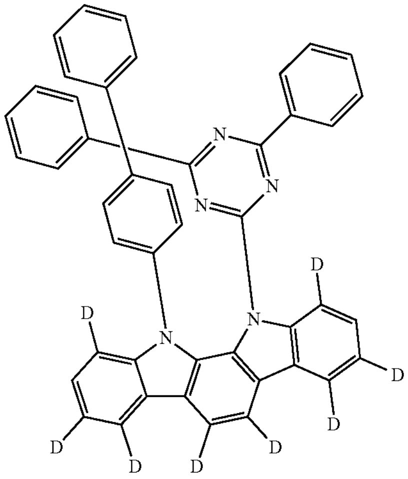
-continued
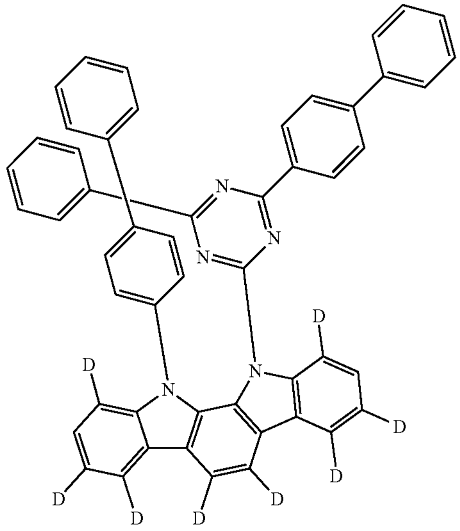
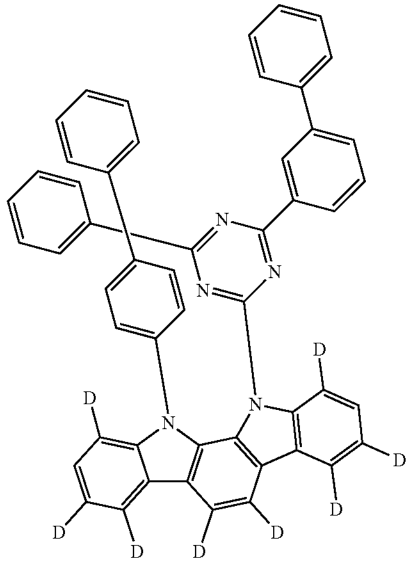
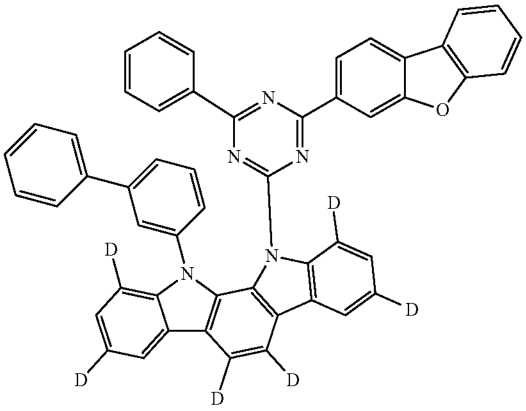

-continued
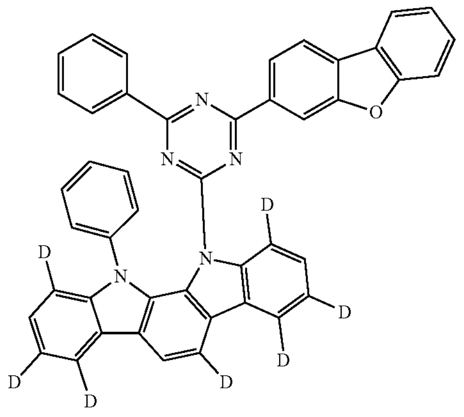
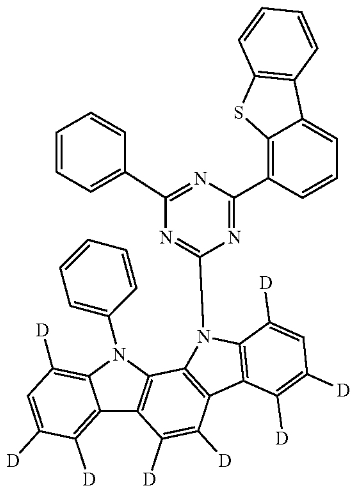
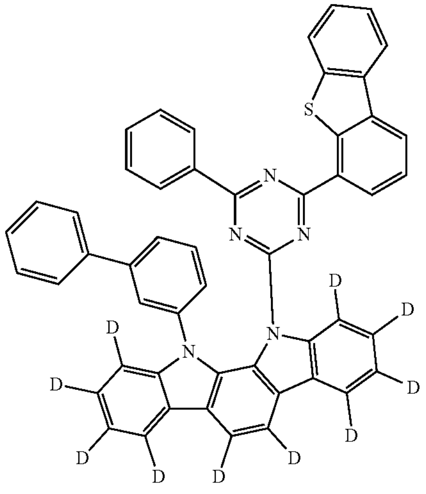
-continued
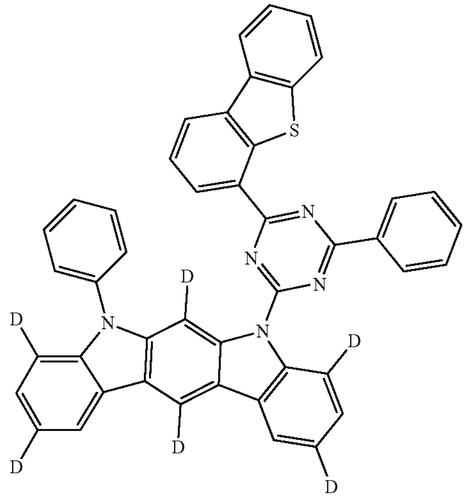
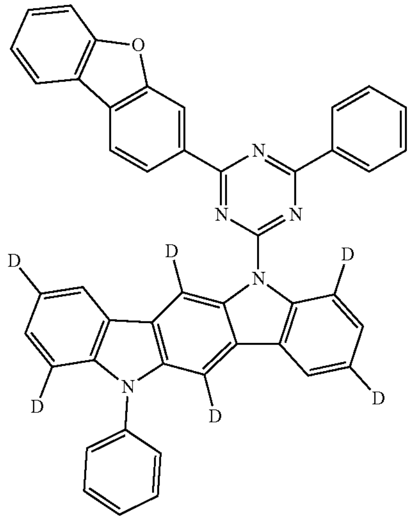
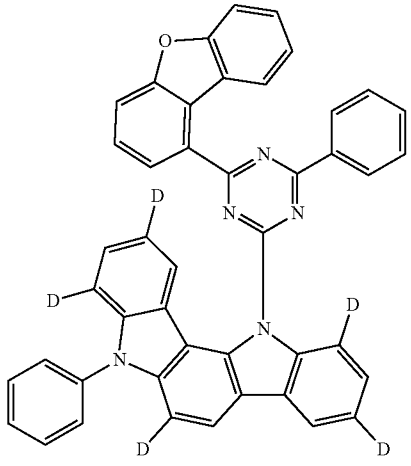

-continued
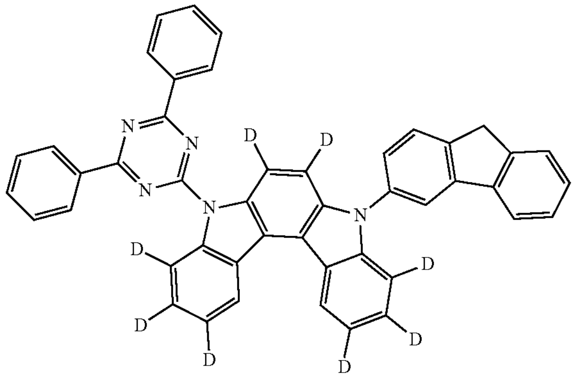
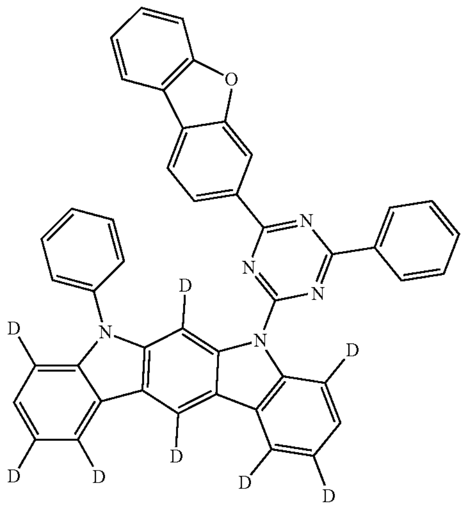
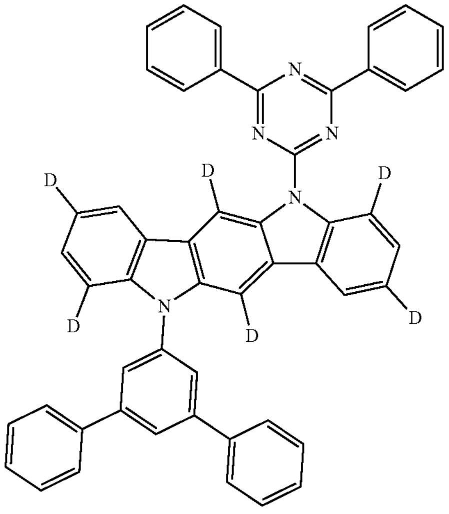
-continued
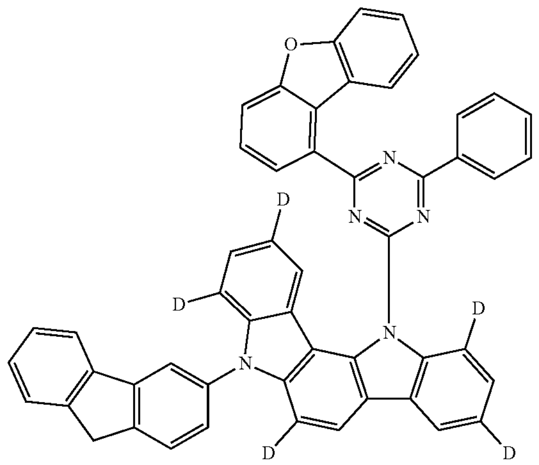
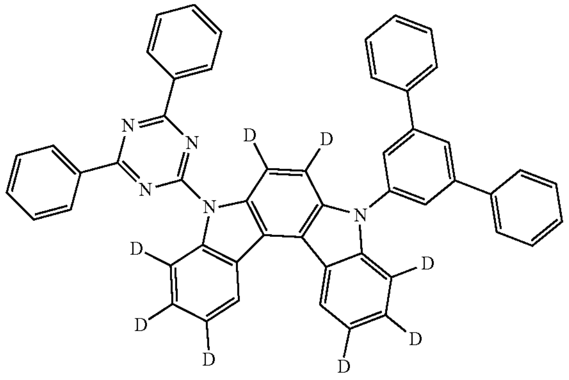
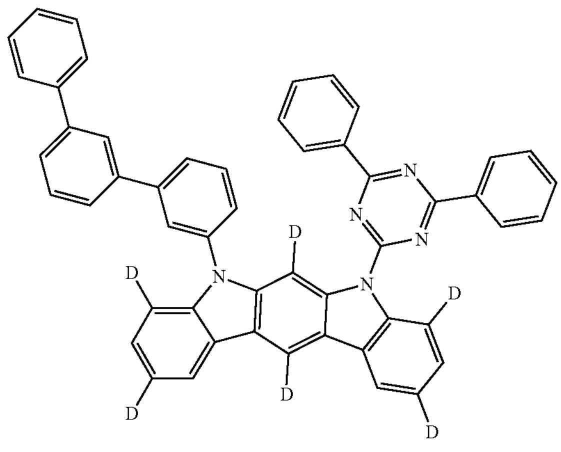

-continued
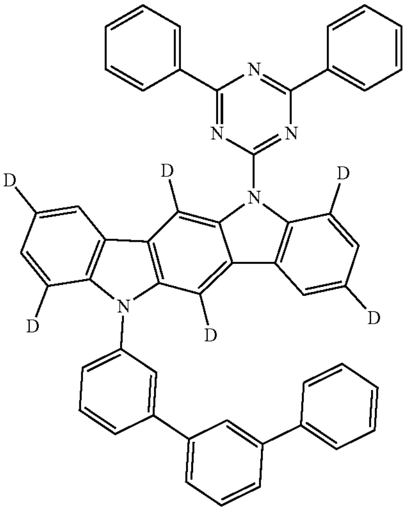
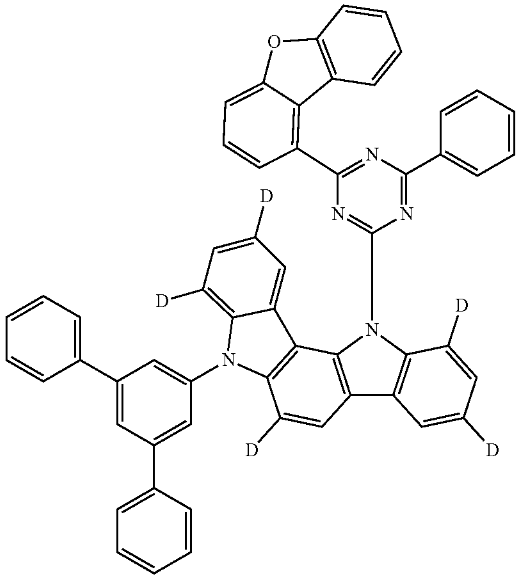
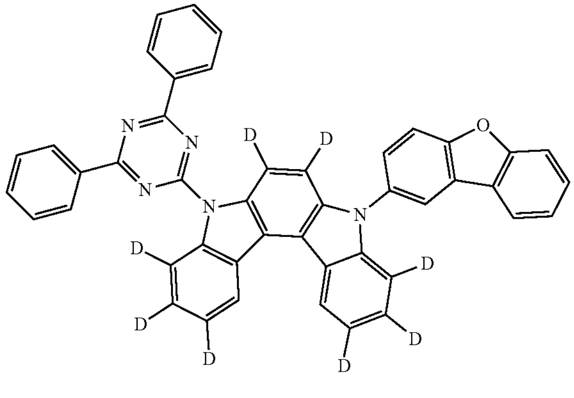
-continued
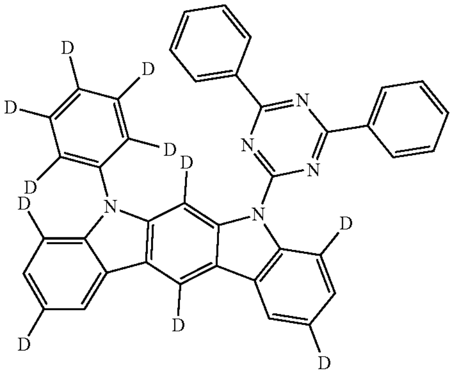
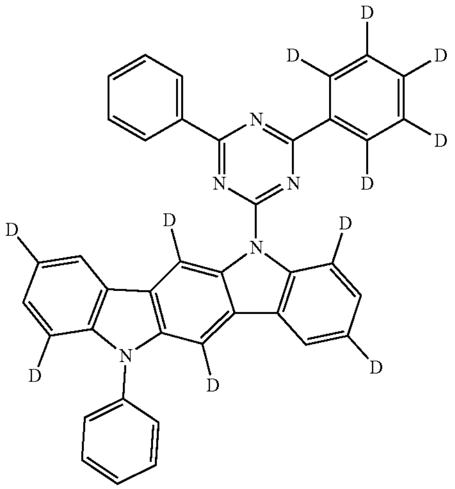
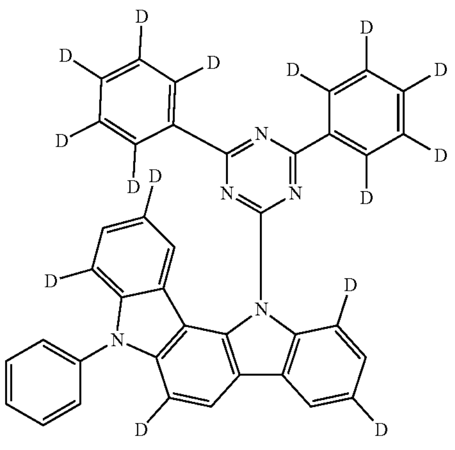

-continued
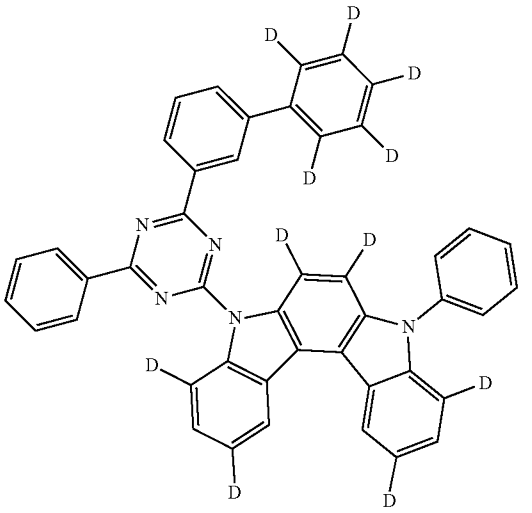
10. The organic light emitting device according to claim 1, wherein all of $R_2$ are hydrogen.
11. The organic light emitting device according to claim 1, wherein the second compound is any one compound selected from the group consisting of the following compounds:
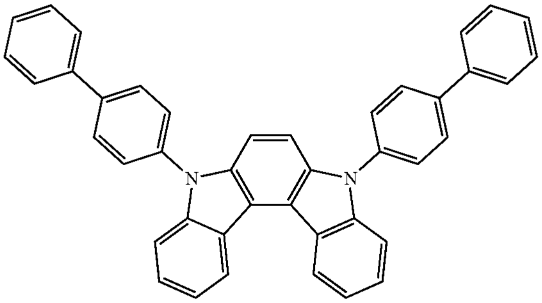
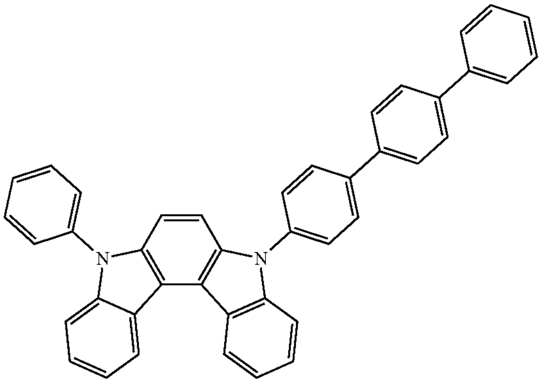
-continued
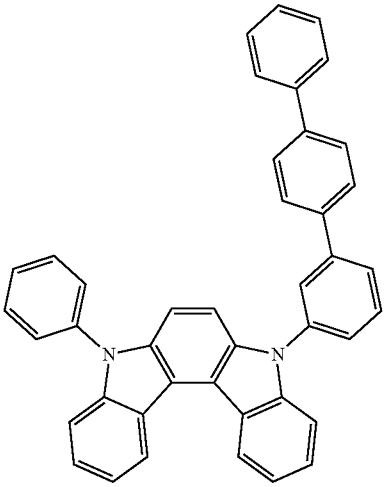
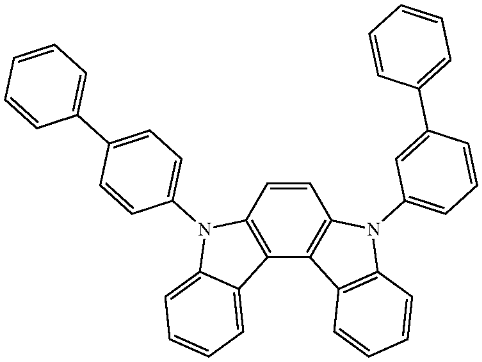
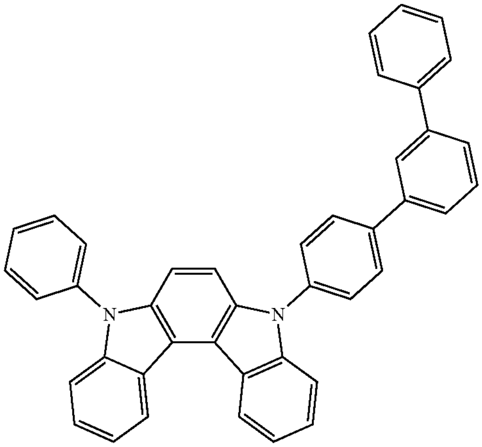

-continued
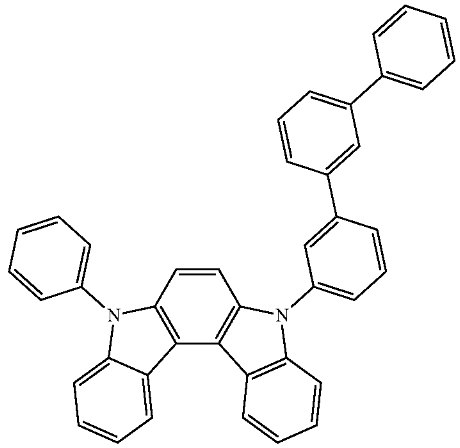
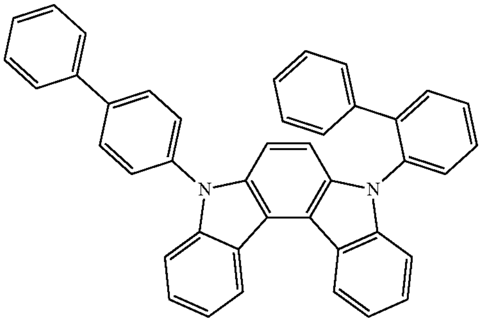
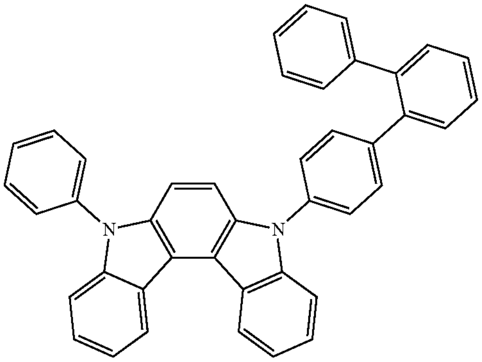
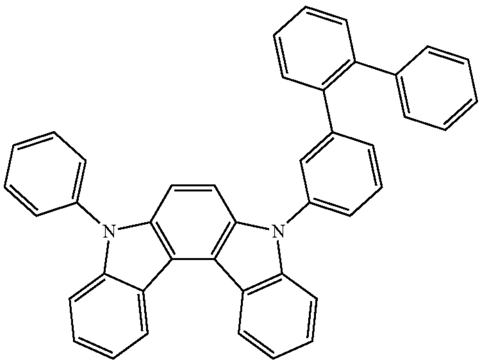
-continued
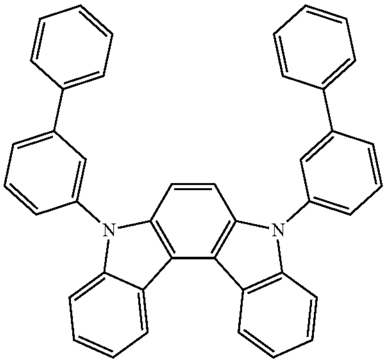
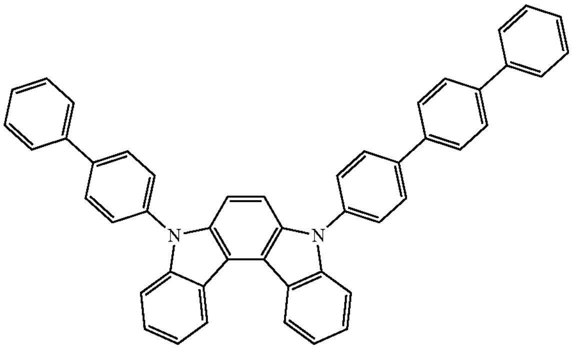
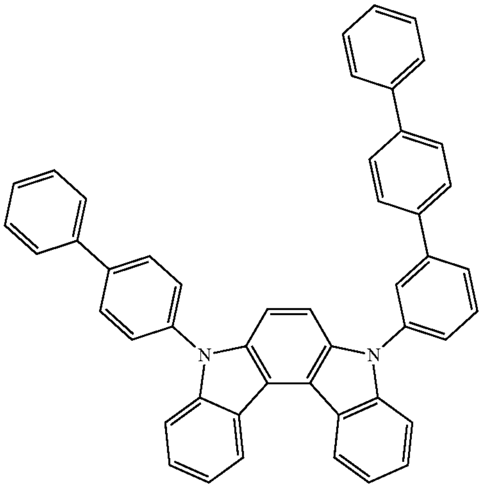
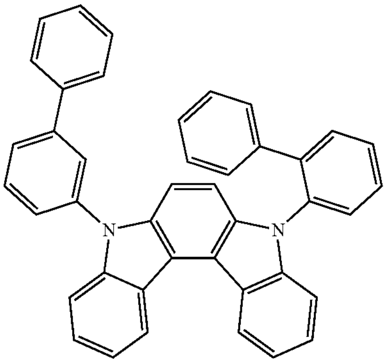

-continued
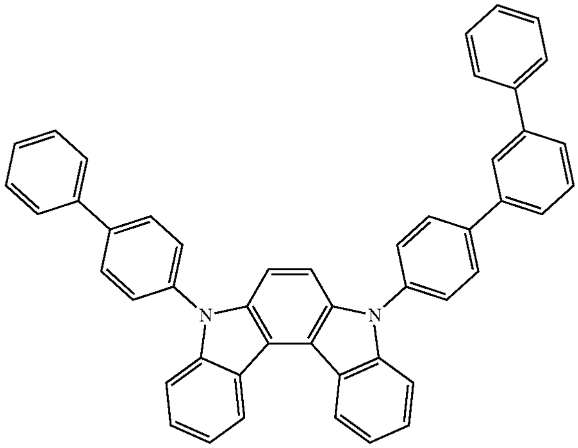
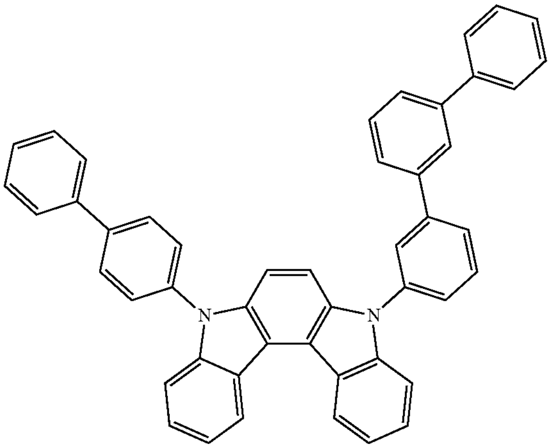
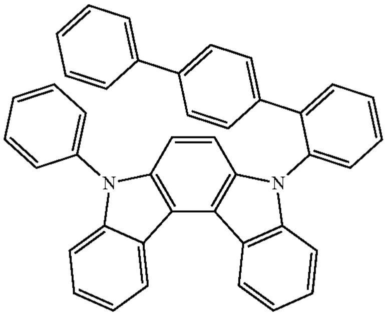
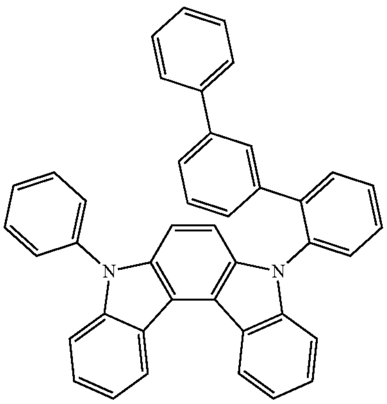
-continued
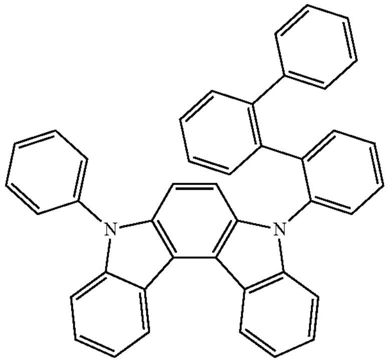
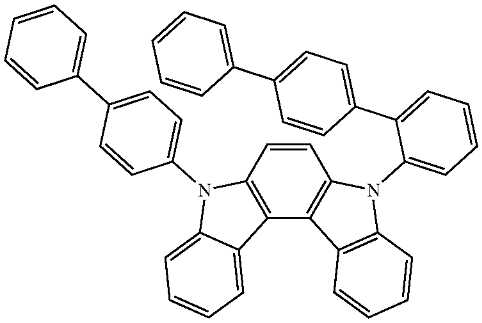
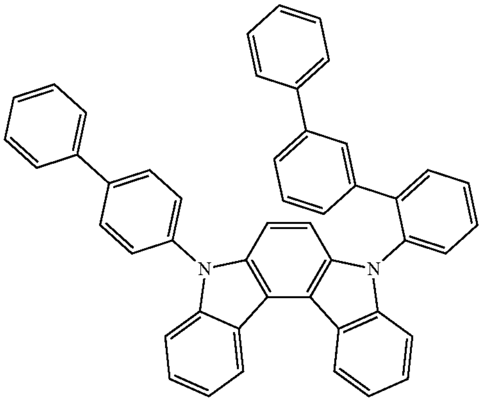
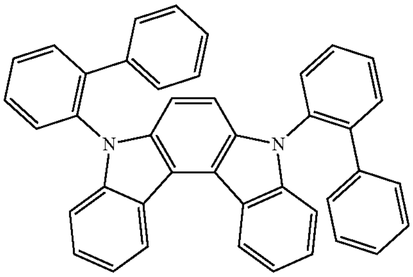
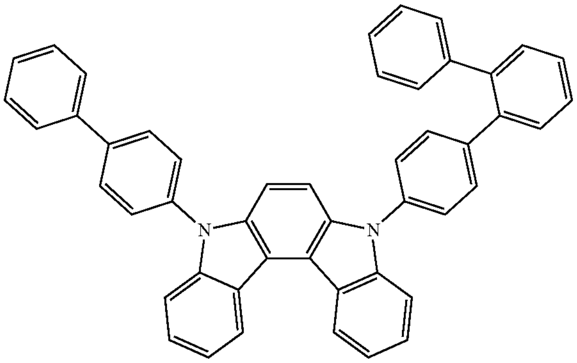

-continued
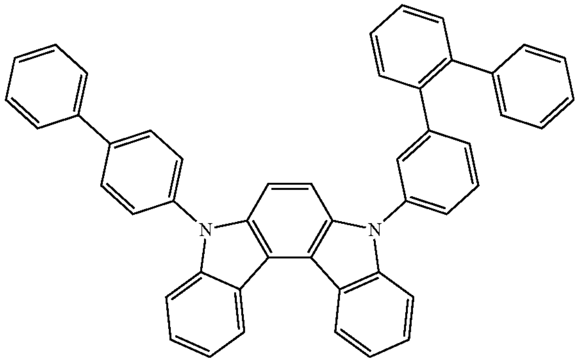
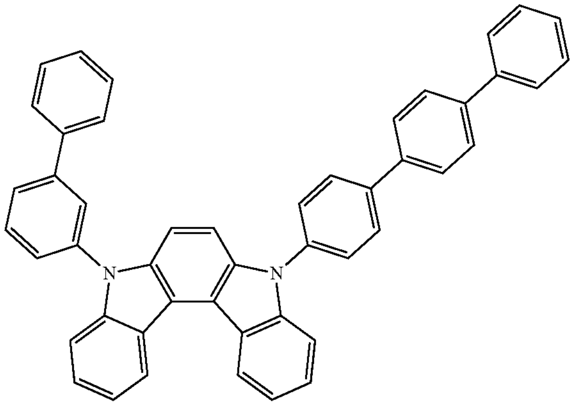
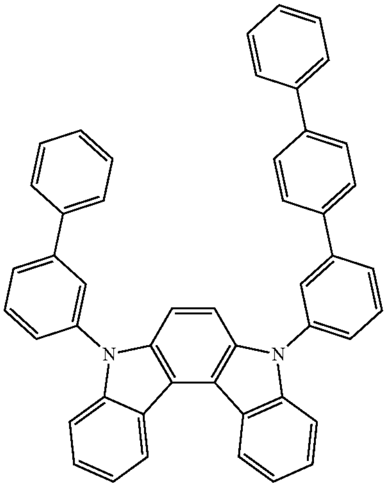
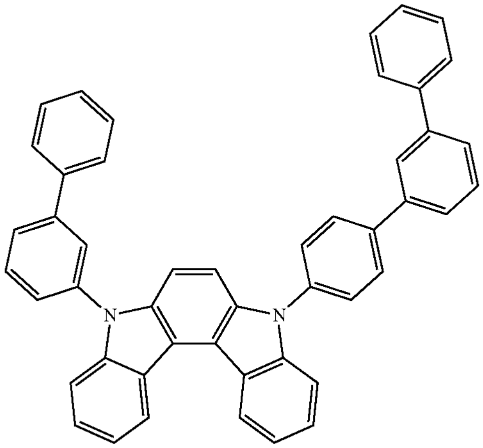
-continued
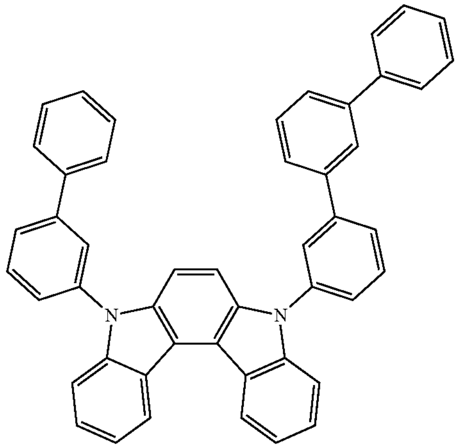
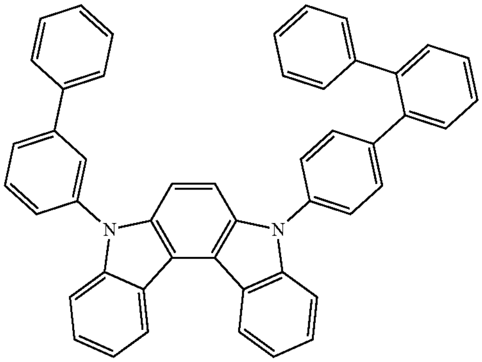
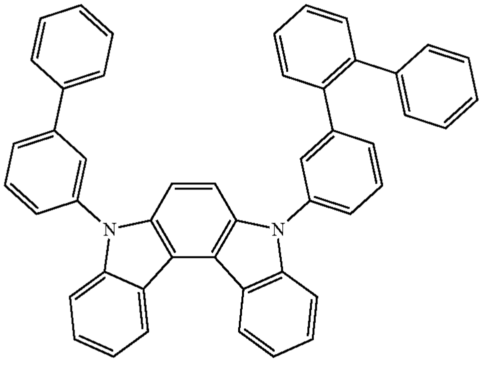

-continued
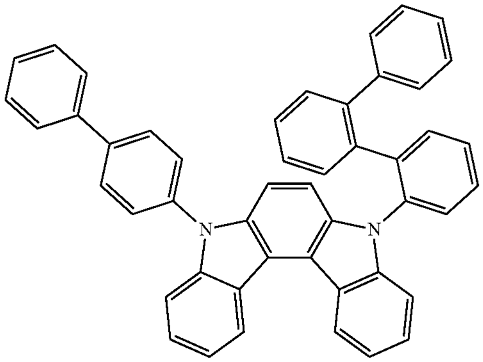
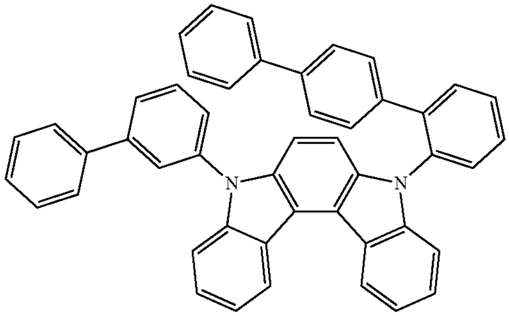
-continued
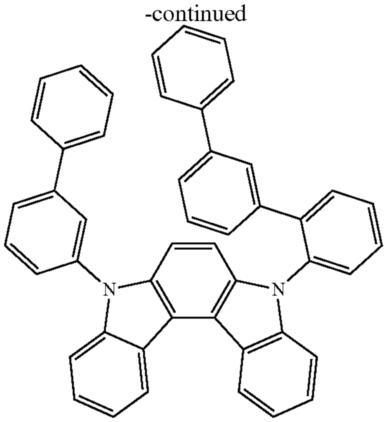
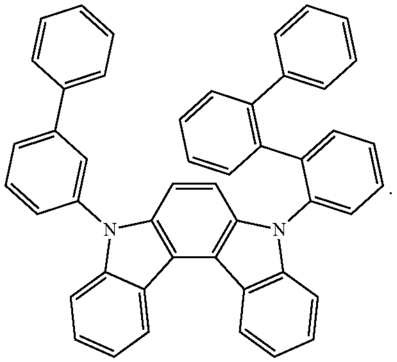
* * * * *